United States Patent
Jensen et al.

(10) Patent No.: US 10,780,118 B2
(45) Date of Patent: *Sep. 22, 2020

(54) METHOD AND COMPOSITIONS FOR CELLULAR IMMUNOTHERAPY

(71) Applicants: Fred Hutchinson Cancer Research Center, Seattle, WA (US); Seattle Children's Hospital, Seattle, WA (US)

(72) Inventors: Michael C. Jensen, Bainbridge Island, WA (US); Stanley R. Riddell, Sammamish, WA (US); Michael Hudecek, Leipzig (DE)

(73) Assignees: Fred Hutchinson Cancer Research Center, Seattle, WA (US); Seattle Children's Hospital, Seattle, WA (US)

( * ) Notice: Subject to any disclaimer, the term of this patent is extended or adjusted under 35 U.S.C. 154(b) by 248 days.

This patent is subject to a terminal disclaimer.

(21) Appl. No.: 14/422,640

(22) PCT Filed: Aug. 20, 2013

(86) PCT No.: PCT/US2013/055862
§ 371 (c)(1),
(2) Date: Feb. 19, 2015

(87) PCT Pub. No.: WO2014/031687
PCT Pub. Date: Feb. 27, 2014

(65) Prior Publication Data
US 2015/0306141 A1    Oct. 29, 2015

Related U.S. Application Data

(60) Provisional application No. 61/691,117, filed on Aug. 20, 2012.

(51) Int. Cl.
| | | |
|---|---|---|
| *A61K 35/17* | (2015.01) | |
| *C07K 14/705* | (2006.01) | |
| *C07K 14/725* | (2006.01) | |
| *C07K 14/715* | (2006.01) | |
| *C07K 16/28* | (2006.01) | |
| *C07K 16/32* | (2006.01) | |
| *C07K 16/40* | (2006.01) | |

(52) U.S. Cl.
CPC ............ *A61K 35/17* (2013.01); *C07K 14/705* (2013.01); *C07K 14/7051* (2013.01); *C07K 14/70521* (2013.01); *C07K 14/7151* (2013.01); *C07K 16/2803* (2013.01); *C07K 16/32* (2013.01); *C07K 16/40* (2013.01); *C07K 2317/622* (2013.01); *C07K 2317/64* (2013.01); *C07K 2319/03* (2013.01); *C07K 2319/30* (2013.01); *C07K 2319/70* (2013.01)

(58) Field of Classification Search
None
See application file for complete search history.

(56) References Cited

U.S. PATENT DOCUMENTS

| | | |
|---|---|---|
| 6,040,177 A | 3/2000 | Riddell et al. |
| 8,822,647 B2 | 9/2014 | Jensen |
| 2003/0148982 A1* | 8/2003 | Brenner ............ A61K 39/0011 514/44 R |
| 2008/0131415 A1 | 6/2008 | Riddell et al. |
| 2011/0059012 A1 | 3/2011 | Turtle et al. |
| 2013/0202622 A1 | 8/2013 | Riddell et al. |
| 2013/0287748 A1 | 10/2013 | June et al. |
| 2014/0314795 A1 | 10/2014 | Riddell et al. |
| 2018/0200298 A1 | 7/2018 | Jensen et al. |

FOREIGN PATENT DOCUMENTS

| | | |
|---|---|---|
| WO | 92/08796 A1 | 5/1992 |
| WO | 1992/015322 | 9/1992 |
| WO | 94/28143 A1 | 12/1994 |
| WO | 1995/021528 | 8/1995 |
| WO | 02/077029 A2 | 10/2002 |
| WO | 2010/025177 A1 | 3/2010 |
| WO | 2011/056894 A2 | 5/2011 |
| WO | 2012/129514 A1 | 9/2012 |
| WO | 2013/123061 A1 | 8/2013 |
| WO | 2013/126712 A1 | 8/2013 |

OTHER PUBLICATIONS

Kowolik et al., Cancer Res., 2006, 66: 10995-11004.*
Wang et al., Blood, online Jun. 7, 2011, 118: 1255-1263.*
Bridgeman et al., Current Gene Therapy, 2010, 10: 77-90.*
Winkler et al., J. Immunol., 2000, 165: 4505-4514.*
Chen et al., J. Exp. Med., 1992, 176: 855-866.*
Solomon et al.,Eur.J. Immunol., 1978, 8: 782-785.*
Hombach et al., Gene Therapy, 2010, 17: 1206-1213.*
Sequence Alignment 1, 2019.*
Sequence Alignment 2, 2019.*
Adlersberg, La Ricerca Clin. Lab., 1976, 6: 191-205.*
Jensen et al., "Antitransgene Rejection Responses Contribute to Attenuated Persistence of Adoptively Transferred CD20/CD19-Specific Chimeric Antigen Receptor Redirected T Cells in Humans," *Biol. Blood Marrow Transplant* 16: 1245-1256, 2010.

(Continued)

*Primary Examiner* — Ileana Popa
(74) *Attorney, Agent, or Firm* — Seed IP Law Group LLP

(57) ABSTRACT

The present invention provides nucleic acids, vectors, host cells, methods and compositions to confer and/or augment immune responses mediated by cellular immunotherapy, such as by adoptively transferring CD8+ central memory T cells or combinations of central memory T cells with CD4+ T cells that are genetically modified to express a chimeric receptor. In embodiments the genetically modified host cell comprises a nucleic acid comprising a polynucleotide coding for a ligand binding domain, a polynucleotide comprising a customized spacer region, a polynucleotide comprising a transmembrane domain, and a polynucleotide comprising an intracellular signaling domain. It has been surprisingly found that the length of the spacer region can affects the ability of chimeric receptor modified T cells to recognize target cells in vitro and affects in vivo efficacy of the chimeric receptor modified T cells. Pharmaceutical formulations produced by the method, and methods of using the same, are also described.

37 Claims, 20 Drawing Sheets

Specification includes a Sequence Listing.

(56) References Cited

OTHER PUBLICATIONS

Bejcek et al., "Development and Characterization of Three Recombinant Single Chain Antibody Fragments (scFvs) Directed against the CD19 Antigen," *Cancer Research* 55:2346-2351, 1995.

Cheadle et al., "Natural Expression of the CD19 Antigen Impacts the Long-Term Engraftment but Not Antitumor Activity of CD19-Specific Engineered T Cells," *Journal of Immunology* 184, 2010, 12 pages.

Cho et al., "Structure of the extracellular region of HER2 alone and in complex with the Herceptin Fab," *Nature* 421:756-760, 2003.

Fitzer-Attas et al., "Harnessing Syk Family Tyrosine Kinases as Signaling Domains for Chimeric Single Chain of the Variable Domain Receptors: Optimal Design for T Cell Activation," *Journal of Immunology* 160:145-154, 1998.

Guest et al., "The Role of Extracellular Spacer Regions in the Optimal Design of Chimeric Immune Receptors," *J Immunother* 28:203-211, 2005.

Hombach et al., "T Cell Activation by Antibody-Like Immunoreceptors: The Position of the binding Epitope within the Target Molecule Determines the Efficiency of Activation of Redirected T Cells," *Journal of Immunology* 178:4650-4657, 2007.

Hudecek et al., "The B-cell tumor-associated antigen ROR1 can be targeted with T cells modified to express a ROR1-specific chimeric antigen receptor," *Blood* 116:4532-4541, 2010.

James et al., "Antigen Sensitivity of CD22-Specific Chimeric TCR is Modulated by Target Epitome Distance from the Cell Membrane," *Journal of Immunology* 180:7028-7038, 2008.

Koehler et al., "Engineered T Cells for the Adoptive Therapy of B-Cell Chronic Lymphocytic Leukaemia," *Advances in Hematology* 2012, 2012, 13 pages.

Lupton et al., "Dominant Positive and Negative Selection Using a Hygromycin Phosphotransferase-Thymidine Kinase Fusion Gene," *Molecular and Cellular Biology* 11(6):3374-3378, 1991.

Pezzutto et al., "CD19 monoclonal antibody HD37 inhibits anti-immunoglobulin-induced B cell activation and proliferation," *The Journal of Immunology* 138:2793-2799, 1987.

Ramos et al., "Chimeric Antigen Receptor (CAR)-Engineered Lymphocytes for Cancer Therapy," *Expert Opin Biol Ther*. 11(7):855-873, 2011. (32 pages).

Riddell et al., "The use of anti-CD28 monoclonal antibodies to clone and expand human antigen-specific T cells," *Journal of Immunological Methods* 128:189-201, 1990.

Riddell et al., "The Fred Hutchinson Cancer Research Center and the University of Washington School of Medicine, Department of Medicine, Division of Oncology Oct. 7, 1991," *Human Gene Therapy* 3:319-338,1992.

Till et al., "Adoptive immunotherapy for indolent non-Hodgkin lymphoma and mantle cell lymphoma using genetically modified autologous CD20-specific T cells," *Blood* 112(6):2261-2271, 2008.

Wilkie et al., "Retargeting of Human T Cells to Tumor-Associated MUC1: The Evolution of a Chimeric Antigen Receptor," *Journal of Immunology* 180:4901-4909, 2008.

Hudecek et al. "The Anti-Tumor Reactivity of ROR1-CAR Modified T Cells Depends on the Targeted Epitope, CAR-Affinity and Design of the CAR Extracellular Domain," *Clinical Lymphoma, Myeloma & Leukemia* 11(Supplement 2), Abstract, 3 pages (Oct. 2011).

Guest et al., "The Role of Extracellular Spacer Regions in the Optimal Design of Chimeric Immune Receptors," *J Immunother* 28(3):203-211 (May/Jun. 2005).

Patel et al., "Impact of chimeric immune receptor extracellular protein domains on T cell function," *Gene Therapy* 6:412-419 (1999).

Nicholson et al., "Construction and characterisation of a functional CD19 specific single chain Fv fragment for immunotherapy of B lineage leukemia and lymphoma." *Molecular Immunology* 24(16-17):1157-1165, 1997.

Yang et al. "Therapeutic Potential and Challenges of Targeting Receptor Tyrosine Kinase ROR1 with Monoclonal Antibodies in B-Cell Malignancies," *PLos One* 6(6):e21018, (15 pages) Jun. 15, 2011.

Altvater et al., "2B4 (CD244) signaling via chimeric receptors costimulates tumor-antigen specific proliferation and in vitro expansion of human T cells," *Cancer Immunol Immunother* 58:1991-2001 (2009).

Altvater et al., "2B4 (CD244) Signaling by Recombinant Antigen-specific Chimeric Receptors Costimulates Natural Killer Cell Activation to Leukemia and Neuroblastoma Cells," *Clin Cancer Res* 15(15):4857-4866 (2009).

Bloom et al., "Intrachain disulfide bond in the core hinge region of human IgG4," *Protein Science* 6:407-415 (1997).

Brentjens et al., "Treatment of Chronic Lymphocytic Leukemia With Genetically Targeted Autologous T Cells: Case Report of an Unforeseen Adverse Event in a Phase I Clinical Trial," *Mol. Ther*., 18(4):666-668 (2010).

Brezski et al., "A monoclonal antibody against hinge-cleaved IgG restores effector function to proteolytically-inactivated IgGs in vitro and in vivo," *mAbs* 6(5):1265-1273 (Sep./Oct. 2014).

Chang et al., "Transgene-enforced co-stimulation of CD4$^+$ T cells leads to enhanced and sustained anti-tumor effector functioning," *Cytotherapy* 9(8):771-784 (2007).

Cheadle et al., "Eradication of Established B-cell Lymphoma by CD19-specific Murine T Cells is Dependent on Host Lymphopenic Environment and Can be Mediated by CD4$^+$ and CD8$^+$ T Cells," *J Immunother* 32(3):207-218 (Apr. 2009).

Cheadle et al., "Killing of non-Hodgkin lymphoma cells by autologous CD19 engineered T cells," *British Journal of Haematology* 129:322-332 (2005).

Cheadle et al., "The combination of cyclophosphamide and human T cells genetically engineered to target CD19 can eradicate established B-cell lymphoma," *British Journal of Haematology* 142(1):65-68 (2008).

Davis et al., "The kinetic-segregation model: TCR triggering and beyond," *Nature Immunology* 7(8):803-809 (Aug. 2006).

Gattenlöhner et al., "Rhabdomyosarcoma Lysis by T Cells Expressing a Human Autoantibody-Based Chimeric Receptor Targeting the Fetal Acetylcholine Receptor," *Cancer Res* 66(1):24-28 (2006).

Gonzalez et al., "Genetic engineering of cytolytic T lymphocytes for adoptive T-cell therapy of neuroblastoma," *The Journal of Gene Medicine* 6:704-711 (2004).

Hoyos et al., "Engineering CD19-specific T lymphocytes with interleukin-15 and a suicide gene to enhance their anti-lymphoma/leukemia effects and safety," *Leukemia* 24:1160-1170 (2010).

Hudecek et al., "The Non-signaling Extracellular Spacer Domain of Chimeric Antigen Receptors is Decisive for in Vivo Antitumor Activity," *Cancer Immunol Res*. 3(2):125-135 (2014).

Imai et al., "Genetic modification of primary natural killer cells overcomes inhibitory signals and induces specific killing of leukemic cells," *Blood* 106(1):376-373 (2005).

Jensen et al., "CD20 is a molecular target for scFvFc:ζ receptor redirected T cells: implications for cellular immunotherapy of CD20+ malignancy," *Biology of Blood and Marrow Transplantation* 4:75-83 (1998).

Kahlon et al., "Specific Recognition and Killing of Glioblastoma Multiforme by Interleukin 13-Zetakine Redirected Cytolytic T Cells," *Cancer Research* 64:9160-9166 (2004).

Kalos et al., "T Cells with Chimeric Antigen Receptors Have Potent Antitumor Effects and Can Establish Memory in Patients with Advanced Leukemia," *Sci. Trans. Med*. 3 95(95ra73):1-13 (2011).

Kochenderfer et al., "Construction and Pre-clinical Evaluation of an Anti-CD19 Chimeric Antigen Receptor," *J Immunother*. 32(7):689-702 (Sep. 2009).

Kochenderfer et al., "Eradication of B-lineage cells and regression of lymphoma in a patient treated with autologous T cells genetically engineered to recognize CD19," *Blood* 116(20):4099-4102 (Nov. 18, 2010).

Kradin et al., "Adoptive Immunotherapy with Interleukin-2 (IL-2) Results in Diminished IL-2 Production by Stimulated Peripheral Blood Lymphocytes," *Journal of Clinical Immunology* 9(5):378-385 (1989).

(56) References Cited

OTHER PUBLICATIONS

Landmeier et al., "Gene-Engineered Varicella-Zoster Virus-Reactive CD4+ Cytotoxic T Cells Exert Tumor-Specific Effector Function," *Cancer Res* 67(17):8335-8343 (2007).
Loskog et al., "Addition of the CD28 signaling domain to chimeric T-cell receptors enhances chimeric T-cell resistance to T regulatory cells," *Leukemia* 20:1819-1828 (2006).
Marin et al., "Enhancement of the anti-leukemic activity of cytokine induced killer cells with an anti-CD19 chimeric receptor delivering a 4-1BB-ζ activating signal," *Experimental Hematology* 35:1388-1397 (2007).
Micklethwaite et al., "Derivation of human T lymphocytes from cord blood and peripheral blood with antiviral and antileukemic specificity from a single culture as protection against infection and relapse after stem cell transplantation," *Blood* 115(13):2695-2703 (Apr. 1, 2010).
Moritz et al., "A spacer region between the single chain antibody- and the CD3ζ-chain domain of chimeric T cell receptor components is required for efficient ligand binding and signaling activity," *Gene Therapy* 2:539-546 (1995).
Park et al., "Adoptive Transfer of Chimeric Antigen Receptor Re-directed Cytolytic T Lymphocyte Clones in Pateints with Neuroblastoma," *Molecular Therapy* 15(4):825-833 (2007).
Pule et al., "A Chimeric T Cell Antigen Receptor That Augments Cytokine Release and Supports Clonal Expansion of Primary Human T Cells," *Molecular Therapy* 12(5):933-941 (2005).
Reddy et al., "Elimination of Fc Receptor-Dependent Effector Functions of a Modified IgG4 Monoclonal Antibody to Human CD4," *The Journal of Immunology* 164:1925-1933 (2000).
Rossig et al., "Target Antigen Expression on a Professional Antigen-Presenting Cell Induces Superior Proliferative Antitumor T-Cell Responses via Chimeric T-Cell Receptors," *J Immunother* 29(1):21-31 (2006).
Salvoldo et al., "CD28 costimulation improves expansion and persistence of chimeric antigen receptor-modified T cells in lymphoma patients," *The Journal of Clinical Investigation* 121(5):1822-1826 (2011).
Salvoldo et al., "Epstein Barr virus-specific cytotoxic T lymphocytes expressing the anti-CD30ζ artificial chimeric T-cell receptor for immunotherapy of Hodgin disease," *Blood* 110(7):2620-2630 (2007).
Tao et al., "The Differential Ability of Human IgG1 and IgG4 to Activate Complement is Determined by the COOH-terminal Sequence of the $C_H2$ Domain," *J. Exp. Med.* 173:1025-1028 (1991).
Till et al., "CD20-specific adoptive immunotherapy for lymphoma using a chimeric antigen receptor with both CD28 and 4-1BB domains: pilot clinical trial results," *Blood* 119(17):3940-3950 (2012).
Vera et al., "T lymphocytes redirected against the k light chain of human immunoglobulin efficiently kill mature B lymphocyte-derived malignant cells," *Blood* 108(12):3890-3897 (2006).
Cartellieri et al., "Chimeric Antigen Receptor-Engineered T Cells for Immunotherapy of Cancer," *Journal of Biomedicine and Biotechnology*, vol. 2010, Article ID 956304 (13 pages) (2010).
Berasain et al., "Specific cleavage sites on human IgG subclasses by cruzipain, the major cysteine proteinase from *Trypanosoma cruzi*," *Molecular & Biochemical Parasitology*, p. 1-7 (2003).
Karlsson et al., "Evaluation of Intracellular Signaling Downstream Chimeric Antigen Receptors," *PLoS One* 10(12):e0144787 (20 pages) (2015).
Rossig et al., "Adoptive Cellular Immunotherapy with CD19-Specific T Cells," *Klin Padiatr* 217:351-356 (2005).
Chmielewski et al., "CD28 cosignalling does not affect the activation threshold in a chimeric antigen receptor-redirected T-cell attack," *Gene Therapy* 18:62-72 (2011).
Zhao et al., "A Herceptin-Based Chimeric Antigen Receptor with Modified Signaling Domains Leads to Enhanced Survival of Transduced T Lymphocytes and Antitumor Activity," *The Journal of Immunology* 183:5563-5574 (2009).

\* cited by examiner

```
                               SEQUENCE LISTING

<160> NUMBER OF SEQ ID NOS: 74

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 1
<223> OTHER INFORMATION: Xaa = glycine, cysteine or arginine
<220> FEATURE:
<221> NAME/KEY: VARIANT
<222> LOCATION: 4
<223> OTHER INFORMATION: Xaa = cysteine or threonine

<400> SEQUENCE: 1

Xaa Pro Pro Xaa Pro
1               5

<210> SEQ ID NO 2
<211> LENGTH: 66
<212> TYPE: DNA
<213> ORGANISM: Artificial Sequence
<220> FEATURE:
<223> OTHER INFORMATION: Synthetic sequence

<400> SEQUENCE: 2
atgctgctgc tggtgaccag cctgctgctg tgcgagctgc ccacccccgc ctttctgctg    60
atcccc                                                              66

<210> SEQ ID NO 3
<211> LENGTH: 735
<212> TYPE: DNA
<213> ORGANISM: Artificial Sequence
<220> FEATURE:
<223> OTHER INFORMATION: Synthetic sequence

<400> SEQUENCE: 3
gacatccaga tgacccagac cacctccagc ctgagcgcca gcctgggcga ccgggtgacc    60
atcagctgcc gggccagcca ggacatcagc aagtacctga actggtatca gcagaagccc   120
gacggcaccg tcaagctgct gatctaccac accagccggc tgcacagcgg cgtgcccagc   180
cggtttagcg gcagcggctc cggcaccgac tacagcctga ccatctccaa cctggaacag   240
gaagatatcg ccacctactt ttgccagcag ggcaacacac tgccctacac ctttggcggc   300
ggaacaaagc tggaaatcac cggcagcacc tccggcagcg gcaagcctgg cagcggcgag   360
ggcagcacca agggcgaggt gaagctgcag gaaagcggcc ctggcctggt ggcccccagc   420
cagagcctga gcgtgacctg caccgtgagc ggcgtgagcc tgcccgacta cggcgtgagc   480
tggatccggc agcccccccag gaagggcctg gaatggctgg gcgtgatctg gggcagcgag   540
accacctact acaacagcgc cctgaagagc cggctgacca tcatcaagga caacagcaag   600
agccaggtgt tcctgaagat gaacagcctg cagaccgacg acaccgccat ctactactgc   660
```

```
gccaagcact actactacgg cggcagctac gccatggact actggggcca gggcaccagc    720
gtgaccgtga gcagc                                                    735

<210> SEQ ID NO 4
<211> LENGTH: 36
<212> TYPE: DNA
<213> ORGANISM: Artificial Sequence
<220> FEATURE:
<223> OTHER INFORMATION: Synthetic sequence

<400> SEQUENCE: 4
gaatctaagt acggaccgcc ctgccccct tgccct                               36

<210> SEQ ID NO 5
<211> LENGTH: 84
<212> TYPE: DNA
<213> ORGANISM: Artificial Sequence
<220> FEATURE:
<223> OTHER INFORMATION: Synthetic sequence

<400> SEQUENCE: 5
atgttctggg tgctggtggt ggtcggaggc gtgctggcct gctacagcct gctggtcacc     60
gtggccttca tcatcttttg ggtg                                           84

<210> SEQ ID NO 6
<211> LENGTH: 126
<212> TYPE: DNA
<213> ORGANISM: Artificial Sequence
<220> FEATURE:
<223> OTHER INFORMATION: Synthetic sequence

<400> SEQUENCE: 6
aaacggggca gaaagaaact cctgtatata ttcaaacaac catttatgag accagtacaa     60
actactcaag aggaagatgg ctgtagctgc cgatttccag aagaagaaga aggaggatgt    120
gaactg                                                              126

<210> SEQ ID NO 7
<211> LENGTH: 336
<212> TYPE: DNA
<213> ORGANISM: Artificial Sequence
<220> FEATURE:
<223> OTHER INFORMATION: Synthetic sequence

<400> SEQUENCE: 7
cgggtgaagt tcagcagaag cgccgacgcc cctgcctacc agcagggcca gaatcagctg     60
tacaacgagc tgaacctggg cagaagggaa gagtacgacg tcctggataa gcggagaggc    120
cgggaccctg agatgggcgg caagcctcgg cggaagaacc cccaggaagg cctgtataac    180
gaactgcaga agacaagat ggccgaggcc tacagcgaga tcggcatgaa gggcgagcgg    240
aggcggggca agggccacga cggcctgtat cagggcctgt ccaccgccac caaggatacc    300
tacgacgccc tgcacatgca ggccctgccc ccaagg                             336

<210> SEQ ID NO 8
<211> LENGTH: 72
<212> TYPE: DNA
<213> ORGANISM: Artificial Sequence
<220> FEATURE:
<223> OTHER INFORMATION: Synthetic sequence

<400> SEQUENCE: 8
```

<210> SEQ ID NO 9
<211> LENGTH: 1074
<212> TYPE: DNA
<213> ORGANISM: Artificial Sequence
<220> FEATURE:
<223> OTHER INFORMATION: Synthetic sequence

<400> SEQUENCE: 9

```
ctcgagggcg gcggagaggg cagaggaagt cttctaacat gcggtgacgt ggaggagaat      60
cccggcccta gg                                                         72
```

<400> SEQUENCE: 9

```
atgcttctcc tggtgacaag ccttctgctc tgtgagttac cacacccagc attcctcctg      60
atcccacgca aagtgtgtaa cggaataggt attggtgaat ttaaagactc actctccata     120
aatgctacga atattaaaca cttcaaaaac tgcacctcca tcagtggcga tctccacatc     180
ctgccggtgg catttagggg tgactccttc acacatactc ctcctctgga tccacaggaa     240
ctggatattc tgaaaaccgt aaaggaaatc acagggtttt tgctgattca ggcttggcct     300
gaaaacagga cggacctcca tgcctttgag aacctagaaa tcatacgcgg caggaccaag     360
caacatggtc agttttctct tgcagtcgtc agcctgaaca taacatcctt gggattacgc     420
tccctcaagg agataagtga tggagatgtg ataatttcag gaaacaaaaa tttgtgctat     480
gcaaatacaa taaactggaa aaaactgttt gggacctccg gtcagaaaac caaaattata     540
agcaacagag gtgaaaacag ctgcaaggcc acaggccagg tctgccatgc cttgtgctcc     600
cccgagggct gctgggggcc ggagcccagg gactgcgtct cttgccggaa tgtcagccga     660
ggcagggaat gcgtggacaa gtgcaacctt ctggagggtg agccaaggga gtttgtggag     720
aactctgagt gcatacagtg ccacccagag tgcctgcctc aggccatgaa catcacctgc     780
acaggacggg gaccagacaa ctgtatccag tgtgcccact acattgacgg cccccactgc     840
gtcaagacct gcccggcagg agtcatggga gaaaacaaca ccctggtctg aagtacgca     900
gacgccggcc atgtgtgcca cctgtgccat ccaaactgca cctacggatg cactgggcca     960
ggtcttgaag ctgtccaacg aatgggcct aagatcccgt ccatcgccac tgggatggtg    1020
ggggcccctcc tcttgctgct ggtggtggcc ctggggatcg gcctcttcat gtga         1074
```

<210> SEQ ID NO 10
<211> LENGTH: 2529
<212> TYPE: DNA
<213> ORGANISM: Artificial Sequence
<220> FEATURE:
<223> OTHER INFORMATION: Synthetic sequence

<400> SEQUENCE: 10

```
atgctgctgc tggtgaccag cctgctgctg tgcgagctgc cccacccgc ctttctgctg      60
atccccgaca tccagatgac ccagaccacc tccagcctga cgccagcct gggcgaccgg     120
gtgaccatca gctgccgggc cagccaggac atcagcaagt acctgaactg gtatcagcag     180
aagcccgacg gcaccgtcaa gctgctgatc taccacacca gcggctgca cagcggcgtg     240
cccagccggt ttagcggcag cggctccggc accgactaca gcctgaccat ctccaacctg     300
gaacaggaag atatcgccac ctactttgc agcagggca cacactgcc ctacacctt      360
ggcggcggaa caaagctgga aatcaccggc agcacctccg gcagcggcaa gcctggcagc     420
ggcgagggca gcaccaaggg cgaggtgaag ctgcaggaaa gcggccctgg cctggtggcc     480
cccagccaga gcctgagcgt gacctgcacc gtgagcggcg tgagcctgcc cgactacggc     540
gtgagctgga tccggcagcc cccccaggaag ggcctggaat ggctgggcgt gatctggggc    600
```

```
agcgagacca cctactacaa cagcgccctg aagagccggc tgaccatcat caaggacaac      660
agcaagagcc aggtgttcct gaagatgaac agcctgcaga ccgacgacac cgccatctac      720
tactgcgcca agcactacta ctacggcggc agctacgcca tggactactg gggccagggc      780
accagcgtga ccgtgagcag cgagagcaag tacggaccgc cctgcccccc ttgcccctatg     840 ttctgggtgc tggtggtggt cggaggcgtg ctggcctgct acagcctgct ggtcaccgtg      900
gccttcatca tcttttgggt gaaacggggc agaaagaaac tcctgtatat attcaaacaa      960
ccatttatga gaccagtaca aactactcaa gaggaagatg gctgtagctg ccgatttcca     1020
gaagaagaag aaggaggatg tgaactgcgg gtgaagttca gcagaagcgc cgacgcccct     1080
gcctaccagc agggccagaa tcagctgtac aacgagctga acctgggcag aagggaagag     1140
tacgacgtcc tggataagcg gagaggccgg gaccctgaga tgggcggcaa gcctcggcgg     1200
aagaaccccc aggaaggcct gtataacgaa ctgcagaaag acaagatggc cgaggcctac     1260
agcgagatcg gcatgaaggg cgagcggagg cggggcaagg ccacgacggg cctgtatcag     1320
ggcctgtcca ccgccaccaa ggatacctac gacgccctgc acatgcaggc cctgccccca     1380
aggctcgagg gcgcggagga gggcagagga agtcttctaa catgcggtga cgtggaggag     1440
aatcccggcc ctaggatgct tctcctggtg acaagccttc tgctctgtga gttaccacac     1500
ccagcattcc tcctgatccc acgcaaagtg tgtaacggaa taggtattgg tgaatttaaa     1560
gactcactct ccataaatgc tacgaatatt aaacacttca aaaactgcac ctccatcagt     1620
ggcgatctcc acatcctgcc ggtggcattt aggggtgact ccttcacaca tactcctcct     1680
ctggatccac aggaactgga tattctgaaa accgtaaagg aaatcacagg ttttttgctg     1740
attcaggctt ggcctgaaaa caggacggac ctccatgcct ttgagaacct agaaatcata     1800
cgcggcagga ccaagcaaca tggtcagttt tctcttgcag tcgtcagcct gaacataaca     1860
tccttgggat tacgctccct caaggagata agtgatggag atgtgataat ttcaggaaac     1920
aaaaatttgt gctatgcaaa tacaataaac tggaaaaaac tgtttgggac ctccggtcag     1980
aaaaccaaaa ttataagcaa cagaggtgaa acagctgcaa aggccacagg ccaggtctgc     2040
catgccttgt gctcccccga gggctgctgg ggccggagc ccagggactg cgtctcttgc     2100
cggaatgtca gccgaggcag ggaatgcgtg gacaagtgca accttctgga gggtgagcca     2160
agggagtttg tggagaactc tgagtgcata cagtgccacc cagagtgcct gcctcaggcc     2220
atgaacatca cctgcacagg acggggacca gacaactgta tccagtgtgc ccactacatt     2280
gacggccccc actgcgtcaa gacctgcccg gcaggagtca tgggagaaaa caacaccctg     2340
gtctggaagt acgcagacgc cggccatgtg tgccacctgt gccatccaaa ctgcacctac     2400
ggatgcactg gccaggtct tgaaggctgt ccaacgaatg gcctaagat cccgtccatc      2460 gccactggga tggtggggc cctcctcttg ctgctggtgg tggccctggg gatcggcctc     2520
ttcatgtga                                                           2529

<210> SEQ ID NO 11
<211> LENGTH: 841
<212> TYPE: PRT
<213> ORGANISM: Artificial Sequence
<220> FEATURE:
<223> OTHER INFORMATION: Synthetic sequence

<400> SEQUENCE: 11

Met Leu Leu Leu Val Thr Ser Leu Leu Leu Cys Glu Leu Pro His Pro
1               5                   10                  15
```

-continued

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
                100                 105                 110

Gly Asn Thr Leu Pro Tyr Thr Phe Gly Gly Gly Thr Lys Leu Glu Ile
                115                 120                 125

Thr Gly Ser Thr Ser Gly Ser Gly Lys Pro Gly Ser Gly Glu Gly Ser
130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
            195                 200                 205

Ala Leu Lys Ser Arg Leu Thr Ile Ile Lys Asp Asn Ser Lys Ser Gln
            210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Glu Ser Lys Tyr Gly
            260                 265                 270

Pro Pro Cys Pro Pro Cys Pro Met Phe Trp Val Leu Val Val Val Gly
            275                 280                 285

Gly Val Leu Ala Cys Tyr Ser Leu Leu Val Thr Val Ala Phe Ile Ile
            290                 295                 300

Phe Trp Val Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

Cys Arg Phe Glu Glu Glu Glu Gly Gly Cys Glu Leu Arg Val Lys Phe
                340                 345                 350

Ser Arg Ser Ala Asp Ala Pro Ala Tyr Gln Gln Gly Gln Asn Gln Leu
            355                 360                 365

Tyr Asn Glu Leu Asn Leu Gly Arg Arg Glu Glu Tyr Asp Val Leu Asp
            370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
            420                 425                 430

```
Gly His Asp Gly Leu Tyr Gln Gly Leu Ser Thr Ala Thr Lys Asp Thr
            435                 440                 445

Tyr Asp Ala Leu His Met Gln Ala Leu Pro Pro Arg Leu Glu Gly Gly
        450                 455                 460

Gly Glu Gly Arg Gly Ser Leu Leu Thr Cys Gly Asp Val Glu Asn
465                 470                 475                 480

Pro Gly Pro Arg Met Leu Leu Leu Val Thr Ser Leu Leu Cys Glu
                    485                 490                 495

Leu Pro His Pro Ala Phe Leu Leu Ile Pro Arg Lys Val Cys Asn Gly
                500                 505                 510

Ile Gly Ile Gly Glu Phe Lys Asp Ser Leu Ser Ile Asn Ala Thr Asn
        515                 520                 525

Ile Lys His Phe Lys Asn Cys Thr Ser Ile Ser Gly Asp Leu His Ile
        530                 535                 540

Leu Pro Val Ala Phe Arg Gly Asp Ser Phe Thr His Thr Pro Pro Leu
545                 550                 555                 560

Asp Pro Gln Glu Leu Asp Ile Leu Lys Thr Val Lys Glu Ile Thr Gly
                565                 570                 575

Phe Leu Leu Ile Gln Ala Trp Pro Glu Asn Arg Thr Asp Leu His Ala
                580                 585                 590

Phe Glu Asn Leu Glu Ile Ile Arg Gly Arg Thr Lys Gln His Gly Gln
            595                 600                 605

Phe Ser Leu Ala Val Val Ser Leu Asn Ile Thr Ser Leu Gly Leu Arg
        610                 615                 620

Ser Leu Lys Glu Ile Ser Asp Gly Asp Val Ile Ile Ser Gly Asn Lys
625                 630                 635                 640

Asn Leu Cys Tyr Ala Asn Thr Ile Asn Trp Lys Lys Leu Phe Gly Thr
                645                 650                 655

Ser Gly Gln Lys Thr Lys Ile Ile Ser Asn Arg Gly Glu Asn Ser Cys
            660                 665                 670

Lys Ala Thr Gly Gln Val Cys His Ala Leu Cys Ser Pro Glu Gly Cys
        675                 680                 685

Trp Gly Pro Glu Pro Arg Asp Cys Val Ser Cys Arg Asn Val Ser Arg
690                 695                 700

Gly Arg Glu Cys Val Asp Lys Cys Asn Leu Leu Glu Gly Glu Pro Arg
705                 710                 715                 720

Glu Phe Val Glu Asn Ser Glu Cys Ile Gln Cys His Pro Glu Cys Leu
                725                 730                 735

Pro Gln Ala Met Asn Ile Thr Cys Thr Gly Arg Gly Pro Asp Asn Cys
                740                 745                 750

Ile Gln Cys Ala His Tyr Ile Asp Gly Pro His Cys Val Lys Thr Cys
        755                 760                 765

Pro Ala Gly Val Met Gly Glu Asn Asn Thr Leu Val Trp Lys Tyr Ala
770                 775                 780

Asp Ala Gly His Val Cys His Leu Cys His Pro Asn Cys Thr Tyr Gly
785                 790                 795                 800

Cys Thr Gly Pro Gly Leu Glu Gly Cys Pro Thr Asn Gly Pro Lys Ile
                805                 810                 815

Pro Ser Ile Ala Thr Gly Met Val Gly Ala Leu Leu Leu Leu Leu Val
                820                 825                 830

Val Ala Leu Gly Ile Gly Leu Phe Met
                835                 840
```

```
<210> SEQ ID NO 12
<211> LENGTH: 15
<212> TYPE: PRT
<213> ORGANISM: Artificial Sequence
<220> FEATURE:
<223> OTHER INFORMATION: Synthetic sequence

<400> SEQUENCE: 12

Gly Gly Gly Gly Ser Gly Gly Gly Ser Gly Gly Gly Gly Ser
1               5                  10                 15

<210> SEQ ID NO 13
<211> LENGTH: 327
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

Leu Ser Leu Ser Leu Gly Lys
              325

<210> SEQ ID NO 14
<211> LENGTH: 220
<212> TYPE: PRT
<213> ORGANISM: Homo sapiens

<400> SEQUENCE: 14

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 15
<211> LENGTH: 255
<212> TYPE: PRT
<213> ORGANISM: Homo sapiens

<400> SEQUENCE: 15

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

```
Ala Gly Cys Ser Met Cys Glu Gln Asp Cys Lys Gln Gly Gln Glu Leu
                100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
                180                 185                 190

Ala Leu Thr Ser Thr Ala Leu Leu Phe Leu Leu Phe Phe Leu Thr Leu
                195                 200                 205

Arg Phe Ser Val Val Lys Arg Gly Arg Lys Lys Leu Leu Tyr Ile Phe
                210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 16
<211> LENGTH: 164
<212> TYPE: PRT
<213> ORGANISM: Homo sapiens

<400> SEQUENCE: 16

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
                35                  40                  45

Leu Phe Leu Arg Val Lys Phe Ser Arg Ser Ala Asp Ala Pro Ala Tyr
50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
                100                 105                 110

Glu Leu Gln Lys Asp Lys Met Ala Glu Ala Tyr Ser Glu Ile Gly Met
                115                 120                 125

Lys Gly Glu Arg Arg Arg Gly Lys Gly His Asp Gly Leu Tyr Gln Gly
                130                 135                 140

Leu Ser Thr Ala Thr Lys Asp Thr Tyr Asp Ala Leu His Met Gln Ala
145                 150                 155                 160

Leu Pro Pro Arg
```

<210> SEQ ID NO 17
<211> LENGTH: 15
<212> TYPE: PRT
<213> ORGANISM: Homo sapiens

<400> SEQUENCE: 17

Glu Pro Lys Ser Cys Asp Lys Thr His Thr Cys Pro Pro Cys Pro
1               5                   10                  15

<210> SEQ ID NO 18
<211> LENGTH: 12
<212> TYPE: PRT
<213> ORGANISM: Artificial Sequence
<220> FEATURE:
<223> OTHER INFORMATION: Synthetic sequence

<400> SEQUENCE: 18

Glu Arg Lys Cys Cys Val Glu Cys Pro Pro Cys Pro
1               5                   10

<210> SEQ ID NO 19
<211> LENGTH: 61
<212> TYPE: PRT
<213> ORGANISM: Homo sapiens

<400> SEQUENCE: 19

Glu Leu Lys Thr Pro Leu Gly Asp Thr His Thr Cys Pro Arg Cys Pro
1               5                   10                  15

Glu Pro Lys Ser Cys Asp Thr Pro Pro Cys Pro Arg Cys Pro Glu
            20                  25                  30

Pro Lys Ser Cys Asp Thr Pro Pro Cys Pro Arg Cys Pro Glu Pro
        35                  40                  45

Lys Ser Cys Asp Thr Pro Pro Cys Pro Arg Cys Pro
    50                  55                  60

<210> SEQ ID NO 20
<211> LENGTH: 12
<212> TYPE: PRT
<213> ORGANISM: Homo sapiens

<400> SEQUENCE: 20

Glu Ser Lys Tyr Gly Pro Pro Cys Pro Ser Cys Pro
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic sequence

<400> SEQUENCE: 21

Glu Ser Lys Tyr Gly Pro Pro Cys Pro Pro Cys Pro
1               5                   10

<210> SEQ ID NO 22
<211> LENGTH: 26
<212> TYPE: DNA
<213> ORGANISM: Artificial Sequence
<220> FEATURE:
<223> OTHER INFORMATION: Primer sequence

<400> SEQUENCE: 22
atcaaaagaa tagaccgaga tagggt                                    26

<210> SEQ ID NO 23
<211> LENGTH: 26
<212> TYPE: DNA
<213> ORGANISM: Artificial Sequence
<220> FEATURE:
<223> OTHER INFORMATION: Primer sequence

<400> SEQUENCE: 23
ccgtaccttt aagaccaatg acttac                                                  26

<210> SEQ ID NO 24
<211> LENGTH: 18
<212> TYPE: DNA
<213> ORGANISM: Artificial Sequence
<220> FEATURE:
<223> OTHER INFORMATION: Primer sequence

<400> SEQUENCE: 24
ttgagagttt tcgccccg                                                           18

<210> SEQ ID NO 25
<211> LENGTH: 24
<212> TYPE: DNA
<213> ORGANISM: Artificial Sequence
<220> FEATURE:
<223> OTHER INFORMATION: Primer sequence

<400> SEQUENCE: 25
aatagacaga tcgctgagat aggt                                                    24

<210> SEQ ID NO 26
<211> LENGTH: 18
<212> TYPE: DNA
<213> ORGANISM: Artificial Sequence
<220> FEATURE:
<223> OTHER INFORMATION: Primer sequence

<400> SEQUENCE: 26
caggtatccg gtaagcgg                                                           18

<210> SEQ ID NO 27
<211> LENGTH: 19
<212> TYPE: DNA
<213> ORGANISM: Artificial Sequence
<220> FEATURE:
<223> OTHER INFORMATION: Primer sequence

<400> SEQUENCE: 27
cgaccagcaa ccatagtcc                                                          19

<210> SEQ ID NO 28
<211> LENGTH: 18
<212> TYPE: DNA
<213> ORGANISM: Artificial Sequence
<220> FEATURE:
<223> OTHER INFORMATION: Primer sequence

<400> SEQUENCE: 28
tagcggtttg actcacgg                                                           18

<210> SEQ ID NO 29
<211> LENGTH: 20
<212> TYPE: DNA
<213> ORGANISM: Artificial Sequence
<220> FEATURE:
<223> OTHER INFORMATION: Primer sequence

<400> SEQUENCE: 29
gcagggagct agaacgattc                                                         20

<210> SEQ ID NO 30

```
<211> LENGTH: 22
<212> TYPE: DNA
<213> ORGANISM: Artificial Sequence
<220> FEATURE:
<223> OTHER INFORMATION: Primer sequence

<400> SEQUENCE: 30
attgtctggt atagtgcagc ag                                        22

<210> SEQ ID NO 31
<211> LENGTH: 16
<212> TYPE: DNA
<213> ORGANISM: Artificial Sequence
<220> FEATURE:
<223> OTHER INFORMATION: Primer sequence

<400> SEQUENCE: 31
tcgcaacggg tttgcc                                               16

<210> SEQ ID NO 32
<211> LENGTH: 21
<212> TYPE: DNA
<213> ORGANISM: Artificial Sequence
<220> FEATURE:
<223> OTHER INFORMATION: Primer sequence

<400> SEQUENCE: 32
aggaagatat cgccacctac t                                         21

<210> SEQ ID NO 33
<211> LENGTH: 20
<212> TYPE: DNA
<213> ORGANISM: Artificial Sequence
<220> FEATURE:
<223> OTHER INFORMATION: Primer sequence

<400> SEQUENCE: 33
cgggtgaagt tcagcagaag                                           20

<210> SEQ ID NO 34
<211> LENGTH: 20
<212> TYPE: DNA
<213> ORGANISM: Artificial Sequence
<220> FEATURE:
<223> OTHER INFORMATION: Primer sequence

<400> SEQUENCE: 34
actgtgtttg ctgacgcaac                                           20

<210> SEQ ID NO 35
<211> LENGTH: 20
<212> TYPE: DNA
<213> ORGANISM: Artificial Sequence
<220> FEATURE:
<223> OTHER INFORMATION: Primer sequence

<400> SEQUENCE: 35
atgcttctcc tggtgacaag                                           20

<210> SEQ ID NO 36
<211> LENGTH: 18
<212> TYPE: PRT
<213> ORGANISM: Artificial Sequence
<220> FEATURE:
<223> OTHER INFORMATION: Synthetic sequence

<400> SEQUENCE: 36
```

```
Gly Ser Thr Ser Gly Ser Gly Lys Pro Gly Ser Gly Glu Gly Ser Thr
1               5                   10                  15

Lys Gly

<210> SEQ ID NO 37
<211> LENGTH: 10051
<212> TYPE: DNA
<213> ORGANISM: Artificial Sequence
<220> FEATURE:
<223> OTHER INFORMATION: Synthetic sequence

<400> SEQUENCE: 37
gttagaccag atctgagcct gggagctctc tggctaacta gggaacccac tgcttaagcc      60
tcaataaagc ttgccttgag tgcttcaagt agtgtgtgcc cgtctgttgt gtgactctgg     120
taactagaga tccctcagac ccttttagtc agtgtggaaa atctctagca gtggcgcccg     180
aacagggact tgaaagcgaa agggaaacca gaggagctct ctcgacgcag gactcggctt     240
gctgaagcgc gcacggcaag aggcgagggg cggcgactgg tgagtacgcc aaaaattttg     300
actagcggag gctagaagga gagagatggg tgcgagagcg tcagtattaa gcggggagaa    360
attagatcga tgggaaaaaa ttcggttaag gccaggggga agaaaaaat ataaattaaa     420
acatatagta tgggcaagca gggagctaga acgattcgca gttaatcctg gcctgttaga     480
aacatcagaa ggctgtagac aaatactggg acagctacaa ccatcccttc agacaggatc     540
agaagaactt agatcattat ataatacagt agcaaccctc tattgtgtgc atcaaaggat     600
agagataaaa gacaccaagg aagctttaga caagatagag gaagagcaaa acaaaagtaa     660
gaaaaaagca cagcaagcag cagctgacac aggacacagc aatcaggtca gccaaaatta     720
ccctatagtg cagaacatcc aggggcaaat ggtacatcag gccatatcac ctagaacttt     780
aaatgcatgg gtaaaagtag tagaagagaa ggctttcagc ccagaagtga tacccatgtt     840
ttcagcatta tcagaaggag ccaccccaca agatttaaac accatgctaa acacagtggg     900
gggacatcaa gcagccatgc aaatgttaaa agagaccatc aatgaggaag ctgcaggcaa     960
agagaagagt ggtgcagaga gaaaaaagag cagtgggaat aggagctttg ttccttgggt    1020
tcttgggagc agcaggaagc actatgggcg cagcgtcaat gacgctgacg gtacaggcca    1080
gacaattatt gtctggtata gtgcagcagc agaacaattt gctgagggct attgaggcgc    1140
aacagcatct gttgcaactc acagtctggg gcatcaagca gctccaggca agaatcctgg    1200
ctgtggaaag atacctaaag gatcaacagc tcctggggat ttggggttgc tctggaaaac    1260
tcatttgcac cactgctgtg ccttggatct acaaatggca gtattcatcc acaattttaa    1320
aagaaaaggg gggattgggg ggtacagtgc aggggaaaga atagtagaca taatagcaac    1380
agacatacaa actaaagaat acaaaaaca aattacaaaa attcaaaatt tcgggttta     1440
ttacagggac agcagagatc cagtttgggg atcaattgca tgaagaatct gcttagggtt    1500
aggcgttttg cgctgcttcg cgaggatctg cgatcgctcc ggtgcccgtc agtgggcaga    1560
gcgcacatcg cccacagtcc ccgagaagtt ggggggaggg gtcggcaatt gaaccggtgc    1620
ctagagaagt ggcgcggggg taaactggga aagtgatgtc gtgtactggc tccgcctttt    1680
tcccgagggt gggggagaac cgtatataag tgcagtagtc gccgtgaacg ttcttttttcg    1740
caacgggttt gccgccagaa cacagctgaa gcttcgaggg gctcgcatct ctccttcacg    1800
cgcccgccgc cctacctgag gccgccatcc acgccggttg agtcgcgttc tgccgcctcc    1860
cgcctgtggt gcctcctgaa ctgcgtccgc cgtctaggta agtttaaagc tcaggtcgag    1920
```

```
accgggcctt tgtccggcgc tcccttggag cctacctaga ctcagccggc tctccacgct   1980
ttgcctgacc ctgcttgctc aactctacgt ctttgtttcg ttttctgttc tgcgccgtta   2040
cagatccaag ctgtgaccgg cgcctacggc tagcgaattc ctcgaggcca ccatgctgct   2100
gctggtgaca agcctgctgc tgtgcgagct gccccacccc gcctttctgc tgatccccca   2160
ggaacagctc gtcgaaagcg gcggcagact ggtgacacct ggcggcagcc tgaccctgag   2220
ctgcaaggcc agcggcttcg acttcagcgc ctactacatg agctgggtcc gccaggcccc   2280
tggcaaggga ctggaatgga tcgccaccat ctaccccagc agcggcaaga cctactacgc   2340
cacctgggtg aacggacggt tcaccatctc cagcgacaac gcccagaaca ccgtggacct   2400
gcagatgaac agcctgacag ccgccgaccg ggccacctac ttttgcgcca gagacagcta   2460
cgccgacgac ggcgccctgt tcaacatctg ggggcctggc accctggtga caatctctag   2520
cggcggaggc ggatctggtg gcggaggaag tggcggcgga ggatctgagc tggtgctgac   2580
ccagagcccc tctgtgtctg ctgccctggg aagccctgcc aagatcacct gtaccctgag   2640
cagcgcccac aagaccgaca ccatcgactg gtatcagcag ctgcagggcg aggccccccag   2700 atacctgatg caggtgcaga gcgacggcag ctacaccaag aggccaggcg tgcccgaccg   2760
gttcagcgga tctagctctg gcgccgaccg ctacctgatc atccccagcg tgcaggccga   2820
tgacgaggcc gattactact gtggcgccga ctacatcggc ggctacgtgt tcggcggagg   2880
cacccagctg accgtgaccg gcgagtctaa gtacggaccg ccctgccccc cttgccctgc   2940
ccccgagttc ctgggcggac ccagcgtgtt cctgttcccc cccaagccca aggacaccct   3000
gatgatcagc cggacccccg aggtgacctg cgtggtggtg gacgtgagcc aggaagatcc   3060
cgaggtccag ttcaattggt acgtggacgg cgtggaagtg cacaacgcca agaccaagcc   3120
cagagaggaa cagttcaaca gcacctaccg ggtggtgtct gtgctgaccg tgctgcacca   3180
ggactggctg aacggcaaag aatacaagtg caaggtgtcc aacaagggcc tgcccagcag   3240
catcgaaaag accatcagca aggccaaggg ccagcctcgc gagccccagg tgtacaccct   3300
gcctccctcc caggaagaga tgaccaagaa ccaggtgtcc ctgacctgcc tggtgaaggg   3360
cttctacccc agcgacatcg ccgtggagtg ggagagcaac ggccagcctg agaacaacta   3420
caagaccacc cctcccgtgc tggacagcga cggcagcttc ttcctgtaca gccggctgac   3480
cgtggacaag agccggtggc aggaaggcaa cgtctttagc tgcagcgtga tgcacgaggc   3540
cctgcacaac cactacaccc agaagagcct gagcctgtcc ctgggcaaga tgttctgggt   3600
gctggtggtg gtgggcgggg tgctggcctg ctacagcctg ctggtgacag tggccttcat   3660
catcttttgg gtgaaacggg gcagaaagaa actcctgtat atattcaaac aaccatttat   3720
gagaccagta caaactactc aagaggaaga tggctgtagc tgccgatttc cagaagaaga   3780
agaaggagga tgtgaactgc gggtgaagtt cagcagaagc gccgacgccc ctgcctacca   3840
gcagggccag aatcagctgt acaacgagct gaacctgggc agaagggaag agtacgacgt   3900
cctggataag cggagaggcc gggaccctga tgggcggc aagcctcggc ggaagaaccc   3960
ccaggaaggc ctgtataacg aactgcagaa agacaagatg gccgaggcct acagcgagat   4020
cggcatgaag ggcgagcgga ggcggggcaa gggccacgac ggcctgtatc agggcctgtc   4080
caccgccacc aaggatacct acgacgccct gcacatgcag gccctgcccc aaggctcga   4140 gggcggcgga gagggcagag gaagtcttct aacatgcggt gacgtggagg agaatcccgg   4200
ccctaggatg cttctcctgg tgacaagcct tctgctctgt gagttaccac acccagcatt   4260
```

```
cctcctgatc ccacgcaaag tgtgtaacgg aataggtatt ggtgaattta aagactcact    4320
ctccataaat gctacgaata ttaaacactt caaaaactgc acctccatca gtggcgatct    4380
ccacatcctg ccggtggcat ttaggggtga ctccttcaca catactcctc ctctggatcc    4440
acaggaactg gatattctga aaaccgtaaa ggaaatcaca gggttttttgc tgattcaggc    4500
ttggcctgaa aacaggacgg acctccatgc ctttgagaac ctagaaatca tacgcggcag    4560
gaccaagcaa catggtcagt tttctcttgc agtcgtcagc ctgaacataa catccttggg    4620
attacgctcc ctcaaggaga taagtgatgg agatgtgata atttcaggaa acaaaaattt    4680
gtgctatgca aatacaataa actgaaaaaa actgtttggg acctccggtc agaaaaccaa    4740
aattataagc aacagaggtg aaaacagctg caaggccaca ggccaggtct gccatgcctt    4800
gtgctccccc gagggctgct ggggcccgga gcccagggac tgcgtctctt gccgaatgt    4860
cagccgaggc agggaatgcg tggacaagtg caaccttctg gagggtgagc caagggagtt    4920
tgtggagaac tctgagtgca tacagtgcca cccagagtgc ctgcctcagg ccatgaacat    4980
cacctgcaca ggacggggac cagacaactg tatccagtgt gcccactaca ttgacggccc    5040
ccactgcgtc aagacctgcc cggcaggagt catgggagaa acaacacccc tggtctggaa    5100
gtacgcagac gccggccatg tgtgccacct gtgccatcca aactgcacct acggatgcac    5160
tgggccaggt cttgaaggct gtccaacgaa tgggcctaag atcccgtcca tcgccactgg    5220
gatggtgggg gccctcctct tgctgctggt ggtggccctg ggatcggcc tcttcatgtg    5280
agcggccgct ctagacccgg gctgcaggaa ttcgatatca agcttatcga taatcaacct    5340
ctggattaca aaatttgtga agattgact ggtattctta actatgttgc tccttttacg    5400
ctatgtggat acgctgcttt aatgcctttg tatcatgcta ttgcttcccg tatggctttc    5460
attttctcct ccttgtataa atcctggttg ctgtctcttt atgaggagtt gtggcccgtt    5520
gtcaggcaac gtggcgtggt gtgcactgtg tttgctgacg caacccccac tggttggggc    5580
attgccacca cctgtcagct cctttccggg actttcgctt tccccctccc tattgccacg    5640
gcggaactca tcgccgcctg ccttgcccgc tgctggacag gggctcggct gttgggcact    5700
gacaattccg tggtgttgtc ggggaaatca tcgtcctttc cttggctgct cgcctgtgtt    5760
gccacctgga ttctgcgcgg gacgtccttc tgctacgtcc cttcggccct caatccagcg    5820
gaccttcctt cccgcggcct gctgccggct ctgcggcctc ttccgcgtct tcgccttcgc    5880
cctcagacga gtcggatctc cctttgggcc gcctccccgc atcgataccg tcgactagcc    5940
gtacctttaa gaccaatgac ttacaaggca gctgtagatc ttagccactt tttaaaagaa    6000
aagggggggac tggaagggct aattcactcc caaagaagac aagatctgct ttttgcctgt    6060
actgggtctc tctggttaga ccagatctga gcctgggagc tctctggcta actagggaac    6120
ccactgctta agcctcaata aagcttgcct tgagtgcttc aagtagtgtg tgcccgtctg    6180
ttgtgtgact ctggtaacta gagatccctc agacccttt agtcagtgtg gaaaatctct    6240
agcagaattc gatatcaagc ttatcgatac cgtcgacctc gagggggggc ccggtaccca    6300
attcgcccta tagtgagtcg tattacaatt cactggccgt cgttttacaa cgtcgtgact    6360
gggaaaaccc tggcgttacc caacttaatc gccttgcagc acatccccct ttcgccagct    6420
ggcgtaatag cgaagaggcc cgcaccgatc gcccttccca acagttgcgc agcctgaatg    6480
gcgaatggaa attgtaagcg ttaatatttt gttaaaattc gcgttaaatt tttgttaaat    6540
cagctcattt tttaaccaat aggccgaaat cggcaaaatc ccttataaat caaaagaata    6600
gaccgagata gggttgagtg ttgttccagt ttggaacaag agtccactat taaagaacgt    6660
```

```
ggactccaac gtcaaagggc gaaaaaccgt ctatcagggc gatggcccac tacgtgaacc    6720
atcaccctaa tcaagttttt tggggtcgag gtgccgtaaa gcactaaatc ggaaccctaa    6780
agggagcccc cgatttagag cttgacgggg aaagccggcg aacgtggcga aaaggaagg    6840 gaagaaagcg aaaggagcgg gcgctagggc gctggcaagt gtagcggtca cgctgcgcgt    6900
aaccaccaca cccgccgcgc ttaatgcgcc gctacagggc gcgtcaggtg cacttttcg    6960 gggaaatgtg cgcggaaccc ctatttgttt attttctaa atacattcaa atatgtatcc    7020
gctcatgaga caataaccct gataaatgct tcaataatat tgaaaaagga agagtatgag    7080
tattcaacat ttccgtgtcg cccttattcc ctttttgcg gcattttgcc ttcctgtttt    7140
tgctcaccca gaaacgctgg tgaaagtaaa agatgctgaa gatcagttgg gtgcacgagt    7200
gggttacatc gaactggatc tcaacagcgg taagatcctt gagagttttc gccccgaaga    7260
acgttttcca atgatgagca cttttaaagt tctgctatgt ggcgcggtat tatcccgtat    7320
tgacgccggg caagagcaac tcggtcgccg catacactat tctcagaatg acttggttga    7380
gtactcacca gtcacagaaa agcatcttac ggatggcatg acagtaagag aattatgcag    7440
tgctgccata accatgagtg ataacactgc ggccaactta cttctgacaa cgatcggagg    7500
accgaaggag ctaaccgctt ttttgcacaa catgggggat catgtaactc gccttgatcg    7560
ttgggaaccg gagctgaatg aagccatacc aaacgacgag cgtgacacca cgatgcctgt    7620
agcaatggca acaacgttgc gcaaactatt aactggcgaa ctacttactc tagcttcccg    7680
gcaacaatta atagactgga tggaggcgga taaagttgca ggaccacttc tgcgctcggc    7740
ccttccggct ggctggttta ttgctgataa atctggagcc ggtgagcgtg gtctcgcgg    7800 tatcattgca gcactggggc cagatggtaa gccctcccgt atcgtagtta tctacacgac    7860
ggggagtcag gcaactatgg atgaacgaaa tagacagatc gctgagatag gtgcctcact    7920
gattaagcat tggtaactgt cagaccaagt ttactcatat atactttaga ttgatttaaa    7980
acttcatttt taatttaaaa ggatctaggt gaagatcctt tttgataatc tcatgaccaa    8040
aatcccttaa cgtgagtttt cgttccactg agcgtcagac cccgtagaaa agatcaaagg    8100
atcttcttga tccttttttt tctgcgcgt aatctgctgc ttgcaaacaa aaaaaccacc    8160
gctaccagcg gtggtttgtt tgccggatca agagctacca actctttttc cgaaggtaac    8220
tggcttcagc agagcgcaga taccaaatac tgttcttcta gtgtagccgt agttaggcca    8280
ccacttcaag aactctgtag caccgcctac atacctcgct ctgctaatcc tgttaccagt    8340
ggctgctgcc agtggcgata gtcgtgtct taccgggttg gactcaagac gatagttacc    8400
ggataaggcg cagcggtcgg gctgaacggg gggttcgtgc acacagccca gcttggagcg    8460
aacgacctac accgaactga gatacctaca gcgtgagcta tgagaaagcg ccacgcttcc    8520
cgaagggaga aaggcggaca ggtatccggt aagcggcagg gtcggaacag gagagcgcac    8580
gagggagctt ccaggggga acgcctggta tctttatagt cctgtcgggt ttcgccacct    8640
ctgacttgag cgtcgatttt tgtgatgctc gtcagggggg cggagcctat ggaaaaacgc    8700
cagcaacgcg gccttttac ggttcctggc cttttgctgg ccttttgctc acatgttctt    8760
tcctgcgtta tccctgatt ctgtggataa ccgtattacc gcctttgagt gagctgatac    8820
cgctcgccgc agccgaacga ccgagcgcag cgagtcagtg agcgaggaag cggaagagcg    8880
cccaatacgc aaaccgcctc tccccgcgcg ttggccgatt cattaatgca gctggcacga    8940
caggtttccc gactggaaag cgggcagtga gcgcaacgca attaatgtga gttagctcac    9000
```

```
tcattaggca ccccaggctt tacactttat gcttccggct cgtatgttgt gtggaattgt  9060
gagcggataa caatttcaca caggaaacag ctatgaccat gattacgcca agctcgaaat  9120
taaccctcac taaagggaac aaaagctgga gctccaccgc ggtggcggcc tcgaggtcga  9180
gatccggtcg accagcaacc atagtcccgc ccctaactcc gcccatcccg ccccctaactc  9240
cgcccagttc cgcccattct ccgccccatg gctgactaat ttttttttatt tatgcagagg  9300
ccgaggccgc ctcggcctct gagctattcc agaagtagtg aggaggcttt tttggaggcc  9360
taggcttttg caaaaagctt cgacggtatc gattggctca tgtccaacat taccgccatg  9420
ttgacattga ttattgacta gttattaata gtaatcaatt acggggtcat tagttcatag  9480
cccatatatg gagttccgcg ttacataact tacggtaaat ggcccgcctg gctgaccgcc  9540
caacgacccc cgcccattga cgtcaataat gacgtatgtt cccatagtaa cgccaatagg  9600
gactttccat tgacgtcaat gggtggagta tttacggtaa actgcccact tggcagtaca  9660
tcaagtgtat catatgccaa gtacgccccc tattgacgtc aatgacggta aatggcccgc  9720
ctggcattat gcccagtaca tgaccttatg ggactttcct acttggcagt acatctacgt  9780
attagtcatc gctattacca tggtgatgcg gttttggcag tacatcaatg ggcgtggata  9840
gcggtttgac tcacggggat ttccaagtct ccaccccatt gacgtcaatg ggagtttgtt  9900
ttggcaccaa aatcaacggg actttccaaa atgtcgtaac aactccgccc cattgacgca  9960
aatgggcggt aggcgtgtac ggaattcgga gtggcgagcc ctcagatcct gcatataagc  10020
agctgctttt tgcctgtact gggtctctct g                                  10051
```

<210> SEQ ID NO 38
<211> LENGTH: 1062
<212> TYPE: PRT
<213> ORGANISM: Artificial Sequence
<220> FEATURE:
<223> OTHER INFORMATION: Synthetic sequence

<400> SEQUENCE: 38

```
Met Leu Leu Leu Val Thr Ser Leu Leu Leu Cys Glu Leu Pro His Pro
1               5                   10                  15

Ala Phe Leu Leu Ile Pro Gln Glu Gln Leu Val Glu Ser Gly Gly Arg
            20                  25                  30

Leu Val Thr Pro Gly Gly Ser Leu Thr Leu Ser Cys Lys Ala Ser Gly
        35                  40                  45

Phe Asp Phe Ser Ala Tyr Tyr Met Ser Trp Val Arg Gln Ala Pro Gly
    50                  55                  60

Lys Gly Leu Glu Trp Ile Ala Thr Ile Tyr Pro Ser Ser Gly Lys Thr
65                  70                  75                  80

Tyr Tyr Ala Thr Trp Val Asn Gly Arg Phe Thr Ile Ser Ser Asp Asn
                85                  90                  95

Ala Gln Asn Thr Val Asp Leu Gln Met Asn Ser Leu Thr Ala Ala Asp
            100                 105                 110

Arg Ala Thr Tyr Phe Cys Ala Arg Asp Ser Tyr Ala Asp Asp Gly Ala
        115                 120                 125

Leu Phe Asn Ile Trp Gly Pro Gly Thr Leu Val Thr Ile Ser Ser Gly
    130                 135                 140

Gly Gly Gly Ser Gly Gly Gly Gly Ser Gly Gly Gly Gly Ser Glu Leu
145                 150                 155                 160

Val Leu Thr Gln Ser Pro Ser Val Ser Ala Ala Leu Gly Ser Pro Ala
                165                 170                 175
```

-continued

```
Lys Ile Thr Cys Thr Leu Ser Ser Ala His Lys Thr Asp Thr Ile Asp
                180                 185                 190
Trp Tyr Gln Gln Leu Gln Gly Glu Ala Pro Arg Tyr Leu Met Gln Val
            195                 200                 205
Gln Ser Asp Gly Ser Tyr Thr Lys Arg Pro Gly Val Pro Asp Arg Phe
        210                 215                 220
Ser Gly Ser Ser Ser Gly Ala Asp Arg Tyr Leu Ile Ile Pro Ser Val
225                 230                 235                 240
Gln Ala Asp Asp Glu Ala Asp Tyr Tyr Cys Gly Ala Asp Tyr Ile Gly
                245                 250                 255
Gly Tyr Val Phe Gly Gly Gly Thr Gln Leu Thr Val Thr Gly Glu Ser
            260                 265                 270
Lys Tyr Gly Pro Pro Cys Pro Pro Cys Pro Ala Pro Glu Phe Leu Gly
        275                 280                 285
Gly Pro Ser Val Phe Leu Phe Pro Pro Lys Pro Lys Asp Thr Leu Met
290                 295                 300
Ile Ser Arg Thr Pro Glu Val Thr Cys Val Val Val Asp Val Ser Gln
305                 310                 315                 320
Glu Asp Pro Glu Val Gln Phe Asn Trp Tyr Val Asp Gly Val Glu Val
                325                 330                 335
His Asn Ala Lys Thr Lys Pro Arg Glu Glu Gln Phe Asn Ser Thr Tyr
            340                 345                 350
Arg Val Val Ser Val Leu Thr Val Leu His Gln Asp Trp Leu Asn Gly
        355                 360                 365
Lys Glu Tyr Lys Cys Lys Val Ser Asn Lys Gly Leu Pro Ser Ser Ile
370                 375                 380
Glu Lys Thr Ile Ser Lys Ala Lys Gly Gln Pro Arg Glu Pro Gln Val
385                 390                 395                 400
Tyr Thr Leu Pro Pro Ser Gln Glu Glu Met Thr Lys Asn Gln Val Ser
                405                 410                 415
Leu Thr Cys Leu Val Lys Gly Phe Tyr Pro Ser Asp Ile Ala Val Glu
            420                 425                 430
Trp Glu Ser Asn Gly Gln Pro Glu Asn Asn Tyr Lys Thr Thr Pro Pro
        435                 440                 445
Val Leu Asp Ser Asp Gly Ser Phe Phe Leu Tyr Ser Arg Leu Thr Val
450                 455                 460
Asp Lys Ser Arg Trp Gln Glu Gly Asn Val Phe Ser Cys Ser Val Met
465                 470                 475                 480
His Glu Ala Leu His Asn His Tyr Thr Gln Lys Ser Leu Ser Leu Ser
                485                 490                 495
Leu Gly Lys Met Phe Trp Val Leu Val Val Val Gly Val Leu Ala
            500                 505                 510
Cys Tyr Ser Leu Leu Val Thr Val Ala Phe Ile Ile Phe Trp Val Lys
        515                 520                 525
Arg Gly Arg Lys Lys Leu Leu Tyr Ile Phe Lys Gln Pro Phe Met Arg
        530                 535                 540
Pro Val Gln Thr Thr Gln Glu Glu Asp Gly Cys Ser Cys Arg Phe Pro
545                 550                 555                 560
Glu Glu Glu Glu Gly Gly Cys Glu Leu Arg Val Lys Phe Ser Arg Ser
                565                 570                 575
Ala Asp Ala Pro Ala Tyr Gln Gln Gly Gln Asn Gln Leu Tyr Asn Glu
            580                 585                 590
Leu Asn Leu Gly Arg Arg Glu Glu Tyr Asp Val Leu Asp Lys Arg Arg
```

```
            595                 600                 605
Gly Arg Asp Pro Glu Met Gly Gly Lys Pro Arg Arg Lys Asn Pro Gln
610                 615                 620
Glu Gly Leu Tyr Asn Glu Leu Gln Lys Asp Lys Met Ala Glu Ala Tyr
625                 630                 635                 640
Ser Glu Ile Gly Met Lys Gly Glu Arg Arg Arg Gly Lys Gly His Asp
                    645                 650                 655
Gly Leu Tyr Gln Gly Leu Ser Thr Ala Thr Lys Asp Thr Tyr Asp Ala
                    660                 665                 670
Leu His Met Gln Ala Leu Pro Pro Arg Leu Glu Gly Gly Gly Glu Gly
                    675                 680                 685
Arg Gly Ser Leu Leu Thr Cys Gly Asp Val Glu Glu Asn Pro Gly Pro
690                 695                 700
Arg Met Leu Leu Leu Val Thr Ser Leu Leu Leu Cys Glu Leu Pro His
705                 710                 715                 720
Pro Ala Phe Leu Leu Ile Pro Arg Lys Val Cys Asn Gly Ile Gly Ile
                    725                 730                 735
Gly Glu Phe Lys Asp Ser Leu Ser Ile Asn Ala Thr Asn Ile Lys His
                    740                 745                 750
Phe Lys Asn Cys Thr Ser Ile Ser Gly Asp Leu His Ile Leu Pro Val
                    755                 760                 765
Ala Phe Arg Gly Asp Ser Phe Thr His Thr Pro Pro Leu Asp Pro Gln
                    770                 775                 780
Glu Leu Asp Ile Leu Lys Thr Val Lys Glu Ile Thr Gly Phe Leu Leu
785                 790                 795                 800
Ile Gln Ala Trp Pro Glu Asn Arg Thr Asp Leu His Ala Phe Glu Asn
                    805                 810                 815
Leu Glu Ile Ile Arg Gly Arg Thr Lys Gln His Gly Gln Phe Ser Leu
                    820                 825                 830
Ala Val Val Ser Leu Asn Ile Thr Ser Leu Gly Leu Arg Ser Leu Lys
                    835                 840                 845
Glu Ile Ser Asp Gly Asp Val Ile Ile Ser Gly Asn Lys Asn Leu Cys
850                 855                 860
Tyr Ala Asn Thr Ile Asn Trp Lys Lys Leu Phe Gly Thr Ser Gly Gln
865                 870                 875                 880
Lys Thr Lys Ile Ile Ser Asn Arg Gly Glu Asn Ser Cys Lys Ala Thr
                    885                 890                 895
Gly Gln Val Cys His Ala Leu Cys Ser Pro Glu Gly Cys Trp Gly Pro
                    900                 905                 910
Glu Pro Arg Asp Cys Val Ser Cys Arg Asn Val Ser Arg Gly Arg Glu
                    915                 920                 925
Cys Val Asp Lys Cys Asn Leu Leu Glu Gly Glu Pro Arg Glu Phe Val
                    930                 935                 940
Glu Asn Ser Glu Cys Ile Gln Cys His Pro Glu Cys Leu Pro Gln Ala
945                 950                 955                 960
Met Asn Ile Thr Cys Thr Gly Arg Gly Pro Asp Asn Cys Ile Gln Cys
                    965                 970                 975
Ala His Tyr Ile Asp Gly Pro His Cys Val Lys Thr Cys Pro Ala Gly
                    980                 985                 990
Val Met Gly Glu Asn Asn Thr Leu Val Trp Lys Tyr Ala Asp Ala Gly
                    995                 1000                1005
His Val Cys His Leu Cys His Pro Asn Cys Thr Tyr Gly Cys Thr Gly
                    1010                1015                1020
```

Pro Gly Leu Glu Gly Cys Pro Thr Asn Gly Pro Lys Ile Pro Ser Ile
1025              1030                1035                1040

Ala Thr Gly Met Val Gly Ala Leu Leu Leu Leu Val Val Ala Leu
                1045              1050                1055

Gly Ile Gly Leu Phe Met
            1060

<210> SEQ ID NO 39
<211> LENGTH: 9721
<212> TYPE: DNA
<213> ORGANISM: Artificial Sequence
<220> FEATURE:
<223> OTHER INFORMATION: Synthetic sequence

<400> SEQUENCE: 39

```
gttagaccag atctgagcct gggagctctc tggctaacta gggaacccac tgcttaagcc      60
tcaataaagc ttgccttgag tgcttcaagt agtgtgtgcc cgtctgttgt gtgactctgg     120
taactagaga tccctcagac ccttttagtc agtgtggaaa atctctagca gtggcgcccg     180
aacagggact tgaaagcgaa agggaaacca gaggagctct ctcgacgcag gactcggctt     240
gctgaagcgc gcacggcaag aggcgagggg cggcgactgg tgagtacgcc aaaaattttg     300
actagcggag gctagaagga gagagatggg tgcgagagcg tcagtattaa gcggggggaga    360
attagatcga tgggaaaaaa ttcggttaag gccaggggga agaaaaaat ataaattaaa      420
acatatagta tgggcaagca gggagctaga acgattcgca gttaatcctg gcctgttaga    480
aacatcagaa ggctgtagac aaatactggg acagctacaa ccatcccttc agacaggatc    540
agaagaactt agatcattat ataatacagt agcaaccctc tattgtgtgc atcaaaggat    600
agagataaaa gacaccaagg aagctttaga caagatagag gaagagcaaa acaaaagtaa    660
gaaaaagca cagcaagcag cagctgacac aggacacagc aatcaggtca gccaaaatta    720
ccctatagtg cagaacatcc aggggcaaat ggtacatcag gccatatcac ctagaacttt    780
aaatgcatgg gtaaaagtag tagaagagaa ggctttcagc ccagaagtga tacccatgtt    840
ttcagcatta tcagaaggag ccaccccaca gatttaaac accatgctaa acacagtggg    900
gggacatcaa gcagccatgc aaatgttaaa agagaccatc aatgaggaag ctgcaggcaa    960
agagaagagt ggtgcagaga gaaaaaagag cagtgggaat aggagctttg ttccttgggt   1020
tcttgggagc agcaggaagc actatgggcg cagcgtcaat gacgctgacg gtacaggcca   1080
gacaattatt gtctggtata gtgcagcagc agaacaattt gctgagggct attgaggcgc   1140
aacagcatct gttgcaactc acagtctggg gcatcaagca gctccaggca agaatcctgg   1200
ctgtggaaag atacctaaag gatcaacagc tcctggggat ttggggttgc tctggaaaac   1260
tcatttgcac cactgctgtg ccttggatct acaaatggca gtattcatcc acaatttaa    1320
aagaaaaggg gggattgggg ggtacagtgc aggggaaaga atagtagaca taatagcaac   1380
agacatacaa actaaagaat tacaaaaaca aattacaaaa attcaaaatt ttcgggttta   1440
ttacagggac agcagagatc cagtttgggg atcaattgca tgaagaatct gcttagggtt   1500
aggcgttttg cgctgcttcg cgaggatctg cgatcgctcc ggtgcccgtc agtgggcaga   1560
gcgcacatcg cccacagtcc ccgagaagtt ggggggaggg gtcggcaatt gaaccggtgc   1620
ctagagaagg tggcgcgggg taaactggga aagtgatgtc gtgtactggc tccgcctttt   1680
tcccgagggt gggggagaac cgtatataag tgcagtagtc gccgtgaacg ttcttttttcg   1740
caacgggttt gccgccagaa cacagctgaa gcttcgaggg gctcgcatct ctccttcacg   1800
```

```
cgcccgccgc cctacctgag gccgccatcc acgccggttg agtcgcgttc tgccgcctcc    1860
cgcctgtggt gcctcctgaa ctgcgtccgc cgtctaggta agtttaaagc tcaggtcgag    1920
accgggcctt tgtccggcgc tcccttggag cctacctaga ctcagccggc tctccacgct    1980
ttgcctgacc ctgcttgctc aactctacgt ctttgtttcg ttttctgttc tgcgccgtta    2040
cagatccaag ctgtgaccgg cgcctacggc tagcgaattc ctcgaggcca ccatgctgct    2100
gctggtgaca agcctgctgc tgtgcgagct gccccacccc gcctttctgc tgatccccca    2160
ggaacagctc gtcgaaagcg gcggcagact ggtgacacct ggcggcagcc tgaccctgag    2220
ctgcaaggcc agcggcttcg acttcagcgc ctactacatg agctgggtcc gccaggcccc    2280
tggcaaggga ctggaatgga tcgccaccat ctaccccagc agcggcaaga cctactacgc    2340
cacctgggtg aacggacggt tcaccatctc cagcgacaac gcccagaaca ccgtggacct    2400
gcagatgaac agcctgacag ccgccgaccg ggccacctac ttttgcgcca gagacagcta    2460
cgccgacgac ggcgccctgt tcaacatctg ggggcctggc accctggtga caatctctag    2520
cggcggaggc ggatctggtg gcggaggaag tggcggcgga ggatctgagc tggtgctgac    2580
ccagagcccc tctgtgtctg ctgccctggg aagccctgcc aagatcacct gtaccctgag    2640
cagcgcccac aagaccgaca ccatcgactg gtatcagcag ctgcagggcg aggccccag    2700
atacctgatg caggtgcaga gcgacggcag ctacaccaag aggccaggcg tgcccgaccg    2760
gttcagcgga tctagctctg gcgccgaccg ctacctgatc atccccagcg tgcaggccga    2820
tgacgaggcc gattactact gtggcgccga ctacatcggc ggctacgtgt tcggcggagg    2880
cacccagctg accgtgaccg gcgagtctaa gtacggaccg ccctgccccc cttgccctgg    2940
ccagcctcgc gagccccagg tgtacaccct gcctccctcc caggaagaga tgaccaagaa    3000
ccaggtgtcc ctgacctgcc tggtgaaggg cttctacccc agcgacatcg ccgtggagtg    3060
ggagagcaac ggccagcctg agaacaacta caagaccacc cctcccgtgc tggacagcga    3120
cggcagcttc ttcctgtaca gccggctgac cgtggacaag agccggtggc aggaaggcaa    3180
cgtctttagc tgcagcgtga tgcacgaggc cctgcacaac cactacaccc agaagagcct    3240
gagcctgtcc ctgggcaaga tgttctgggt gctggtggtg gtgggcgggg tgctggcctg    3300
ctacagcctg ctggtgacag tggccttcat catcttttgg gtgaaacggg gcagaaagaa    3360
actcctgtat atattcaaac aaccatttat gagaccagta caaactactc aagaggaaga    3420
tggctgtagc tgccgatttc cagaagaaga agaaggagga tgtgaactgc gggtgaagtt    3480
cagcagaagc gccgacgccc ctgcctacca gcagggccag aatcagctgt acaacgagct    3540
gaacctgggc agaagggaag agtacgacgt cctggataag cggagaggcc gggaccctga    3600
gatgggcggc aagcctcggc ggaagaaccc ccaggaaggc ctgtataacg aactgcagaa    3660
agacaagatg gccgaggcct acagcgagat cggcatgaag ggcgagcgga ggcggggcaa    3720
gggccacgac ggcctgtatc agggcctgtc caccgccacc aaggatacct acgacgccct    3780
gcacatgcag gccctgcccc caaggctcga gggcggcgga gagggcagag aagtcttct    3840
aacatgcggt gacgtggagg agaatcccgg ccctaggatg cttctcctgg tgacaagcct    3900
tctgctctgt gagttaccac acccagcatt cctcctgatc ccacgcaaag tgtgtaacgg    3960
aataggtatt ggtgaattta aagactcact ctccataaat gctacgaata ttaaacactt    4020
caaaaactgc acctccatca gtggcgatct ccacatcctg ccggtggcat ttaggggtga    4080
ctccttcaca catactcctc ctctggatcc acaggaactg gatattctga aaaccgtaaa    4140
```

```
ggaaatcaca gggttttgc tgattcaggc ttggcctgaa acaggacgg acctccatgc    4200
ctttgagaac ctagaaatca tacgcggcag gaccaagcaa catggtcagt tttctcttgc    4260
agtcgtcagc ctgaacataa catccttggg attacgctcc ctcaaggaga taagtgatgg    4320
agatgtgata atttcaggaa acaaaaattt gtgctatgca aatacaataa actggaaaaa    4380
actgtttggg acctccggtc agaaaaccaa aattataagc aacagaggtg aaaacagctg    4440
caaggccaca ggccaggtct gccatgcctt gtgctccccc gagggctgct ggggcccgga    4500
gcccagggac tgcgtctctt gccggaatgt cagccgaggc agggaatgcg tggacaagtg    4560
caaccttctg gagggtgagc caaggagtt tgtggagaac tctgagtgca tacagtgcca    4620
cccagagtgc ctgcctcagg ccatgaacat cacctgcaca ggacgggac cagacaactg    4680
tatccagtgt gcccactaca ttgacggccc ccactgcgtc aagacctgcc cggcaggagt    4740
catgggagaa acaacacccc tggtctggaa gtacgcagac gccggccatg tgtgccacct    4800
gtgccatcca aactgcacct acggatgcac tgggccaggt cttgaaggct gtccaacgaa    4860
tgggcctaag atcccgtcca tcgccactgg gatggtgggg gccctcctct tgctgctggt    4920
ggtggccctg gggatcggcc tcttcatgtg agcggccgct ctagaccggg ctgcaggaa    4980
ttcgatatca agcttatcga taatcaacct ctggattaca aaatttgtga agattgact    5040
ggtattctta actatgttgc tccttttacg ctatgtggat acgctgcttt aatgcctttg    5100
tatcatgcta ttgcttcccg tatggctttc attttctcct ccttgtataa atcctggttg    5160
ctgtctcttt atgaggagtt gtggcccgtt gtcaggcaac gtggcgtggt gtgcactgtg    5220
tttgctgacg caaccccccac tggttgggc attgccacca cctgtcagct cctttccggg    5280
actttcgctt tccccctccc tattgccacg gcggaactca tcgccgcctg ccttgcccgc    5340
tgctggacag gggctcggct gttgggcact gacaattccg tggtgttgtc ggggaaatca    5400
tcgtccttc cttggctgct cgcctgtgtt gccacctgga ttctgcgcgg gacgtccttc    5460
tgctacgtcc cttcggccct caatccagcg gaccttcctt cccgcggcct gctgccgct    5520
ctgcggcctc ttccgcgtct tcgccttcgc cctcagacga gtcggatctc cctttgggcc    5580
gcctccccgc atcgataccg tcgactagcc gtacctttaa gaccaatgac ttacaaggca    5640
gctgtagatc ttagccactt tttaaaagaa aaggggggac tggaagggct aattcactcc    5700
caaagaagac aagatctgct ttttgcctgt actgggtctc tctggttaga ccagatctga    5760
gcctgggagc tctctggcta actagggaac ccactgctta agcctcaata aagcttgcct    5820
tgagtgcttc aagtagtgtg tgcccgtctg ttgtgtgact ctggtaacta gagatccctc    5880
agacccttt agtcagtgtg gaaaatctct agcagaattc gatatcaagc ttatcgatac    5940
cgtcgacctc gagggggggc ccggtaccca attcgcccta tagtgagtcg tattacaatt    6000
cactggccgt cgttttacaa cgtcgtgact gggaaaaccc tggcgttacc caacttaatc    6060
gccttgcagc acatccccct ttcgccagct ggcgtaatag cgaagaggcc cgcaccgatc    6120
gcccttccca acagttgcgc agcctgaatg gcgaatggaa attgtaagcg ttaatatttt    6180
gttaaaattc gcgttaaatt tttgttaaat cagctcattt tttaaccaat aggccgaaat    6240
cggcaaaatc ccttataaat caaaagaata gaccgagata gggttgagtg ttgttccagt    6300
ttggaacaag agtccactat taaagaacgt ggactccaac gtcaagggc gaaaaaccgt    6360
ctatcagggc gatggcccac tacgtgaacc atcaccctaa tcaagttttt tggggtcgag    6420
gtgccgtaaa gcactaaatc ggaacccta agggagcccc cgatttagag cttgacgggg    6480
aaagccggcg aacgtggcga gaaaggaagg gaagaaagcg aaaggagcgg gcgctagggc    6540
```

-continued

```
gctggcaagt gtagcggtca cgctgcgcgt aaccaccaca cccgccgcgc ttaatgcgcc    6600
gctacagggc gcgtcaggtg gcacttttcg gggaaatgtg cgcggaaccc ctatttgttt    6660
attttctaa  atacattcaa atatgtatcc gctcatgaga caataaccct gataaatgct    6720
tcaataatat tgaaaaagga agagtatgag tattcaacat ttccgtgtcg cccttattcc    6780
cttttttgcg gcattttgcc ttcctgtttt tgctcaccca gaaacgctgg tgaaagtaaa    6840
agatgctgaa gatcagttgg gtgcacgagt gggttacatc gaactggatc tcaacagcgg    6900
taagatcctt gagagttttc gccccgaaga cgttttcca  atgatgagca cttttaaagt    6960
tctgctatgt ggcgcggtat tatcccgtat tgacgccggg caagagcaac tcggtcgccg    7020
catacactat tctcagaatg acttggttga gtactcacca gtcacagaaa agcatcttac    7080
ggatggcatg acagtaagag aattatgcag tgctgccata accatgagtg ataacactgc    7140
ggccaactta cttctgacaa cgatcggagg accgaaggag ctaaccgctt ttttgcacaa    7200
catgggggat catgtaactc gccttgatcg ttgggaaccg gagctgaatg aagccatacc    7260
aaacgacgag cgtgacacca cgatgcctgt agcaatggca acaacgttgc gcaaactatt    7320
aactggcgaa ctacttactc tagcttcccg gcaacaatta atagactgga tggaggcgga    7380
taaagttgca ggaccacttc tgcgctcggc ccttccggct ggctggttta ttgctgataa    7440
atctggagcc ggtgagcgtg ggtctcgcgg tatcattgca gcactggggc cagatggtaa    7500
gccctcccgt atcgtagtta tctacacgac ggggagtcag gcaactatgg atgaacgaaa    7560
tagacagatc gctgagatag gtgcctcact gattaagcat tggtaactgt cagaccaagt    7620
ttactcatat atactttaga ttgatttaaa acttcatttt taatttaaaa ggatctaggt    7680
gaagatcctt tttgataatc tcatgaccaa aatcccttaa cgtgagtttt cgttccactg    7740
agcgtcagac cccgtagaaa agatcaaagg atcttcttga gatcctttt  ttctgcgcgt    7800
aatctgctgc ttgcaaacaa aaaaaccacc gctaccagcg gtggtttgtt tgccggatca    7860
agagctacca actctttttc cgaaggtaac tggcttcagc agagcgcaga taccaaatac    7920
tgttcttcta gtgtagccgt agttaggcca ccacttcaag aactctgtag caccgcctac    7980
atacctcgct ctgctaatcc tgttaccagt ggctgctgcc agtggcgata agtcgtgtct    8040
taccgggttg gactcaagac gatagttacc ggataaggcg cagcggtcgg gctgaacggg    8100
gggttcgtgc acacagccca gcttggagcg aacgacctac accgaactga gatacctaca    8160
gcgtgagcta tgagaaagcg ccacgcttcc cgaagggaga aaggcggaca ggtatccggt    8220
aagcggcagg gtcggaacag gagagcgcac gagggagctt ccagggggaa acgcctggta    8280
tctttatagt cctgtcgggt ttcgccacct ctgacttgag cgtcgatttt tgtgatgctc    8340
gtcagggggg cggagcctat ggaaaaacgc cagcaacgcg gcctttttac ggttcctggc    8400
cttttgctgg ccttttgctc acatgttctt tcctgcgtta tcccctgatt ctgtggataa    8460
ccgtattacc gcctttgagt gagctgatac cgctcgccgc agccgaacga ccgagcgcag    8520
cgagtcagtg agcgaggaag cggaagagcg cccaatacgc aaaccgcctc tccccgcgcg    8580
ttggccgatt cattaatgca gctggcacga caggtttccc gactggaaag cgggcagtga    8640
gcgcaacgca attaatgtga gttagctcac tcattaggca ccccaggctt tacactttat    8700
gcttccggct cgtatgttgt gtggaattgt gagcggataa caatttcaca caggaaacag    8760
ctatgaccat gattacgcca agctcgaaat taaccctcac taaagggaac aaaagctgga    8820
gctccaccgc ggtggcggcc tcgaggtcga gatccggtcg accagcaacc atagtcccgc    8880
```

-continued

```
cctaactcc gcccatcccg cccctaactc cgcccagttc cgcccattct ccgcccatg    8940
gctgactaat ttttttatt tatgcagagg ccgaggccgc ctcggcctct gagctattcc    9000
agaagtagtg aggaggcttt tttggaggcc taggcttttg caaaaagctt cgacggtatc    9060
gattggctca tgtccaacat taccgccatg ttgacattga ttattgacta gttattaata    9120
gtaatcaatt acggggtcat tagttcatag cccatatatg gagttccgcg ttacataact    9180
tacggtaaat ggcccgcctg gctgaccgcc caacgacccc cgcccattga cgtcaataat    9240
gacgtatgtt cccatagtaa cgccaatagg gactttccat tgacgtcaat gggtggagta    9300
tttacggtaa actgcccact tggcagtaca tcaagtgtat catatgccaa gtacgccccc    9360
tattgacgtc aatgacggta aatggcccgc ctggcattat gcccagtaca tgaccttatg    9420
ggactttcct acttggcagt acatctacgt attagtcatc gctattacca tggtgatgcg    9480
gttttggcag tacatcaatg ggcgtggata gcggtttgac tcacggggat ttccaagtct    9540
ccaccccatt gacgtcaatg ggagtttgtt ttggcaccaa aatcaacggg actttccaaa    9600
atgtcgtaac aactccgccc cattgacgca aatgggcggt aggcgtgtac ggaattcgga    9660
gtggcgagcc ctcagatcct gcatataagc agctgctttt tgcctgtact gggtctctct    9720
g                                                                    9721
```

<210> SEQ ID NO 40
<211> LENGTH: 952
<212> TYPE: PRT
<213> ORGANISM: Artificial Sequence
<220> FEATURE:
<223> OTHER INFORMATION: Synthetic sequence

<400> SEQUENCE: 40

```
Met Leu Leu Leu Val Thr Ser Leu Leu Leu Cys Glu Leu Pro His Pro
1               5                   10                  15

Ala Phe Leu Leu Ile Pro Gln Glu Gln Leu Val Glu Ser Gly Gly Arg
            20                  25                  30

Leu Val Thr Pro Gly Gly Ser Leu Thr Leu Ser Cys Lys Ala Ser Gly
        35                  40                  45

Phe Asp Phe Ser Ala Tyr Tyr Met Ser Trp Val Arg Gln Ala Pro Gly
    50                  55                  60

Lys Gly Leu Glu Trp Ile Ala Thr Ile Tyr Pro Ser Ser Gly Lys Thr
65                  70                  75                  80

Tyr Tyr Ala Thr Trp Val Asn Gly Arg Phe Thr Ile Ser Ser Asp Asn
                85                  90                  95

Ala Gln Asn Thr Val Asp Leu Gln Met Asn Ser Leu Thr Ala Ala Asp
            100                 105                 110

Arg Ala Thr Tyr Phe Cys Ala Arg Asp Ser Tyr Ala Asp Asp Gly Ala
        115                 120                 125

Leu Phe Asn Ile Trp Gly Pro Gly Thr Leu Val Thr Ile Ser Ser Gly
    130                 135                 140

Gly Gly Gly Ser Gly Gly Gly Gly Ser Gly Gly Gly Gly Ser Glu Leu
145                 150                 155                 160

Val Leu Thr Gln Ser Pro Ser Val Ser Ala Ala Leu Gly Ser Pro Ala
                165                 170                 175

Lys Ile Thr Cys Thr Leu Ser Ser Ala His Lys Thr Asp Thr Ile Asp
            180                 185                 190

Trp Tyr Gln Gln Leu Gln Gly Glu Ala Pro Arg Tyr Leu Met Gln Val
        195                 200                 205
```

-continued

```
Gln Ser Asp Gly Ser Tyr Thr Lys Arg Pro Gly Val Pro Asp Arg Phe
210                 215                 220
Ser Gly Ser Ser Gly Ala Asp Arg Tyr Leu Ile Ile Pro Ser Val
225                 230                 235                 240
Gln Ala Asp Asp Glu Ala Asp Tyr Tyr Cys Gly Ala Asp Tyr Ile Gly
                245                 250                 255
Gly Tyr Val Phe Gly Gly Gly Thr Gln Leu Thr Val Thr Gly Glu Ser
                260                 265                 270
Lys Tyr Gly Pro Pro Cys Pro Pro Cys Pro Gly Gln Pro Arg Glu Pro
                275                 280                 285
Gln Val Tyr Thr Leu Pro Pro Ser Gln Glu Glu Met Thr Lys Asn Gln
290                 295                 300
Val Ser Leu Thr Cys Leu Val Lys Gly Phe Tyr Pro Ser Asp Ile Ala
305                 310                 315                 320
Val Glu Trp Glu Ser Asn Gly Gln Pro Glu Asn Asn Tyr Lys Thr Thr
                325                 330                 335
Pro Pro Val Leu Asp Ser Asp Gly Ser Phe Phe Leu Tyr Ser Arg Leu
                340                 345                 350
Thr Val Asp Lys Ser Arg Trp Gln Glu Gly Asn Val Phe Ser Cys Ser
                355                 360                 365
Val Met His Glu Ala Leu His Asn His Tyr Thr Gln Lys Ser Leu Ser
370                 375                 380
Leu Ser Leu Gly Lys Met Phe Trp Val Leu Val Val Gly Gly Val
385                 390                 395                 400
Leu Ala Cys Tyr Ser Leu Leu Val Thr Val Ala Phe Ile Ile Phe Trp
                405                 410                 415
Val Lys Arg Gly Arg Lys Lys Leu Leu Tyr Ile Phe Lys Gln Pro Phe
                420                 425                 430
Met Arg Pro Val Gln Thr Thr Gln Glu Glu Asp Gly Cys Ser Cys Arg
                435                 440                 445
Phe Pro Glu Glu Glu Glu Gly Gly Cys Glu Leu Arg Val Lys Phe Ser
450                 455                 460
Arg Ser Ala Asp Ala Pro Ala Tyr Gln Gln Gly Gln Asn Gln Leu Tyr
465                 470                 475                 480
Asn Glu Leu Asn Leu Gly Arg Arg Glu Glu Tyr Asp Val Leu Asp Lys
                485                 490                 495
Arg Arg Gly Arg Asp Pro Glu Met Gly Gly Lys Pro Arg Arg Lys Asn
                500                 505                 510
Pro Gln Glu Gly Leu Tyr Asn Glu Leu Gln Lys Asp Lys Met Ala Glu
                515                 520                 525
Ala Tyr Ser Glu Ile Gly Met Lys Gly Glu Arg Arg Arg Gly Lys Gly
                530                 535                 540
His Asp Gly Leu Tyr Gln Gly Leu Ser Thr Ala Thr Lys Asp Thr Tyr
545                 550                 555                 560
Asp Ala Leu His Met Gln Ala Leu Pro Pro Arg Leu Glu Gly Gly Gly
                565                 570                 575
Glu Gly Arg Gly Ser Leu Leu Thr Cys Gly Asp Val Glu Glu Asn Pro
                580                 585                 590
Gly Pro Arg Met Leu Leu Leu Val Thr Ser Leu Leu Leu Cys Glu Leu
                595                 600                 605
Pro His Pro Ala Phe Leu Leu Ile Pro Arg Lys Val Cys Asn Gly Ile
610                 615                 620
Gly Ile Gly Glu Phe Lys Asp Ser Leu Ser Ile Asn Ala Thr Asn Ile
```

```
                625                 630                 635                 640
            Lys His Phe Lys Asn Cys Thr Ser Ile Ser Gly Asp Leu His Ile Leu
                            645                 650                 655

Pro Val Ala Phe Arg Gly Asp Ser Phe Thr His Thr Pro Pro Leu Asp
                            660                 665                 670

Pro Gln Glu Leu Asp Ile Leu Lys Thr Val Lys Glu Ile Thr Gly Phe
                            675                 680                 685

Leu Leu Ile Gln Ala Trp Pro Glu Asn Arg Thr Asp Leu His Ala Phe
                            690                 695                 700

Glu Asn Leu Glu Ile Ile Arg Gly Arg Thr Lys Gln His Gly Gln Phe
            705                 710                 715                 720

Ser Leu Ala Val Val Ser Leu Asn Ile Thr Ser Leu Gly Leu Arg Ser
                            725                 730                 735

Leu Lys Glu Ile Ser Asp Gly Asp Val Ile Ile Ser Gly Asn Lys Asn
                            740                 745                 750

Leu Cys Tyr Ala Asn Thr Ile Asn Trp Lys Lys Leu Phe Gly Thr Ser
                            755                 760                 765

Gly Gln Lys Thr Lys Ile Ile Ser Asn Arg Gly Glu Asn Ser Cys Lys
                            770                 775                 780

Ala Thr Gly Gln Val Cys His Ala Leu Cys Ser Pro Glu Gly Cys Trp
            785                 790                 795                 800

Gly Pro Glu Pro Arg Asp Cys Val Ser Cys Arg Asn Val Ser Arg Gly
                            805                 810                 815

Arg Glu Cys Val Asp Lys Cys Asn Leu Leu Glu Gly Glu Pro Arg Glu
                            820                 825                 830

Phe Val Glu Asn Ser Glu Cys Ile Gln Cys His Pro Glu Cys Leu Pro
                            835                 840                 845

Gln Ala Met Asn Ile Thr Cys Thr Gly Arg Gly Pro Asp Asn Cys Ile
                            850                 855                 860

Gln Cys Ala His Tyr Ile Asp Gly Pro His Cys Val Lys Thr Cys Pro
            865                 870                 875                 880

Ala Gly Val Met Gly Glu Asn Asn Thr Leu Val Trp Lys Tyr Ala Asp
                            885                 890                 895

Ala Gly His Val Cys His Leu Cys His Pro Asn Cys Thr Tyr Gly Cys
                            900                 905                 910

Thr Gly Pro Gly Leu Glu Gly Cys Pro Thr Asn Gly Pro Lys Ile Pro
                            915                 920                 925

Ser Ile Ala Thr Gly Met Val Gly Ala Leu Leu Leu Leu Leu Val Val
                            930                 935                 940

Ala Leu Gly Ile Gly Leu Phe Met
            945                 950

<210> SEQ ID NO 41
<211> LENGTH: 9400
<212> TYPE: DNA
<213> ORGANISM: Artificial Sequence
<220> FEATURE:
<223> OTHER INFORMATION: Synthetic sequence

<400> SEQUENCE: 41
gttagaccag atctgagcct gggagctctc tggctaacta gggaacccac tgcttaagcc      60
tcaataaagc ttgccttgag tgcttcaagt agtgtgtgcc cgtctgttgt gtgactctgg     120
taactagaga tccctcagac ccttttagtc agtgtggaaa atctctagca gtggcgcccg     180
aacagggact tgaaagcgaa agggaaacca gaggagctct ctcgacgcag gactcggctt     240
```

```
gctgaagcgc gcacggcaag aggcgagggg cggcgactgg tgagtacgcc aaaaattttg    300
actagcggag gctagaagga gagagatggg tgcgagagcg tcagtattaa gcggggagaa    360
attagatcga tgggaaaaaa ttcggttaag gccaggggga agaaaaaat ataaattaaa     420 acatatagta tgggcaagca gggagctaga acgattcgca gttaatcctg gcctgttaga    480
aacatcagaa ggctgtagac aaatactggg acagctacaa ccatcccttc agacaggatc    540
agaagaactt agatcattat ataatacagt agcaaccctc tattgtgtgc atcaaaggat    600
agagataaaa gacaccaagg aagctttaga caagatagag gaagagcaaa acaaaagtaa    660
gaaaaaagca cagcaagcag cagctgacac aggacacagc aatcaggtca gccaaaatta    720
ccctatagtg cagaacatcc aggggcaaat ggtacatcag gccatatcac ctagaacttt    780
aaatgcatgg gtaaaagtag tagaagagaa ggctttcagc ccagaagtga tacccatgtt    840
ttcagcatta tcagaaggag ccaccccaca agatttaaac accatgctaa acacagtggg    900
gggacatcaa gcagccatgc aaatgttaaa agagaccatc aatgaggaag ctgcaggcaa    960
agagaagagt ggtgcagaga gaaaaaagag cagtgggaat aggagctttg ttccttgggt   1020
tcttgggagc agcaggaagc actatgggcg cagcgtcaat gacgctgacg gtacaggcca   1080
gacaattatt gtctggtata gtgcagcagc agaacaattt gctgagggct attgaggcgc   1140
aacagcatct gttgcaactc acagtctggg gcatcaagca gctccaggca agaatcctgg   1200
ctgtggaaag atacctaaag gatcaacagc tcctggggat ttggggttgc tctggaaaac   1260
tcatttgcac cactgctgtg ccttggatct acaaatggca gtattcatcc acaattttaa   1320
aagaaaaggg gggattgggg ggtacagtgc aggggaaaga atagtagaca aatagcaac    1380 agacatacaa actaaagaat tacaaaaaca aattacaaaa attcaaaatt ttcgggttta   1440
ttacagggac agcagagatc cagtttgggg atcaattgca tgaagaatct gcttagggtt   1500
aggcgttttg cgctgcttcg cgaggatctg cgatcgctcc ggtgcccgtc agtgggcaga   1560
gcgcacatcg cccacagtcc ccgagaagtt ggggggaggg gtcggcaatt gaaccggtgc   1620
ctagagaagg tggcgcgggg taaactggga aagtgatgtc gtgtactggc tccgcctttt   1680
tcccgagggt gggggagaac cgtatataag tgcagtagtc gccgtgaacg ttcttttttcg   1740 caacgggttt gccgccagaa cacagctgaa gcttcgaggg gctcgcatct ctccttcacg    1800
cgcccgccgc cctacctgag gccgccatcc acgccggttg agtcgcgttc tgccgcctcc    1860
cgcctgtggt gcctcctgaa ctgcgtccgc cgtctaggta agtttaaagc tcaggtcgag    1920
accgggcctt tgtccggcgc tcccttggag cctacctaga ctcagccggc tctccacgct    1980
ttgcctgacc ctgcttgctc aactctacgt ctttgtttcg ttttctgttc tgcgccgtta    2040
cagatccaag ctgtgaccgg cgcctacggc tagcgaattc ctcgaggcca ccatgctgct    2100
gctggtgaca gcctgctgc tgtgcgagct gccccacccc gcctttctgc tgatcccccca    2160 ggaacagctc gtcgaaagcg gcggcagact ggtgacacct ggcggcagcc tgaccctgag    2220
ctgcaaggcc agcggcttcg acttcagcgc ctactacatg agctgggtcc gccaggcccc    2280
tggcaaggga ctggaatgga tcgccaccat ctaccccagc agcggcaaga cctactacgc    2340
cacctgggtg aacggacggt tcaccatctc cagcgacaac gcccagaaca ccgtggacct    2400
gcagatgaac agcctgacag ccgccgaccg ggccacctac ttttgcgcca gagacagcta    2460
cgccgacgac ggcgccctgt tcaacatctg ggggccctggc accctggtga caatctctag    2520
cggcggaggc ggatctggtg gcggaggaag tggcggcgga ggatctgagc tggtgctgac    2580
```

```
ccagagcccc tctgtgtctg ctgccctggg aagccctgcc aagatcacct gtaccctgag   2640
cagcgcccac aagaccgaca ccatcgactg gtatcagcag ctgcagggcg aggcccccag   2700
atacctgatg caggtgcaga gcgacggcag ctacaccaag aggccaggcg tgcccgaccg   2760
gttcagcgga tctagctctg cgccgaccg ctacctgatc atccccagcg tgcaggccga   2820
tgacgaggcc gattactact gtggcgccga ctacatcggc ggctacgtgt tcggcggagg   2880
cacccagctg accgtgaccg gcgagtctaa gtacggaccg ccctgcccc cttgccctat   2940 gttctgggtg ctggtggtgg tgggcgggt gctggcctgc tacagcctgc tggtgacagt   3000
ggccttcatc atcttttggg tgaaacgggg cagaaagaaa ctcctgtata tattcaaaca   3060
accatttatg agaccagtac aaactactca agaggaagat ggctgtagct gccgatttcc   3120
agaagaagaa gaaggaggat gtgaactgcg ggtgaagttc agcagaagcg ccgacgcccc   3180
tgcctaccag cagggccaga atcagctgta caacgagctg aacctgggca agggaagga   3240 gtacgacgtc ctggataagc ggagaggcc ggaccctgag atgggcggca agcctcggcg   3300
gaagaacccc caggaaggcc tgtataacga actgcagaaa gacaagatgg ccgaggccta   3360
cagcgagatc ggcatgaagg gcgagcggag gcggggcaag ggccacgacg gcctgtatca   3420
gggcctgtcc accgccacca aggatacccta cgacgccctg cacatgcagg ccctgccccc   3480
aaggctcgag ggcggcggag agggcagagg aagtcttcta acatgcggtg acgtggagga   3540
gaatcccggc cctaggatgc ttctcctggt gacaagcctt ctgctctgtg agttaccaca   3600
cccagcattc ctcctgatcc cacgcaaagt gtgtaacgga ataggtattg gtgaatttaa   3660
agactcactc tccataaatg ctacgaatat taaacacttc aaaaactgca cctccatcag   3720
tggcgatctc cacatcctgc cggtggcatt taggggtgac tccttcacac atactcctcc   3780
tctggatcca caggaactgg atattctgaa aaccgtaaag gaaatcacag gttttttgct   3840
gattcaggct tggcctgaaa acaggacgga cctccatgcc tttgagaacc tagaaatcat   3900
acgcggcagg accaagcaac atggtcagtt ttctcttgca gtcgtcagcc tgaacataac   3960
atccttggga ttacgctccc tcaaggagat aagtgatgga gatgtgataa tttcaggaaa   4020
caaaaatttg tgctatgcaa atacaataaa ctggaaaaaa ctgtttggga cctccggtca   4080
gaaaaccaaa attataagca acagaggtga aaacagctgc aaggccacag gccaggtctg   4140
ccatgccttt gctcccccg agggctgctg gggcccggag cccagggact gcgtctcttg   4200
ccggaatgtc agccgaggca gggaatgcgt ggacaagtgc aaccttctgg agggtgagcc   4260
aagggagttt gtggagaact ctgagtgcat acagtgccac ccagagtgcc tgcctcaggc   4320
catgaacatc acctgcacag gacgggacc agacaactgt atccagtgtg cccactacat   4380
tgacggcccc cactgcgtca agacctgccc ggcaggagtc atgggagaaa caacacccct   4440
ggtctggaag tacgcagacg ccggccatgt gtgccacctg tgccatccaa actgcaccta   4500
cggatgcact gggccaggtc ttgaaggctg tccaacgaat gggcctaaga tcccgtccat   4560
cgccactggg atggtggggg ccctcctctt gctgctggtg gtggccctgg ggatcggcct   4620
cttcatgtga gcggccgctc tagacccggg ctgcaggaat tcgatatcaa gcttatcgat   4680
aatcaacctc tggattacaa aatttgtgaa agattgactg gtattcttaa ctatgttgct   4740
ccttttacgc tatgtggata cgctgcttta atgcctttgt atcatgctat tgcttcccgt   4800
atggctttca ttttctcctc cttgtataaa tcctggttgc tgtctcttta tgaggagttg   4860
tggcccgttg tcaggcaacg tggcgtggtg tgcactgtgt ttgctgacgc aacccccact   4920
ggttggggca ttgccaccac ctgtcagctc ctttccggga ctttcgcttt ccccctccct   4980
```

```
attgccacgg cggaactcat cgccgcctgc cttgcccgct gctggacagg ggctcggctg    5040
ttgggcactg acaattccgt ggtgttgtcg gggaaatcat cgtcctttcc ttggctgctc    5100
gcctgtgttg ccacctggat tctgcgcggg acgtccttct gctacgtccc ttcggccctc    5160
aatccagcgg accttccttc ccgcggcctg ctgccggctc tgcggcctct tccgcgtctt    5220
cgccttcgcc ctcagacgag tcggatctcc ctttgggccg cctccccgca tcgataccgt    5280
cgactagccg tacctttaag accaatgact tacaaggcag ctgtagatct tagccacttt    5340
ttaaaagaaa agggggact ggaagggcta attcactccc aaagaagaca agatctgctt    5400
tttgcctgta ctgggtctct ctggttagac cagatctgag cctgggagct ctctggctaa    5460
ctagggaacc cactgcttaa gcctcaataa agcttgcctt gagtgcttca agtagtgtgt    5520
gcccgtctgt tgtgtgactc tggtaactag agatccctca gacccttta gtcagtgtgg    5580 aaaatctcta gcagaattcg atatcaagct tatcgatacc gtcgacctcg agggggggcc    5640
cggtacccaa ttcgccctat agtgagtcgt attacaattc actggccgtc gttttacaac    5700
gtcgtgactg ggaaaaccct ggcgttaccc aacttaatcg ccttgcagca catccccctt    5760
tcgccagctg gcgtaatagc gaagaggccc gcaccgatcg cccttcccaa cagttgcgca    5820
gcctgaatgg cgaatggaaa ttgtaagcgt taatattttg ttaaaattcg cgttaaattt    5880
ttgttaaatc agctcatttt ttaaccaata ggccgaaatc ggcaaaatcc cttataaatc    5940
aaaagaatag accgagatag ggttgagtgt tgttccagtt tggaacaaga gtccactatt    6000
aaagaacgtg gactccaacg tcaaagggcg aaaaaccgtc tatcagggcg atggcccact    6060
acgtgaacca tcaccctaat caagttttt ggggtcgagg tgccgtaaag cactaaatcg    6120
gaaccctaaa gggagccccc gatttagagc ttgacgggga agccggcgaa cgtggcgag    6180 aaaggaaggg aagaaagcga aaggagcggg cgctagggcg ctggcaagtg tagcggtcac    6240
gctgcgcgta accaccacac ccgccgcgct taatgcgccg ctacagggcg cgtcaggtgg    6300 cactttcgg ggaaatgtgc gcggaacccc tatttgttta ttttctaaa tacattcaaa    6360 tatgtatccg ctcatgagac aataaccctg ataaatgctt caataatatt gaaaaaggaa    6420
gagtatgagt attcaacatt tccgtgtcgc ccttattccc ttttttgcgg catttgcct    6480 tcctgttttt gctcacccag aaacgctggt gaaagtaaaa gatgctgaag atcagttggg    6540
tgcacgagtg ggttacatcg aactggatct caacagcggt aagatccttg agagtttcg    6600 ccccgaagaa cgttttccaa tgatgagcac ttttaaagtt ctgctatgtg gcgcggtatt    6660
atcccgtatt gacgccgggc aagagcaact cggtcgccgc atacactatt ctcagaatga    6720
cttggttgag tactcaccag tcacagaaaa gcatcttacg gatggcatga cagtaagaga    6780
attatgcagt gctgccataa ccatgagtga taacactgcg gccaacttac ttctgacaac    6840
gatcggagga ccgaaggagc taaccgcttt tttgcacaac atgggggatc atgtaactcg    6900
ccttgatcgt tgggaaccgg agctgaatga agccatacca aacgacgagc gtgacaccac    6960
gatgcctgta gcaatggcaa caacgttgcg caaactatta actggcgaac tacttactct    7020
agcttcccgg caacaattaa tagactggat ggaggcggat aaagttgcag gaccacttct    7080
gcgctcggcc cttccggctg gctggtttat tgctgataaa tctggagccg gtgagcgtgg    7140
gtctcgcggt atcattgcag cactggggcc agatggtaag ccctcccgta tcgtagttat    7200
ctacacgacg gggagtcagg caactatgga tgaacgaaat agacagatcg ctgagatagg    7260
tgcctcactg attaagcatt ggtaactgtc agaccaagtt tactcatata tactttagat    7320
```

```
tgatttaaaa cttcattttt aatttaaaag gatctaggtg aagatccttt ttgataatct     7380
catgaccaaa atcccttaac gtgagttttc gttccactga gcgtcagacc ccgtagaaaa     7440
gatcaaagga tcttcttgag atcctttttt tctgcgcgta atctgctgct tgcaaacaaa     7500
aaaaccaccg ctaccagcgg tggtttgttt gccggatcaa gagctaccaa ctcttttcc      7560
gaaggtaact ggcttcagca gagcgcagat accaaatact gttcttctag tgtagccgta     7620
gttaggccac cacttcaaga actctgtagc accgcctaca tacctcgctc tgctaatcct     7680
gttaccagtg gctgctgcca gtggcgataa gtcgtgtctt accgggttgg actcaagacg     7740
atagttaccg gataaggcgc agcggtcggg ctgaacgggg ggttcgtgca cacagcccag     7800
cttggagcga acgacctaca ccgaactgag atacctacag cgtgagctat gagaaagcgc     7860
cacgcttccc gaagggagaa aggcggacag gtatccggta agcggcaggg tcggaacagg     7920
agagcgcacg agggagcttc cagggggaaa cgcctggtat ctttatagtc ctgtcgggtt     7980
tcgccacctc tgacttgagc gtcgattttt gtgatgctcg tcaggggggc ggagcctatg     8040
gaaaaacgcc agcaacgcgg cctttttacg gttcctggcc ttttgctggc cttttgctca     8100
catgttcttt cctgcgttat cccctgattc tgtggataac cgtattaccg cctttgagtg     8160
agctgatacc gctcgccgca gccgaacgac cgagcgcagc gagtcagtga gcgaggaagc     8220
ggaagagcgc ccaatacgca aaccgcctct ccccgcgcgt tggccgattc attaatgcag     8280
ctggcacgac aggtttcccg actggaaagc gggcagtgag cgcaacgcaa ttaatgtgag     8340
ttagctcact cattaggcac cccaggcttt acactttatg cttccggctc gtatgttgtg     8400
tggaattgtg agcggataac aatttcacac aggaaacagc tatgaccatg attacgccaa     8460
gctcgaaatt aaccctcact aaagggaaca aaagctggag ctccaccgcg gtggcggcct     8520
cgaggtcgag atccggtcga ccagcaacca tagtcccgcc cctaactccg cccatcccgc     8580
ccctaactcc gcccagttcc gcccattctc cgccccatgg ctgactaatt ttttttattt     8640
atgcagaggc cgaggccgcc tcggcctctg agctattcca gaagtagtga ggaggctttt     8700
ttggaggcct aggcttttgc aaaaagcttc gacggtatcg attggctcat gtccaacatt     8760
accgccatgt tgacattgat tattgactag ttattaatag taatcaatta cggggtcatt     8820
agttcatagc ccatatatgg agttccgcgt tacataactt acggtaaatg gcccgcctgg     8880
ctgaccgccc aacgaccccc gcccattgac gtcaataatg acgtatgttc ccatagtaac     8940
gccaataggg actttccatt gacgtcaatg ggtggagtat ttacggtaaa ctgcccactt     9000
ggcagtacat caagtgtatc atatgccaag tacgccccct attgacgtca atgacggtaa     9060
atggcccgcc tggcattatg cccagtacat gaccttatgg gactttccta cttggcagta     9120
catctacgta ttagtcatcg ctattaccat ggtgatgcgg ttttggcagt acatcaatgg     9180
gcgtggatag cggtttgact cacggggatt tccaagtctc caccccattg acgtcaatgg     9240
gagtttgttt tggcaccaaa atcaacggga ctttccaaaa tgtcgtaaca actccgcccc     9300
attgacgcaa atgggcggta ggcgtgtacg gaattcggag tggcgagccc tcagatcctg     9360
catataagca gctgcttttt gcctgtactg ggtctctctg                           9400
```

<210> SEQ ID NO 42
<211> LENGTH: 845
<212> TYPE: PRT
<213> ORGANISM: Artificial Sequence
<220> FEATURE:
<223> OTHER INFORMATION: Synthetic sequence

<400> SEQUENCE: 42

```
Met Leu Leu Leu Val Thr Ser Leu Leu Leu Cys Glu Leu Pro His Pro
1               5                   10                  15

Ala Phe Leu Leu Ile Pro Gln Glu Gln Leu Val Glu Ser Gly Gly Arg
            20                  25                  30

Leu Val Thr Pro Gly Gly Ser Leu Thr Leu Ser Cys Lys Ala Ser Gly
            35                  40                  45

Phe Asp Phe Ser Ala Tyr Tyr Met Ser Trp Val Arg Gln Ala Pro Gly
50                  55                  60

Lys Gly Leu Glu Trp Ile Ala Thr Ile Tyr Pro Ser Ser Gly Lys Thr
65                  70                  75                  80

Tyr Tyr Ala Thr Trp Val Asn Gly Arg Phe Thr Ile Ser Ser Asp Asn
            85                  90                  95

Ala Gln Asn Thr Val Asp Leu Gln Met Asn Ser Leu Thr Ala Ala Asp
            100                 105                 110

Arg Ala Thr Tyr Phe Cys Ala Arg Asp Ser Tyr Ala Asp Asp Gly Ala
            115                 120                 125

Leu Phe Asn Ile Trp Gly Pro Gly Thr Leu Val Thr Ile Ser Ser Gly
    130                 135                 140

Gly Gly Gly Ser Gly Gly Gly Ser Gly Gly Gly Ser Glu Leu
145                 150                 155                 160

Val Leu Thr Gln Ser Pro Ser Val Ser Ala Ala Leu Gly Ser Pro Ala
                165                 170                 175

Lys Ile Thr Cys Thr Leu Ser Ser Ala His Lys Thr Asp Thr Ile Asp
                180                 185                 190

Trp Tyr Gln Gln Leu Gln Gly Glu Ala Pro Arg Tyr Leu Met Gln Val
                195                 200                 205

Gln Ser Asp Gly Ser Tyr Thr Lys Arg Pro Gly Val Pro Asp Arg Phe
    210                 215                 220

Ser Gly Ser Ser Ser Gly Ala Asp Arg Tyr Leu Ile Ile Pro Ser Val
225                 230                 235                 240

Gln Ala Asp Asp Glu Ala Asp Tyr Tyr Cys Gly Ala Asp Tyr Ile Gly
                245                 250                 255

Gly Tyr Val Phe Gly Gly Gly Thr Gln Leu Thr Val Thr Gly Glu Ser
                260                 265                 270

Lys Tyr Gly Pro Pro Cys Pro Pro Cys Pro Met Phe Trp Val Leu Val
                275                 280                 285

Val Val Gly Gly Val Leu Ala Cys Tyr Ser Leu Leu Val Thr Val Ala
    290                 295                 300

Phe Ile Ile Phe Trp Val Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
                340                 345                 350

Arg Val Lys Phe Ser Arg Ser Ala Asp Ala Pro Ala Tyr Gln Gln Gly
                355                 360                 365

Gln Asn Gln Leu Tyr Asn Glu Leu Asn Leu Gly Arg Arg Glu Glu Tyr
    370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415
```

```
Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
            435                 440                 445

Thr Lys Asp Thr Tyr Asp Ala Leu His Met Gln Ala Leu Pro Pro Arg
            450                 455                 460

Leu Glu Gly Gly Gly Glu Gly Arg Gly Ser Leu Leu Thr Cys Gly Asp
465                 470                 475                 480

Val Glu Glu Asn Pro Gly Pro Arg Met Leu Leu Val Thr Ser Leu
                485                 490                 495

Leu Leu Cys Glu Leu Pro His Pro Ala Phe Leu Leu Ile Pro Arg Lys
            500                 505                 510

Val Cys Asn Gly Ile Gly Ile Gly Glu Phe Lys Asp Ser Leu Ser Ile
            515                 520                 525

Asn Ala Thr Asn Ile Lys His Phe Lys Asn Cys Thr Ser Ile Ser Gly
            530                 535                 540

Asp Leu His Ile Leu Pro Val Ala Phe Arg Gly Asp Ser Phe Thr His
545                 550                 555                 560

Thr Pro Pro Leu Asp Pro Gln Glu Leu Asp Ile Leu Lys Thr Val Lys
                565                 570                 575

Glu Ile Thr Gly Phe Leu Leu Ile Gln Ala Trp Pro Glu Asn Arg Thr
            580                 585                 590

Asp Leu His Ala Phe Glu Asn Leu Glu Ile Ile Arg Gly Arg Thr Lys
            595                 600                 605

Gln His Gly Gln Phe Ser Leu Ala Val Val Ser Leu Asn Ile Thr Ser
            610                 615                 620

Leu Gly Leu Arg Ser Leu Lys Glu Ile Ser Asp Gly Asp Val Ile Ile
625                 630                 635                 640

Ser Gly Asn Lys Asn Leu Cys Tyr Ala Asn Thr Ile Asn Trp Lys Lys
                645                 650                 655

Leu Phe Gly Thr Ser Gly Gln Lys Thr Lys Ile Ile Ser Asn Arg Gly
            660                 665                 670

Glu Asn Ser Cys Lys Ala Thr Gly Gln Val Cys His Ala Leu Cys Ser
            675                 680                 685

Pro Glu Gly Cys Trp Gly Pro Glu Pro Arg Asp Cys Val Ser Cys Arg
            690                 695                 700

Asn Val Ser Arg Gly Arg Glu Cys Val Asp Lys Cys Asn Leu Leu Glu
705                 710                 715                 720

Gly Glu Pro Arg Glu Phe Val Glu Asn Ser Glu Cys Ile Gln Cys His
                725                 730                 735

Pro Glu Cys Leu Pro Gln Ala Met Asn Ile Thr Cys Thr Gly Arg Gly
            740                 745                 750

Pro Asp Asn Cys Ile Gln Cys Ala His Tyr Ile Asp Gly Pro His Cys
            755                 760                 765

Val Lys Thr Cys Pro Ala Gly Val Met Gly Glu Asn Asn Thr Leu Val
            770                 775                 780

Trp Lys Tyr Ala Asp Ala Gly His Val Cys His Leu Cys His Pro Asn
785                 790                 795                 800

Cys Thr Tyr Gly Cys Thr Gly Pro Gly Leu Glu Gly Cys Pro Thr Asn
                805                 810                 815

Gly Pro Lys Ile Pro Ser Ile Ala Thr Gly Met Val Gly Ala Leu Leu
            820                 825                 830

Leu Leu Leu Val Val Ala Leu Gly Ile Gly Leu Phe Met
```

835         840         845

<210> SEQ ID NO 43
<211> LENGTH: 10015
<212> TYPE: DNA
<213> ORGANISM: Artificial Sequence
<220> FEATURE:
<223> OTHER INFORMATION: Synthetic sequence

<400> SEQUENCE: 43

| | |
|---|---|
| gttagaccag atctgagcct gggagctctc tggctaacta gggaacccac tgcttaagcc | 60 |
| tcaataaagc ttgccttgag tgcttcaagt agtgtgtgcc cgtctgttgt gtgactctgg | 120 |
| taactagaga tccctcagac ccttttagtc agtgtggaaa atctctagca gtggcgcccg | 180 |
| aacagggact tgaaagcgaa agggaaacca gaggagctct ctcgacgcag gactcggctt | 240 |
| gctgaagcgc gcacggcaag aggcgagggg cggcgactgg tgagtacgcc aaaaattttg | 300 |
| actagcggag gctagaagga gagagatggg tgcgagagcg tcagtattaa gcggggagaa | 360 |
| attagatcga tgggaaaaaa ttcggttaag gccaggggga agaaaaaat ataaattaaa | 420 |
| acatatagta tgggcaagca gggagctaga acgattcgca gttaatcctg gcctgttaga | 480 |
| aacatcagaa ggctgtagac aaatactggg acagctacaa ccatcccttc agacaggatc | 540 |
| agaagaactt agatcattat ataatacagt agcaaccctc tattgtgtgc atcaaaggat | 600 |
| agagataaaa gacaccaagg aagctttaga caagatagag gaagagcaaa acaaaagtaa | 660 |
| gaaaaagca cagcaagcag cagctgacac aggacacagc aatcaggtca gccaaaatta | 720 |
| ccctatagtg cagaacatcc aggggcaaat ggtacatcag gccatatcac ctagaacttt | 780 |
| aaatgcatgg gtaaaagtag tagaagagaa ggctttcagc ccagaagtga tacccatgtt | 840 |
| ttcagcatta tcagaaggag ccaccccaca agatttaaac accatgctaa acacagtggg | 900 |
| gggacatcaa gcagccatgc aaatgttaaa agagaccatc aatgaggaag ctgcaggcaa | 960 |
| agagaagagt ggtgcagaga gaaaaaagag cagtgggaat aggagctttg ttccttgggt | 1020 |
| tcttgggagc agcaggaagc actatgggcg cagcgtcaat gacgctgacg gtacaggcca | 1080 |
| gacaattatt gtctggtata gtgcagcagc agaacaattt gctgagggct attgaggcgc | 1140 |
| aacagcatct gttgcaactc acagtctggg gcatcaagca gctccaggca agaatcctgg | 1200 |
| ctgtggaaag atacctaaag gatcaacagc tcctggggat ttggggttgc tctggaaaac | 1260 |
| tcatttgcac cactgctgtg ccttggatct acaaatggca gtattcatcc acaattttaa | 1320 |
| aagaaaaggg gggattgggg ggtacagtgc aggggaaaga atagtagaca taatagcaac | 1380 |
| agacatacaa actaaagaat tacaaaaaca aattacaaaa attcaaaatt ttcgggttta | 1440 |
| ttacagggac agcagagatc cagtttgggg atcaattgca tgaagaatct gcttagggtt | 1500 |
| aggcgttttg cgctgcttcg cgaggatctg cgatcgctcc ggtgcccgtc agtgggcaga | 1560 |
| gcgcacatcg cccacagtcc ccgagaagtt ggggggaggg gtcggcaatt gaaccggtgc | 1620 |
| ctagagaagg tggcgcgggg taaactggga aagtgatgtc gtgtactggc tccgcctttt | 1680 |
| tcccgagggt gggggagaac cgtatataag tgcagtagtc gccgtgaacg ttcttttttcg | 1740 |
| caacgggttt gccgccagaa cacagctgaa gcttcgaggg gctcgcatct ctccttcacg | 1800 |
| cgcccgccgc cctacctgag gccgccatcc acgccggttg agtcgcgttc tgccgcctcc | 1860 |
| cgcctgtggt gcctcctgaa ctgcgtccgc cgtctaggta agtttaaagc tcaggtcgag | 1920 |
| accgggcctt tgtccggcgc tcccttggag cctacctaga ctcagccggc tctccacgct | 1980 |
| ttgcctgacc ctgcttgctc aactctacgt ctttgtttcg ttttctgttc tgcgccgtta | 2040 |

```
cagatccaag ctgtgaccgg cgcctacggc tagcgaattc gccaccatgc tgctgctggt    2100
gacaagcctg ctgctgtgcg agctgcccca ccccgccttt ctgctgatcc cccagagcgt    2160
gaaagagtcc gagggcgacc tggtcacacc agccggcaac ctgaccctga cctgtaccgc    2220
cagcggcagc gacatcaacg actacccccat ctcttgggtc cgccaggctc ctggcaaggg    2280
actggaatgg atcggcttca tcaacagcgg cggcagcact tggtacgcca gctgggtcaa    2340
aggccggttc accatcagcc ggaccagcac caccgtggac ctgaagatga caagcctgac    2400
caccgacgac accgccacct acttttgcgc cagaggctac agcacctact acggcgactt    2460
caacatctgg ggccctggca ccctggtcac aatctctagc ggcggaggcg gcagcggagg    2520
tggaggaagt ggcggcggag gatccgagct ggtcatgacc cagaccccca gcagcacatc    2580
tggcgccgtg ggcggcaccg tgaccatcaa ttgccaggcc agccagagca tcgacagcaa    2640
cctggcctgg ttccagcaga agcccggcca gccccccacc ctgctgatct acagagcctc    2700
caacctggcc agcggcgtgc caagcagatt cagcggcagc agatctggca ccgagtacac    2760
cctgaccatc tccggcgtgc agagagagga cgccgctacc tattactgcc tgggcggcgt    2820
gggcaacgtg tcctacagaa ccagcttcgg cggaggtact gaggtggtcg tcaaatacgg    2880
accgccctgc cccccttgcc ctgccccccga gttcctgggc ggacccagcg tgttcctgtt    2940 ccccccaag cccaaggaca ccctgatgat cagcccggacc cccgaggtga cctgcgtggt    3000
ggtggacgtg agccaggaag atcccgaggt ccagttcaat tggtacgtgg acggcgtgga    3060
agtgcacaac gccaagacca gcccagaga ggaacagttc aacagcacct accgggtggt    3120
gtctgtgctg accgtgctgc accaggactg gctgaacggc aaagaataca agtgcaaggt    3180
gtccaacaag ggcctgccca gcagcatcga aaagaccatc agcaaggcca agggccagcc    3240
tcgcgagccc caggtgtaca ccctgcctcc ctcccaggaa gagatgacca gaaccaggt    3300 gtccctgacc tgcctggtga agggcttcta ccccagcgac atcgccgtgg agtgggagag    3360
caacggccag cctgagaaca actacaagac caccccctccc gtgctggaca cgacggcag    3420 cttcttcctg tacagccggc tgaccgtgga caagagccgg tggcaggaag caacgtctt    3480 tagctgcagc gtgatgcacg aggccctgca caaccactac acccagaaga gcctgagcct    3540
gtccctgggc aagatgttct gggtgctggt ggtggtgggc ggggtgctgg cctgctacag    3600
cctgctggtg acagtggcct tcatcatctt ttgggtgaaa cggggcagaa agaaactcct    3660
gtatatattc aaacaaccat ttatgagacc agtacaaact actcaagagg aagatggctg    3720
tagctgccga tttccagaag aagaagaagg aggatgtgaa ctgcgggtga agttcagcag    3780
aagcgccgac gcccctgcct accagcaggg ccagaatcag ctgtacaacg agctgaacct    3840
gggcagaagg gaagagtacg acgtcctgga taagcggaga ggccgggacc ctgagatggg    3900
cggcaagcct cggcggaaga accccccagga aggcctgtat aacgaactgc agaaagacaa    3960
gatggccgag gcctacagcg agatcggcat gaagggcgag cggaggcggg gcaagggcca    4020
cgacggcctg tatcagggcc tgtccaccgc caccaaggat acctacgacg ccctgcacat    4080
gcaggccctg ccccaaggc tcgagggcgg cggagagggc agaggaagtc ttctaacatg    4140
cggtgacgtg gaggagaatc ccggccctag gatgcttctc ctggtgacaa gccttctgct    4200
ctgtgagtta ccacacccag cattcctcct gatcccacgc aaagtgtgta acggaatagg    4260
tattggtgaa tttaaagact cactctccat aaatgtacg aatattaaac acttcaaaaa    4320
ctgcacctcc atcagtggcg atctccacat cctgccggtg gcatttaggg gtgactcctt    4380
```

```
cacacatact cctcctctgg atccacagga actggatatt ctgaaaaccg taaggaaat     4440 cacagggttt ttgctgattc aggcttggcc tgaaaacagg acggacctcc atgcctttga    4500
gaacctagaa atcatacgcg gcaggaccaa gcaacatggt cagttttctc ttgcagtcgt    4560
cagcctgaac ataacatcct tgggattacg ctccctcaag gagataagtg atggagatgt    4620
gataatttca ggaaacaaaa atttgtgcta tgcaaataca ataaactgga aaaaactgtt    4680
tgggacctcc ggtcagaaaa ccaaaattat aagcaacaga ggtgaaaaca gctgcaaggc    4740
cacaggccag gtctgccatg ccttgtgctc ccccgagggc tgctgggcc cggagcccag     4800 ggactgcgtc tcttgccgga atgtcagccg aggcagggaa tgcgtggaca gtgcaacct     4860 tctggagggt gagccaaggg agtttgtgga gaactctgag tgcatacagt gccacccaga    4920
gtgcctgcct caggccatga acatcacctg cacaggacgg ggaccagaca actgtatcca    4980
gtgtgcccac tacattgacg gcccccactg cgtcaagacc tgcccggcag gagtcatggg    5040
agaaaacaac ccctggtctg gaagtacgc agacgccggc catgtgtgcc acctgtgcca     5100
tccaaactgc acctacggat gcactgggcc aggtcttgaa ggctgtccaa cgaatgggcc    5160
taagatcccg tccatcgcca ctgggatggt gggggccctc ctcttgctgc tggtggtggc    5220
cctggggatc ggcctcttca tgtgagcggc cgctctagac ccgggctgca ggaattcgat    5280
atcaagctta tcgataatca acctctggat tacaaaattt gtgaaagatt gactggtatt    5340
cttaactatg ttgctccttt tacgctatgt ggatacgctg ctttaatgcc tttgtatcat    5400
gctattgctt cccgtatggc tttcattttc tcctccttgt ataaatcctg gttgctgtct    5460
ctttatgagg agttgtggcc cgttgtcagg caacgtggcg tggtgtgcac tgtgtttgct    5520
gacgcaaccc ccactggttg ggcattgcc accacctgtc agctccttc cggactttc      5580 gctttccccc tccctattgc cacggcggaa ctcatcgccg cctgccttgc ccgctgctgg    5640 acagggctc ggctgttggg cactgacaat tccgtggtgt tgtcgggaa atcatcgtcc      5700 tttccttggc tgctcgcctg tgttgccacc tggattctgc gcgggacgtc cttctgctac    5760
gtcccttcgg ccctcaatcc agcggacctt ccttcccgcg gcctgctgcc ggctctgcgg    5820
cctcttccgc gtcttcgcct tcgccctcag acgagtcgga tctccctttg ggccgcctcc    5880
ccgcatcgat accgtcgact agccgtacct ttaagaccaa tgacttacaa ggcagctgta    5940
gatcttagcc actttttaaa agaaaagggg ggactgaag gctaattca ctcccaaaga     6000 agacaagatc tgcttttgc ctgtactggg tctctctggt tagaccagat ctgagcctgg     6060
gagctctctg gctaactagg gaacccactg cttaagcctc aataaagctt gccttgagtg    6120
cttcaagtag tgtgtgcccg tctgttgtgt gactctggta actagagatc cctcagaccc    6180
ttttagtcag tgtggaaaat ctctagcaga attcgatatc aagcttatcg ataccgtcga    6240
cctcgagggg gggcccggta cccaattcgc cctatagtga gtcgtattac aattcactgg    6300
ccgtcgtttt acaacgtcgt gactgggaaa accctggcgt tacccaactt aatcgccttg    6360
cagcacatcc ccctttcgcc agctggcgta atagcgaaga ggcccgcacc gatcgccctt    6420
cccaacagtt gcgcagcctg aatggcgaat ggaaattgta agcgttaata ttttgttaaa    6480
attcgcgtta atttttgtt aaatcagctc atttttaac caataggccg aaatcggcaa      6540
aatcccttat aaatcaaaag aatagaccga gatagggttg agtgttgttc cagtttggaa    6600
caagagtcca ctattaaaga acgtggactc caacgtcaaa gggcgaaaaa ccgtctatca    6660
gggcgatggc ccactacgtg aaccatcacc ctaatcaagt ttttggggt cgaggtgccg     6720 taaagcacta aatcggaacc ctaaagggag cccccgattt agagcttgac ggggaaagcc    6780
```

```
ggcgaacgtg gcgagaaagg aagggaagaa agcgaaagga gcgggcgcta gggcgctggc    6840
aagtgtagcg gtcacgctgc gcgtaaccac cacacccgcc gcgcttaatg cgccgctaca    6900
gggcgcgtca ggtggcactt ttcggggaaa tgtgcgcgga acccctattt gtttatttt     6960 ctaaatacat tcaaatatgt atccgctcat gagacaataa ccctgataaa tgcttcaata    7020
atattgaaaa aggaagagta tgagtattca acatttccgt gtcgcccta ttccctttt      7080 tgcggcattt tgccttcctg ttttgctca cccagaaacg ctggtgaaag taaaagatgc     7140
tgaagatcag ttgggtgcac gagtgggtta catcgaactg gatctcaaca gcggtaagat    7200
ccttgagagt tttcgccccg aagaacgttt tccaatgatg agcacttta aagttctgct     7260 atgtggcgcg gtattatccc gtattgacgc cgggcaagag caactcggtc gccgcataca    7320
ctattctcag aatgacttgg ttgagtactc accagtcaca gaaaagcatc ttacggatgg    7380
catgacagta agagaattat gcagtgctgc cataaccatg agtgataaca ctgcggccaa    7440
cttacttctg acaacgatcg gaggaccgaa ggagctaacc gcttttttgc acaacatggg    7500
ggatcatgta actcgccttg atcgttggga accggagctg aatgaagcca taccaaacga    7560
cgagcgtgac accacgatgc ctgtagcaat ggcaacaacg ttgcgcaaac tattaactgg    7620
cgaactactt actctagctt cccggcaaca attaatagac tggatggagg cggataaagt    7680
tgcaggacca cttctgcgct cggcccttcc ggctggctgg tttattgctg ataaatctgg    7740
agccggtgag cgtgggtctc gcggtatcat tgcagcactg gggccagatg gtaagccctc    7800
ccgtatcgta gttatctaca cgacggggag tcaggcaact atggatgaac gaaatagaca    7860
gatcgctgag ataggtgcct cactgattaa gcattggtaa ctgtcagacc aagtttactc    7920
atatatactt tagattgatt taaaacttca tttttaattt aaaaggatct aggtgaagat    7980
cctttttgat aatctcatga ccaaaatccc ttaacgtgag ttttcgttcc actgagcgtc    8040 agacccgta gaaaagatca aaggatcttc ttgagatcct tttttttctgc gcgtaatctg    8100 ctgcttgcaa acaaaaaaac caccgctacc agcggtggtt tgtttgccgg atcaagagct    8160
accaactctt tttccgaagg taactggctt cagcagagcg cagataccaa atactgttct    8220
tctagtgtag ccgtagttag gccaccactt caagaactct gtagcaccgc ctacatacct    8280
cgctctgcta atcctgttac cagtggctgc tgccagtggc gataagtcgt gtcttaccgg    8340
gttggactca agacgatagt taccggataa ggcgcagcgg tcgggctgaa cggggggttc    8400
gtgcacacag cccagcttgg agcgaacgac ctacaccgaa ctgagatacc tacagcgtga    8460
gctatgagaa agcgccacgc ttcccgaagg agaaaggcg gacaggtatc cggtaagcgg    8520
cagggtcgga acaggagagc gcacgaggga gcttccaggg ggaaacgcct ggtatcttta    8580
tagtcctgtc gggtttcgcc acctctgact tgagcgtcga ttttgtgat gctcgtcagg    8640 ggggcggagc ctatggaaaa acgccagcaa cgcggccttt ttacggttcc tggccttttg    8700
ctggcctttt gctcacatgt tctttcctgc gttatcccct gattctgtgg ataaccgtat    8760
taccgccttt gagtgagctg ataccgctcg ccgcagccga acgaccgagc gcagcgagtc    8820
agtgagcgag gaagcggaag agcgcccaat acgcaaaccg cctctccccg cgcgttggcc    8880
gattcattaa tgcagctggc acgacaggtt tcccgactgg aaagcgggca gtgagcgcaa    8940
cgcaattaat gtgagttagc tcactcatta ggcacccag gctttacact ttatgcttcc    9000
ggctcgtatg ttgtgtggaa ttgtgagcgg ataacaattt cacacaggaa acagctatga    9060
ccatgattac gccaagctcg aaattaaccc tcactaaagg gaacaaaagc tggagctcca    9120
```

```
ccgcggtggc ggcctcgagg tcgagatccg gtcgaccagc aaccatagtc ccgcccctaa    9180
ctccgcccat cccgccccta actccgccca gttccgccca ttctccgccc catggctgac    9240
taattttttt tatttatgca gaggccgagg ccgcctcggc ctctgagcta ttccagaagt    9300
agtgaggagg cttttttgga ggcctaggct tttgcaaaaa gcttcgacgg tatcgattgg    9360
ctcatgtcca acattaccgc catgttgaca ttgattattg actagttatt aatagtaatc    9420
aattacgggg tcattagttc atagcccata tatggagttc cgcgttacat aacttacggt    9480
aaatggcccg cctggctgac cgcccaacga cccccgccca ttgacgtcaa taatgacgta    9540
tgttcccata gtaacgccaa tagggacttt ccattgacgt caatgggtgg agtatttacg    9600
gtaaactgcc cacttggcag tacatcaagt gtatcatatg ccaagtacgc ccctattga    9660
cgtcaatgac ggtaaatggc ccgcctggca ttatgcccag tacatgacct tatgggactt    9720
tcctacttgg cagtacatct acgtattagt catcgctatt accatggtga tgcggttttg    9780
gcagtacatc aatgggcgtg gatagcggtt tgactcacgg ggatttccaa gtctccaccc    9840
cattgacgtc aatgggagtt tgttttggca ccaaaatcaa cgggactttc caaaatgtcg    9900
taacaactcc gccccattga cgcaaatggg cggtaggcgt gtacggaatt cggagtggcg    9960
agccctcaga tcctgcatat aagcagctgc tttttgcctg tactgggtct ctctg         10015
```

<210> SEQ ID NO 44
<211> LENGTH: 1055
<212> TYPE: PRT
<213> ORGANISM: Artificial Sequence
<220> FEATURE:
<223> OTHER INFORMATION: Synthetic sequence

<400> SEQUENCE: 44

```
Met Leu Leu Leu Val Thr Ser Leu Leu Leu Cys Glu Leu Pro His Pro
1               5                   10                  15

Ala Phe Leu Leu Ile Pro Gln Ser Val Lys Glu Ser Glu Gly Asp Leu
            20                  25                  30

Val Thr Pro Ala Gly Asn Leu Thr Leu Thr Cys Thr Ala Ser Gly Ser
        35                  40                  45

Asp Ile Asn Asp Tyr Pro Ile Ser Trp Val Arg Gln Ala Pro Gly Lys
    50                  55                  60

Gly Leu Glu Trp Ile Gly Phe Ile Asn Ser Gly Ser Thr Trp Tyr
65                  70                  75                  80

Ala Ser Trp Val Lys Gly Arg Phe Thr Ile Ser Arg Thr Ser Thr Thr
                85                  90                  95

Val Asp Leu Lys Met Thr Ser Leu Thr Thr Asp Thr Ala Thr Tyr
            100                 105                 110

Phe Cys Ala Arg Gly Tyr Ser Thr Tyr Tyr Gly Asp Phe Asn Ile Trp
        115                 120                 125

Gly Pro Gly Thr Leu Val Thr Ile Ser Ser Gly Gly Gly Gly Ser Gly
    130                 135                 140

Gly Gly Gly Ser Gly Gly Gly Ser Glu Leu Val Met Thr Gln Thr
145                 150                 155                 160

Pro Ser Ser Thr Ser Gly Ala Val Gly Gly Thr Val Thr Ile Asn Cys
                165                 170                 175

Gln Ala Ser Gln Ser Ile Asp Ser Asn Leu Ala Trp Phe Gln Gln Lys
            180                 185                 190

Pro Gly Gln Pro Pro Thr Leu Leu Ile Tyr Arg Ala Ser Asn Leu Ala
        195                 200                 205
```

```
Ser Gly Val Pro Ser Arg Phe Ser Gly Ser Arg Ser Gly Thr Glu Tyr
    210                 215                 220
Thr Leu Thr Ile Ser Gly Val Gln Arg Glu Asp Ala Ala Thr Tyr Tyr
225                 230                 235                 240
Cys Leu Gly Gly Val Gly Asn Val Ser Tyr Arg Thr Ser Phe Gly Gly
                245                 250                 255
Gly Thr Glu Val Val Lys Glu Ser Lys Tyr Gly Pro Pro Cys Pro
                260                 265                 270
Pro Cys Pro Ala Pro Glu Phe Leu Gly Gly Pro Ser Val Phe Leu Phe
            275                 280                 285
Pro Pro Lys Pro Lys Asp Thr Leu Met Ile Ser Arg Thr Pro Glu Val
290                 295                 300
Thr Cys Val Val Val Asp Val Ser Gln Glu Asp Pro Glu Val Gln Phe
305                 310                 315                 320
Asn Trp Tyr Val Asp Gly Val Glu Val His Asn Ala Lys Thr Lys Pro
                325                 330                 335
Arg Glu Glu Gln Phe Asn Ser Thr Tyr Arg Val Val Ser Val Leu Thr
                340                 345                 350
Val Leu His Gln Asp Trp Leu Asn Gly Lys Glu Tyr Lys Cys Lys Val
            355                 360                 365
Ser Asn Lys Gly Leu Pro Ser Ser Ile Glu Lys Thr Ile Ser Lys Ala
370                 375                 380
Lys Gly Gln Pro Arg Glu Pro Gln Val Tyr Thr Leu Pro Pro Ser Gln
385                 390                 395                 400
Glu Glu Met Thr Lys Asn Gln Val Ser Leu Thr Cys Leu Val Lys Gly
                405                 410                 415
Phe Tyr Pro Ser Asp Ile Ala Val Glu Trp Glu Ser Asn Gly Gln Pro
            420                 425                 430
Glu Asn Asn Tyr Lys Thr Thr Pro Pro Val Leu Asp Ser Asp Gly Ser
                435                 440                 445
Phe Phe Leu Tyr Ser Arg Leu Thr Val Asp Lys Ser Arg Trp Gln Glu
            450                 455                 460
Gly Asn Val Phe Ser Cys Ser Val Met His Glu Ala Leu His Asn His
465                 470                 475                 480
Tyr Thr Gln Lys Ser Leu Ser Leu Ser Leu Gly Lys Met Phe Trp Val
                485                 490                 495
Leu Val Val Val Gly Gly Val Leu Ala Cys Tyr Ser Leu Leu Val Thr
                500                 505                 510
Val Ala Phe Ile Ile Phe Trp Val Lys Arg Gly Arg Lys Lys Leu Leu
            515                 520                 525
Tyr Ile Phe Lys Gln Pro Phe Met Arg Pro Val Gln Thr Thr Gln Glu
            530                 535                 540
Glu Asp Gly Cys Ser Cys Arg Phe Pro Glu Glu Glu Gly Gly Cys
545                 550                 555                 560
Glu Leu Arg Val Lys Phe Ser Arg Ser Ala Asp Ala Pro Ala Tyr Gln
                565                 570                 575
Gln Gly Gln Asn Gln Leu Tyr Asn Glu Leu Asn Leu Gly Arg Arg Glu
                580                 585                 590
Glu Tyr Asp Val Leu Asp Lys Arg Arg Gly Arg Asp Pro Glu Met Gly
            595                 600                 605
Gly Lys Pro Arg Arg Lys Asn Pro Gln Glu Gly Leu Tyr Asn Glu Leu
        610                 615                 620
Gln Lys Asp Lys Met Ala Glu Ala Tyr Ser Glu Ile Gly Met Lys Gly
```

-continued

```
        625                 630                 635                 640
Glu Arg Arg Arg Gly Lys Gly His Asp Gly Leu Tyr Gln Gly Leu Ser
                    645                 650                 655

Thr Ala Thr Lys Asp Thr Tyr Asp Ala Leu His Met Gln Ala Leu Pro
                    660                 665                 670

Pro Arg Leu Glu Gly Gly Gly Glu Gly Arg Gly Ser Leu Leu Thr Cys
                    675                 680                 685

Gly Asp Val Glu Glu Asn Pro Gly Pro Arg Met Leu Leu Val Thr
                    690                 695                 700

Ser Leu Leu Leu Cys Glu Leu Pro His Pro Ala Phe Leu Leu Ile Pro
705                 710                 715                 720

Arg Lys Val Cys Asn Gly Ile Gly Ile Gly Glu Phe Lys Asp Ser Leu
                    725                 730                 735

Ser Ile Asn Ala Thr Asn Ile Lys His Phe Lys Asn Cys Thr Ser Ile
                    740                 745                 750

Ser Gly Asp Leu His Ile Leu Pro Val Ala Phe Arg Gly Asp Ser Phe
                    755                 760                 765

Thr His Thr Pro Pro Leu Asp Pro Gln Glu Leu Asp Ile Leu Lys Thr
                    770                 775                 780

Val Lys Glu Ile Thr Gly Phe Leu Leu Ile Gln Ala Trp Pro Glu Asn
785                 790                 795                 800

Arg Thr Asp Leu His Ala Phe Glu Asn Leu Glu Ile Ile Arg Gly Arg
                    805                 810                 815

Thr Lys Gln His Gly Gln Phe Ser Leu Ala Val Val Ser Leu Asn Ile
                    820                 825                 830

Thr Ser Leu Gly Leu Arg Ser Leu Lys Glu Ile Ser Asp Gly Asp Val
                    835                 840                 845

Ile Ile Ser Gly Asn Lys Asn Leu Cys Tyr Ala Asn Thr Ile Asn Trp
                    850                 855                 860

Lys Lys Leu Phe Gly Thr Ser Gly Gln Lys Thr Lys Ile Ile Ser Asn
865                 870                 875                 880

Arg Gly Glu Asn Ser Cys Lys Ala Thr Gly Gln Val Cys His Ala Leu
                    885                 890                 895

Cys Ser Pro Glu Gly Cys Trp Gly Pro Glu Pro Arg Asp Cys Val Ser
                    900                 905                 910

Cys Arg Asn Val Ser Arg Gly Arg Glu Cys Val Asp Lys Cys Asn Leu
                    915                 920                 925

Leu Glu Gly Glu Pro Arg Glu Phe Val Glu Asn Ser Glu Cys Ile Gln
                    930                 935                 940

Cys His Pro Glu Cys Leu Pro Gln Ala Met Asn Ile Thr Cys Thr Gly
945                 950                 955                 960

Arg Gly Pro Asp Asn Cys Ile Gln Cys Ala His Tyr Ile Asp Gly Pro
                    965                 970                 975

His Cys Val Lys Thr Cys Pro Ala Gly Val Met Gly Glu Asn Asn Thr
                    980                 985                 990

Leu Val Trp Lys Tyr Ala Asp Ala Gly His Val Cys His Leu Cys His
                    995                 1000                1005

Pro Asn Cys Thr Tyr Gly Cys Thr Gly Pro Gly Leu Glu Gly Cys Pro
                    1010                1015                1020

Thr Asn Gly Pro Lys Ile Pro Ser Ile Ala Thr Gly Met Val Gly Ala
1025                1030                1035                1040

Leu Leu Leu Leu Leu Val Val Ala Leu Gly Ile Gly Leu Phe Met
                    1045                1050                1055
```

<210> SEQ ID NO 45
<211> LENGTH: 10015
<212> TYPE: DNA
<213> ORGANISM: Artificial Sequence
<220> FEATURE:
<223> OTHER INFORMATION: Synthetic sequence

<400> SEQUENCE: 45

```
gttagaccag atctgagcct gggagctctc tggctaacta gggaacccac tgcttaagcc      60
tcaataaagc ttgccttgag tgcttcaagt agtgtgtgcc cgtctgttgt gtgactctgg     120
taactagaga tccctcagac ccttttagtc agtgtggaaa atctctagca gtggcgcccg     180
aacagggact tgaaagcgaa agggaaacca gaggagctct ctcgacgcag gactcggctt     240
gctgaagcgc gcacggcaag aggcgagggg cggcgactgg tgagtacgcc aaaaattttg     300
actagcggag gctagaagga gagagatggg tgcgagagcg tcagtattaa gcggggggaga    360
attagatcga tgggaaaaaa ttcggttaag gccaggggga agaaaaaat ataaattaaa      420
acatatagta tgggcaagca gggagctaga acgattcgca gttaatcctg gcctgttaga    480
aacatcagaa ggctgtagac aaatactggg acagctacaa ccatcccttc agacaggatc    540
agaagaactt agatcattat ataatacagt agcaaccctc tattgtgtgc atcaaaggat    600
agagataaaa gacaccaagg aagctttaga caagatagag gaagagcaaa acaaaagtaa    660
gaaaaaagca cagcaagcag cagctgacac aggacacagc aatcaggtca gccaaaatta    720
ccctatagtg cagaacatcc aggggcaaat ggtacatcag gccatatcac ctagaacttt    780
aaatgcatgg gtaaaagtag tagaagagaa ggctttcagc ccagaagtga tacccatgtt    840
ttcagcatta tcagaaggag ccaccccaca agatttaaac accatgctaa acacagtggg    900
gggacatcaa gcagccatgc aaatgttaaa agagaccatc aatgaggaag ctgcaggcaa    960
agagaagagt ggtgcagaga gaaaaaagag cagtgggaat aggagctttg ttccttgggt   1020
tcttgggagc agcaggaagc actatgggcg cagcgtcaat gacgctgacg gtacaggcca   1080
gacaattatt gtctggtata gtgcagcagc agaacaattt gctgagggct attgaggcgc   1140
aacagcatct gttgcaactc acagtctggg gcatcaagca gctccaggca agaatcctgg   1200
ctgtggaaag atacctaaag gatcaacagc tcctggggat ttggggttgc tctggaaaac   1260
tcatttgcac cactgctgtg ccttggatct acaaatggca gtattcatcc acaattttaa   1320
aagaaagggg gggattgggg ggtacagtgc aggggaaaga atagtagaca taatagcaac   1380
agacatacaa actaaagaat tacaaaaaca aattacaaaa attcaaaatt ttcgggttta   1440
ttacagggac agcagagatc cagtttgggg atcaattgca tgaagaatct gcttagggtt   1500
aggcgttttg cgctgcttcg cgaggatctg cgatcgctcc ggtgcccgtc agtgggcaga   1560
gcgcacatcg cccacagtcc ccgagaagtt ggggggaggg gtcggcaatt gaaccggtgc   1620
ctagagaagg tggcgcgggg taaactggga aagtgatgtc gtgtactggc tccgcctttt   1680
tcccgagggt gggggagaac cgtatataag tgcagtagtc gccgtgaacg ttcttttcg    1740
caacgggttt gccgccagaa cacagctgaa gcttcgaggg gctcgcatct ctccttcacg   1800
cgcccgccgc cctacctgag gccgccatcc acgccggttg agtcgcgttc tgccgcctcc   1860
cgcctgtggt gcctcctgaa ctgcgtccgc cgtctaggta agtttaaagc tcaggtcgag   1920
accgggcctt tgtccggcgc tcccttggag cctacctaga ctcagccggc tctccacgct   1980
ttgcctgacc ctgcttgctc aactctacgt ctttgtttcg ttttctgttc tgcgccgtta   2040
```

```
cagatccaag ctgtgaccgg cgcctacggc tagcgaattc gccaccatgc tgctgctggt    2100
gacaagcctg ctgctgtgcg agctgcccca ccccgccttt ctgctgatcc cccagagcgt    2160
gaaagagtcc gagggcgacc tggtcacacc agccggcaac ctgaccctga cctgtaccgc    2220
cagcggcagc gacatcaacg actacccat ctcttgggtc cgccaggctc ctggcaaggg    2280
actggaatgg atcggcttca tcaacagcgg cggcagcact tggtacgcca gctgggtcaa    2340
aggccggttc accatcagcc ggaccagcac caccgtggac ctgaagatga caagcctgac    2400
caccgacgac accgccacct acttttgcgc cagaggctac agcacctact acggcgactt    2460
caacatctgg ggccctggca ccctggtcac aatctctagc ggcggaggcg gcagcggagg    2520
tggaggaagt ggcggcggag gatccgagct ggtcatgacc cagaccccca gcagcacatc    2580
tggcgccgtg ggcggcaccg tgaccatcaa ttgccaggcc agccagagca tcgacagcaa    2640
cctggcctgg ttccagcaga agcccggcca gcccccacc ctgctgatct acagagcctc    2700
caacctggcc agcggcgtgc caagcagatt cagcggcagc agatctggca ccgagtacac    2760
cctgaccatc tccggcgtgc agagagagga cgccgctacc tattactgcc tgggcggcgt    2820
gggcaacgtg tcctacagaa ccagcttcgg cggaggtact gaggtggtcg tcaaatacgg    2880
accgccctgc ccccttgcc ctgccccga gttcctgggc ggaccagcg tgttcctgtt    2940 ccccccaag cccaaggaca ccctgatgat cagccggacc cccgaggtga cctgcgtggt    3000
ggtggacgtg agccaggaag atcccgaggt ccagttcaat tggtacgtgg acggcgtgga    3060
agtgcacaac gccaagacca gcccagaga ggaacagttc aacagcacct accgggtggt    3120
gtctgtgctg accgtgctgc accaggactg gctgaacggc aaagaatca agtgcaaggt    3180 gtccaacaag ggcctgccca gcagcatcga aaagaccatc agcaaggcca agggccagcc    3240
tcgcgagccc caggtgtaca ccctgcctcc ctcccaggaa gagatgacca agaaccaggt    3300
gtccctgacc tgcctggtga agggcttcta ccccagcgac atcgccgtgg agtgggagag    3360
caacggccag cctgagaaca actacaagac caccctccc gtgctggaca cgacggcag    3420 cttcttcctg tacagccggc tgaccgtgga caagagccgg tggcaggaag caacgtctt    3480 tagctgcagc gtgatgcacg aggccctgca caaccactac acccagaaga gcctgagcct    3540
gtccctgggc aagatgttct gggtgctggt ggtggtgggc ggggtgctgg cctgctacag    3600
cctgctggtg acagtggcct tcatcatctt ttgggtgaaa cggggcagaa agaaactcct    3660
gtatatattc aaacaaccat ttatgagacc agtacaaact actcaagagg aagatggctg    3720
tagctgccga tttccagaag aagaagaagg aggatgtgaa ctgcgggtga agttcagcag    3780
aagcgccgac gcccctgcct accagcaggg ccagaatcag ctgtacaacg agctgaacct    3840
gggcagaagg gaagagtacg acgtcctgga taagcggaga ggccgggacc tgagatgggg    3900
cggcaagcct cggcggaaga accccagga aggcctgtat aacgaactgc agaaagacaa    3960
gatggccgag gcctacagcg agatcggcat gaagggcgag cggaggcggg caagggcca    4020 cgacggcctg tatcagggcc tgtccaccgc caccaaggat acctacgacg ccctgcacat    4080
gcaggccctg ccccaaggc tcgagggcgg cggagagggc agaggaagtc ttctaacatg    4140
cggtgacgtg gaggagaatc ccggccctag gatgcttctc ctggtgacaa gccttctgct    4200
ctgtgagtta ccacacccag cattcctcct gatcccacgc aaagtgtgta cggaataggt    4260
tattggtgaa tttaaagact cactctccat aaatgctacg aatattaaac acttcaaaaa    4320
ctgcacctcc atcagtggcg atctccacat cctgccggtg gcatttaggg gtgactcctt    4380
cacacatact cctcctctgg atccacagga actggatatt ctgaaaaccg taaggaaat    4440
```

```
cacagggttt ttgctgattc aggcttggcc tgaaaacagg acggacctcc atgcctttga    4500
gaacctagaa atcatacgcg gcaggaccaa gcaacatggt cagttttctc ttgcagtcgt    4560
cagcctgaac ataacatcct tgggattacg ctccctcaag gagataagtg atggagatgt    4620
gataatttca ggaaacaaaa atttgtgcta tgcaaataca ataaactgga aaaaactgtt    4680
tgggacctcc ggtcagaaaa ccaaaattat aagcaacaga ggtgaaaaca gctgcaaggc    4740
cacaggccag gtctgccatg ccttgtgctc ccccgagggc tgctgggggcc cggagcccag    4800 ggactgcgtc tcttgccgga atgtcagccg aggcagggaa tgcgtggaca agtgcaacct    4860
tctggagggt gagccaaggg agtttgtgga gaactctgag tgcatacagt gccacccaga    4920
gtgcctgcct caggccatga acatcacctg cacaggacgg ggaccagaca actgtatcca    4980
gtgtgcccac tacattgacg gcccccactg cgtcaagacc tgcccggcag gagtcatggg    5040
agaaaacaac accctggtct ggaagtacgc agacgccggc catgtgtgcc acctgtgcca    5100
tccaaactgc acctacggat gcactgggcc aggtcttgaa ggctgtccaa cgaatgggcc    5160
taagatcccg tccatcgcca ctgggatggt gggggccctc ctcttgctgc tggtggtggc    5220
cctggggatc ggcctcttca tgtgagcggc cgctctagac ccgggctgca ggaattcgat    5280
atcaagctta tcgataatca acctctggat tacaaaattt gtgaaagatt gactggtatt    5340
cttaactatg ttgctccttt tacgctatgt ggatacgctg ctttaatgcc tttgtatcat    5400
gctattgctt cccgtatggc tttcattttc tcctccttgt ataaatcctg gttgctgtct    5460
ctttatgagg agttgtggcc cgttgtcagg caacgtggcg tggtgtgcac tgtgtttgct    5520
gacgcaaccc ccactggttg gggcattgcc accacctgtc agctcctttc cgggactttc    5580
gctttccccc tccctattgc cacggcggaa ctcatcgccg cctgccttgc ccgctgctgg    5640
acaggggctc ggctgttggg cactgacaat tccgtggtgt tgtcggggaa atcatcgtcc    5700
tttccttggc tgctcgcctg tgttgccacc tggattctgc gcgggacgtc ttctgctac     5760 gtcccttcgg ccctcaatcc agcggacctt ccttcccgcg gcctgctgcc ggctctgcgg    5820
cctcttccgc gtcttcgcct tcgccctcag acgagtcgga tctccctttg ggccgcctcc    5880
ccgcatcgat accgtcgact agccgtacct ttaagaccaa tgacttacaa ggcagctgta    5940
gatcttagcc acttttttaaa agaaaagggg ggactggaag gctaattca ctcccaaaga    6000 agacaagatc tgcttttttgc ctgtactggg tctctctggt tagaccagat ctgagcctgg    6060
gagctctctg gctaactagg gaacccactg cttaagcctc aataaagctt gccttgagtg    6120
cttcaagtag tgtgtgcccg tctgttgtgt gactctggta actagagatc cctcagaccc    6180
ttttagtcag tgtggaaaat ctctagcaga attcgatatc aagcttatcg ataccgtcga    6240
cctcgagggg gggcccggta cccaattcgc cctatagtga gtcgtattac aattcactgg    6300
ccgtcgtttt acaacgtcgt gactgggaaa accctggcgt tacccaactt aatcgccttg    6360
cagcacatcc cctttcgcc agctggcgta atagcgaaga ggcccgcacc gatcgccctt    6420
cccaacagtt gcgcagcctg aatggcgaat ggaaattgta agcgttaata ttttgttaaa    6480
attcgcgtta aattttttgtt aaatcagctc attttttaac caataggccg aaatcggcaa    6540
aatcccttat aaatcaaaag aatagaccga gatagggttg agtgttgttc cagtttggaa    6600
caagagtcca ctattaaaga acgtggactc caacgtcaaa gggcgaaaaa ccgtctatca    6660
gggcgatggc ccactacgtg aaccatcacc ctaatcaagt tttttggggt cgaggtgccg    6720
taaagcacta aatcggaacc ctaaagggag cccccgattt agagcttgac ggggaaagcc    6780
```

-continued

```
ggcgaacgtg gcgagaaagg aagggaagaa agcgaaagga gcgggcgcta gggcgctggc    6840
aagtgtagcg gtcacgctgc gcgtaaccac cacacccgcc gcgcttaatg cgccgctaca    6900
gggcgcgtca ggtggcactt tcggggaaa tgtgcgcgga accccattt gttatttt       6960 ctaaatacat tcaaatatgt atccgctcat gagacaataa ccctgataaa tgcttcaata    7020
atattgaaaa aggaagagta tgagtattca acatttccgt gtcgcccta ttcccttttt    7080 tgcggcattt tgccttcctg tttttgctca cccagaaacg ctggtgaaag taaaagatgc    7140
tgaagatcag ttgggtgcac gagtgggtta catcgaactg gatctcaaca gcggtaagat    7200
ccttgagagt tttcgccccg aagaacgttt tccaatgatg agcactttta aagttctgct    7260
atgtggcgcg gtattatccc gtattgacgc cgggcaagag caactcggtc gccgcataca    7320
ctattctcag aatgacttgg ttgagtactc accagtcaca gaaaagcatc ttacggatgg    7380
catgacagta agagaattat gcagtgctgc cataaccatg agtgataaca ctgcggccaa    7440
cttacttctg acaacgatcg gaggaccgaa ggagctaacc gcttttttgc acaacatggg    7500
ggatcatgta actcgccttg atcgttggga accggagctg aatgaagcca taccaaacga    7560
cgagcgtgac accacgatgc ctgtagcaat ggcaacaacg ttgcgcaaac tattaactgg    7620
cgaactactt actctagctt cccggcaaca attaatagac tggatggagg cggataaagt    7680
tgcaggacca cttctgcgct cggcccttcc ggctggctgg tttattgctg ataaatctgg    7740
agccggtgag cgtgggtctc gcggtatcat tgcagcactg gggccagatg gtaagccctc    7800
ccgtatcgta gttatctaca cgacggggag tcaggcaact atggatgaac gaaatagaca    7860
gatcgctgag ataggtgcct cactgattaa gcattggtaa ctgtcagacc aagtttactc    7920
atatatactt tagattgatt taaaacttca ttttaattt aaaaggatct aggtgaagat    7980
cctttttgat aatctcatga ccaaaatccc ttaacgtgag ttttcgttcc actgagcgtc    8040
agaccccgta gaaaagatca aaggatcttc ttgagatcct tttttctgc gcgtaatctg    8100 ctgcttgcaa acaaaaaaac caccgctacc agcggtggtt tgtttgccgg atcaagagct    8160
accaactctt tttccgaagg taactggctt cagcagagcg cagataccaa atactgttct    8220
tctagtgtag ccgtagttag gccaccactt caagaactct gtagcaccgc ctacatacct    8280
cgctctgcta atcctgttac cagtggctgc tgccagtggc gataagtcgt gtcttaccgg    8340
gttggactca agacgatagt taccggataa ggcgcagcgg tcgggctgaa cggggggttc    8400
gtgcacacag cccagcttgg agcgaacgac ctacaccgaa ctgagatacc tacagcgtga    8460
gctatgagaa agcgccacgc ttcccgaagg gagaaaggcg gacaggtatc cggtaagcgg    8520
cagggtcgga acaggagagc gcacgaggga gcttccaggg ggaaacgcct ggtatcttta    8580
tagtcctgtc gggtttcgcc acctctgact tgagcgtcga tttttgtgat gctcgtcagg    8640
ggggcggagc ctatggaaaa acgccagcaa cgcggccttt ttacggttcc tggccttttg    8700
ctggcctttt gctcacatgt tctttcctgc gttatcccct gattctgtgg ataaccgtat    8760
taccgccttt gagtgagctg ataccgctcg ccgcagccga acgaccgagc gcagcgagtc    8820
agtgagcgag gaagcggaag agcgcccaat acgcaaaccg cctctccccg cgcgttggcc    8880
gattcattaa tgcagctggc acgacaggtt tcccgactgg aaagcgggca gtgagcgcaa    8940
cgcaattaat gtgagttagc tcactcatta ggcacccag gctttacact ttatgcttcc    9000
ggctcgtatg ttgtgtggaa ttgtgagcgg ataacaattt cacacaggaa acagctatga    9060
ccatgattac gccaagctcg aaattaaccc tcactaaagg gaacaaaagc tggagctcca    9120
ccgcggtggc ggcctcgagg tcgagatccg gtcgaccagc aaccatagtc ccgcccctaa    9180
```

```
ctccgcccat cccgcccta actccgccca gttccgccca ttctccgccc catggctgac    9240 taatttttt tatttatgca gaggccgagg ccgcctcggc ctctgagcta ttccagaagt    9300
agtgaggagg cttttttgga ggcctaggct tttgcaaaaa gcttcgacgg tatcgattgg    9360
ctcatgtcca acattaccgc catgttgaca ttgattattg actagttatt aatagtaatc    9420
aattacgggg tcattagttc atagcccata tatggagttc cgcgttacat aacttacggt    9480
aaatggcccg cctggctgac cgcccaacga ccccgccca ttgacgtcaa taatgacgta    9540
tgttcccata gtaacgccaa tagggacttt ccattgacgt caatgggtgg agtatttacg    9600
gtaaactgcc cacttggcag tacatcaagt gtatcatatg ccaagtacgc ccctattga    9660 cgtcaatgac ggtaaatggc ccgcctggca ttatgcccag tacatgacct tatgggactt    9720
tcctacttgg cagtacatct acgtattagt catcgctatt accatggtga tgcggttttg    9780
gcagtacatc aatgggcgtg gatagcggtt tgactcacgg ggatttccaa gtctccaccc    9840
cattgacgtc aatgggagtt tgttttggca ccaaaatcaa cgggactttc caaaatgtcg    9900
taacaactcc gccccattga cgcaaatggg cggtaggcgt gtacggaatt cggagtggcg    9960
agccctcaga tcctgcatat aagcagctgc tttttgcctg tactgggtct ctctg         10015
```

<210> SEQ ID NO 46
<211> LENGTH: 945
<212> TYPE: PRT
<213> ORGANISM: Artificial Sequence
<220> FEATURE:
<223> OTHER INFORMATION: Synthetic sequence

<400> SEQUENCE: 46

```
Met Leu Leu Leu Val Thr Ser Leu Leu Leu Cys Glu Leu Pro His Pro
1               5                   10                  15

Ala Phe Leu Leu Ile Pro Gln Ser Val Lys Glu Ser Glu Gly Asp Leu
            20                  25                  30

Val Thr Pro Ala Gly Asn Leu Thr Leu Thr Cys Thr Ala Ser Gly Ser
        35                  40                  45

Asp Ile Asn Asp Tyr Pro Ile Ser Trp Val Arg Gln Ala Pro Gly Lys
    50                  55                  60

Gly Leu Glu Trp Ile Gly Phe Ile Asn Ser Gly Ser Thr Trp Tyr
65                  70                  75                  80

Ala Ser Trp Val Lys Gly Arg Phe Thr Ile Ser Arg Thr Ser Thr Thr
                85                  90                  95

Val Asp Leu Lys Met Thr Ser Leu Thr Thr Asp Thr Ala Thr Tyr
            100                 105                 110

Phe Cys Ala Arg Gly Tyr Ser Thr Tyr Tyr Gly Asp Phe Asn Ile Trp
        115                 120                 125

Gly Pro Gly Thr Leu Val Thr Ile Ser Ser Gly Gly Gly Ser Gly
    130                 135                 140

Gly Gly Gly Ser Gly Gly Gly Ser Glu Leu Val Met Thr Gln Thr
145                 150                 155                 160

Pro Ser Ser Thr Ser Gly Ala Val Gly Gly Thr Val Thr Ile Asn Cys
                165                 170                 175

Gln Ala Ser Gln Ser Ile Asp Ser Asn Leu Ala Trp Phe Gln Gln Lys
            180                 185                 190

Pro Gly Gln Pro Pro Thr Leu Leu Ile Tyr Arg Ala Ser Asn Leu Ala
        195                 200                 205

Ser Gly Val Pro Ser Arg Phe Ser Gly Ser Arg Ser Gly Thr Glu Tyr
```

```
            210                 215                 220
Thr Leu Thr Ile Ser Gly Val Gln Arg Glu Asp Ala Thr Tyr Tyr
225                 230                 235                 240

Cys Leu Gly Gly Val Gly Asn Val Ser Tyr Arg Thr Ser Phe Gly Gly
                245                 250                 255

Gly Thr Glu Val Val Lys Glu Ser Lys Tyr Gly Pro Pro Cys Pro
                260                 265                 270

Pro Cys Pro Gly Gln Pro Arg Glu Pro Gln Val Tyr Thr Leu Pro Pro
            275                 280                 285

Ser Gln Glu Glu Met Thr Lys Asn Gln Val Ser Leu Thr Cys Leu Val
        290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Tyr Ser Arg Leu Thr Val Asp Lys Ser Arg Trp
            340                 345                 350

Gln Glu Gly Asn Val Phe Ser Cys Ser Val Met His Glu Ala Leu His
        355                 360                 365

Asn His Tyr Thr Gln Lys Ser Leu Ser Leu Ser Leu Gly Lys Met Phe
370                 375                 380

Trp Val Leu Val Val Val Gly Val Leu Ala Cys Tyr Ser Leu Leu
385                 390                 395                 400

Val Thr Val Ala Phe Ile Ile Phe Trp Val Lys Arg Gly Arg Lys Lys
                405                 410                 415

Leu Leu Tyr Ile Phe Lys Gln Pro Phe Met Arg Pro Val Gln Thr Thr
            420                 425                 430

Gln Glu Glu Asp Gly Cys Ser Cys Arg Phe Pro Glu Glu Glu Gly
        435                 440                 445

Gly Cys Glu Leu Arg Val Lys Phe Ser Arg Ser Ala Asp Ala Pro Ala
            450                 455                 460

Tyr Gln Gln Gly Gln Asn Gln Leu Tyr Asn Glu Leu Asn Leu Gly Arg
465                 470                 475                 480

Arg Glu Glu Tyr Asp Val Leu Asp Lys Arg Arg Gly Arg Asp Pro Glu
                485                 490                 495

Met Gly Gly Lys Pro Arg Arg Lys Asn Pro Gln Glu Gly Leu Tyr Asn
            500                 505                 510

Glu Leu Gln Lys Asp Lys Met Ala Glu Ala Tyr Ser Glu Ile Gly Met
        515                 520                 525

Lys Gly Glu Arg Arg Arg Gly Lys Gly His Asp Gly Leu Tyr Gln Gly
530                 535                 540

Leu Ser Thr Ala Thr Lys Asp Thr Tyr Asp Ala Leu His Met Gln Ala
545                 550                 555                 560

Leu Pro Pro Arg Leu Glu Gly Gly Gly Glu Gly Arg Gly Ser Leu Leu
                565                 570                 575

Thr Cys Gly Asp Val Glu Glu Asn Pro Gly Pro Arg Met Leu Leu Leu
            580                 585                 590

Val Thr Ser Leu Leu Leu Cys Glu Leu Pro His Pro Ala Phe Leu Leu
        595                 600                 605

Ile Pro Arg Lys Val Cys Asn Gly Ile Gly Ile Gly Glu Phe Lys Asp
610                 615                 620

Ser Leu Ser Ile Asn Ala Thr Asn Ile Lys His Phe Lys Asn Cys Thr
625                 630                 635                 640
```

Ser Ile Ser Gly Asp Leu His Ile Leu Pro Val Ala Phe Arg Gly Asp
            645                 650                 655

Ser Phe Thr His Thr Pro Pro Leu Asp Pro Gln Glu Leu Asp Ile Leu
        660                 665                 670

Lys Thr Val Lys Glu Ile Thr Gly Phe Leu Leu Ile Gln Ala Trp Pro
    675                 680                 685

Glu Asn Arg Thr Asp Leu His Ala Phe Glu Asn Leu Glu Ile Ile Arg
690                 695                 700

Gly Arg Thr Lys Gln His Gly Gln Phe Ser Leu Ala Val Val Ser Leu
705                 710                 715                 720

Asn Ile Thr Ser Leu Gly Leu Arg Ser Leu Lys Glu Ile Ser Asp Gly
                725                 730                 735

Asp Val Ile Ile Ser Gly Asn Lys Asn Leu Cys Tyr Ala Asn Thr Ile
            740                 745                 750

Asn Trp Lys Lys Leu Phe Gly Thr Ser Gly Gln Lys Thr Lys Ile Ile
        755                 760                 765

Ser Asn Arg Gly Glu Asn Ser Cys Lys Ala Thr Gly Gln Val Cys His
    770                 775                 780

Ala Leu Cys Ser Pro Glu Gly Cys Trp Gly Pro Glu Pro Arg Asp Cys
785                 790                 795                 800

Val Ser Cys Arg Asn Val Ser Arg Gly Arg Glu Cys Val Asp Lys Cys
                805                 810                 815

Asn Leu Leu Glu Gly Glu Pro Arg Glu Phe Val Glu Asn Ser Glu Cys
            820                 825                 830

Ile Gln Cys His Pro Glu Cys Leu Pro Gln Ala Met Asn Ile Thr Cys
        835                 840                 845

Thr Gly Arg Gly Pro Asp Asn Cys Ile Gln Cys Ala His Tyr Ile Asp
    850                 855                 860

Gly Pro His Cys Val Lys Thr Cys Pro Ala Gly Val Met Gly Glu Asn
865                 870                 875                 880

Asn Thr Leu Val Trp Lys Tyr Ala Asp Ala Gly His Val Cys His Leu
                885                 890                 895

Cys His Pro Asn Cys Thr Tyr Gly Cys Thr Gly Pro Gly Leu Glu Gly
            900                 905                 910

Cys Pro Thr Asn Gly Pro Lys Ile Pro Ser Ile Ala Thr Gly Met Val
        915                 920                 925

Gly Ala Leu Leu Leu Leu Leu Val Ala Leu Gly Ile Gly Leu Phe
    930                 935                 940

Met
945

<210> SEQ ID NO 47
<211> LENGTH: 9685
<212> TYPE: DNA
<213> ORGANISM: Artificial Sequence
<220> FEATURE:
<223> OTHER INFORMATION: Synthetic sequence

<400> SEQUENCE: 47
gttagaccag atctgagcct gggagctctc tggctaacta gggaacccac tgcttaagcc      60
tcaataaagc ttgccttgag tgcttcaagt agtgtgtgcc cgtctgttgt gtgactctgg     120
taactagaga tccctcagac ccttttagtc agtgtggaaa atctctagca gtggcgcccg     180
aacagggact tgaaagcgaa agggaaacca gaggagctct ctcgacgcag gactcggctt     240

```
gctgaagcgc gcacggcaag aggcgagggg cggcgactgg tgagtacgcc aaaaattttg    300
actagcggag gctagaagga gagagatggg tgcgagagcg tcagtattaa gcggggagaa    360
attagatcga tgggaaaaaa ttcggttaag gccagggggga agaaaaaat ataaattaaa    420
acatatagta tgggcaagca gggagctaga acgattcgca gttaatcctg gcctgttaga    480
aacatcagaa ggctgtagac aaatactggg acagctacaa ccatcccttc agacaggatc    540
agaagaactt agatcattat ataatacagt agcaaccctc tattgtgtgc atcaaaggat    600
agagataaaa gacaccaagg aagctttaga caagatagag gaagagcaaa acaaaagtaa    660
gaaaaaagca cagcaagcag cagctgacac aggacacagc aatcaggtca gccaaaatta    720
ccctatagtg cagaacatcc aggggcaaat ggtacatcag gccatatcac ctagaacttt    780
aaatgcatgg gtaaaagtag tagaagagaa ggctttcagc ccagaagtga tacccatgtt    840
ttcagcatta tcagaaggag ccaccccaca agatttaaac accatgctaa acacagtggg    900
gggacatcaa gcagccatgc aaatgttaaa agagaccatc aatgaggaag ctgcaggcaa    960
agagaagagt ggtgcagaga gaaaaaagag cagtgggaat aggagctttg ttccttgggt   1020
tcttgggagc agcaggaagc actatgggcg cagcgtcaat gacgctgacg gtacaggcca   1080
gacaattatt gtctggtata gtgcagcagc agaacaattt gctgagggct attgaggcgc   1140
aacagcatct gttgcaactc acagtctggg gcatcaagca gctccaggca agaatcctgg   1200
ctgtggaaag atacctaaag gatcaacagc tcctggggat ttggggttgc tctggaaaac   1260
tcatttgcac cactgctgtg ccttggatct acaaatggca gtattcatcc acaattttaa   1320
aagaaaaggg gggattgggg ggtacagtgc aggggaaaga atagtagaca taatagcaac   1380
agacatacaa actaaagaat tacaaaaaca aattacaaaa attcaaaatt tcgggttta   1440
ttacaggac agcagagatc cagtttgggg atcaattgca tgaagaatct gcttaggtt   1500
aggcgttttg cgctgcttcg cgaggatctg cgatcgctcc ggtgccgtc agtgggcaga    1560
gcgcacatcg cccacagtcc ccgagaagtt gggggaggg tcggcaatt gaaccggtgc    1620
ctagagaagg tggcgcgggg taaactggga aagtgatgtc gtgtactggc tccgcctttt   1680
tcccgagggt gggggagaac cgtatataag tgcagtagtc gccgtgaacg ttcttttttcg   1740
caacgggttt gccgccagaa cacagctgaa gcttcgaggg gctcgcatct ctccttcacg   1800
cgcccgccgc cctacctgag gccgccatcc acgccggttg agtcgcgttc tgccgcctcc   1860
cgcctgtggt gcctcctgaa ctgcgtccgc cgtctaggta agtttaaagc tcaggtcgag   1920
accgggcctt tgtccggcgc tcccttggag cctacctaga ctcagccggc tctccacgct   1980
ttgcctgacc ctgcttgctc aactctacgt cttttgtttcg ttttctgttc tgcgccgtta   2040
cagatccaag ctgtgaccgg cgcctacggc tagcgaattc gccaccatgc tgctgctggt   2100
gacaagcctg ctgctgtgcg agctgccccca ccccgccttt ctgctgatcc cccagagcgt   2160
gaaagagtcc gagggcgacc tggtcacacc agcggcaac ctgaccctga cctgtaccgc   2220
cagcggcagc gacatcaacg actacccat ctcttgggtc cgccaggctc ctggcaaggg   2280
actggaatgg atcggcttca tcaacagcgg cggcagcact tggtacgcca gctgggtcaa   2340
aggccggttc accatcagcc ggaccagcac caccgtggac ctgaagatga acagcctgac   2400
caccgacgac accgccacct actttttgcgc cagaggctac agcacctact acggcgactt   2460
caacatctgg ggccctggca ccctggtcac aatctctagc ggcggaggcg gcagcggagg   2520
tggaggaagt ggcggcggag gatccgagct ggtcatgacc cagaccccca gcagcacatc   2580
tggcgccgtg ggcggcaccg tgaccatcaa ttgccaggcc agccagagca tcgacagcaa   2640
```

-continued

```
cctggcctgg ttccagcaga agcccggcca gccccccacc ctgctgatct acagagcctc    2700
caacctggcc agcggcgtgc caagcagatt cagcggcagc agatctggca ccgagtacac    2760
cctgaccatc tccggcgtgc agagagagga cgccgctacc tattactgcc tgggcggcgt    2820
gggcaacgtg tcctacagaa ccagcttcgg cggaggtact gaggtggtcg tcaaatacgg    2880
accgccctgc ccccttgccc tggccagcct cgcgagccc caggtgtaca ccctgcctcc    2940
ctcccaggaa gagatgacca agaaccaggt gtccctgacc tgcctggtga agggcttcta    3000
ccccagcgac atcgccgtgg agtgggagag caacggccag cctgagaaca actacaagac    3060
cacccctccc gtgctggaca cgacggcag cttcttcctg tacagccggc tgaccgtgga    3120
caagagccgg tggcaggaag gcaacgtctt tagctgcagc gtgatgcacg aggccctgca    3180
caaccactac acccagaaga gcctgagcct gtccctgggc aagatgttct gggtgctggt    3240
ggtggtgggc ggggtgctgg cctgctacag cctgctggtg acagtggcct tcatcatctt    3300
ttgggtgaaa cggggcagaa agaaactcct gtatatattc aaacaaccat ttatgagacc    3360
agtacaaact actcaagagg aagatggctg tagctgccga tttccagaag aagaagaagg    3420
aggatgtgaa ctgcgggtga agttcagcag aagcgccgac gcccctgcct accagcaggg    3480
ccagaatcag ctgtacaacg agctgaacct gggcagaagg gaagagtacg acgtcctgga    3540
taagcggaga ggccgggacc ctgagatggg cggcaagcct cggcggaaga ccccccagga    3600
aggcctgtat aacgaactgc agaaagacaa gatggccgag gcctacagcg agatcggcat    3660
gaagggcgag cggaggcggg gcaagggcca cgacggcctg tatcagggcc tgtccaccgc    3720
caccaaggat acctacgacg ccctgcacat gcaggccctg cccccaaggc tcgagggcgg    3780
cggagagggc agaggaagtc ttctaacatg cggtgacgtg gaggagaatc ccggccctag    3840
gatgcttctc ctggtgacaa gccttctgct ctgtgagtta ccacacccag cattcctcct    3900
gatcccacgc aaagtgtgta acggaatagg tattggtgaa tttaaagact cactctccat    3960
aaatgctacg aatattaaac acttcaaaaa ctgcacctcc atcagtggcg atctccacat    4020
cctgccggtg gcatttaggg gtgactcctt cacacatact cctcctctgg atccacagga    4080
actggatatt ctgaaaaccg taaggaaat cacagggttt ttgctgattc aggcttggcc    4140
tgaaaacagg acggacctcc atgcctttga gaacctagaa atcatacgcg gcaggaccaa    4200
gcaacatggt cagttttctc ttgcagtcgt cagcctgaac ataacatcct tgggattacg    4260
ctccctcaag gagataagtg atggagatgt gataatttca ggaaacaaaa atttgtgcta    4320
tgcaaataca ataaactgga aaaactgtt tgggacctcc ggtcagaaaa ccaaaattat    4380
aagcaacaga ggtgaaaaca gctgcaaggc cacaggccag gtctgccatg ccttgtgctc    4440
ccccgagggc tgctgggcc ggagcccag ggactgcgtc tcttgccgga atgtcagccg    4500
aggcagggaa tgcgtggaca gtgcaacct tctggagggt gagccaaggg agtttgtgga    4560
gaactctgag tgcatacagt gccacccaga gtgcctgcct caggccatga acatcacctg    4620
cacaggacgg ggaccagaca actgtatcca gtgtgcccac tacattgacg ccccccactg    4680
cgtcaagacc tgcccggcag gagtcatggg agaaaacaac accctggtct ggaagtacgc    4740
agacgccggc catgtgtgcc acctgtgcca tccaaactgc acctacgat gcactgggcc    4800 aggtcttgaa ggctgtccaa cgaatgggcc taagatcccg tccatcgcca ctgggatggt    4860
gggggccctc ctcttgctgc tggtggtggc cctggggatc ggcctcttca tgtgagcggc    4920
cgctctagac ccgggctgca ggaattcgat atcaagctta tcgataatca acctctggat    4980
```

```
tacaaaattt gtgaaagatt gactggtatt cttaactatg ttgctccttt tacgctatgt    5040
ggatacgctg ctttaatgcc tttgtatcat gctattgctt cccgtatggc tttcattttc    5100
tcctccttgt ataaatcctg gttgctgtct ctttatgagg agttgtggcc cgttgtcagg    5160
caacgtggcg tggtgtgcac tgtgtttgct gacgcaaccc ccactggttg gggcattgcc    5220
accacctgtc agctcctttc cgggactttc gctttccccc tccctattgc cacggcggaa    5280
ctcatcgccg cctgccttgc ccgctgctgg acagggctc ggctgttggg cactgacaat    5340
tccgtggtgt tgtcggggaa atcatcgtcc tttccttggc tgctcgcctg tgttgccacc    5400
tggattctgc gcgggacgtc cttctgctac gtcccttcgg ccctcaatcc agcggacctt    5460
ccttcccgcg gcctgctgcc ggctctgcgg cctcttccgc gtcttcgcct tcgccctcag    5520
acgagtcgga tctcccttttg ggccgcctcc ccgcatcgat accgtcgact agccgtacct    5580
ttaagaccaa tgacttacaa ggcagctgta gatcttagcc acttttttaaa agaaaagggg    5640 ggactggaag ggctaattca ctcccaaaga agacaagatc tgcttttttgc ctgtactggg    5700 tctctctggt tagaccagat ctgagcctgg gagctctctg gctaactagg gaacccactg    5760
cttaagcctc aataaagctt gccttgagtg cttcaagtag tgtgtgcccg tctgttgtgt    5820
gactctggta actagagatc cctcagaccc ttttagtcag tgtggaaaat ctctagcaga    5880
attcgatatc aagcttatcg ataccgtcga cctcgagggg gggcccggta cccaattcgc    5940
cctatagtga gtcgtattac aattcactgg ccgtcgtttt acaacgtcgt gactgggaaa    6000
accctggcgt tacccaactt aatcgccttg cagcacatcc cctttcgcc agctggcgta    6060 atagcgaaga ggcccgcacc gatcgccctt cccaacagtt gcgcagcctg aatggcgaat    6120
ggaaattgta agcgttaata ttttgttaaa attcgcgtta aatttttgtt aaatcagctc    6180
attttttaac caataggccg aaatcggcaa aatcccttat aaatcaaaag aatagaccga    6240
gatagggttg agtgttgttc cagtttggaa caagagtcca ctattaaaga acgtggactc    6300
caacgtcaaa gggcgaaaaa ccgtctatca gggcgatggc ccactacgtg aaccatcacc    6360
ctaatcaagt ttttttggggt cgaggtgccg taaagcacta aatcggaacc ctaaagggag    6420
cccccgattt agagcttgac ggggaaagcc ggcgaacgtg gcgagaaagg aagggaagaa    6480
agcgaaagga gcgggcgcta gggcgctggc aagtgtagcg gtcacgctgc gcgtaaccac    6540
cacacccgcc gcgcttaatg cgccgctaca gggcgcgtca ggtggcactt tcggggaaa    6600 tgtgcgcgga accctattt gtttatttt ctaaatacat tcaaatatgt atccgctcat    6660
gagacaataa ccctgataaa tgcttcaata atattgaaaa aggaagagta tgagtattca    6720
acatttccgt gtcgccctta ttcccttttt tgcggcattt tgccttcctg tttttgctca    6780
cccagaaacg ctggtgaaag taaaagatgc tgaagatcag ttgggtgcac gagtgggtta    6840
catcgaactg gatctcaaca gcggtaagat ccttgagagt tttcgccccg aagaacgttt    6900
tccaatgatg agcactttta aagttctgct atgtggcgcg gtattatccc gtattgacgc    6960
cgggcaagag caactcggtc gccgcataca ctattctcag aatgacttgg ttgagtactc    7020
accagtcaca gaaaagcatc ttacggatgg catgacagta agagaattat gcagtgctgc    7080
cataaccatg agtgataaca ctgcggccaa cttacttctg acaacgatcg gaggaccgaa    7140
ggagctaacc gcttttttgc acaacatggg ggatcatgta actcgccttg atcgttggga    7200
accggagctg aatgaagcca taccaaacga cgagcgtgac accacgatgc ctgtagcaat    7260
ggcaacaacg ttgcgcaaac tattaactgg cgaactactt actctagctt cccggcaaca    7320
attaatagac tggatggagg cggataaagt tgcaggacca cttctgcgct cggcccttcc    7380
```

```
ggctggctgg tttattgctg ataaatctgg agccggtgag cgtgggtctc gcggtatcat    7440
tgcagcactg gggccagatg gtaagccctc ccgtatcgta gttatctaca cgacggggag    7500
tcaggcaact atggatgaac gaaatagaca gatcgctgag ataggtgcct cactgattaa    7560
gcattggtaa ctgtcagacc aagtttactc atatatactt tagattgatt taaaacttca    7620
tttttaattt aaaaggatct aggtgaagat cctttttgat aatctcatga ccaaaatccc    7680
ttaacgtgag ttttcgttcc actgagcgtc agacccccgta gaaaagatca aaggatcttc    7740
ttgagatcct ttttttctgc gcgtaatctg ctgcttgcaa acaaaaaaac caccgctacc    7800
agcggtggtt tgtttgccgg atcaagagct accaactctt tttccgaagg taactggctt    7860
cagcagagcg cagataccaa atactgttct tctagtgtag ccgtagttag gccaccactt    7920
caagaactct gtagcaccgc ctacatacct cgctctgcta atcctgttac cagtggctgc    7980
tgccagtggc gataagtcgt gtcttaccgg gttggactca agacgatagt taccggataa    8040
ggcgcagcgg tcgggctgaa cggggggttc gtgcacacag cccagcttgg agcgaacgac    8100
ctacaccgaa ctgagatacc tacagcgtga gctatgagaa agcgccacgc ttcccgaagg    8160
gagaaaggcg gacaggtatc cggtaagcgg cagggtcgga acaggagagc gcacgaggga    8220
gcttccaggg ggaaacgcct ggtatcttta tagtcctgtc gggtttcgcc acctctgact    8280
tgagcgtcga tttttgtgat gctcgtcagg gggcggagc ctatggaaaa acgccagcaa    8340
cgcggccttt ttacggttcc tggccttttg ctggcctttt gctcacatgt tctttcctgc    8400
gttatcccct gattctgtgg ataaccgtat taccgccttt gagtgagctg ataccgctcg    8460
ccgcagccga acgaccgagc gcagcgagtc agtgagcgag gaagcggaag agcgcccaat    8520
acgcaaaccg cctctccccg cgcgttggcc gattcattaa tgcagctggc acgacaggtt    8580
tcccgactgg aaagcgggca gtgagcgcaa cgcaattaat gtgagttagc tcactcatta    8640
ggcaccccag gctttacact ttatgcttcc ggctcgtatg ttgtgtggaa ttgtgagcgg    8700
ataacaattt cacacaggaa acagctatga ccatgattac gccaagctcg aaattaaccc    8760
tcactaaagg gaacaaaagc tggagctcca ccgcggtggc ggcctcgagg tcgagatccg    8820
gtcgaccagc aaccatagtc ccgcccctaa ctccgcccat cccgcccta actccgccca    8880 gttccgccca ttctccgccc catggctgac taatttttttt tatttatgca gaggccgagg    8940
ccgcctcggc ctctgagcta ttccagaagt agtgaggagg cttttttgga ggcctaggct    9000
tttgcaaaaa gcttcgacgg tatcgattgg ctcatgtcca acattaccgc catgttgaca    9060
ttgattattg actagttatt aatagtaatc aattacgggg tcattagttc atagcccata    9120
tatggagttc cgcgttacat aacttacggt aaatggcccg cctggctgac cgcccaacga    9180
cccccgccca ttgacgtcaa taatgacgta tgttcccata gtaacgccaa tagggacttt    9240
ccattgacgt caatgggtgg agtatttacg gtaaactgcc cacttggcag tacatcaagt    9300
gtatcatatg ccaagtacgc ccctattga cgtcaatgac ggtaaatggc ccgcctggca    9360
ttatgcccag tacatgacct tatgggactt tcctacttgg cagtacatct acgtattagt    9420
catcgctatt accatggtga tgcggttttg gcagtacatc aatgggcgtg gatagcggtt    9480
tgactcacgg ggatttccaa gtctccaccc cattgacgtc aatgggagtt tgttttggca    9540
ccaaaatcaa cgggactttc caaaatgtcg taacaactcc gccccattga cgcaaatggg    9600
cggtaggcgt gtacggaatt cggagtggcg agccctcaga tcctgcatat aagcagctgc    9660 ttttttgcctg tactgggtct ctctg                                        9685
```

<210> SEQ ID NO 48
<211> LENGTH: 838
<212> TYPE: PRT
<213> ORGANISM: Artificial Sequence
<220> FEATURE:
<223> OTHER INFORMATION: Synthetic sequence

<400> SEQUENCE: 48

```
Met Leu Leu Leu Val Thr Ser Leu Leu Leu Cys Glu Leu Pro His Pro
1               5                   10                  15

Ala Phe Leu Leu Ile Pro Gln Ser Val Lys Glu Ser Glu Gly Asp Leu
            20                  25                  30

Val Thr Pro Ala Gly Asn Leu Thr Leu Thr Cys Thr Ala Ser Gly Ser
        35                  40                  45

Asp Ile Asn Asp Tyr Pro Ile Ser Trp Val Arg Gln Ala Pro Gly Lys
    50                  55                  60

Gly Leu Glu Trp Ile Gly Phe Ile Asn Ser Gly Ser Thr Trp Tyr
65              70                  75                  80

Ala Ser Trp Val Lys Gly Arg Phe Thr Ile Ser Arg Thr Ser Thr Thr
                85                  90                  95

Val Asp Leu Lys Met Thr Ser Leu Thr Thr Asp Thr Ala Thr Tyr
            100                 105                 110

Phe Cys Ala Arg Gly Tyr Ser Thr Tyr Tyr Gly Asp Phe Asn Ile Trp
        115                 120                 125

Gly Pro Gly Thr Leu Val Thr Ile Ser Ser Gly Gly Gly Gly Ser Gly
    130                 135                 140

Gly Gly Gly Ser Gly Gly Gly Ser Glu Leu Val Met Thr Gln Thr
145                 150                 155                 160

Pro Ser Ser Thr Ser Gly Ala Val Gly Gly Thr Val Thr Ile Asn Cys
                165                 170                 175

Gln Ala Ser Gln Ser Ile Asp Ser Asn Leu Ala Trp Phe Gln Gln Lys
            180                 185                 190

Pro Gly Gln Pro Pro Thr Leu Leu Ile Tyr Arg Ala Ser Asn Leu Ala
        195                 200                 205

Ser Gly Val Pro Ser Arg Phe Ser Gly Ser Arg Ser Gly Thr Glu Tyr
    210                 215                 220

Thr Leu Thr Ile Ser Gly Val Gln Arg Glu Asp Ala Ala Thr Tyr Tyr
225                 230                 235                 240

Cys Leu Gly Gly Val Gly Asn Val Ser Tyr Arg Thr Ser Phe Gly Gly
                245                 250                 255

Gly Thr Glu Val Val Val Lys Glu Ser Lys Tyr Gly Pro Pro Cys Pro
            260                 265                 270

Pro Cys Pro Met Phe Trp Val Leu Val Val Gly Gly Val Leu Ala
        275                 280                 285

Cys Tyr Ser Leu Leu Val Thr Val Ala Phe Ile Ile Phe Trp Val Lys
    290                 295                 300

Arg Gly Arg Lys Lys Leu Leu Tyr Ile Phe Lys Gln Pro Phe Met Arg
305                 310                 315                 320

Pro Val Gln Thr Thr Gln Glu Glu Asp Gly Cys Ser Cys Arg Phe Pro
                325                 330                 335

Glu Glu Glu Glu Gly Gly Cys Glu Leu Arg Val Lys Phe Ser Arg Ser
            340                 345                 350

Ala Asp Ala Pro Ala Tyr Gln Gln Gly Gln Asn Gln Leu Tyr Asn Glu
        355                 360                 365
```

```
Leu Asn Leu Gly Arg Arg Glu Glu Tyr Asp Val Leu Asp Lys Arg Arg
    370                 375                 380

Gly Arg Asp Pro Glu Met Gly Gly Lys Pro Arg Arg Lys Asn Pro Gln
385                 390                 395                 400

Glu Gly Leu Tyr Asn Glu Leu Gln Lys Asp Lys Met Ala Glu Ala Tyr
                405                 410                 415

Ser Glu Ile Gly Met Lys Gly Glu Arg Arg Arg Gly Lys Gly His Asp
            420                 425                 430

Gly Leu Tyr Gln Gly Leu Ser Thr Ala Thr Lys Asp Thr Tyr Asp Ala
        435                 440                 445

Leu His Met Gln Ala Leu Pro Pro Arg Leu Glu Gly Gly Gly Glu Gly
    450                 455                 460

Arg Gly Ser Leu Leu Thr Cys Gly Asp Val Glu Glu Asn Pro Gly Pro
465                 470                 475                 480

Arg Met Leu Leu Leu Val Thr Ser Leu Leu Leu Cys Glu Leu Pro His
                485                 490                 495

Pro Ala Phe Leu Leu Ile Pro Arg Lys Val Cys Asn Gly Ile Gly Ile
                500                 505                 510

Gly Glu Phe Lys Asp Ser Leu Ser Ile Asn Ala Thr Asn Ile Lys His
            515                 520                 525

Phe Lys Asn Cys Thr Ser Ile Ser Gly Asp Leu His Ile Leu Pro Val
    530                 535                 540

Ala Phe Arg Gly Asp Ser Phe Thr His Thr Pro Leu Asp Pro Gln
545                 550                 555                 560

Glu Leu Asp Ile Leu Lys Thr Val Lys Glu Ile Thr Gly Phe Leu Leu
                565                 570                 575

Ile Gln Ala Trp Pro Glu Asn Arg Thr Asp Leu His Ala Phe Glu Asn
            580                 585                 590

Leu Glu Ile Ile Arg Gly Arg Thr Lys Gln His Gly Gln Phe Ser Leu
        595                 600                 605

Ala Val Val Ser Leu Asn Ile Thr Ser Leu Gly Leu Arg Ser Leu Lys
    610                 615                 620

Glu Ile Ser Asp Gly Asp Val Ile Ile Ser Gly Asn Lys Asn Leu Cys
625                 630                 635                 640

Tyr Ala Asn Thr Ile Asn Trp Lys Lys Leu Phe Gly Thr Ser Gly Gln
                645                 650                 655

Lys Thr Lys Ile Ile Ser Asn Arg Gly Glu Asn Ser Cys Lys Ala Thr
            660                 665                 670

Gly Gln Val Cys His Ala Leu Cys Ser Pro Glu Gly Cys Trp Gly Pro
        675                 680                 685

Glu Pro Arg Asp Cys Val Ser Cys Arg Asn Val Ser Arg Gly Arg Glu
    690                 695                 700

Cys Val Asp Lys Cys Asn Leu Leu Glu Gly Glu Pro Arg Glu Phe Val
705                 710                 715                 720

Glu Asn Ser Glu Cys Ile Gln Cys His Pro Glu Cys Leu Pro Gln Ala
                725                 730                 735

Met Asn Ile Thr Cys Thr Gly Arg Gly Pro Asp Asn Cys Ile Gln Cys
            740                 745                 750

Ala His Tyr Ile Asp Gly Pro His Cys Val Lys Thr Cys Pro Ala Gly
        755                 760                 765

Val Met Gly Glu Asn Asn Thr Leu Val Trp Lys Tyr Ala Asp Ala Gly
    770                 775                 780

His Val Cys His Leu Cys His Pro Asn Cys Thr Tyr Gly Cys Thr Gly
```

```
                785                 790                 795                 800
Pro Gly Leu Glu Gly Cys Pro Thr Asn Gly Pro Lys Ile Pro Ser Ile
                    805                 810                 815

Ala Thr Gly Met Val Gly Ala Leu Leu Leu Leu Val Val Ala Leu
                820                 825                 830

Gly Ile Gly Leu Phe Met
            835

<210> SEQ ID NO 49
<211> LENGTH: 119
<212> TYPE: PRT
<213> ORGANISM: Artificial Sequence
<220> FEATURE:
<223> OTHER INFORMATION: Synthetic sequence

<400> SEQUENCE: 49

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
                20                  25                  30

Asn Gln Val Ser Leu Thr Cys Leu Val Lys Gly Phe Tyr Pro Ser Asp
            35                  40                  45

Ile Ala Val Glu Trp Glu Ser Asn Gly Gln Pro Glu Asn Asn Tyr Lys
        50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 50
<211> LENGTH: 229
<212> TYPE: PRT
<213> ORGANISM: Artificial Sequence
<220> FEATURE:
<223> OTHER INFORMATION: Synthetic sequence

<400> SEQUENCE: 50

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125
```

```
Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220

Leu Ser Leu Gly Lys
225

<210> SEQ ID NO 51
<211> LENGTH: 9
<212> TYPE: PRT
<213> ORGANISM: Artificial Sequence
<220> FEATURE:
<223> OTHER INFORMATION: Synthetic sequence

<400> SEQUENCE: 51

Tyr Gly Pro Pro Cys Pro Pro Cys Pro
1               5

<210> SEQ ID NO 52
<211> LENGTH: 10
<212> TYPE: PRT
<213> ORGANISM: Artificial Sequence
<220> FEATURE:
<223> OTHER INFORMATION: Synthetic sequence

<400> SEQUENCE: 52

Lys Tyr Gly Pro Pro Cys Pro Pro Cys Pro
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Synthetic sequence

<400> SEQUENCE: 53

Glu Val Val Val Lys Tyr Gly Pro Pro Cys Pro Cys Pro
1               5                   10

<210> SEQ ID NO 54
<211> LENGTH: 2529
<212> TYPE: DNA
<213> ORGANISM: Artificial Sequence
<220> FEATURE:
<223> OTHER INFORMATION: Synthetic sequence

<400> SEQUENCE: 54
atgcttctcc tggtgacaag ccttctgctc tgtgagttac cacacccagc attcctcctg      60
atcccagata tccagatgac ccagtccccg agctccctgt ccgcctctgt gggcgatagg     120
gtcaccatca cctgccgtgc cagtcaggat gtgaatactg ctgtagcctg gtatcaacag     180
aaaccaggaa aagctccgaa actactgatt tactcggcat ccttcctcta ctctggagtc     240
ccttctcgct tctctggttc cagatctggg acggatttca ctctgaccat cagcagtctg     300
```

```
cagccggaag acttcgcaac ttattactgt cagcaacatt atactactcc tcccacgttc    360
ggacagggta ccaaggtgga gatcaaaggc agtactagcg gcggtggctc cgggggcgga    420
tccggtgggg gcggcagcag cgaggttcag ctggtggagt ctggcggtgg cctggtgcag    480 ccaggggct cactccgttt gtcctgtgca gcttctggct tcaacattaa agacacctat     540
atacactggg tgcgtcaggc cccgggtaag ggcctggaat gggttgcaag gatttatcct    600
acgaatggtt atactagata tgccgatagc gtcaagggcc gtttcactat aagcgcagac    660
acatccaaaa acacagccta cctgcagatg aacagcctgc gtgctgagga cactgccgtc    720
tattattgtt ctagatgggg aggggacggc ttctatgcta tggactactg gggtcaagga    780
accctggtca ccgtctcgag tgagagcaag tacgaccgc cctgccccc ttgccctatg      840 ttctgggtgc tggtggtggt cggaggcgtg ctggcctgct acagcctgct ggtcaccgtg    900
gccttcatca tcttttgggt gaaacggggc agaagaaac tcctgtatat attcaaacaa     960
ccatttatga ccagtacaa aactactcaa gaggaagatg gctgtagctg ccgatttcca    1020
gaagaagaag aaggaggatg tgaactgcgg gtgaagttca gcagaagcgc cgacgcccct   1080
gcctaccagc agggccagaa tcagctgtac aacgagctga acctgggcag aagggaagag   1140
tacgacgtcc tggataagcg gagaggccgg gaccctgaga tgggcggcaa gcctcggcgg   1200 aagaacccc aggaaggcct gtataacgaa ctgcagaaag acaagatggc cgaggcctac    1260
agcgagatcg gcatgaaggg cgagcggagg cggggcaagg gccacgacgg cctgtatcag   1320
ggcctgtcca ccgccaccaa ggataccctac gacgccctgc acatgcaggc cctgcccca   1380 aggctcgagg gcggcggaga gggcagagga agtcttctaa catgcggtga cgtggaggag   1440
aatcccggcc ctaggatgct tctcctggtg acaagccttc tgctctgtga gttaccacac   1500
ccagcattcc tcctgatccc acgcaaagtg tgtaacggaa taggtattgg tgaatttaaa   1560
gactcactct ccataaatgc tacgaatatt aaacacttca aaaactgcac ctccatcagt   1620
ggcgatctcc acatcctgcc ggtggcattt aggggtgact ccttcacaca tactcctcct   1680
ctggatccac aggaactgga tattctgaaa accgtaaagg aaatcacagg ttttttgctg   1740
attcaggctt ggcctgaaaa caggacggac ctccatgcct tgagaaccct agaaatcata   1800
cgcggcagga ccaagcaaca tggtcagttt tctcttgcag tcgtcagcct gaacataaca   1860
tccttgggat tacgctccct caaggagata agtgatggag atgtgataat ttcaggaaac   1920
aaaaatttgt gctatgcaaa tacaataaac tggaaaaaac tgtttgggac ctccggtcag   1980
aaaaccaaaa ttataagcaa cagaggtgaa aacagctgca aggccacagg ccaggtctgc   2040
catgccttgt gctcccccga gggctgctgg ggcccggagc ccaggactg cgtctcttgc   2100 cggaatgtca gccgaggcag ggaatgcgtg gacaagtgca accttctgga gggtgagcca   2160
agggagtttg tggagaactc tgagtgcata cagtgccacc cagagtgcct gcctcaggcc   2220
atgaacatca cctgcacagg acggggacca gacaactgta tccagtgtgc ccactacatt   2280
gacggccccc actgcgtcaa gacctgcccg gcaggagtca tgggagaaaa caacaccctg   2340
gtctggaagt acgcagacgc cggccatgtg tgccacctgt gccatccaaa ctgcacctac   2400
ggatgcactg ggccaggtct tgaaggctgt ccaacgaatg gcctaagat cccgtccatc    2460 gccactggga tggtggggc cctcctcttg ctgctggtgg tggccctggg gatcggcctc   2520
ttcatgtga                                                           2529
```

<210> SEQ ID NO 55

<211> LENGTH: 2850
<212> TYPE: DNA
<213> ORGANISM: Artificial Sequence
<220> FEATURE:
<223> OTHER INFORMATION: Synthetic sequence

<400> SEQUENCE: 55

| | | | | | |
|---|---|---|---|---|---|
| atgcttctcc | tggtgacaag | ccttctgctc | tgtgagttac | cacacccagc | attcctcctg | 60 |
| atcccagata | tccagatgac | ccagtccccg | agctccctgt | ccgcctctgt | gggcgatagg | 120 |
| gtcaccatca | cctgccgtgc | cagtcaggat | gtgaatactg | ctgtagcctg | gtatcaacag | 180 |
| aaaccaggaa | aagctccgaa | actactgatt | tactcggcat | ccttcctcta | ctctggagtc | 240 |
| ccttctcgct | tctctggttc | cagatctggg | acggatttca | ctctgaccat | cagcagtctg | 300 |
| cagccggaag | acttcgcaac | ttattactgt | cagcaacatt | atactactcc | tcccacgttc | 360 |
| ggacagggta | ccaaggtgga | gatcaaaggc | agtactagcg | gcggtggctc | cggggcgga | 420 |
| tccggtgggg | gcggcagcag | cgaggttcag | ctggtggagt | ctgcggtgg | cctggtgcag | 480 |
| ccagggggct | cactccgttt | gtcctgtgca | gcttctggct | tcaacattaa | agacacctat | 540 |
| atacactggg | tgcgtcaggc | ccgggtaag | ggcctggaat | gggttgcaag | gatttatcct | 600 |
| acgaatggtt | atactagata | tgccgatagc | gtcaagggcc | gtttcactat | aagcgcagac | 660 |
| acatccaaaa | acacagccta | cctgcagatg | aacagcctgc | gtgctgagga | cactgccgtc | 720 |
| tattattgtt | ctagatgggg | aggggacgg | ttctatgcta | tggactactg | ggtcaagga | 780 |
| accctggtca | ccgtctcgag | tgagagcaag | tacggaccgc | cctgcccccc | ttgccctggc | 840 |
| cagcctagag | aacccaggt | gtacaccctg | cctcccagcc | aggaagagat | gaccaagaac | 900 |
| caggtgtccc | tgacctgcct | ggtcaaaggc | ttctacccca | gcgatatcgc | cgtggaatgg | 960 |
| gagagcaacg | gccagccga | gaacaactac | aagaccaccc | ccctgtgct | ggacagcgac | 1020 |
| ggcagcttct | tcctgtactc | ccggctgacc | gtggacaaga | gccggtggca | ggaaggcaac | 1080 |
| gtcttcagct | gcagcgtgat | gcacgaggcc | ctgcacaacc | actacaccca | gaagtccctg | 1140 |
| agcctgagcc | tgggcaagat | gttctgggtg | ctggtggtgg | tcggaggcgt | gctggcctgc | 1200 |
| tacagcctgc | tggtcaccgt | ggccttcatc | atcttttggg | tgaaacgggg | cagaaagaaa | 1260 |
| ctcctgtata | tattcaaaca | accatttatg | agaccagtac | aaactactca | agaggaagat | 1320 |
| ggctgtagct | gccgatttcc | agaagaagaa | gaaggaggat | gtgaactgcg | ggtgaagttc | 1380 |
| agcagaagcg | ccgacgcccc | tgcctaccag | cagggccaga | atcagctgta | caacgagctg | 1440 |
| aacctgggca | gagggaaga | gtacgacgtc | ctggataagc | ggagaggccg | ggaccctgag | 1500 |
| atgggcggca | agcctcggcg | gaagaacccc | caggaaggcc | tgtataacga | actgcagaaa | 1560 |
| gacaagatgg | ccgaggccta | cagcgagatc | ggcatgaagg | gcgagcggag | cggggcaag | 1620 |
| ggccacgacg | gcctgtatca | gggcctgtcc | accgccacca | aggatacccta | cgacgccctg | 1680 |
| cacatgcagg | ccctgccccc | aaggctcgag | ggcggcggag | agggcagagg | aagtcttcta | 1740 |
| acatgcggtg | acgtggagga | gaatcccggc | cctaggatgc | ttctcctggt | gacaagcctt | 1800 |
| ctgctctgtg | agttaccaca | cccagcattc | ctcctgatcc | cacgcaaagt | gtgtaacgga | 1860 |
| ataggtattg | tgaatttaa | agactcactc | tccataaatg | ctacgaatat | aaacacttc | 1920 |
| aaaaactgca | cctccatcag | tggcgatctc | cacatcctgc | cggtggcatt | tagggtgac | 1980 |
| tccttcacac | atactcctcc | tctggatcca | caggaactgg | atattctgaa | accgtaaag | 2040 |
| gaaatcacag | ggttttgct | gattcaggct | tggcctgaaa | acaggacgga | cctccatgcc | 2100 |
| tttgagaacc | tagaaatcat | acgcggcagg | accaagcaac | atggtcagtt | ttctcttgca | 2160 |

```
gtcgtcagcc tgaacataac atccttggga ttacgctccc tcaaggagat aagtgatgga   2220
gatgtgataa tttcaggaaa caaaaatttg tgctatgcaa atacaataaa ctggaaaaaa   2280
ctgtttggga cctccggtca gaaaaccaaa attataagca acagaggtga aaacagctgc   2340
aaggccacag gccaggtctg ccatgccttg tgctccccg  agggctgctg gggcccggag   2400
cccagggact gcgtctcttg ccggaatgtc agccgaggca gggaatgcgt ggacaagtgc   2460
aaccttctgg agggtgagcc aagggagttt gtggagaact ctgagtgcat acagtgccac   2520
ccagagtgcc tgcctcaggc catgaacatc acctgcacag gacgggggacc agacaactgt   2580 atccagtgtg cccactacat tgacggcccc cactgcgtca agacctgccc ggcaggagtc   2640
atgggagaaa acaacaccct ggtctggaag tacgcagacg ccggccatgt gtgccacctg   2700
tgccatccaa actgcaccta cggatgcact gggccaggtc ttgaaggctg tccaacgaat   2760
gggcctaaga tcccgtccat cgccactggg atggtggggg ccctcctctt gctgctggtg   2820
gtggccctgg ggatcggcct cttcatgtga                                    2850
```

<210> SEQ ID NO 56
<211> LENGTH: 3180
<212> TYPE: DNA
<213> ORGANISM: Artificial Sequence
<220> FEATURE:
<223> OTHER INFORMATION: Synthetic sequence

<400> SEQUENCE: 56

```
atgcttctcc tggtgacaag ccttctgctc tgtgagttac cacacccagc attcctcctg     60
atcccagata tccagatgac ccagtccccg agctccctgt ccgcctctgt gggcgatagg    120
gtcaccatca cctgccgtgc cagtcaggat gtgaatactg ctgtagccctg gtatcaacag    180 aaaccaggaa aagctccgaa actactgatt tactcggcat ccttcctcta ctctggagtc    240
ccttctcgct tctctggttc cagatctggg acggatttca ctctgaccat cagcagtctg    300
cagccggaag acttcgcaac ttattactgt cagcaacatt atactactcc tcccacgttc    360
ggacagggta ccaaggtgga gatcaaaggc agtactagcg gcggtggctc cggggggcgga    420 tccggtgggg gcggcagcag cgaggttcag ctggtggagt ctggcggtgg cctggtgcag    480
ccagggggct cactccgttt gtcctgtgca gcttctggct tcaacattaa agacacctat    540
atacactggg tgcgtcaggc cccgggtaag ggcctggaat gggttgcaag gatttatcct    600
acgaatggtt atactagata tgccgatagc gtcaagggcc gtttcactat aagcgcagac    660
acatccaaaa acacagccta cctgcagatg aacagcctgc gtgctgagga cactgccgtc    720
tattattgtt ctagatgggg aggggacggc ttctatgcta tggactactg gggtcaagga    780
accctggtca ccgtctcgag tgagagcaag tacggaccgc cctgcccccc ttgccctgcc    840
cccgagttcc tgggcggacc cagcgtgttc ctgttccccc caagcccaa  ggacaccctg    900 atgatcagcc ggacccccga ggtgacctgc gtggtggtgg acgtgagcca ggaagatccc    960
gaggtccagt tcaattggta cgtggacggc gtggaagtgc acaacgccaa gaccaagccc   1020
agagaggaac agttcaacag cacctaccgg gtggtgtctg tgctgaccgt gctgcaccag   1080
gactggctga acggcaaaga atacaagtgc aaggtgtcca acaagggcct gcccagcagc   1140
atcgaaaaga ccatcagcaa ggccaagggc cagcctcgcg agccccaggt gtacaccctg   1200
cctccctccc aggaagagat gaccaagaac caggtgtccc tgacctgcct ggtgaagggc   1260
ttctacccca gcgacatcgc cgtggagtgg gagagcaacg gccagcctga gaacaactac   1320
aagaccaccc ctcccgtgct ggacagcgac ggcagcttct tcctgtacag ccggctgacc   1380
```

```
gtggacaaga gccggtggca ggaaggcaac gtctttagct gcagcgtgat gcacgaggcc    1440
ctgcacaacc actacaccca gaagagcctg agcctgtccc tgggcaagat gttctgggtg    1500
ctggtggtgg tgggcggggt gctggcctgc tacagcctgc tggtgacagt ggccttcatc    1560
atcttttggg tgaaacgggg cagaaagaaa ctcctgtata tattcaaaca accatttatg    1620
agaccagtac aaactactca agaggaagat ggctgtagct gccgatttcc agaagaagaa    1680
gaaggaggat gtgaactgcg ggtgaagttc agcagaagcg ccgacgcccc tgcctaccag    1740
cagggccaga atcagctgta caacgagctg aacctgggca agggaagaa gtacgacgtc     1800 ctggataagc ggagaggccg ggaccctgag atgggcggca agcctcggcg aagaaccccc    1860
caggaaggcc tgtataacga actgcagaaa gacaagatgg ccgaggccta cagcgagatc    1920
ggcatgaagg gcgagcggag gcggggcaag ggccacgacg gcctgtatca gggcctgtcc    1980
accgccacca aggataccta cgacgccctg cacatgcagg ccctgccccc aaggctcgag    2040
ggcggcggag agggcagagg aagtcttcta acatgcggtg acgtggagga gaatcccggc    2100
cctaggatgc ttctcctggt gacaagcctt ctgctctgtg agttaccaca cccagcattc    2160
ctcctgatcc cacgcaaagt gtgtaacgga ataggtattg gtgaatttaa agactcactc    2220
tccataaatg ctacgaatat taaacacttc aaaaactgca cctccatcag tggcgatctc    2280
cacatcctgc cggtggcatt tagggtgac tccttcacac atactcctcc tctggatcca     2340
caggaactga atattctgaa aaccgtaaag gaaatcacag ggttttttgct gattcaggct    2400 tggcctgaaa acaggacgga cctccatgcc tttgagaacc tagaaatcat acgcggcagg    2460
accaagcaac atggtcagtt ttctcttgca gtcgtcagcc tgaacataac atccttggga    2520
ttacgctccc tcaaggagat aagtgatgga gatgtgataa tttcaggaaa caaaaatttg    2580
tgctatgcaa atacaataaa ctggaaaaaa ctgtttggga cctccggtca gaaaaccaaa    2640
attataagca acagaggtga aaacagctgc aaggccacag gccaggtctg ccatgccttg    2700
tgctcccccg agggctgctg gggcccggag cccagggact gcgtctcttg ccggaatgtc    2760
agccgaggca gggaatgcgt ggacaagtgc aaccttctgg agggtgagcc aagggagttt    2820
gtggagaact ctgagtgcat acagtgccac ccagagtgcc tgcctcaggc catgaacatc    2880
acctgcacag gacggggacc agacaactgt atccagtgtg cccactacat tgacggcccc    2940
cactgcgtca agacctgccc ggcaggagtc atgggagaaa acaacaccct ggtctggaag    3000
tacgcagacg ccggccatgt gtgccacctg tgccatccaa actgcaccta cggatgcact    3060
gggccaggtc ttgaaggctg tccaacgaat gggcctaaga tcccgtccat cgccactggg    3120
atggtggggg ccctcctctt gctgctggtg gtggccctgg ggatcggcct cttcatgtga    3180
```

<210> SEQ ID NO 57
<211> LENGTH: 11
<212> TYPE: PRT
<213> ORGANISM: Artificial Sequence
<220> FEATURE:
<223> OTHER INFORMATION: Synthetic sequence

<400> SEQUENCE: 57

Arg Ala Ser Gln Asp Ile Ser Lys Tyr Leu Asn
1               5                   10

<210> SEQ ID NO 58
<211> LENGTH: 7
<212> TYPE: PRT
<213> ORGANISM: Artificial Sequence

```
<220> FEATURE:
<223> OTHER INFORMATION: Synthetic sequence

<400> SEQUENCE: 58

Ser Arg Leu His Ser Gly Val
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic sequence

<400> SEQUENCE: 59

Gly Asn Thr Leu Pro Tyr Thr Phe Gly
1               5

<210> SEQ ID NO 60
<211> LENGTH: 16
<212> TYPE: PRT
<213> ORGANISM: Artificial Sequence
<220> FEATURE:
<223> OTHER INFORMATION: Synthetic sequence

<400> SEQUENCE: 60

Val Ile Trp Gly Ser Glu Thr Thr Tyr Tyr Asn Ser Ala Leu Lys Ser
1               5                   10                  15

<210> SEQ ID NO 61
<211> LENGTH: 7
<212> TYPE: PRT
<213> ORGANISM: Artificial Sequence
<220> FEATURE:
<223> OTHER INFORMATION: Synthetic sequence

<400> SEQUENCE: 61

Tyr Ala Met Asp Tyr Trp Gly
1               5

<210> SEQ ID NO 62
<211> LENGTH: 11
<212> TYPE: PRT
<213> ORGANISM: Artificial Sequence
<220> FEATURE:
<223> OTHER INFORMATION: Synthetic sequence

<400> SEQUENCE: 62

Ala Ser Gly Phe Asp Phe Ser Ala Tyr Tyr Met
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Synthetic sequence

<400> SEQUENCE: 63

Thr Ile Tyr Pro Ser Ser Gly
1               5

<210> SEQ ID NO 64
<211> LENGTH: 9
<212> TYPE: PRT
<213> ORGANISM: Artificial Sequence
```

```
<220> FEATURE:
<223> OTHER INFORMATION: Synthetic sequence

<400> SEQUENCE: 64

Ala Asp Arg Ala Thr Tyr Phe Cys Ala
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic sequence

<400> SEQUENCE: 65

Asp Thr Ile Asp Trp Tyr
1               5

<210> SEQ ID NO 66
<211> LENGTH: 16
<212> TYPE: PRT
<213> ORGANISM: Artificial Sequence
<220> FEATURE:
<223> OTHER INFORMATION: Synthetic sequence

<400> SEQUENCE: 66

Val Gln Ser Asp Gly Ser Tyr Thr Lys Arg Pro Gly Val Pro Asp Arg
1               5                   10                  15

<210> SEQ ID NO 67
<211> LENGTH: 8
<212> TYPE: PRT
<213> ORGANISM: Artificial Sequence
<220> FEATURE:
<223> OTHER INFORMATION: Synthetic sequence

<400> SEQUENCE: 67

Tyr Ile Gly Gly Tyr Val Phe Gly
1               5

<210> SEQ ID NO 68
<211> LENGTH: 11
<212> TYPE: PRT
<213> ORGANISM: Artificial Sequence
<220> FEATURE:
<223> OTHER INFORMATION: Synthetic sequence

<400> SEQUENCE: 68

Ser Gly Ser Asp Ile Asn Asp Tyr Pro Ile Ser
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Synthetic sequence

<400> SEQUENCE: 69

Ile Asn Ser Gly Gly Ser Thr
1               5

<210> SEQ ID NO 70
<211> LENGTH: 8
<212> TYPE: PRT
<213> ORGANISM: Artificial Sequence
```

```
<220> FEATURE:
<223> OTHER INFORMATION: Synthetic sequence

<400> SEQUENCE: 70

Tyr Phe Cys Ala Arg Gly Tyr Ser
1               5

<210> SEQ ID NO 71
<211> LENGTH: 5
<212> TYPE: PRT
<213> ORGANISM: Artificial Sequence
<220> FEATURE:
<223> OTHER INFORMATION: Synthetic sequence

<400> SEQUENCE: 71

Ser Asn Leu Ala Trp
1               5

<210> SEQ ID NO 72
<211> LENGTH: 16
<212> TYPE: PRT
<213> ORGANISM: Artificial Sequence
<220> FEATURE:
<223> OTHER INFORMATION: Synthetic sequence

<400> SEQUENCE: 72

Arg Ala Ser Asn Leu Ala Ser Gly Val Pro Ser Arg Phe Ser Gly Ser
1               5                   10                  15

<210> SEQ ID NO 73
<211> LENGTH: 8
<212> TYPE: PRT
<213> ORGANISM: Artificial Sequence
<220> FEATURE:
<223> OTHER INFORMATION: Synthetic sequence

<400> SEQUENCE: 73

Asn Val Ser Tyr Arg Thr Ser Phe
1               5

<210> SEQ ID NO 74
<211> LENGTH: 5
<212> TYPE: PRT
<213> ORGANISM: Artificial Sequence
<220> FEATURE:
<223> OTHER INFORMATION: Synthetic sequence

<400> SEQUENCE: 74

Asp Tyr Gly Val Ser
1               5
```

METHOD AND COMPOSITIONS FOR CELLULAR IMMUNOTHERAPY

This application is being filed on 20 Aug. 2013, as a PCT International Patent application and claims priority to U.S. Patent Application Ser. No. 61/691,117 filed on 20 Aug. 2012, the disclosure of which is incorporated herein by reference in its entirety.

STATEMENT REGARDING FEDERALLY SPONSORED RESEARCH

This invention was made with government support under CA136551 and CA114536 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056 425USPC_SEQUENCE_LISTING.txt. The text file is 159 KB, was created on Apr. 5, 2018, and is being submitted electronically via EFS-Web.

FIELD OF THE INVENTION

The present invention relates to the field of biomedicine and specifically methods useful for cancer therapy. In particular, embodiments of the invention relate to methods and compositions for carrying out cellular immunotherapy comprising T cells modified with tumor targeting receptors.

BACKGROUND OF THE INVENTION

The adoptive transfer of human T lymphocytes that are engineered by gene transfer to express chimeric antigen receptors (chimeric receptors) specific for surface molecules expressed on tumor cells has the potential to effectively treat advanced malignancies. Chimeric receptors are synthetic receptors that include an extracellular ligand binding domain, most commonly a single chain variable fragment of a monoclonal antibody (scFv) linked to intracellular signaling components, most commonly CD3ζ alone or combined with one or more costimulatory domains. Much of the research in the design of chimeric receptors has focused on defining scFvs and other ligand binding elements that target malignant cells without causing serious toxicity to essential normal tissues, and on defining the optimal composition of intracellular signaling modules to activate T cell effector functions. However, it is uncertain whether the variations in chimeric receptor design that mediate superior in vitro function will translate reproducibly into improved in vivo therapeutic activity in clinical applications of chimeric receptor-modified T cells.

There is a need to identify methods for determining elements of chimeric receptor design that are important for therapeutic activity and cell populations to genetically modify and adoptively transfer that provide enhanced survival and efficacy in vivo.

SUMMARY OF THE INVENTION

In one aspect, the present disclosure relates to methods and compositions to confer and/or augment immune responses mediated by cellular immunotherapy, such as by adoptively transferring tumor-specific, genetically modified subsets of CD8+ or CD4+ T cells alone, or in combination. The disclosure provides for chimeric receptor nucleic acids, and vectors and host cells including such nucleic acids. The nucleic acid sequence that encodes the chimeric receptor links together a number of modular components that can be excised and replaced with other components in order to customize the chimeric receptor for efficient T cell activation and recognition of a specific target molecule or an epitope on the target molecule.

In embodiments, a chimeric receptor nucleic acid comprises a polynucleotide coding for a ligand binding domain, wherein the ligand is a molecule expressed on malignant or infected cells, a polynucleotide coding for a polypeptide spacer wherein the polypeptide spacer is about 200 amino acids or less, a polynucleotide coding for a transmembrane domain; and a polynucleotide coding for intracellular signaling domains. In embodiments, the polypeptide spacer comprises a modified IgG4 hinge region containing an amino acid sequence $X_1PPX_2P$ (SEQ ID NO: 1) that may be linked to other amino acid sequences including but not limited to the CH2 and CH3 or CH3 only sequences of the Ig Fc. It has been surprisingly found that the length of the spacer region that is presumed not to have signaling capability affects the in vivo efficacy of the T cells modified to express the chimeric receptor and needs to be customized for individual target molecules for optimal tumor or target cell recognition.

Another aspect of the disclosure provides an isolated chimeric receptor nucleic acid comprising: a polynucleotide coding for a ligand binding domain, wherein the ligand is a tumor specific antigen, viral antigen, or any other molecule expressed on a target cell population that is suitable to mediate recognition and elimination by a lymphocyte; a polynucleotide coding for a polypeptide spacer wherein the polypeptide spacer is of a customized length that is specific for each targeted ligand, wherein the spacer provides for enhanced T cell proliferation and/or cytokine production as compared to a reference chimeric receptor; a polynucleotide coding for a transmembrane domain; and a polynucleotide coding for one or more intracellular signaling domains. In embodiments, a long spacer is employed if the epitope on the target ligand is in a membrane proximal position and a short spacer is employed if the epitope on the target ligand is in a membrane distal position. The disclosure includes expression vectors and host cells comprising the isolated chimeric receptor as described herein.

Another aspect of the disclosure provides a chimeric receptor polypeptide comprising a ligand binding domain, wherein the ligand is a tumor specific antigen, viral antigen or any other molecule that is expressed on a target cell population and can be targeted to mediate recognition and elimination by lymphocytes; a polypeptide spacer wherein the polypeptide spacer is about 10-229 amino acids; a transmembrane domain; and one or more intracellular signaling domains. In embodiments, the polypeptide spacer comprises a modified IgG hinge region containing the amino acid sequence $X_1PPX_2P$ (SEQ ID NO: 1).

In another aspect, the present disclosure provides compositions to confer and/or augment immune responses mediated by cellular immunotherapy, such as by adoptively transferring tumor-specific, subset specific genetically modified CD4+ T cells, wherein the CD4+ T cells confer and/or augment the ability of CD8+ T cells to sustain anti-tumor reactivity and increase and/or maximize tumor-specific proliferation. In embodiments, the CD4+ cells are genetically modified to express a chimeric receptor nucleic acid and/or chimeric receptor polypeptide as described herein.

In another aspect, the present disclosure provides compositions to confer and/or augment immune responses mediated by cellular immunotherapy, such as by adoptively transferring tumor-specific, subset specific genetically modified CD8+ T cells. In embodiments, the CD8+ cells express a chimeric receptor nucleic acid and/or chimeric receptor polypeptide as described herein.

In another embodiment, the present invention provides an adoptive cellular immunotherapy composition having a genetically modified CD8+ cytotoxic T lymphocyte cell preparation to confer and/or augment immune responses, wherein the cytotoxic T lymphocyte cell preparation comprises CD8+ T cells that express a chimeric receptor comprising a ligand binding domain for a ligand associated with the disease or disorder, a customized spacer region, a transmembrane domain; and an intracellular signaling domain of a T cell or other receptors, such as a costimulatory domain, and/or a genetically modified helper T lymphocyte cell preparation, wherein the helper T lymphocyte cell preparation has CD4+ T cells that express a chimeric receptor comprising an antibody variable domain specific for the ligand associated with the disease or disorder, a customized spacer region, a transmembrane domain; and one or more intracellular signaling domains.

In one embodiment, the present invention provides a method of performing cellular immunotherapy in a subject having a disease or disorder by administering to the subject a genetically modified cytotoxic T lymphocyte cell preparation that provides a cellular immune response, wherein the cytotoxic T lymphocyte cell preparation comprises CD8+ T cells that have a chimeric receptor comprising a polynucleotide coding for a ligand binding domain, wherein the ligand is a tumor specific antigen, viral antigen, or any other molecule expressed on a target cell population that is suitable to mediate recognition and elimination by a lymphocyte; a polynucleotide coding for a polypeptide spacer wherein the polypeptide spacer is of a customized length that is specific for each targeted ligand, wherein the spacer provides for enhanced T cell proliferation and/or cytokine production as compared to a reference chimeric receptor, a polynucleotide coding for a transmembrane domain; and a polynucleotide coding for one or more intracellular signaling domains. In embodiment, the ligand binding domain is an extracellular antibody variable domain specific for a ligand associated with the disease or disorder. An embodiment includes a genetically modified helper T lymphocyte cell preparation that wherein the helper T lymphocyte cell preparation comprises CD4+ T cells that have a chimeric receptor comprising an a polynucleotide coding for a ligand binding domain, wherein the ligand is a tumor specific antigen, viral antigen, or any other molecule expressed on a target cell population that is suitable to mediate recognition and elimination by a lymphocyte; a polynucleotide coding for a polypeptide spacer wherein the polypeptide spacer is of a customized length that is specific for each targeted ligand, wherein the spacer provides for enhanced T cell proliferation and/or cytokine production as compared to a reference chimeric receptor; a polynucleotide coding for a transmembrane domain; and a polynucleotide coding for one or more intracellular signaling domains. In embodiments, the genetically modified CD8+ and genetically modified CD4+ cell population are coadministered. In embodiments, the T cells are autologous or allogeneic T cells.

Various modifications of the above method are possible. For example, the chimeric receptor that is expressed by the CD4+ T cell and the CD8+ T cell can be the same or different.

In another aspect, the present invention provides a method of manufacturing an adoptive immunotherapy composition by obtaining a chimeric receptor modified tumor-specific CD8+ cytotoxic T lymphocyte cell preparation that elicits a cellular immune response and expresses an antigen-reactive chimeric receptor, wherein the modified cytotoxic T lymphocyte cell preparation comprises CD8+ T cells that have a chimeric receptor comprising a ligand binding domain, wherein the ligand is a tumor specific antigen, viral antigen, or any other molecule expressed on a target cell population that is suitable to mediate recognition and elimination by a lymphocyte; a polypeptide spacer wherein the polypeptide spacer is of a customized length that is specific for each targeted ligand, wherein the spacer provides for enhanced T cell proliferation and/or cytokine production as compared to a reference chimeric receptor; a transmembrane domain; and one or more intracellular signaling domains; and/or obtaining a modified naïve or memory CD4+ T helper cell wherein the modified helper T lymphocyte cell preparation comprises CD4+ cells that have a chimeric receptor comprising a ligand binding domain, wherein the ligand is a tumor specific antigen, viral antigen, or any other molecule expressed on a target cell population that is suitable to mediate recognition and elimination by a lymphocyte; a polypeptide spacer wherein the polypeptide spacer is of a customized length that is specific for each targeted ligand, wherein the spacer provides for enhanced T cell proliferation and/or cytokine production as compared to a reference chimeric receptor, a transmembrane domain; and one or more intracellular signaling domains.

These and other embodiments of the invention are described further in the accompanying specification, drawings and claims.

(A) Design of lentiviral transgene inserts encoding a panel of CD19-specific chimeric receptors that differ in extracellular spacer length and intracellular co-stimulation. Each chimeric receptor encoded the CD19-specific single chain variable fragment derived from the FMC63 mAb in a VL-VH orientation, an IgG4-derived spacer domain of Hinge-CH2-CH3 (long spacer, 229 AA) or Hinge only (short spacer, 12 AA), and a signaling module containing CD3ζ with CD28 or 4-1BB alone or in tandem. Each chimeric receptor cassette contains a truncated EGFR marker encoded downstream of a cleavable 2A element. (B, C) Polyclonal T cell lines modified with each of the CD19-chimeric receptor constructs were prepared from purified CD8+ CD45RO+ CD62L+ central memory T cells ($T_{CM}$) of normal donors. Following lentiviral transduction, transgene-positive T cells in each cell line were purified using the tEGFR marker and expanded for in vitro and in vivo experiments. (D) MFI after staining for the tEGFR marker shows equivalent transgene expression in T cells modified with each of the CD19-chimeric receptors.

Figure 14:
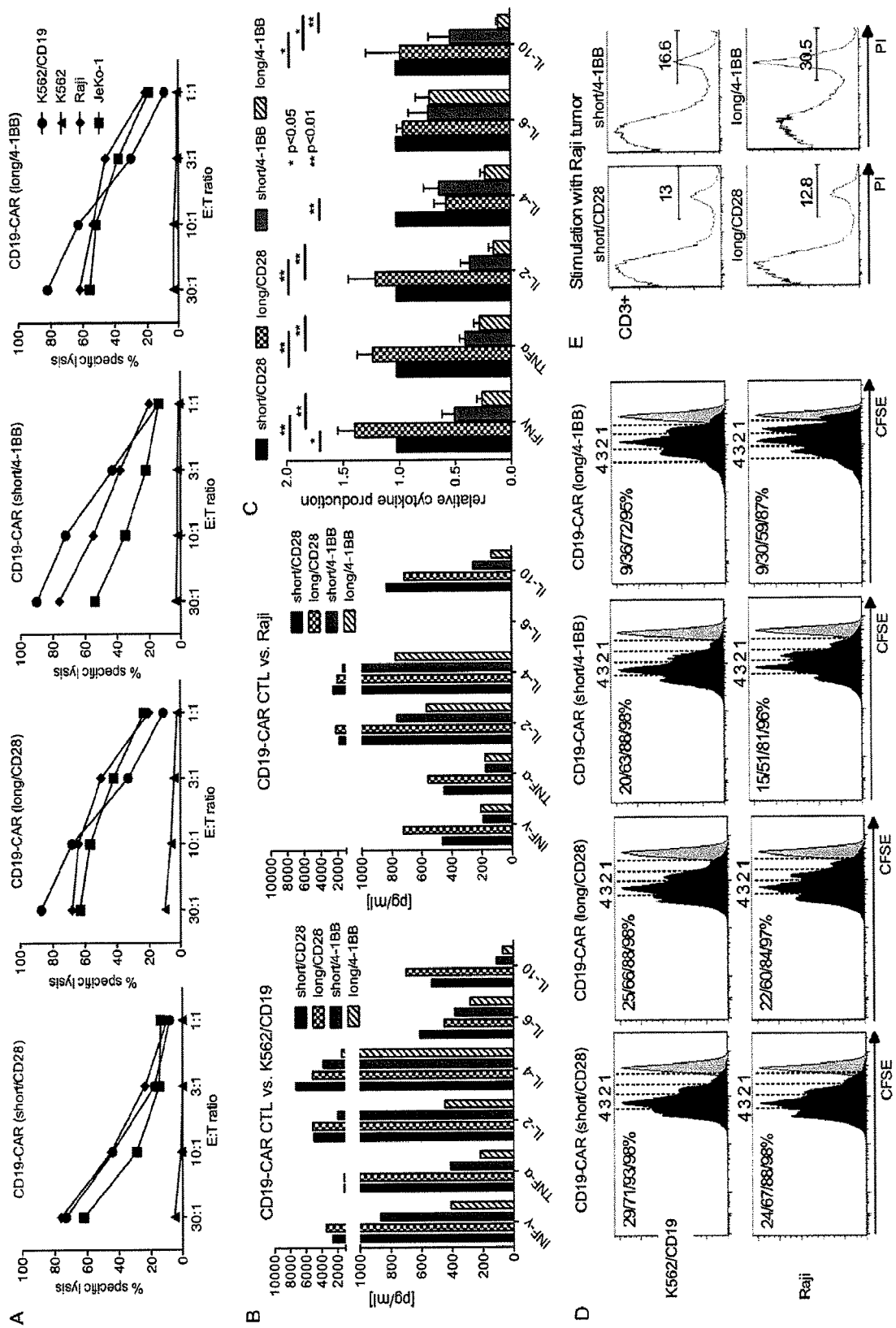

FIG. 14: In vitro cytotoxicity, cytokine production, and proliferation of T cells modified with distinct CD19-chimeric receptors. (A) Cytolytic activity of T cells expressing the various CD19-chimeric receptors against CD19+ and control target cells. (B) Multiplex cytokine assay of supernatants obtained after 24 hours from triplicate co-cultures of T cells expressing the various CD19-chimeric receptors and K562 cells transfected with CD19, and CD19+ Raji cells. (C) Comparison of cytokine production by T cells expressing the various CD19-chimeric receptors. Multiplex cytokine data from 6 independent experiments were normalized (cytokine release by CD19-chimeric receptor 'short/CD28' CTL=1) and analyzed by Student's t-test. (D) CFSE dye dilution was used to measure proliferation of CD19-chimeric receptor T cells 72 hours after stimulation with K562/CD19 (upper panel) and CD19+ Raji tumor cells (lower panel) without addition of exogenous cytokines. For analysis, triplicate wells were pooled and the proliferation of live (PI−), CD8+ T cells analyzed. Numbers above each histogram indicate the number of cell divisions the proliferating subset underwent, and the fraction of T cells in each gate that underwent ≥4/3/2/1 cell divisions is provided in the upper left of each plot. (E) PI staining was performed at the end of a 72-hour co-culture of T cells expressing the various CD19-chimeric receptors with Raji tumor cells. The percentage of PI+ cells within in chimeric receptor T cell line (CD3+) is provided in each histogram.

Figure 15:
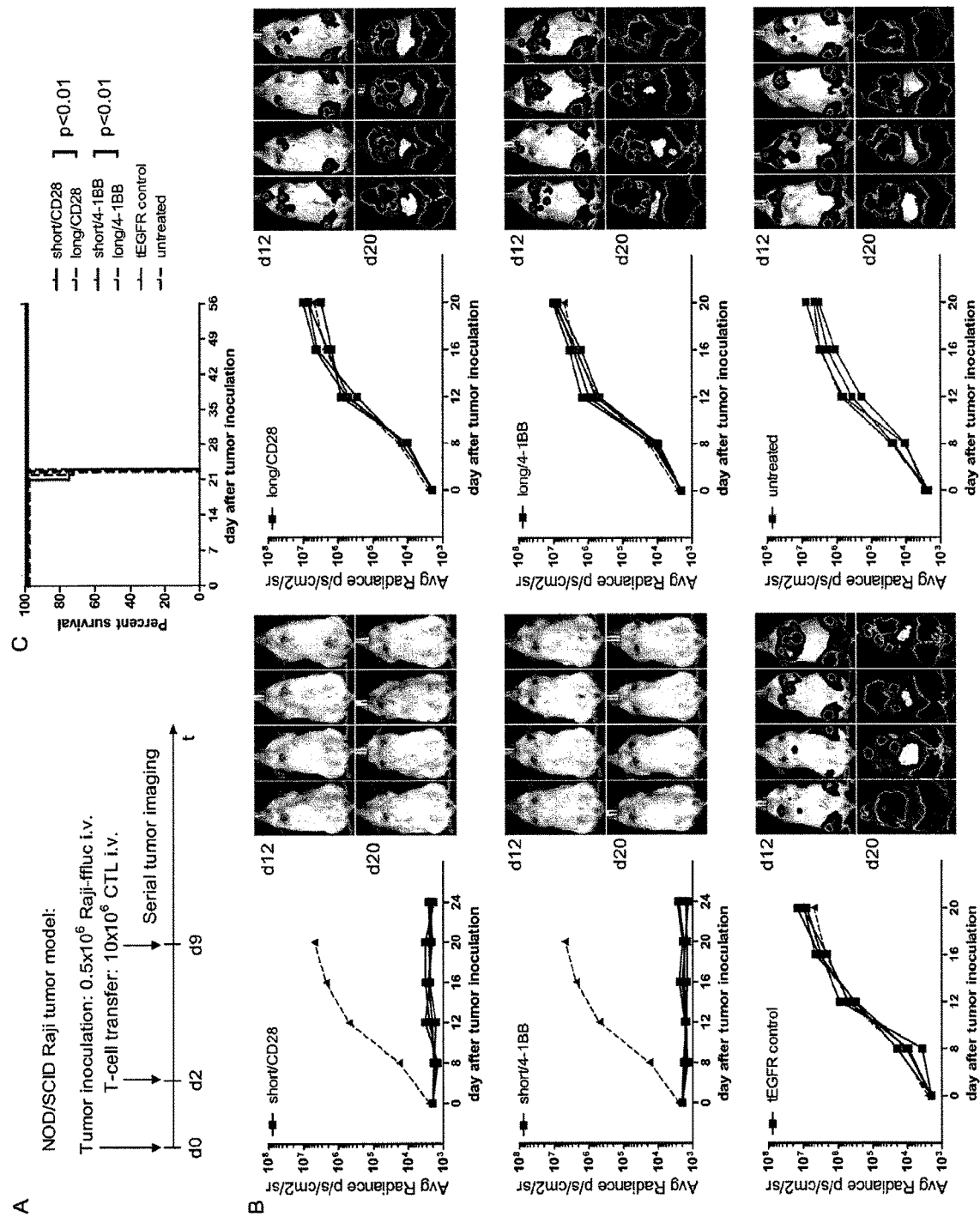

FIG. 15: CD19-chimeric receptor T cells with a short extracellular spacer domain eradicate Raji tumors in NOD/SCID mice. (A) Cohorts of mice were inoculated with Raji-ffluc via tail vein injection, and T cells transduced with CD19-chimeric receptors containing long and short spacer domains or with tEGFR alone were administered 2 and 9 days after tumor inoculation by tail vein injection. Tumor progression and distribution was evaluated by serial bioluminescence imaging after injection of luciferin substrate. (B) Serial bioluminescence imaging of tumor in cohorts of mice either treated with T cells expressing CD19-chimeric receptors with short spacer ('short/CD28' and 'short/4-1BB') and long spacer ('long/CD28' and 'long/4-1BB') domains, with T cells transduced with the tEGFR control vector, or untreated. Each diagram representing cohorts of mice treated with CD19-chimeric receptor or tEGFR transduced T cells also shows the mean of tumor progression in untreated mice for comparison (red triangles). (C) Kaplan-Meier analyses of survival of untreated mice and mice treated with T cells expressing CD19-chimeric receptors with short spacer ('short/CD28' and 'short/4-1BB'), long spacer ('long/CD28' and 'long/4-1BB') domains, and with control tEGFR. Statistical analyses were performed using the log-rank test. The data shown in B and C are representative of results obtained in 3 independent experiments.

Figure 16:
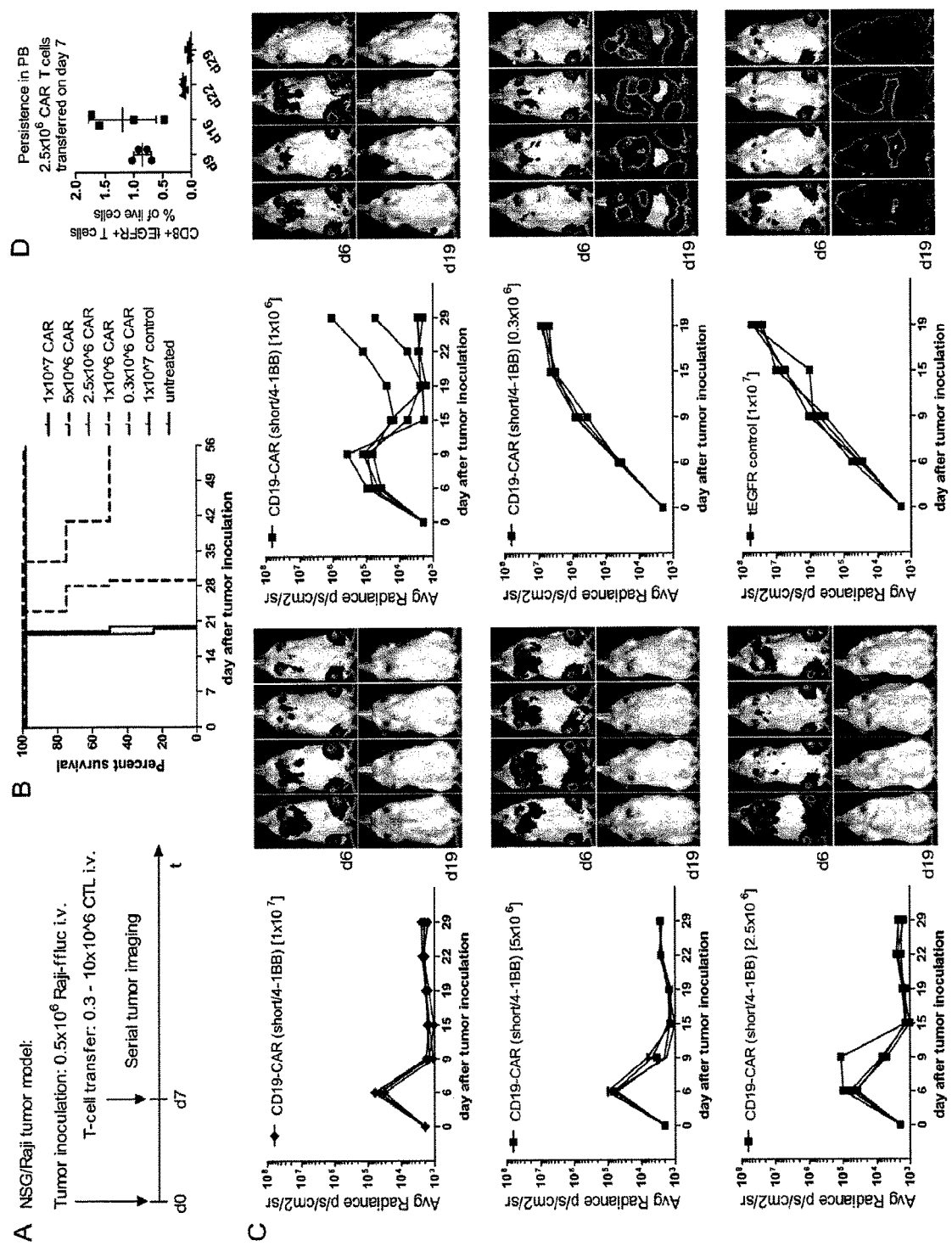

FIG. 16: CD19-chimeric receptor T cells with a short spacer (short/4-1BB) eradicate established Raji tumors in NSG mice in a dose-dependent manner. (A) Mice were inoculated with Raji-ffluc via tail vein injection and tumor engraftment confirmed by bioluminescence imaging on day 6. On day 7, mice received a single i.v. injection of various doses of T cells transduced with the CD19-chimeric receptor 'short/4-1BB' or with the tEGFR-control lentivirus. (B, C) Dose dependent anti-tumor efficacy of T cells expressing the CD19-chimeric receptor 'short/4-1BB'. A control cohort of mice received a single high dose of T cells modified with tEGFR alone. (D) Persistence of CD19-chimeric receptor T cells following adoptive transfer into NSG/Raji mice. Flow cytometric analysis of peripheral blood (eye bleeds) in the cohort of mice treated with $2.5 \times 10^6$ CD19-chimeric receptor 'short/4-1BB' T cells. The frequency of CD8+ tEGFR+ T cells is shown as percentage of live peripheral blood cells.

Figure 17:
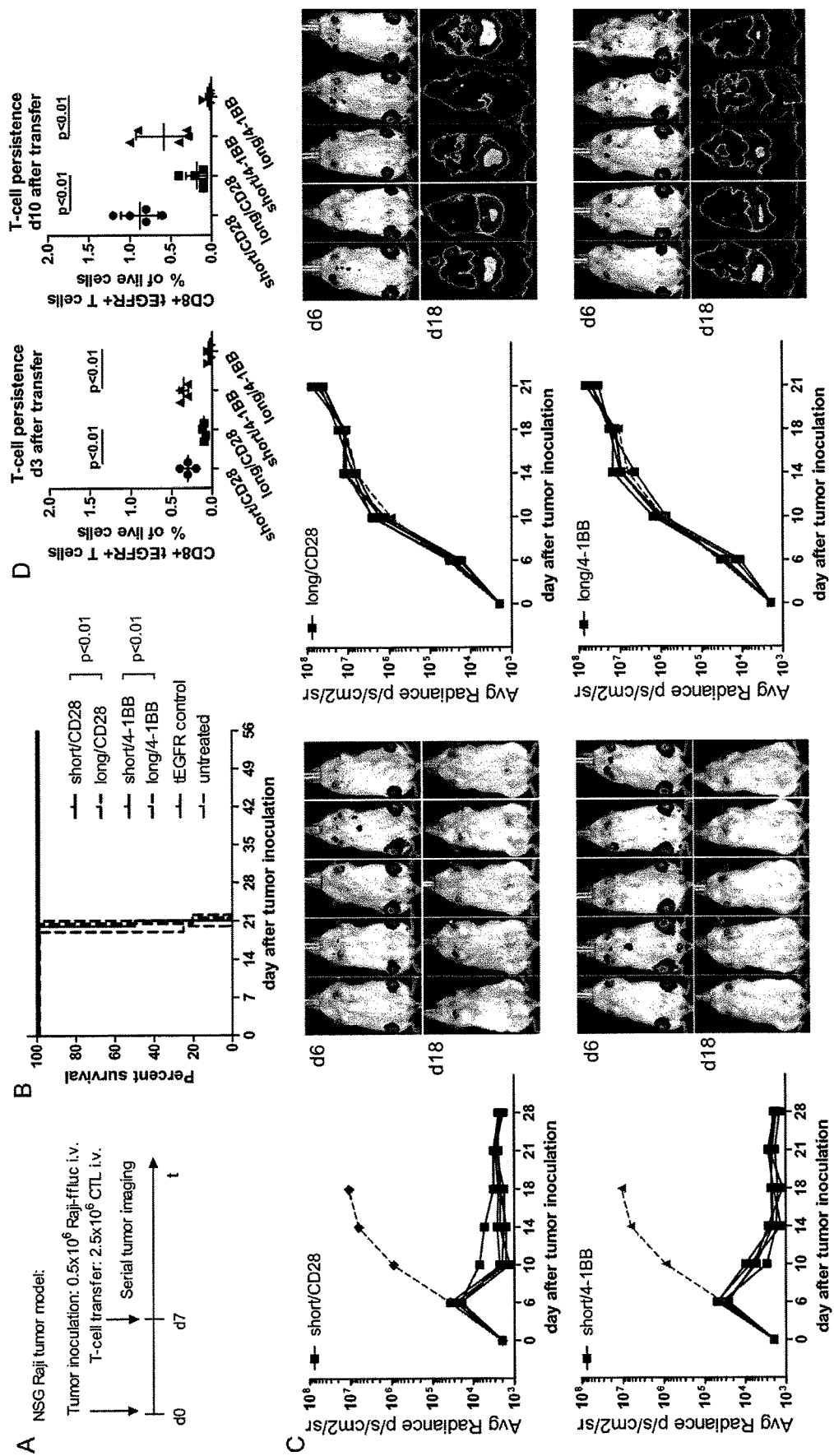

FIG. 17: T cells expressing CD19-chimeric receptors with a short spacer and either CD28 or 4-1BB are more effective against established lymphoma than those expressing CD19-chimeric receptors with a long spacer. (A) NSG mice were inoculated with Raji-ffluc on day 0, and treated on day 7 with one dose of $2.5 \times 10^6$ CD19 chimeric receptor T cells expressing short or long spacer and either CD28 or 4-1BB costimulatory domain. (B) Kaplan-Meier analyses of survival of mice in each of the treatment groups. Statistical analyses were performed using the log-rank test. (C) Bioluminescence imaging of cohorts of mice treated with T cells expressing CD19-chimeric receptors with short spacers ('short/CD28' and 'short/4-1BB'), and long spacers ('long/CD28' and 'long/4-1BB'). The mean tumor burden observed in untreated mice at each time point is shown in each diagram for comparison (triangles). (D) In vivo persistence of T cells expressing CD19-chimeric receptor with short spacer domain is enhanced compared to T cells expressing CD19-chimeric receptors with long spacer domain. The frequency of CD8+ tEGFR+ T cells in the peripheral blood obtained at day 3 and 10 after transfer was determined by flow cytometry and is shown as percentage of live (PI−) peripheral blood cells. Statistical analyses were performed by Student's t-test. The data shown in B-D are representative for results obtained in 3 independent experiments.

Figure 18:
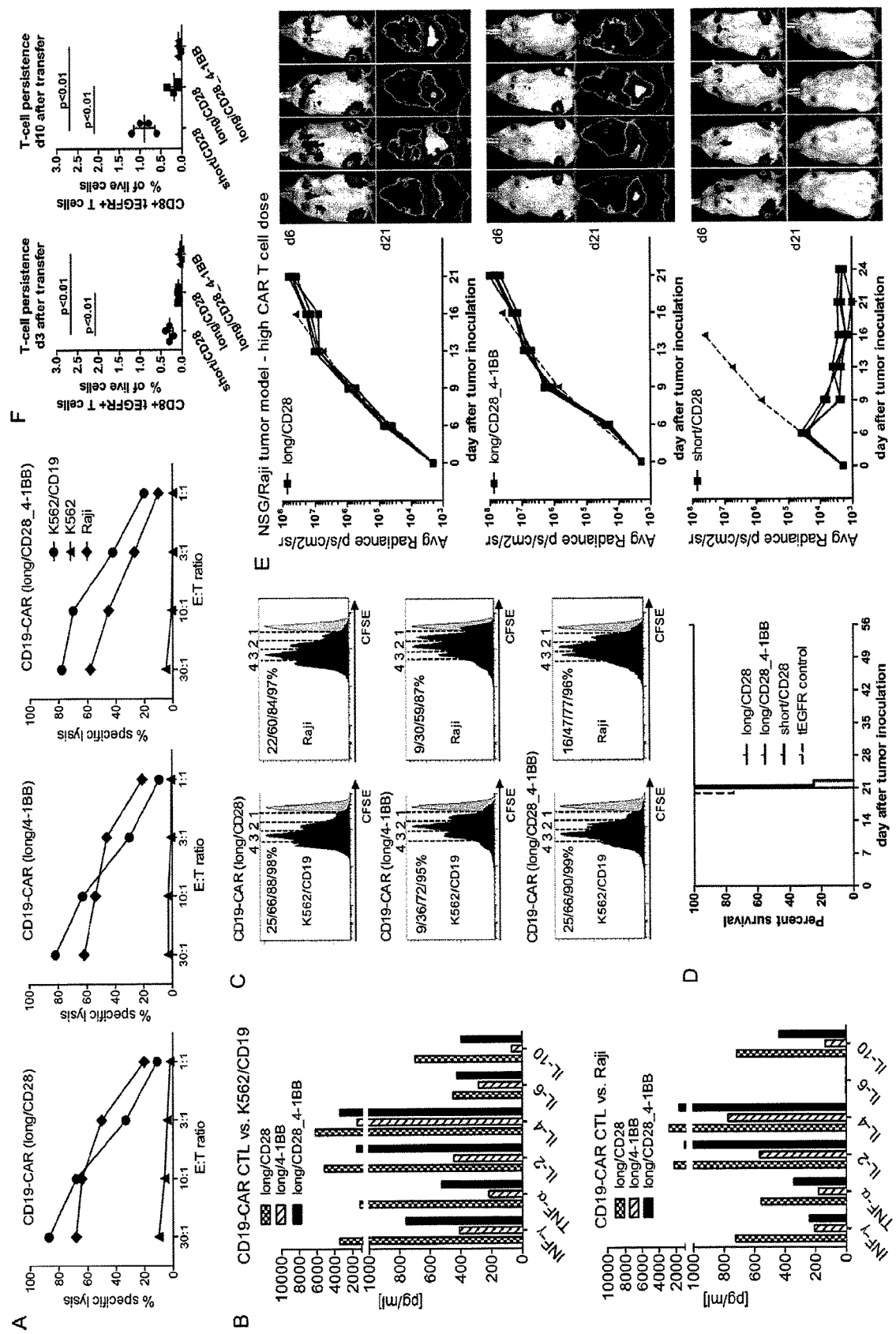

FIG. 18: Increasing chimeric receptor T cell dose or augmenting costimulatory signaling does not improve the anti-tumor efficacy of CD19-chimeric receptors with a long spacer domain against established lymphoma. (A) Cytolytic activity of T cells expressing 'long/CD28', 'long/4-1BB' and 'long/CD28_4-1BB' CD19 chimeric receptors against CD19+ and control target cells. (B) Multiplex cytokine assay of supernatant obtained after 24 hours from triplicate co-cultures of K562/CD19 and Raji tumor cells with T cells expressing the various CD19-chimeric receptors. (C) Evaluation of proliferation of CD19-chimeric receptor T cells 72 hours after stimulation with CD19+ tumor cells (K562/CD19—left panel; Raji—right panel) by CFSE dye dilution. For analysis, triplicate wells were pooled and the proliferation of live (PI−) CD8+ T cells analyzed. Numbers above each histogram indicate the number of cell divisions the proliferating subset underwent, and the fraction of T cells in each gate that underwent ≥4/3/2/1 cell divisions is provided in the upper left of each plot. (D) Kaplan-Meier analyses of survival of mice treated with T cells expressing CD19-chimeric receptors with short ('short/CD28') and long spacer domain ('long/CD28' and 'long/CD28_4-1BB'), or T cells modified with a tEGFR-encoding control lentiviral vector. Statistical analyses were performed using the log-rank test. (E) Bioluminescence imaging of cohorts of mice treated with T cells expressing CD19-chimeric receptors with short spacer ('short/CD28'), and long spacers ('long/CD28 and 'long/CD28_4-1BB'). Diagrams show mean tumor progression in untreated mice for comparison (red triangles). (F) In vivo persistence of T cells expressing the various CD19-chimeric receptors. The frequency of CD8+ tEGFR+ T cells in the peripheral blood obtained at day 3 and 10 after transfer was determined by flow cytometry and is shown as percentage of live (PI−) peripheral blood cells. Statistical analyses were performed by Student's t-test.

Figure 19:
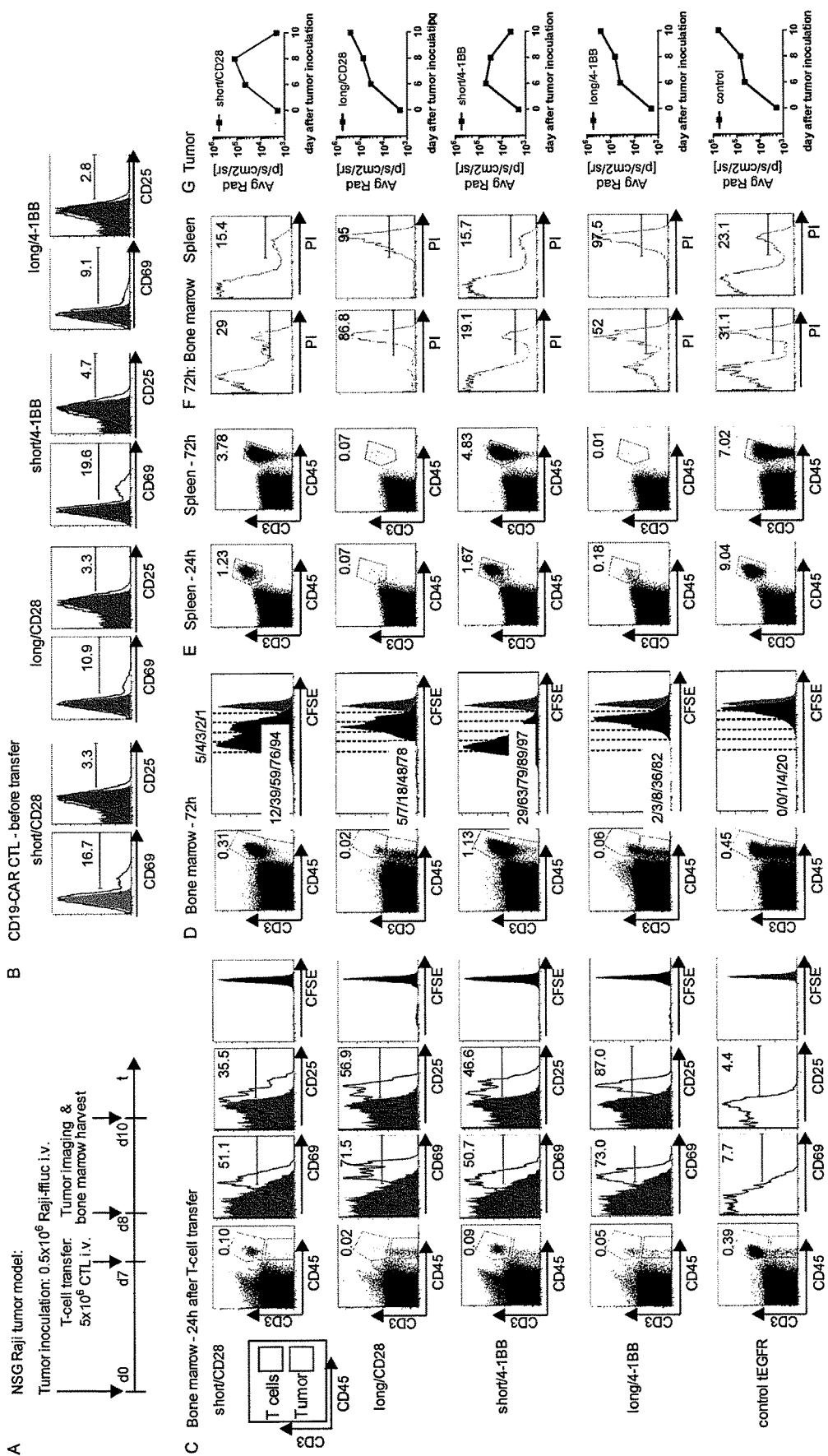

FIG. 19: CD19-chimeric receptor T cells with a long spacer domain are activated by tumor in vivo but fail to increase in cell number. (A) Expression of CD69 and CD25 on T cells modified with each CD19-chimeric receptor prior to transfer into NSG/Raji mice. (B) Cohorts of mice were inoculated with Raji-ffluc tumor cells and 7 days later received CFSE-labeled CD19-chimeric receptor transduced or control T cells. Bone marrow and spleens were harvested from subgroups of mice 24 and 72 hours after T cell administration. (C, D) Multiparameter flow cytometric analysis of bone marrow mononuclear cells obtained 24 hours (C) and 72 hours (D) after T cell transfer. Dot plots show anti CD3 and anti CD45 staining after gating on Pr cells to detect viable human T cells. The $CD3^+$ $CD45^+$ gate contains Raji tumor cells. Expression of CD25 and CD69 on live ($PI^-$) $CD3^+$ $CD45^+$ T cells is shown in the histograms. (E) Frequency of $CD3^+$ $CD45^+$ T cells in spleens obtained 24 and 72 hours after T cell transfer. Dot plots are gated on live $PI^-$ splenocytes and the percentage of $CD3^+$ $CD45^+$ T cells is shown in each plot. (F) PI staining of bone marrow and splenocytes hours after T cell transfer into NSG/Raji mice. The numbers in the histograms indicate the percentage of $PI^+$ cells within the $CD3^+$ population. (G) Bioluminescence imaging of cohorts of mice treated with T cells expressing CD19-chimeric receptors with short spacer ('short/CD28' and 'short/4-1BB'), long spacers ('long/CD28 and 'long/4-1BB'), or control T cells.

Figure 20:
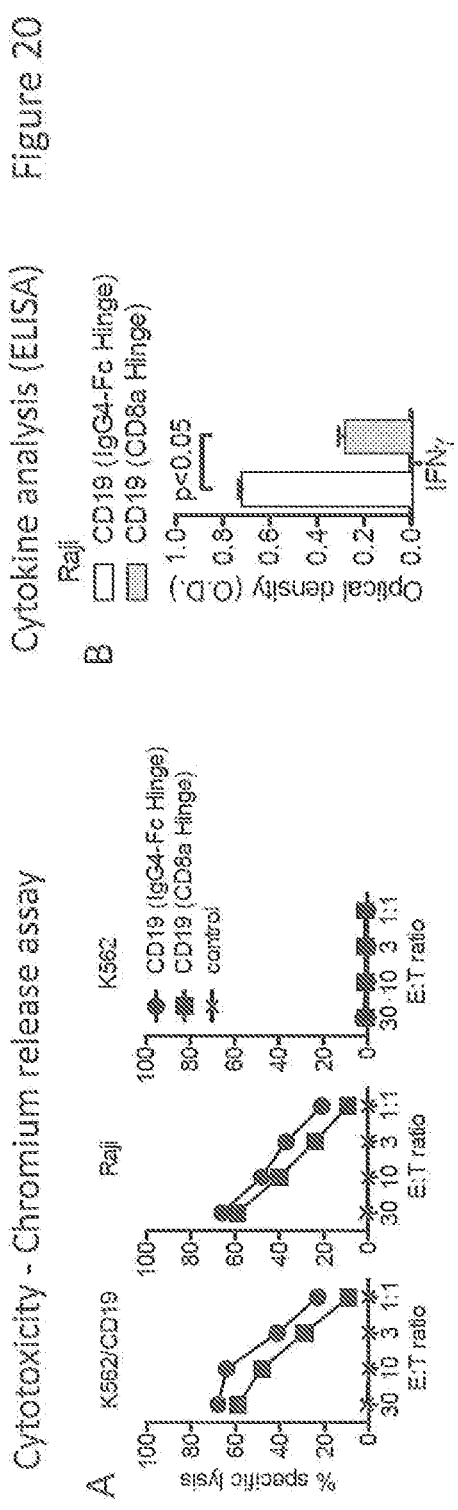
Figure 20:
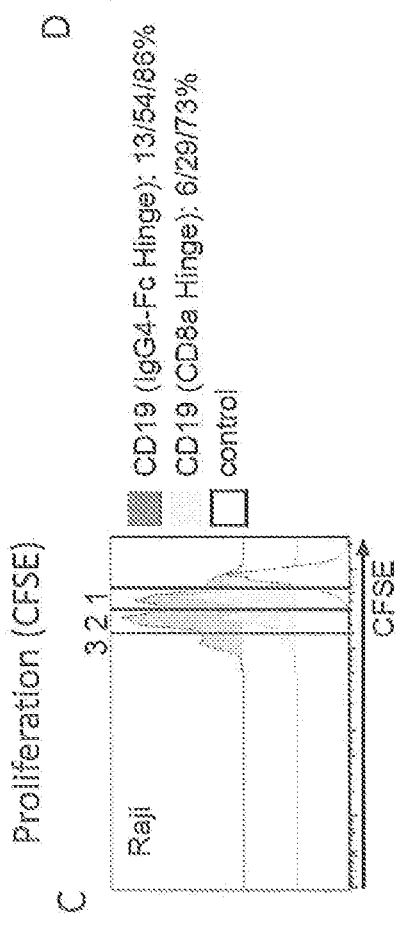
Figure 20:
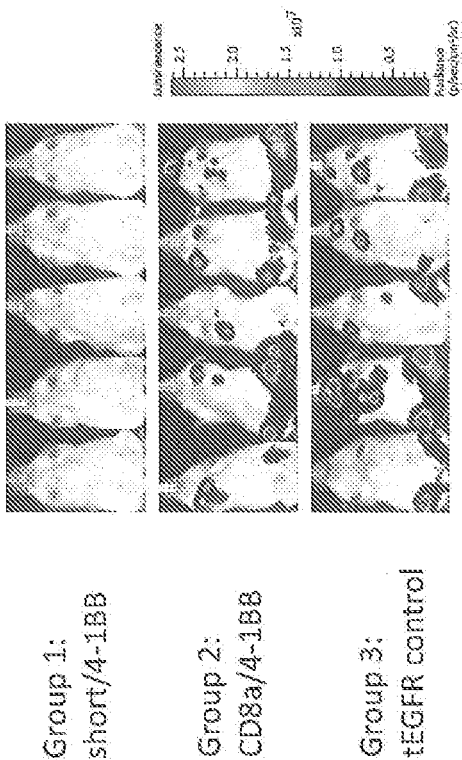

FIG. 20: T cells expressing CD19 chimeric receptors with 4-1BB and CD3zeta and a modified IgG4-Fc binge exhibit superior in vitro and in vivo function compared to T cells expressing CD19 chimeric receptors with 4-1BB and CD3zeta and a CD8 alpha hinge. A. Cytolytic activity of CD19 chimeric receptor modified T-cells with IgG4 Fc hinge, CD8 alpha hinge and control T cells against $Cr^{51}$-labeled K562 cells transfected with CD19, Raji lymphoma cells that express CD19, and K562 control T cells. Lysis is shown at different E/T ratios in a 4 hour $Cr^{51}$ release assay. B. Interferon gamma production by $5 \times 10^4$ T cells expressing a CD19 chimeric receptor with an IgG4 Fc hinge or CD8 alpha hinge after a 24-hour coculture with Raji tumor cells. O.D. of 1 corresponds to ~500 pg/ml of interferon gamma. C. CFSE dye dilution assay to measure proliferation of T cells expressing a CD19 chimeric receptor with an IgG4 Fc hinge or CD8 alpha hinge and T cells that express tEGFR alone (control) after 72 hours coculture with CD19 positive Raji lymphoma cells. Numbers above each histogram indicate the number of cell divisions the proliferating cell subset underwent. The fraction of T cells in each gate that underwent ≥3/2/1 cell divisions is provided next to the plot. D. In vivo antitumor activity of T cells expressing a CD19 chimeric receptor with an IgG4 Fc hinge (group 1) or CD8 alpha hinge (group 2) and T cells that express tEGFR alone (group 3) in NSG mice inoculated with Raji tumor cells expressing firefly luciferase (ffluc). Mice were imaged 17 days after tumor inoculation and 10 days after T cell inoculation. The data shows greater tumor burden in mice treated with control tEGFR T cells (group 3) or with CD19 chimeric receptor CD8 alpha hinge T cells (group 2) compared with mice treated with CD19 chimeric receptor IgG4 Fc hinge T cells (group 1).

DETAILED DESCRIPTION

Unless defined otherwise, all technical and scientific terms used herein have the same meaning as commonly understood by one of ordinary skill in the art to which the invention pertains.

"About" as used herein when referring to a measurable value is meant to encompass variations of ±20% or ±10%, more preferably ±5%, even more preferably ±1%, and still more preferably ±0.1% from the specified value.

"Activation", as used herein, refers to the state of a T cell that has been sufficiently stimulated to induce detectable cellular proliferation, cytokine production or expression of cell surface markers such as CD69 and CD25, or detectable effector functions.

"Activation Induced cell death" as used herein refers to a state of a T cell that is activated but is not able to proliferate for more than 2 generations and exhibits markers of apoptosis.

"Antigen" or "Ag" as used herein refers to a molecule that provokes an immune response. This immune response may involve either antibody production, or the activation of specific immunologically-competent cells, or both. It is readily apparent that an antigen can be generated synthesized, produced recombinantly or can be derived from a biological sample. Such a biological sample can include, but is not limited to a tissue sample, a tumor sample, a cell or a biological fluid.

"Anti-tumor effect" as used herein, refers to a biological effect, which can be manifested by a decrease in tumor volume, a decrease in the number of tumor cells, a decrease in the number of metastases, an increase in life expectancy, or a decrease of various physiological symptoms associated with the cancerous condition. An "anti-tumor effect" can also be manifested by a decrease in recurrence or an increase in the time before recurrence.

"Chimeric receptor" as used herein refers to a synthetically designed receptor comprising a ligand binding domain of an antibody or other protein sequence that binds to a molecule associated with the disease or disorder and is linked via a spacer domain to one ore more intracellular signaling domains of a T cell or other receptors, such as a costimulatory domain.

"Co-stimulatory domain," as the term is used herein refers to a signaling moiety that provides to T cells a signal which, in addition to the primary signal provided by for instance the CD3 zeta chain of the TCR/CD3 complex, mediates a T cell response, including, but not limited to, activation, proliferation, differentiation, cytokine secretion, and the like. A co-stimulatory domain can include all or a portion of, but is not limited to, CD27, CD28, 4-1BB, OX40, CD30, CD40, ICOS, lymphocyte function-associated antigen-1 (LFA-1), CD2, CD7, LIGHT, NKG2C, B7-H3, and a ligand that specifically binds with CD83. In embodiments, the co-stimulatory domain is an intracellular signaling domain that interacts with other intracellular mediators to mediate a cell response including activation, proliferation, differentiation and cytokine secretion, and the like.

"Coding for" are used herein refers to the property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system. A "nucleic acid sequence coding for a polypeptide" includes all nucleotide sequences that are degenerate versions of each other and that code for the same amino acid sequence.

"Cytotoxic T lymphocyte" (CTL) as used herein refers to a T lymphocyte that expresses CD8 on the surface thereof (i.e., a $CD8^+$ T cell). In some embodiments such cells are preferably "memory" T cells ($T_M$ cells) that are antigen-experienced.

"Central memory" T cell (or "$T_{CM}$") as used herein refers to an antigen experienced CTL that expresses CD62L or CCR-7 and CD45RO on the surface thereof, and does not express or has decreased expression of CD45RA as compared to naive cells. In embodiments, central memory cells are positive for expression of CD62L, CCR7, CD28, CD127, CD45RO, and CD95, and have decreased expression of CD54RA as compared to naïve cells.

"Effector memory" T cell (or "$T_{EM}$") as used herein refers to an antigen experienced T cell that does not express or has decreased expression of CD62L on the surface thereof as compared to central memory cells, and does not express or has decreased expression of CD45RA as compared to naïve cell. In embodiments, effector memory cells are negative for expression of CD62L and CCR7, compared to naïve cells or central memory cells, and have variable expression of CD28 and CD45RA.

"Naïve" T cells as used herein refers to a non antigen experienced T lymphocyte that expresses CD62L and CD45RA, and does not express CD45RO– as compared to central or effector memory cells. In some embodiments, naïve CD8+ T lymphocytes are characterized by the expression of phenotypic markers of naïve T cells including CD62L, CCR7, CD28, CD127, and CD45RA.

"Effector" "$T_E$" T cells as used herein refers to a antigen experienced cytotoxic T lymphocyte cells that do not express or have decreased expression of CD62L, CCR7, CD28, and are positive for granzyme B and perforin as compared to central memory or naïve T cells.

"Enriched" and "depleted" as used herein to describe amounts of cell types in a mixture refers to the subjecting of the mixture of the cells to a process or step which results in an increase in the number of the "enriched" type and a decrease in the number of the "depleted" cells. Thus, depending upon the source of the original population of cells subjected to the enriching process, a mixture or composition may contain about 60, 70, 80, 90, 95, or 99 percent or more (in number or count) of the "enriched" cells and about 40, 30, 20, 10, 5 or 1 percent or less (in number or count) of the "depleted" cells.

"Epitope" as used herein refers to a part of an antigen or molecule that is recognized by the immune system including antibodies, T cells, and/or B cells. Epitopes usually have at least 7 amino acids and can be linear or conformational.

"Isolated," when used to describe the various polypeptides disclosed herein, means polypeptide or nucleic acid that has been identified and separated and/or recovered from a component of its natural environment. Preferably, the isolated polypeptide or nucleic acid is free of association with all components with which it is naturally associated. Contaminant components of its natural environment are materials that would typically interfere with diagnostic or therapeutic uses for the polypeptide or nucleic acid, and may include enzymes, hormones, and other proteinaceous or non-proteinaceous solutes.

"Intracellular signaling domain" as used herein refers to all or a portion of one or more domains of a molecule (here the chimeric receptor molecule) that provides for activation of a lymphocyte. Intracellular domains of such molecules mediate a signal by interacting with cellular mediators to result in proliferation, differentiation, activation and other effector functions. In embodiments, such molecules include all or portions of CD28, CD3, 4-1BB, and combinations thereof.

"Ligand" as used herein refers to a substance that binds specifically to another substance to form a complex. Example of ligands include epitopes on antigens, molecules that bind to receptors, substrates, inhibitors, hormones, and activators. "Ligand binding domain" as used herein refers to substance or portion of a substance that binds to a ligand. Examples of ligand binding domains include antigen binding portions of antibodies, extracellular domains of receptors, and active sites of enzymes.

"Operably linked" as used herein refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Percent (%) amino acid sequence identity" with respect to the chimeric receptor polypeptide sequences identified herein is defined as the percentage of amino acid residues in a candidate sequence that are identical with the amino acid residues in the reference sequence for each of the ligand binding domain, spacer, transmembrane domain, and/or the lymphocyte activating domain, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, % amino acid sequence identity values generated using the WU-BLAST-2 computer program [Altschul et al., Methods in Enzymology, 266:460-480 (1996)] uses several search parameters, most of which are set to the default values. Those that are not set to default values (i.e., the adjustable parameters) are set with the following values: overlap span=1, overlap fraction=0.125, word threshold (T)=11 and scoring matrix=BLOSUM62. A % amino acid sequence identity value is determined by dividing (a) the number of matching identical amino acid residues between the each or all of the polypeptide amino acid sequence of the reference chimeric receptor sequence provided in Table 2 and the comparison amino acid sequence of interest as determined by WU-BLAST-2 by (b) the total number of amino acid residues of the polypeptide of interest.

"Chimeric receptor variant polynucleotide" or "chimeric receptor variant nucleic acid sequence" as used herein refers to a polypeptide-encoding nucleic acid molecule as defined below having at least about 80% nucleic acid sequence identity with the polynucleotide acid sequence shown in Table 1 or a specifically derived fragment thereof, such as polynucleotide coding for an antigen binding domain, a polynucleotide encoding a spacer domain, a polynucleotide coding for a transmembrane domain and/or a polynucleotide coding for a lymphocyte stimulatory domain. Ordinarily, a chimeric receptor variant of polynucleotide or fragment thereof will have at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with the nucleic acid sequence as shown in Table or a derived fragment thereof. Variants do not encompass the native nucleotide sequence. In this regard, due to the degeneracy of the genetic code, one of ordinary skill in the art will immediately recognize that a large number of chimeric receptor variant polynucleotides having at least about 80% nucleic acid sequence identity to the nucleotide sequence of Table 1 will encode a polypeptide having an amino acid sequence which is identical to the amino acid sequence of Table 2.

"Substantially purified" refers to a molecule that is essentially free of other molecule types or a cell that is essentially free of other cell types. A substantially purified cell also refers to a cell, which has been separated from other cell types with which it is normally associated in its naturally occurring state. In some instances, a population of substantially purified cells refers to a homogenous population of cells.

"Not substantially found" when used in reference the presence of a tumor antigen or other molecules on normal cells refers to the percentage of a normal cell type that has the antigen or molecule, and/or the density of the antigen on the cells. In embodiments, not substantially found means that the antigen or molecule is found on less than 50% of normal cell type and/or at a 50% less density as compared to the amount of cells or antigen found on a tumor cell or other diseased cell.

"T cells" or "T lymphocytes" as used herein may be from any mammalian, preferably primate, species, including monkeys, dogs, and humans. In some embodiments the T cells are allogeneic (from the same species but different donor) as the recipient subject; in some embodiments the T cells are autologous (the donor and the recipient are the same); in some embodiments the T cells are syngeneic (the donor and the recipients are different but are identical twins).

MODES OF THE DISCLOSURE

The disclosure provides for chimeric receptor nucleic acids, and vectors and host cells including such nucleic acids. The chimeric receptor nucleic acid comprises a number of modular components that can be excised and replaced with other components in order to customize the chimeric receptor for a specific target molecule. The disclosure provides that one of the modular components is the spacer component. It has been surprisingly found that the length of the spacer region that is presumed not to have signaling capability affects the in vivo efficacy of the T cells modified to express the chimeric receptor and needs to be customized for individual target molecules for enhanced therapeutic activity.

In one aspect, methods and nucleic acid constructs are provided to design a chimeric receptor that has improved tumor recognition, increased T cell proliferation and/or cytokine production in response to the ligand as compared to a reference chimeric receptor. In embodiments, a library of nucleic acids is provided, wherein each nucleic acid codes for a spacer region that differs from the others in sequence and length. Each of the nucleic acids can then be used to form a chimeric receptor nucleic acid construct that can be tested in vivo (in an animal model) and/or in vitro so that a spacer can be selected that provides for improved tumor recognition, increased T cell proliferation and/or cytokine production in response to the ligand.

In embodiments, a chimeric receptor nucleic acid comprises a polynucleotide coding for a ligand binding domain, wherein the ligand is a tumor or viral specific antigen or molecule, a polynucleotide coding for a customized polypeptide spacer, wherein the spacer provides for enhanced T cell proliferation; a polynucleotide coding for a transmembrane domain; and a polynucleotide coding for one or more intracellular signaling domains. In embodiments, a long spacer is employed if the epitope of the target molecule is membrane proximal on the target cell and a short spacer is employed if the epitope of the target molecule is membrane distal on the target cell.

The design of a chimeric receptor can be customized depending on the type of tumor or virus, the target antigen or molecule present on the tumor, the affinity of the antibody for the target molecule, the flexibility needed for the antigen binding domain, and/or the intracellular signaling domain. In embodiments, a number of chimeric receptor constructs are tested in vitro and in in vivo models to determine the ability of T cells modified with the receptor to kill tumor cells in immunodeficient mice and to proliferate and persist after adoptive transfer. In embodiments, a chimeric receptor is selected that provides for capability of at least 30% of the cells to proliferate through at least two generations in vitro and/or within 72 hours after introduction in vivo. In embodiments, a chimeric receptor is not selected that results in greater than 50% of the cells undergoing activation induced cell death (AICD) within 72 hours in vivo in immunodeficient mice, and fails to eradicate tumor cells.

Depending on whether the target molecule is present on a subject's tumor cells, the chimeric receptor includes a ligand binding domain that specifically binds to that target molecule. In embodiments, a subject's tumor cells are characterized for cell surface tumor molecules. The target molecule may be selected based on a determination of its presence on a particular subject's tumor cells. In embodiments, a target molecule is selected that is a cell surface molecule found predominantly on tumor cells and not found on normal tissues to any substantial degree. In embodiments, an antibody is selected to bind to an epitope on the targeted cell surface molecule. In some cases, the epitope is characterized with respect to its proximity to the cell membrane. An epitope is characterized as proximal to the membrane when it is predicted or known by structural analysis to reside closer to the target cell membrane than alternative epitopes that are predicted or known by structural analysis to reside a greater distance from the target cell membrane. In embodiments, the affinity of the antibody from which the scFV is constructed is compared by binding assays, and antibodies with different affinities are examined in chimeric receptor formats expressed in T cells to determine which affinity confers optimal tumor recognition, based on superior cytotoxicity of target cells, and/or T cell cytokine production and proliferation.

In addition, the spacer region of the chimeric receptor may be varied to optimize T cell recognition of the ligand on the target cell. In embodiments, when an antibody binds to an epitope on the target cell that is very proximal to the membrane, a spacer is selected that is longer than about 15 amino acids. For example, in embodiments, if the epitope or portion thereof on the target antigen is in the first 100 amino acids of the linear sequence of the extracellular domain adjacent to the transmembrane domain, a long spacer region may be selected. In embodiments, when an antibody binds to an epitope on the target cell that is distal to the membrane, a spacer is selected that is about 119 or 15 amino acids or less. For example, in embodiments, when the epitope or portion thereof is found in the 150 amino acids of the linear sequence of the extracellular domain from the terminus, a short or inetermediate spacer may be utilized. In embodiments, a spacer comprises an amino acid sequence $X_1PPX_2P$ (SEQ ID NO: 1).

A variety of combinations of primary and costimulatory intracellular signaling domain may be employed to enhance the in vivo efficacy of the chimeric receptor. In embodiments, different constructs of the chimeric receptor can be tested in an in vivo animal model to determine efficacy for tumor killing. In embodiments, a costimulatory intracellular signaling domain is selected from the group consisting of CD28 and modified versions thereof, 4-1BB and modified versions thereof and combinations thereof. Other costimulatory domains, such as OX40 may be incorporated.

CD8+ central memory T cells have an intrinsic programming that allows them to persist for extended periods after administration, which makes them a preferred subset of CD8+ T cells for immunotherapy. In embodiments, CD19 specific chimeric receptor modified cytotoxic T cells prepared from sort purified CD8+ central memory T cells are administered in the presence or absence of CD4+CD19 specific chimeric receptor-modified T cells. In embodiments, tumor-specific CD4+ T cells exert anti-tumor reactivity and provide help to tumor-specific CD8+ T cells in vitro and in vivo. In a specific embodiment, tumor-specific CD4+ T cells or $CD4^+$ T cells selected from the naïve or the central memory subsets are utilized alone or in combination with $CD8^+$ $T_{CM}$.

Nucleic Acids, Vectors, and Polypeptides

The disclosure provides a chimeric receptor nucleic acid useful for transforming or transducing lymphocytes for use in adoptive immunotherapy. In embodiments, the nucleic acid contains a number of modular components that provide for easy substitution of elements of the nucleic acid. While not meant to limit the scope of the disclosure, it is believed that the chimeric receptor for each tumor antigen is desirably customized in terms of components in order to provide for in vivo efficacy and efficient expression in mammalian cells. For example, in a specific embodiment, for efficacy of a chimeric receptor comprising a scFV that binds to a ROR1 epitope located in the membrane distal Ig/Frizzled domain, a spacer that is about 15 amino acids or less is employed. In another specific embodiment, for efficacy of a chimeric receptor comprising a scFV that binds to a ROR1 epitope located in the membrane proximal Kringle domain, a spacer that is longer than 15 amino acids is employed. In another embodiment, for efficacy of a chimeric receptor comprising a scFV that binds to CD19, a spacer that is 15 amino acids or less is employed.

In embodiments, an isolated chimeric receptor nucleic acid comprises a polynucleotide coding for a ligand binding domain, wherein the target molecule is a tumor specific antigen, a polynucleotide coding for a polypeptide spacer wherein the polypeptide spacer is about 229 amino acids or less; a polynucleotide coding for a transmembrane domain; and a polynucleotide coding for an intracellular signaling domain. In embodiments, an expression vector comprises a chimeric nucleic acid as described herein. Polypeptides encoded by all of or a portion of the chimeric receptor nucleic acids are also included herein.

Ligand Binding Domain

In embodiments, the chimeric receptor nucleic acid comprises a polynucleotide coding for a ligand binding domain. In embodiments, the ligand binding domain specifically binds to a tumor or viral specific antigen. In embodiments, the ligand binding domain is an antibody or fragment thereof. A nucleic acid sequence coding for an antibody or antibody fragment can readily be determined. In a specific embodiment, the polynucleotide codes for a single chain Fv that specifically binds CD19. In other specific embodiments, the polynucleotide codes for a single chain Fv that specifically binds ROR1. The sequences of these antibodies are known to or can readily be determined by those of skill in the art.

Tumor antigens are proteins that are produced by tumor cells that elicit an immune response. The selection of the ligand binding domain of the invention will depend on the type of cancer to be treated, and may target tumor antigens or other tumor cell surface molecules. A tumor sample from a subject may be characterized for the presence of certain biomarkers or cell surface markers. For example, breast cancer cells from a subject may be positive or negative for each of Her2Neu, Estrogen receptor, and/or the Progesterone receptor. A tumor antigen or cell surface molecule is selected that is found on the individual subject's tumor cells. Tumor antigens and cell surface molecules are well known in the art and include, for example, carcinoembryonic antigen (CEA), prostate specific antigen, PSMA, Her2/neu, estrogen receptor, progesterone receptor, ephrinB2, CD19, CD20, CD22, CD23, CD123, CS-1, ROR1, mesothelin, c-Met, GD-2, and MAGE A3 TCR. In embodiments a target molecule is a cell surface molecule that is found on tumor cells and is not substantially found on normal tissues, or restricted in its expression to non-vital normal tissues.

Other target molecules include but are not limited to antigens derived from infectious pathogens such as HIV (human immunodeficiency virus), HBV (hepatitis B virus), HPV (human papilloma virus) and Hepatitis C virus.

In one embodiment, the target molecule on the tumor comprises one or more epitopes associated with a malignant tumor. Malignant tumors express a number of proteins that can serve as target antigens for T cell receptor or chimeric receptor mediated recognition. Other target molecules belong to the group of cell transformation-related molecules such as the oncogene HER-2/Neu/ErbB2. In embodiments, the tumor antigen is selectively expressed or overexpressed on the tumor cells as compared to control cells of the same tissue type. In other embodiments, the tumor antigen is a cell surface polypeptide.

Once a tumor cell surface molecule that might be targeted with a chimeric receptor is identified, an epitope of the target molecule is selected and characterized. In embodiments, an epitope is selected that is proximal to the tumor cell membrane. In other embodiments, an epitope is selected that is distal to the tumor cell membrane. An epitope is characterized as proximal to the membrane when it is predicted or known by structural analysis to reside closer to the target cell membrane than alternative epitopes that are predicted or known by structural analysis to reside a greater distance from the target cell membrane.

Antibodies that specifically bind a tumor cell surface molecule can be prepared using methods of obtaining monoclonal antibodies, methods of phage display, methods to generate human or humanized antibodies, or methods using a transgenic animal or plant engineered to produce human antibodies. Phage display libraries of partially or fully synthetic antibodies are available and can be screened for an antibody or fragment thereof that can bind to the target molecule. Phage display libraries of human antibodies are also available. In embodiments, antibodies specifically bind to a tumor cell surface molecule and do not cross react with nonspecific components such as bovine serum albumin or other unrelated antigens. Once identified, the amino acid sequence or polynucleotide sequence coding for the antibody can be isolated and/or determined.

Antibodies or antigen binding fragments include all or a portion of polyclonal antibodies, a monoclonal antibody, a human antibody, a humanized antibody, a synthetic antibody, a chimeric antibody, a bispecific antibody, a minibody, and a linear antibody. Antibody fragments" comprise a portion of an intact antibody, preferably the antigen binding or variable region of the intact antibody and can readily be prepared. Examples of antibody fragments include Fab, Fab', F(ab')$_2$, and Fv fragments; diabodies; linear antibodies; single-chain antibody molecules; and multispecific antibodies formed from antibody fragments.

In embodiments, a number of different antibodies that bind to a particular tumor cell surface molecules can be isolated and characterized. In embodiments, the antibodies are characterized based on epitope specificity of the targeted molecule. In addition, in some cases, antibodies that bind to the same epitope can be selected based on the affinity of the antibody for that epitope. In embodiments, an antibody has an affinity of at least 1 mM, and preferably <50 nM. In embodiments, an antibody is selected that has a higher affinity for the epitope as compared to other antibodies. For example, an antibody is selected that has at least a 2 fold, at least a 5 fold, at least a 10 fold, at least a 20 fold, at least a 30 fold, at least a 40 fold, or at least a 50 fold greater affinity than a reference antibody that binds to the same epitope.

In embodiments, target molecules are selected from the group consisting of CD19, CD20, CD22, CD23, CD123, CS-1, ROR1, mesothelin, Her2, c-Met, PSMA, GD-2, MAGE A3 TCR and combinations thereof.

In specific embodiments, the target antigen is CD19. A number of antibodies specific for CD19 are known to those of skill in the art and can be readily characterized for sequence, epitope binding, and affinity. In a specific embodiment, the chimeric receptor construct includes a scFV sequence from FMC63 antibody. In other embodiments, the scFV is a human or humanized ScFv comprising a variable light chain comprising a CDRL1 sequence of RASQDISKYLN (SEQ ID NO: 57), CDRL2 sequence of SRLHSGV (SEQ ID NO: 58), and a CDRL3 sequence of GNTLPYTFG (SEQ ID NO: 59). In other embodiments, the scFV is a human or humanized ScFv comprising a variable heavy chain comprising CDRH1 sequence of DYGVS (SEQ ID NO: 74), CDRH2 sequence of VIWGSETTYYNSALKS (SEQ ID NO: 60), and a CDRH3 sequence of YAMDYWG (SEQ ID NO: 61). The disclosure also contemplates variable regions that have at least 90% amino acid sequence identity to that of the scFv for FMC63 and that have at least the same affinity for CD19. In embodiments, the chimeric receptor has a short or intermediate spacer of 119 amino acids or less, or 12 amino acids or less. In a specific embodiment, the spacer is 12 amino acid or less and has a sequence of SEQ ID NO:4.

In embodiments, CDR regions are found within antibody regions as numbered by Kabat as follows: for the light chain; CDRL1 amino acids 24-34; CDRL2 amino acids 50-56; CDRL3 at amino acids 89-97; for the heavy chain at CDRH1 at amino acids 31-35; CDRH2 at amino acids 50-65; and for CDRH3 at amino acids 95-102. CDR regions in antibodies can be readily determined.

In specific embodiments, the target antigen is ROR1. A number of antibodies specific for ROR1 are known to those of skill in the art and can be readily characterized for sequence, epitope binding, and affinity. In a specific embodiment, the chimeric receptor construct includes a scFV sequence from R12 antibody. In other embodiments, the scFV is a human or humanized ScFv comprising a variable light chain comprising a CDRL1 sequence of ASGFDFSAYYM (SEQ ID NO: 62), CDRL2 sequence of TIYPSSG (SEQ ID NO: 63), and a CDRL3 sequence of ADRATYFCA (SEQ ID NO: 64). In other embodiments, the scFV is a human or humanized ScFv comprising a variable heavy chain comprising CDRH1 sequence of DTIDWY (SEQ ID NO: 65), CDRH2 sequence of VQSDGSYTKRPGVPDR (SEQ ID NO: 66), and a CDRH3 sequence of YIGGYVFG (SEQ ID NO: 67). The disclosure also contemplates variable regions that have at least 90% amino acid sequence identity to that of the scFv for R12 and that have at least the same affinity for ROR1. In embodiments, the chimeric receptor has a short or intermediate spacer of 119 amino acids or less, or 12 amino acids or less. In a specific embodiment, the spacer is 12 amino acid or less and has a sequence of SEQ ID NO:4.

In specific embodiments, the target antigen is ROR1. A number of antibodies specific for ROR1 are known to those of skill in the art and can be readily characterized for sequence, epitope binding, and affinity. In a specific embodiment, the chimeric receptor construct includes a scFV sequence from R11 antibody. In other embodiments, the scFV is a human or humanized ScFv comprising a variable light chain comprising a CDRL1 sequence of SGSDINDYPIS (SEQ ID NO: 68$), CDRL2 sequence of INSGGST (SEQ ID NO: 69), and a CDRL3 sequence of YFCARGYS (SEQ ID NO: 70). In other embodiments, the scFV is a human or humanized ScFv comprising a variable heavy chain comprising CDRH1 sequence of SNLAW (SEQ ID NO 71), CDRH2 sequence of RASNLASGVPSRFSGS (SEQ ID NO: 72), and a CDRH3 sequence of NVSYRTSF (SEQ ID NO: 73). The disclosure also contemplates variable regions that have at least 90% amino acid sequence identity to that of the scFv for R11 and that have at least the same affinity for ROR1. In embodiments, the chimeric receptor has a long spacer of 229 amino acids or less. In a specific embodiment, the spacer is 229 amino acids and has a sequence of SEQ ID NO:50.

In specific embodiments, the target antigen is Her2. A number of antibodies specific for Her2 are known to those of skill in the art and can be readily characterized for sequence, epitope binding, and affinity. In a specific embodiment, the chimeric receptor construct includes a scFV sequence from Herceptin antibody. In other embodiments, the scFV is a human or humanized ScFv comprising a variable light chain comprising a CDRL1 sequence, CDRL2 sequence and a CDRL3 sequence of the Herceptin antibody. In other embodiments, the scFV is a human or humanized ScFv comprising a variable heavy chain comprising CDRH1 sequence, CDRH2, and a CDRH3 sequence of Herceptin. The CDR sequences can readily be determined from the amino acid sequence of Herceptin. The disclosure also contemplates variable regions that have at least 90% amino acid sequence identity to that of the scFv for Herceptin and that have at least the same affinity for Her2. In embodiments, the chimeric receptor has a long spacer of 229 amino acids or less. In a specific embodiment, the spacer is 229 amino acids and has a sequence of SEQ ID NO:50.

In embodiments, a polynucleotide coding for a ligand binding domain is operably linked to a polynucleotide coding for a spacer region. In embodiments, the polynucleotide coding for a ligand binding domain may also have one or more restriction enzyme sites at the 5' and/or 3' ends of the coding sequence in order to provide for easy excision and replacement of the polynucleotide with another polynucleotide coding for a ligand binding domain coding for a different antigen or that has different binding characteristics. For example, a restriction site, NheI, is encoded upstream of the leader sequence; and a 3' RsrII located within the hinge region allows subcloning of any desirable scFv into a chimeric receptor vector. In embodiments, the polynucleotide is codon optimized for expression in mammalian cells.

In embodiments, the polynucleotide coding for a ligand binding domain is operably linked to a signal peptide. In embodiments the signal peptide is a signal peptide for granulocyte colony stimulating factor. Polynucleotides coding for other signal peptides such as CD8 alpha can be utilized.

In embodiments, the polynucleotide coding for a ligand binding domain is operably linked to a promoter. A promoter is selected that provides for expression of the chimeric antigen receptor in a mammalian cell. In a specific embodiment the promoter is the elongation growth factor promoter (EF-1). Another example of a suitable promoter is the immediate early cytomegalovirus (CMV) promoter sequence. However, other constitutive promoter sequences may also be used, including, but not limited to the simian virus 40 (SV 40) early promoter, mouse mammary tumor virus (MMTV), human immunodeficiency virus (HIV) long terminal repeat (LTR) promoter, MuMoLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Inducible promoters are also contemplated. Examples of inducible promoters include, but are not limited to a metallothionine promoter, a glucocorticoid promoter, a progesterone promoter, and a tetracycline promoter.

A specific embodiment of a polynucleotide coding for a ligand binding domain is shown in Table 1 as the scFv from an antibody that specifically binds CD19, such as FMC63. A polynucleotide encoding for a flexible linker including the amino acids GSTSGSGKPGSGEGSTKG (SEQ ID NO:36) separates the VH and VL chains in the scFV. The amino acid sequence of the scFv including the linker is shown in Table 2. (SEQ ID NO: 11) Other CD19-targeting antibodies such as SJ25C1 and HD37 are known. (SJ25C1: Bejcek et al. Cancer Res 2005, PMID 7538901; HD37: Pezutto et al. JI 1987, PMID 2437199).

Spacer

In embodiments, the chimeric receptor nucleic acid comprises a polynucleotide coding for a spacer region. It has been surprisingly found that the length of the spacer region that is presumed not to have signaling capability affects the in vivo efficacy of the T cells modified to express the chimeric receptor and needs to be customized for individual target molecules for optimal tumor or target cell recognition. In embodiments, the chimeric receptor nucleic acid comprises a polynucleotide coding for a customizable spacer region selected from a library of polynucleotides coding for spacer regions. In embodiments, a spacer length is selected based upon the location of the epitope, affinity of the antibody for the epitope, and/or the ability of the T cells expressing the chimeric receptor to proliferate in vitro and/or in vivo in response to antigen recognition.

Typically a spacer region is found between the ligand binding domain and the transmembrane domain of the chimeric receptor. In embodiments, a spacer region provides for flexibility of the ligand binding domain, allows for high expression levels in lymphocytes. A CD19-specific chimeric receptor having a spacer domain of about 229 amino acids had less antitumor activity than a CD19-specific chimeric receptor with a short spacer region comprised of the modified IgG4 hinge only. Other chimeric receptors, such as those constructed from the R12 or 2A2 scFvs also require a short spacer for optimal triggering of T cell effector functions, while a chimeric receptor constructed with the R11 ROR1 scFv requires a long spacer domain of about 229 amino acids for tumor recognition.

In embodiments, a spacer region has at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In embodiments, a spacer region has about 12 amino acids or less, about 119 amino acids or less, or about 229 amino acids or less.

In some embodiments, the spacer region is derived from a hinge region of an immunoglobulin like molecule. In embodiments, a spacer region comprises all or a portion of the hinge region from a human IgG1, human IgG2, a human IgG3, or a human IgG4, and may contain one or more amino acid substitutions. Exemplary sequences of the hinge regions are provided in Table 8. In embodiments, a portion of the hinge region includes the upper hinge amino acids found between the variable heavy chain and the core, and the core hinge amino acids including a polyproline region. Typically, the upper hinge region has about 3 to 10 amino acids. In some cases, the spacer region comprises an amino acid sequence of $X_1PPX_2P$ (SEQ ID NO:1). In embodiments, $X_1$ is a cysteine, glycine, or arginine and X2 is a cysteine or a threonine.

In embodiments, hinge region sequences can be modified in one or more amino acids in order to avoid undesirable structural interactions such as dimerization. In a specific embodiment, the spacer region comprises a portion of a modified human hinge region from IgG4, for example, as shown in Table 2 or Table 8 (SEQ ID NO:21). A representative of a polynucleotide coding for a portion of a modified IgG4 hinge region is provided in Table 1. (SEQ ID NO:4) In embodiments, a hinge region can have at least about 90%, 92%, 95%, or 100% sequence identity with a hinge region amino acid sequence identified in Table 2 or Table 8. In a specific embodiment, a portion of a human hinge region from IgG4 has an amino acid substitution in the core amino acids from CPSP to CPPC.

In some embodiments, all or a portion of the hinge region is combined with one or more domains of a constant region of an immunoglobulin. For example, a portion of a hinge region can be combined with all or a portion of a CH2 or CH3 domain or variant thereof. In embodiments, the spacer region does not include the 47-48 amino acid hinge region sequence from CD8 alpha or the spacer region consisting of an extracellular portion of the CD28 molecule.

In embodiments, a short spacer region has about 12 amino acids or less and comprises all or a portion of a IgG4 hinge region sequence or variant thereof, an intermediate spacer region has about 119 amino acids or less and comprises all or a portion of a IgG4 hinge region sequence and a CH3 region or variant thereof, and a long spacer has about 229 amino acids or less and comprises all or a portion of a IgG4 hinge region sequence, a CH2 region, and a CH3 region or variant thereof.

A polynucleotide coding for a spacer region can be readily prepared by synthetic or recombinant methods from the amino acid sequence. In embodiments, a polynucleotide coding for a spacer region is operably linked to a polynucleotide coding for a transmembrane region. In embodiments, the polynucleotide coding for the spacer region may also have one or more restriction enzyme sites at the 5' and/or 3' ends of the coding sequence in order to provide for easy excision and replacement of the polynucleotide with another polynucleotide coding for a different spacer region. In embodiments, the polynucleotide coding for the spacer region is codon optimized for expression in mammalian cells.

In embodiments, a library of polynucleotides, each coding for different spacer region is provided. In an embodiment, the spacer region is selected from the group consisting of a hinge region sequence from IgG1, IgG2, IgG3, or IgG4 or portion thereof, a hinge region sequence from IgG1, IgG2, IgG3, or IgG4 in combination with all or a portion of a CH2 region or variant thereof, a hinge region sequence from IgG1, IgG2, IgG3, or IgG4 in combination with all or a portion of a CH3 region or variant thereof, and a hinge region sequence from IgG1, IgG2, IgG3, or IgG4 in combination with all or a portion of a CH2 region or variant thereof, and a CH3 region or variant thereof. In embodiments, a short spacer region is a modified IgG4 hinge sequence (SEQ ID NO:4) having 12 amino acids or less, an intermediate sequence is a IgG4 hinge sequence with a CH3 sequence having 119 amino acids or less (SEQ ID NO:49); or a IgG4 hinge sequence with a CH2 and CH3 region having 229 amino acids or less (SEQ ID NO:50)

In embodiments, a method of selecting a spacer region for a chimeric receptor is provided herein. Surprisingly some chimeric receptor constructs, although effective to activate T cells and direct their killing of tumor cells in vitro, were not effective in vivo. In addition, the side effect profile of the chimeric receptor modified T cells can be such as to result in more cells undergoing activation induced cell death or causing an increase in in vivo cytokines. In embodiments, a method comprises providing a plurality of chimeric receptor nucleic acids, wherein the chimeric receptor nucleic acids differ only in the spacer region; introducing each of the chimeric receptor nucleic acids into a separate T lymphocyte population; expanding each separate lymphocyte population in vitro, and introducing each lymphocyte population into an animal bearing a tumor to determine the anti-tumor efficacy of each of the chimeric receptors when expressed in T cells, and selecting a chimeric receptor that provides anti-tumor efficacy as compared to each of the other separate lymphocyte populations modified with each of the other chimeric receptors.

Animal models of different tumors are known. Anti-tumor efficacy can be measured by identifying a decrease in tumor volume, by determining animal death, persistence of the genetically modified T cells in vivo, activation of genetically modified T cells (for example, by detecting an increase in expression of CD25 and/CD69), and/or proliferation of genetically modified T cells in vivo. In an embodiment, a chimeric receptor is selected that provides for the best anti-tumor efficacy in vivo as determined by one or more of these parameters. Lack of anti-tumor efficacy can be determined by lack of persistence of the genetically modified lymphocytes in vivo, animal death, an increase in apoptosis as measured by an increase in induction of caspase-3, and/or a decrease in proliferation of genetically modified lymphocytes.

In other embodiments, a method for selecting a spacer comprises selecting an epitope of a target molecule and characterizing the location of the epitope with respect to the cell membrane, selecting a spacer region that is long or short depending on the location of the epitope with respect to the cell membrane, selecting an antibody or fragment thereof that has an affinity for the epitope that is higher or lower as compared to a reference antibody, and determining whether the chimeric receptor construct provides for enhanced T cell proliferation or cytokine production in vitro and/or in vivo.

In some embodiments, if the target epitope or portion thereof is located proximal to the membrane it is located in the first 100 amino acids of the linear sequence of the extracellular domain adjacent to the transmembrane domain. If the epitope is located proximal to the membrane, a long spacer (e.g. 229 amino acids or less and greater than 119 amino acids) is selected. In some embodiments, if the target epitope is located distal to the membrane, it is located in the first 150 amino acids of the linear sequence of the extracellular domain terminus. If the epitope is located distal to the membrane, an intermediate or short spacer is selected (e.g. 119 amino acids or less or 12-15 amino acids or less). Alternatively, whether the epitope is proximal or distal to the membrane can be determined by modeling of the three dimensional structure or based on analysis of the crystal structure.

In some embodiments, a chimeric receptor is selected that provides for at least 30% of the cells proliferating through two generations in vitro and/or in vivo. In other embodiments a chimeric receptor is not selected if it results in at least 50% of the cells undergoing activation induced cell death in 72 hours. In embodiments, a short spacer (e.g. 15 amino acids or less) is selected if the epitope is distal to the membrane. In embodiments, a long spacer (e.g. 229 amino acid or less and greater than 119 amino acids) is selected if the epitope is proximal to the membrane.

In embodiments, providing a plurality of chimeric receptor nucleic acids, wherein the chimeric receptor nucleic acids differ only in the spacer region comprises providing a chimeric receptor construct comprising a polynucleotide coding for a ligand binding domain, wherein the ligand is a tumor specific antigen, viral antigen, or any other molecule expressed on a target cell population that is suitable to mediate recognition and elimination by a lymphocyte; a polynucleotide coding for a first polypeptide spacer having a defined restriction site at the 5' and 3' end of the coding sequence for the first polypeptide spacer; a polynucleotide coding for a transmembrane domain; and a polynucleotide coding for one or more intracellular signaling domains.

In embodiments, a method further comprises providing one or more polynucleotides, each encoding a different spacer region. In embodiments, the different spacer regions are selected from the group consisting of a hinge region sequence from IgG1, IgG2, IgG3, or IgG4 or variant thereof or portion thereof, a hinge region sequence from IgG1, IgG2, IgG3, or IgG4 in combination with all or a portion of a CH2 region or variant thereof, a hinge region sequence from IgG1, IgG2, IgG3, or IgG4 in combination with all or a portion of a CH3 region or variant thereof, and a hinge region sequence from IgG1, IgG2, IgG3, or IgG4 in combination with all or a portion of a CH2 region or variant thereof and a CH3 region or variant thereof. In embodiments, CH2 or CH3 regions may be modified by one or more deletions or amino acid substitutions in order to provide for expression in lymphocytes and/or in order to minimize interactions with other molecules. In embodiments, a portion of a hinge region comprises at least the upper amino acids and the core sequence. In embodiments, a hinge region comprises the sequence $X_1PPX_2P$ (SEQ ID NO: 1).

In embodiments, a method further comprises replacing the polynucleotide coding for the spacer region with a polynucleotide encoding a different spacer region to form a chimeric receptor nucleic acid with a different spacer region. The method can be repeated to form any number of chimeric receptor nucleic acids, each differing in the spacer region. In embodiments, the chimeric receptor nucleic acids differ from one another only in the spacer region.

Transmembrane Domain

In embodiments, the chimeric receptor nucleic acid comprises a polynucleotide coding for a transmembrane domain. The transmembrane domain provides for anchoring of the chimeric receptor in the membrane.

In an embodiment, the transmembrane domain that naturally is associated with one of the domains in the chimeric receptor is used. In some cases, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or a synthetic source. When the source is natural, the domain may be derived from any membrane-bound or transmembrane protein. Transmembrane regions comprise at least the transmembrane region(s) of the alpha, beta or zeta chain of the T-cell receptor, CD28, CD3, CD45, CD4, CD8, CD9, CD16, CD22; CD33, CD37, CD64, CD80, CD86, CD134, CD137 and CD154. In a specific embodiment, the transmembrane domain comprises the amino acid sequence of the CD28 transmembrane domain as shown in Table 2. A representative polynucleotide sequence coding for the CD28 transmembrane domain is shown in Table 1 (SEQ ID NO:5).

A transmembrane domain may be synthetic or a variant of a naturally occurring transmembrane domain. In embodiments, synthetic or variant transmembrane domains comprise predominantly hydrophobic residues such as leucine and valine. In embodiments, a transmembrane domain can have at least about 80%, 85%, 90%, 95%, or 100% amino acid sequence identity with a transmembrane domain as shown in Table 2 or Table 6. Variant transmembrane domains preferably have a hydrophobic score of at least 50 as calculated by Kyte Doolittle.

A polynucleotide coding for a transmembrane domain can be readily prepared by synthetic or recombinant methods. In embodiments, a polynucleotide coding for a transmembrane domain is operably linked to a polynucleotide coding for a intracellular signaling region. In embodiments, the polynucleotide coding for a transmembrane domain may also have one or more restriction enzyme sites at the 5' and/or 3' ends of the coding sequence in order to provide for easy excision and replacement of the polynucleotide coding for a transmembrane domain with another polynucleotide coding for a different transmembrane domain. In embodiments, the polynucleotide coding for a transmembrane domain is codon optimized for expression in mammalian cells.

Intracellular Signaling Domain

In embodiments, the chimeric receptor nucleic acid comprises a polynucleotide coding for an intracellular signaling domain. The intracellular signaling domain provides for activation of one function of the transduced cell expressing the chimeric receptor upon binding to the ligand expressed on tumor cells. In embodiments, the intracellular signaling domain contains one or more intracellular signaling domains. In embodiments, the intracellular signaling domain is a portion of and/or a variant of an intracellular signaling domain that provides for activation of at least one function of the transduced cell.

Examples of intracellular signaling domains for use in a chimeric receptor of the disclosure include the cytoplasmic sequences of the CD3 zeta chain, and/or co-receptors that act in concert to initiate signal transduction following chimeric receptor engagement, as well as any derivative or variant of these sequences and any synthetic sequence that has the same functional capability. T cell activation can be said to be mediated by two distinct classes of cytoplasmic signaling sequence: those that initiate antigen-dependent primary activation and provide a T cell receptor like signal (primary cytoplasmic signaling sequences) and those that act in an antigen-independent manner to provide a secondary or co-stimulatory signal (secondary cytoplasmic signaling sequences). Primary cytoplasmic signaling sequences that act in a stimulatory manner may contain signaling motifs which are known as receptor tyrosine-based activation motifs or ITAMs. Examples of ITAM containing primary cytoplasmic signaling sequences include those derived from CD3 zeta, FcR gamma, CD3 gamma, CD3 delta, CD3 epsilon, CD5, CD22, CD79a, CD79b, and CD66d. In embodiments, the primary signaling intracellular domain can have at least about 80%, 85%, 90%, or 95% sequence identity to CD3zeta having a sequence provided in Table 2. In embodiments variants, of CD3 zeta retain at least one, two, three or all ITAM regions as shown in Table 7.

In a preferred embodiment, the intracellular signaling domain of the chimeric receptor can be designed to comprise the CD3-zeta signaling domain by itself or combined with any other desired cytoplasmic domain(s). For example, the intracellular signaling domain of the chimeric receptor can comprise a CD3zeta chain and a costimulatory signaling region.

The costimulatory signaling region refers to a portion of the chimeric receptor comprising the intracellular domain of a costimulatory molecule. A costimulatory molecule is a cell surface molecule other than an antigen receptor or their ligands that is required for a response of lymphocytes to an antigen. Examples of such molecules include CD27, CD28, 4-1BB (CD 137), OX40, CD30, CD40, lymphocyte function-associated antigen-1 (LFA-1), CD2, CD7, LIGHT, NKG2C, B7-H3, and a ligand that specifically binds with CD83. In embodiments, the costimulatory signaling domain can have at least about 80%, 85%, 90%, or 95% amino acid sequence identity to the intracellular domain of CD28 as shown in Table 5 or to 4-1BB having a sequence provided in Table 2. In an embodiment, a variant of the CD28 intracellular domain comprises an amino acid substitution at positions 186-187, wherein LL is substituted with GG.

The intracellular signaling sequences of the chimeric receptor may be linked to each other in a random or specified order. Optionally, a short oligo- or polypeptide linker, preferably between 2 and 10 amino acids in length may form the linkage. In one embodiment, the intracellular signaling domains comprises all or a portion of the signaling domain of CD3-zeta or variant thereof and all or a portion of the signaling domain of CD28 or a variant thereof. In another embodiment, the intracellular signaling domain comprises all or a portion of the signaling domain of CD3-zeta or variant thereof and all or a portion of the signaling domain of 4-1BB or variant thereof. In yet another embodiment, the intracellular signaling domain comprises all or a portion of the signaling domain of CD3-zeta or variant thereof, all or a portion of the signaling domain of CD28 or variant thereof, and all or a portion of the signaling domain of 4-1BB or variant thereof. In a specific embodiment, the amino acid sequence of the intracellular signaling domain comprising a variant of CD3zeta and a portion of the 4-1BB intracellular signaling domain is provided in Table 2. A representative nucleic acid sequence is provided in Table 1 (SEQ ID NO:6; SEQ ID NO:7).

In an embodiment, a polynucleotide coding for an intracellular signaling domain comprises a 4-1BB intracellular domain linked to a portion of a CD3zeta domain. In other embodiments, a 4-1BB intracellular domain and a CD28 intracellular domain are linked to a portion of a CD3 zeta domain.

A polynucleotide coding for an intracellular signaling domain can be readily prepared by synthetic or recombinant methods from the amino acid sequence. In embodiments, the polynucleotide coding for an intracellular signaling domain may also have one or more restriction enzyme sites at the 5' and/or 3' ends of the coding sequence in order to provide for easy excision and replacement of the polynucleotide coding for an intracellular signaling domain with another polynucleotide coding for a different intracellular signaling domain. In embodiments, the polynucleotide coding for an intracellular signaling domain is codon optimized for expression in mammalian cells.

Marker Sequences

In embodiments, the chimeric receptor nucleic acid optionally further comprises a polynucleotide sequence coding for a marker sequence. A marker sequence can provide for selection of transduced cells, and identification of transduced cells. In embodiments, the marker sequence is operably linked to a polynucleotide sequence coding for a linker sequence. In embodiments, the linker sequence is a cleavable linker sequence.

A number of different marker sequences can be employed. Typically a marker sequence has a functional characteristic that allows for selection of transduced cells and/or detection of transduced cells. In embodiments, the marker sequence is compatible with transduction of human lymphocytes.

The positive selectable marker may be a gene, which upon being introduced into the host cell, expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

In an embodiment, a chimeric receptor nucleic acid further comprises a polynucleotide coding for a marker sequence. In an embodiment, the marker sequence is a truncated epidermal growth factor receptor as shown in Table 2. An exemplary polynucleotide for the truncated epidermal growth factor receptor is shown in Table 1. (SEQ ID NO:9) In embodiments, the polynucleotide coding for the marker sequence is operably linked to a polynucleotide coding for a linker sequence. In a specific embodiment, the linker sequence is a cleavable linker sequence T2A as shown in Table 2. An exemplary polynucleotide sequence coding for the T2A linker is provided in Table 1. (SEQ ID NO:8)

A polynucleotide coding for marker sequence can be readily prepared by synthetic or recombinant methods from the amino acid sequence. In embodiments a polynucleotide coding for a marker sequence is operably linked to a polynucleotide coding for an intracellular signaling domain. In embodiments, the polynucleotide coding for a marker sequence may also have one or more restriction enzyme sites at the 5' and/or 3' ends of the coding sequence in order to provide for easy excision and replacement of the polynucleotide coding for a marker sequence with another polynucleotide coding for a different marker sequence. In embodiments, the polynucleotide coding for a marker sequence is codon optimized for expression in mammalian cells.

Vectors, Cells and Methods of Transducing Cells

Selection and Sorting of T Lymphocyte Populations

The compositions described herein provide for CD4+ and/or CD8+ T lymphocytes. T lymphocytes can be collected in accordance with known techniques and enriched or depleted by known techniques such as affinity binding to antibodies such as flow cytometry and/or immunomagnetic selection. After enrichment and/or depletion steps, in vitro expansion of the desired T lymphocytes can be carried out in accordance with known techniques (including but not limited to those described in U.S. Pat. No. 6,040,177 to Riddell et al.), or variations thereof that will be apparent to those skilled in the art. In embodiments, the T cells are autologous T cells obtained from the patient.

For example, the desired T cell population or subpopulation may be expanded by adding an initial T lymphocyte population to a culture medium in vitro, and then adding to the culture medium feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). The non-dividing feeder cells can comprise gamma-irradiated PBMC feeder cells. In some embodiments, the PBMC are irradiated with gamma rays in the range of about 3000 to 3600 rads to prevent cell division. The order of addition of the T cells and feeder cells to the culture media can be reversed if desired. The culture can typically be incubated under conditions of temperature and the like that are suitable for the growth of T lymphocytes. For the growth of human T lymphocytes, for example, the temperature will generally be at least about 25 degrees Celsius, preferably at least about 30 degrees, more preferably about 37 degrees.

The T lymphocytes expanded include $CD8^+$ cytotoxic T lymphocytes (CTL) and $CD4^+$ helper T lymphocytes that may be specific for an antigen present on a human tumor or a pathogen.

Optionally, the expansion method may further comprise the step of adding non-dividing EBV-transformed lymphoblastoid cells (LCL) as feeder cells. LCL can be irradiated with gamma rays in the range of about 6000 to 10,000 rads. The LCL feeder cells may be provided in any suitable amount, such as a ratio of LCL feeder cells to initial T lymphocytes of at least about 10:1.

Optionally, the expansion method may further comprise the step of adding anti-CD3 and/or anti CD28 antibody to the culture medium (e.g., at a concentration of at least about 0.5 ng/ml). Optionally, the expansion method may further comprise the step of adding IL-2 and/or IL-15 to the culture medium (e.g., wherein the concentration of IL-2 is at least about 10 units/ml).

After isolation of T lymphocytes both cytotoxic and helper T lymphocytes can be sorted into naïve, memory, and effector T cell subpopulations either before or after expansion.

CD8+ cells can be obtained by using standard methods. In some embodiments, CD8+ cells are further sorted into naïve, central memory, and effector memory cells by identifying cell surface antigens that are associated with each of those types of CD8+ cells. In embodiments, memory T cells are present in both CD62L+ and CD62L− subsets of CD8+ peripheral blood lymphocytes. PBMC are sorted into CD62L−CD8+ and CD62L+CD8+ fractions after staining with anti-CD8 and anti-CD62L antibodies. In some embodiments, the expression of phenotypic markers of central memory $T_{CM}$ include CD45RO, CD62L, CCR7, CD28, CD3, and CD127 and are negative or low for granzyme B. In some embodiments, central memory T cells are CD45RO+, CD62L+, CD8+ T cells. In some embodiments, effector $T_E$ are negative for CD62L, CCR7, CD28, and CD127, and positive for granzyme B and perforin. In some embodiments, naïve CD8+ T lymphocytes are characterized by the expression of phenotypic markers of naïve T cells including CD62L, CCR7, CD28, CD3, CD127, and CD45RA.

Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, positive refers to uniform staining of the cell population above the isotype control. In some embodiments, a decrease in expression of one or markers refers to loss of 1 log 10 in the mean fluorescence intensity and/or decrease of percentage of cells that exhibit the marker of at least about 20% of the cells, 25% of-the cells, 30% of the cells, 35% of the cells, 40% of the cells, 45% of the cells, 50% of the cells, 55% of the cells, 60% of the cells, 65% of the cells, 70% of the cells, 75% of the cells, 80%. of the cells, 85% of the cells, 90% of the cell, 95% of the cells, and 100% of the cells and any % between 20 and 100% when compared to a reference cell population. In some embodiments, a cell population positive for one or markers refers to a percentage of cells that exhibit the marker of at least about 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 50 and 1000% when compared to a reference cell population.

CD4+ T helper cells are sorted into naïve, central memory, and effector cells by identifying cell populations that have cell surface antigens. CD4+ lymphocytes can be obtained by standard methods. In some embodiments, naïve CD4+ T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO−.

In embodiments, populations of CD4+ and CD8+ that are antigen specific can be obtained by stimulating naïve or antigen specific T lymphocytes with antigen. For example, antigen-specific T cell lines or clones can be generated to Cytomegalovirus antigens by isolating T cells from infected subjects and stimulating the cells in vitro with the same antigen. Naïve T cells may also be used. Any number of antigens from tumor cells may be utilized as targets to elicit T cell responses. In some embodiments, the adoptive cellular immunotherapy compositions are useful in the treatment of a disease or disorder including a solid tumor, hematologic malignancy, breast cancer or melanoma.

Modification of T Lymphocyte Populations

In some embodiments it may be desired to introduce functional genes into the T cells to be used in immunotherapy in accordance with the present disclosure. For example, the introduced gene or genes may improve the efficacy of therapy by promoting the viability and/or function of transferred T cells; or they may provide a genetic marker to permit selection and/or evaluation of in vivo survival or migration; or they may incorporate functions that improve the safety of immunotherapy, for example, by making the cell susceptible to negative selection in vivo as described by Lupton S. D. et al., *Mol. and Cell Biol.*, 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. This can be carried out in accordance with known techniques (see, e.g., U.S. Pat. No. 6,040,177 to Riddell et al. at columns 14-17) or variations thereof that will be apparent to those skilled in the art based upon the present disclosure.

In embodiments, T cells are modified with chimeric receptors as described herein. In some embodiments, the T cells are obtained from the subject to be treated, in other embodiments, the lymphocytes are obtained from allogeneic human donors, preferably healthy human donors.

In some embodiments, chimeric receptors comprise a ligand binding domain that specifically binds to a tumor cell surface molecule, a polypeptide spacer region, a transmembrane domain and an intracellular signaling domain as described herein. In embodiments, the ligand binding domain is a single-chain antibody fragment (scFv) that is derived from the variable heavy (VH) and variable light (VL) chains of a monoclonal antibody (mAb). Costimulatory signals can also be provided through the chimeric receptor by fusing the costimulatory domain of CD28 and/or 4-1BB to the CD3ζ chain. Chimeric receptors are specific for cell surface molecules independent from HLA, thus overcoming the limitations of TCR-recognition including HLA-restriction and low levels of HLA-expression on tumor cells.

Chimeric receptors can be constructed with a specificity for any cell surface marker by utilizing antigen binding fragments or antibody variable domains of, for example, antibody molecules. The antigen binding molecules can be linked to one or more cell signaling modules. In embodiments, cell signaling modules include CD3 transmembrane domain, CD3 intracellular signaling domains, and CD28 transmembrane domains. In embodiments, the intracellular signaling domain comprises a CD28 transmembrane and signaling domain linked to a CD3 zeta intracellular domain. In some embodiments, a chimeric receptor can also include a transduction marker such as tEGFR.

In embodiments, the same or a different chimeric receptor can be introduced into each of population of CD4+ and CD8+ T lymphocytes. In embodiments, the chimeric receptor in each of these populations has a ligand binding domain that specifically binds to the same ligand on the tumor or infected cell. The cellular signaling modules can differ. In embodiments, the intracellular signaling domain of the CD8+ cytotoxic T cells is the same as the intracellular signaling domain of the CD4+ helper T cells. In other embodiments, the intracellular signaling domain of the CD8+ cytotoxic T cells is different than the intracellular signaling domain of the CD4+ helper T cells.

In embodiments each of the CD4 or CD8 T lymphocytes can be sorted in to naïve, central memory, effector memory or effector cells prior to transduction as described herein. In alternative embodiments, each of the CD4 or CD8 T lymphocytes can be sorted in to naïve, central memory, effector memory, or effector cells after transduction.

Various transduction techniques have been developed which utilize recombinant infectious virus particles for gene delivery. This represents a currently preferred approach to the transduction of T lymphocytes of the present invention. The viral vectors which have been used in this way include virus vectors derived from simian virus 40, adenoviruses, adeno-associated virus (AAV), lentiviral vectors, and retroviruses. Thus, gene transfer and expression methods are numerous but essentially function to introduce and express genetic material in mammalian cells. Several of the above techniques have been used to transduce hematopoietic or lymphoid cells, including calcium phosphate transfection, protoplast fusion, electroporation, and infection with recombinant adenovirus, adeno-associated virus and retrovirus vectors. Primary T lymphocytes have been successfully transduced by electroporation and by retroviral or lentiviral infection.

Retroviral and lentiviral vectors provide a highly efficient method for gene transfer into eukaryotic cells. Moreover, retroviral or lentiviral integration takes place in a controlled fashion and results in the stable integration of one or a few copies of the new genetic information per cell.

It is contemplated that overexpression of a stimulatory factor (for example, a lymphokine or a cytokine) may be toxic to the treated individual. Therefore, it is within the scope of the invention to include gene segments that cause the T cells of the invention to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-I TK) gene, which confers ganciclovir sensitivity; the cellular hypoxanthine phosphoribosyltransferase (HPRT) gene, the cellular adenine phosphoribosyltransferase (APRT) gene, and bacterial cytosine deaminase, In some embodiments it may be useful to include in the T cells a positive marker that enables the selection of cells of the negative selectable phenotype in vitro. The positive selectable marker may be a gene that upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

A variety of methods can be employed for transducing T lymphocytes, as well known in the art. In embodiments, transduction is carried out using lentiviral vectors.

In embodiments, CD4+ and CD8+ cells each can separately be modified with an expression vector encoding a chimeric receptor to form defined populations. In embodiments, these cells are then further sorted into subpopulations of naïve, central memory and effector cells as described above by sorting for cell surface antigens unique to each of those cell populations. In addition, CD4+ or CD8+ cell populations may be selected by their cytokine profile or proliferative activities. For example, CD4+ T lymphocytes that have enhanced production of cytokines such as IL-2, IL-4, IL-10, TNFα, and IFNγ as compared to sham transduced cells or transduced CD8+ cells when stimulated with antigen can be selected. In other embodiments, naïve or central memory CD4+ T cells that have enhanced production of IL-2 and/or TNFα are selected. Likewise, CD8+ cells that have enhanced IFNγ production are selected as compared to sham transduced CD8+ cells.

In embodiments, CD4+ and CD8+ cells that proliferate in response to antigen or tumor targets are selected. For example, CD4+ cells that proliferate vigorously when stimulated with antigen or tumor targets as compared to sham transduced cells, or CD8+ transduced cells are selected. In some embodiments, CD4+ and CD8+ cells are selected that are cytotoxic for antigen bearing cells. In embodiments, CD4+ are expected to be weakly cytotoxic as compared to CD8+ cells.

In a preferred embodiment, transduced lymphocytes, such as CD8+ central memory cells, are selected that provide for tumor cell killing in vivo using an animal model established for the particular type of cancer. Such animal models are known to those of skill in the art and exclude human beings. As described herein, not all chimeric receptor constructs transduced into lymphocytes confer the ability to kill tumor cells in vivo despite the ability to become activated and kill tumor cells in vitro. In particular, for some target molecules T cells having chimeric receptor constructs with a long spacer region were less effective at killing tumor cells in vivo as compared to T cells having a chimeric receptor with short spacer region. For other target molecules, T cells having chimeric receptor constructs with a short spacer region were less effective at killing tumor cells in vivo as compared to T cells having chimeric receptors with a long spacer region.

In yet other embodiments, transduced chimeric receptor expressing T cells are selected that can persist in vivo using an animal model established for the particular type of cancer. In embodiments, transduced chimeric receptor CD8+ central memory cells with a short spacer region have been shown to persist in vivo after introduction into the animal for about 3 day or more, 10 days or more, 20 days or more, 30 days or more, 40 days or more, or 50 days or more.

The disclosure contemplates that combinations of CD4+ and CD8+ T cells will be utilized in the compositions. In one embodiment, combinations of chimeric receptor transduced CD4+ cells can be combined with chimeric receptor transduced CD8+ cells of the same ligand specificity or combined with CD8+ T cells that are specific for a distinct tumor ligand. In other embodiments, chimeric receptor transduced CD8+ cells are combined with chimeric receptor transduced CD4+ cells specific for a different ligand expressed on the tumor. In yet another embodiment, chimeric receptor modified CD4+ and CD8+ cells are combined. In embodiments CD8+ and CD4+ cells can be combined in different ratios for example, a 1:1 ratio of CD8+ and CD4+, a ratio of 10:1 of CD8+ to CD4+, or a ratio of 100:1 of CD8+ to CD4+. In embodiments, the combined population is tested for cell proliferation in vitro and/or in vivo, and the ratio of cells that provides for proliferation of cells is selected.

As described herein, the disclosure contemplates that CD4+ and CD8+ cells can be further separated into subpopulations, such as naïve, central memory, and effector memory cell populations. As described herein, in some embodiments, naïve CD4+ cells are CD45RO−, CD45RA+, CD62L+, CD4+ positive T cells. In some embodiments, central memory CD4+ cells are CD62L positive and CD45RO positive. In some embodiments, effector CD4+ cells are CD62L negative and CD45RO positive. Each of these populations may be independently modified with a chimeric receptor.

As described herein, in embodiments, memory T cells are present in both CD62L+ and CD62L− subsets of CD8+ peripheral blood lymphocytes. PBMC are sorted into CD62L−CD8+ and CD62L−CD8+ fractions after staining with anti-CD8 and anti-CD62L antibodies. In some embodiments, the expression of phenotypic markers of central memory T cells (TCM) include CD62L, CCR7, CD28, CD3, and CD127 and are negative or low for granzyme B. In some embodiments, central memory T cells are CD45RO+, CD62L+, CD8+ T cells. In some embodiments, effector T cells ($T_E$) are negative for CD62L, CCR7, CD28, and CD127, and positive for granzyme B and perforin. In some embodiments, naïve CD8+ T lymphocytes are characterized by CD8+, CD62L+, CD45RO+, CCR7+, CD28+CD127+, and CD45RO+. Each of these populations may be independently modified with a chimeric receptor.

After transduction and/or selection for chimeric receptor bearing cells, the cell populations are preferably expanded in vitro until a sufficient number of cells are obtained to provide for at least one infusion into a human subject, typically around $10^4$ cells/kg to $10^9$ cells/kg In embodiments, the transduced cells are cultured in the presence of antigen bearing cells, anti CD3, anti CD28, and IL 2, IL-7, IL 15, IL-21 and combinations thereof.

Each of the subpopulations of CD4+ and CD8+ cells can be combined with one another. In a specific embodiment, modified naïve or central memory CD4+ cells are combined with modified central memory CD8+ T cells to provide a synergistic cytotoxic effect on antigen bearing cells, such as tumor cells.

Compositions

The disclosure provides for an adoptive cellular immunotherapy composition comprising a genetically modified T lymphocyte cell preparation as described herein.

In embodiments, the T lymphocyte cell preparation comprises CD4+ T cells that have a chimeric receptor comprising an extracellular antibody variable domain specific for a ligand associated with the disease or disorder, a customizable spacer region, a transmembrane domain, and an intracellular signaling domain of a T cell receptor or other receptors as described herein. In other embodiments, an adoptive cellular immunotherapy composition further comprises a chimeric receptor modified tumor-specific CD8+ cytotoxic T lymphocyte cell preparation that provides a cellular immune response, wherein the cytotoxic T lymphocyte cell preparation comprises CD8+ T cells that have a chimeric receptor comprising an extracellular single chain antibody specific for a ligand associated with the disease or disorder, a customizable spacer region, a transmembrane domain, and an intracellular signaling domain of a T cell receptor as described herein. In embodiments, the chimeric receptor modified T cell population of the disclosure can persist in vivo for at least about 3 days or longer.

In some embodiments, an adoptive cellular immunotherapy composition comprises a chimeric receptor modified tumor-specific CD8+ cytotoxic T lymphocyte cell preparation that provides a cellular immune response, wherein the cytotoxic T lymphocyte cell preparation comprises CD8+ T cells that have a chimeric receptor comprising an extracellular single chain antibody specific for a ligand associated with the disease or disorder, a customizable spacer region, a transmembrane domain, and an intracellular signaling domain of a T cell receptor, in combination with an antigen-reactive chimeric receptor modified naïve CD4+ T helper cell derived from CD45RO− CD62L+ CD4+ T cells, and a pharmaceutically acceptable carrier.

In other embodiments, an adoptive cellular immunotherapy composition comprises an antigen specific CD8+ cytotoxic T lymphocyte cell preparation that provides a cellular immune response derived from the patient combined with an antigen-reactive chimeric receptor modified naïve CD4+ T helper cell that augments the CD8+ immune response, wherein the helper T lymphocyte cell preparation comprises CD4+ T cells that have a chimeric receptor comprising an extracellular antibody variable domain specific for the antigen associated with the disease or disorder, a customizable spacer region, a transmembrane domain, and an intracellular signaling domain of a T cell receptor.

In a further embodiment, an adoptive cellular immunotherapy composition comprises an antigen-reactive chimeric receptor modified naïve CD4+ T helper cell that augments the CD8+ immune response, wherein the helper T lymphocyte cell preparation comprises CD4+ T cells that have a chimeric receptor comprising an extracellular antibody variable domain specific for a ligand associated with a disease or disorder, a customizable spacer region, a transmembrane domain, and an intracellular signaling domain of a T cell receptor.

In embodiments, the CD4+ T helper lymphocyte cell is selected from the group consisting of naïve CD4+ T cells, central memory CD4+ T cells, effector memory CD4+ T cells, or bulk CD4+ T cells. In some embodiments, CD4+ helper lymphocyte cell is a naïve CD4+ T cell, wherein the naïve CD4+ T cell comprises a CD45RO−, CD45RA+, CD62L+CD4+ T cell. In embodiments, the CD8+ T cytotoxic lymphocyte cell is selected from the group consisting of naïve CD8+ T cells, central memory CD8+ T cells, effector memory CD8+ T cells or bulk CD8+ T cells. In some embodiments, the CD8+ cytotoxic T lymphocyte cell is a central memory T cell wherein the central memory T cell comprises a CD45RO+, CD62L+, CD8+ T cell. In yet other embodiments, the CD8+ cytotoxic T lymphocyte cell is a central memory T cell and the CD4+ helper T lymphocyte cell is a naïve or central memory CD4+ T cell.

Methods

The disclosure provides methods of making adoptive immunotherapy compositions and uses or methods of using these compositions for performing cellular immunotherapy in a subject having a disease or disorder. In embodiments, the chimeric receptor modified T cells as described herein are able to persist in vivo for at least 3 days, or at least 10 days. In embodiments, the chimeric receptor modified T cells as described herein can proliferate in vivo through at least 2, or at least 3 generations as determined by CFSE dye dilution. Proliferation and persistence of the chimeric receptor modified T cells can be determined by using an animal model of the disease or disorder and administering the cells and determining persistence and/or proliferative capacity of the transferred cells. In other embodiments, proliferation and activation can be tested in vitro by going through multiple cycles of activation with antigen bearing cells.

In embodiments, a method of manufacturing the compositions comprises obtaining a modified naïve CD4+ T helper cell, wherein the modified helper T lymphocyte cell preparation comprises CD4+ T cells that have a chimeric receptor comprising a ligand binding domain specific for a tumor cell surface molecule, a customized spacer domain, a transmembrane domain, and an intracellular signaling domain as described herein.

In another embodiment, a method further comprises obtaining a modified CD8+ cytotoxic T cell, wherein the modified cytotoxic T lymphocyte cell preparation comprises CD8+ cells that have a chimeric receptor comprising a ligand binding domain specific for a tumor cell surface molecule, a customized spacer domain, a transmembrane domain, and an intracellular signaling domain as described herein.

In another embodiment, a method comprises obtaining a modified CD8+ cytotoxic T cell, wherein the modified cytotoxic T lymphocyte cell preparation comprises CD8+ T cells that have a chimeric receptor comprising a ligand binding domain specific for a tumor cell surface molecule, a customized spacer domain, a transmembrane domain, and an intracellular signaling domain as described herein, and further comprising combining the modified CD8+ cytotoxic T cells with a CD4+ helper cell lymphocyte cell preparation.

The preparation of the CD4+ and CD8+ cells that are modified with a chimeric receptor has been described above as well as in the examples. Antigen specific T lymphocytes can be obtained from a patient having the disease or disorder or can be prepared by in vitro stimulation of T lymphocytes in the presence of antigen. Subpopulations of CD4+ and CD8+ T lymphocytes that are not selected for antigen specificity can also be isolated as described herein and combined in the methods of manufacturing. In embodiments, the combination of cell populations can be evaluated for uniformity of cell surface makers, the ability to proliferate through at least two generations, to have a uniform cell differentiation status. Quality control can be performed by coculturing an cell line expressing the target ligand with chimeric receptor modified T cells to determine if the chimeric receptor modified T cells recognize the cell line using cytotoxicity, proliferation, or cytokine production assays that are known in the field. Cell differentiation status and cell surface markers on the chimeric receptor modified T cells can be determined by flow cytometry. In embodiments, the markers and cell differentiation status on the CD8+ cells include CD3, CD8, CD62L, CD28, CD27, CD69, CD25, PD-1, CTLA-4, CD45RO, and CD45RA. In embodiments, the markers and the cell differentiation status on the CD4+ cells include CD3, CD4, CD62L, CD28, CD27, CD69, CD25, PD-1, CTLA-4 CD45RO, and CD45RA.

In embodiments, a method of selecting a spacer region for a chimeric receptor is provided herein. Surprisingly some chimeric receptor constructs, although effective to activate T cells in vitro, were not effective in vivo. In embodiments, a method comprises providing a plurality of chimeric receptor nucleic acids, wherein the chimeric receptor nucleic acids differ only in the spacer region; introducing each of the chimeric receptor nucleic acids into a separate T lymphocyte population; expanding each separate lymphocyte population in vitro, and introducing each lymphocyte population into an animal bearing a tumor to determine the anti-tumor efficacy of each of the chimeric receptor modified T cells, and selecting a chimeric receptor that provides anti-tumor efficacy as compared to each of the other separate lymphocyte populations modified with each of the other chimeric receptor modified T cells.

Animal models of different tumors are known. Anti-tumor efficacy can be measured by identifying a decrease in tumor volume, by determining animal death, persistence of the genetically modified T cells in vivo, activation of genetically modified T cells (for example, by detecting an increase in expression of CD25 and/CD69), and/or proliferation of genetically modified T cells in vivo. In an embodiment, a chimeric receptor is selected that provides for the best anti-tumor efficacy in vivo as determined by one or more of these parameters. Lack of anti-tumor efficacy can be determined by lack of persistence of the genetically modified lymphocytes in vivo, animal death, an increase in apoptosis as measured by an increase in induction of caspase-3, and/or a decrease in proliferation of genetically modified lymphocytes.

In embodiments, providing a plurality of chimeric receptor nucleic acids, wherein the chimeric receptor nucleic acids differ only in the spacer region comprises providing a chimeric receptor construct comprising a polynucleotide coding for a ligand binding domain, wherein the ligand is a tumor specific antigen, viral antigen, or any other molecule expressed on a target cell population that is suitable to mediate recognition and elimination by a lymphocyte; a polynucleotide coding for a first polypeptide spacer having a defined restriction site at the 5' and 3' end of the coding sequence for the first polypeptide spacer, a polynucleotide coding for a transmembrane domain; and a polynucleotide coding for an intracellular signaling domain.

The disclosure also provides methods of performing cellular immunotherapy in a subject having a disease or disorder comprising: administering a composition of lymphocytes expressing a chimeric receptor as described herein. In other embodiments, a method comprises administering to the subject a genetically modified cytotoxic T lymphocyte cell preparation that provides a cellular immune response, wherein the cytotoxic T lymphocyte cell preparation comprises CD8+ T cells that have a chimeric receptor comprising a ligand binding domain specific for a tumor cell surface molecule, a customized spacer domain, a transmembrane domain, and an intracellular signaling domain as described herein, and a genetically modified helper T lymphocyte cell preparation that elicits direct tumor recognition and augments the genetically modified cytotoxic T lymphocyte cell preparations ability to mediate a cellular immune response, wherein the helper T lymphocyte cell preparation comprises CD4+ T cells that have a chimeric receptor comprising a ligand binding domain specific for a tumor cell surface molecule, a customized spacer domain, a transmembrane domain, and an intracellular signaling domain as described herein.

While not limiting the scope of the disclosure, it is believed by selecting the chimeric receptor modified T cell population that can persist and proliferate in vivo prior to administration may result in the ability to use a lower dose of T cells and provide more uniform therapeutic activity. In embodiments, the dose of T cells can be reduced at least 10%, 20%, or 30% or greater. Reduction in the dose of T cells may be beneficial to reduce the risk or tumor lysis syndrome and cytokine storm.

In another embodiment, a method of performing cellular immunotherapy in subject having a disease or disorder comprises: administering to the subject a genetically modified helper T lymphocyte cell preparation, wherein the modified helper T lymphocyte cell preparation comprises CD4+ T cells that have a chimeric receptor comprising a ligand binding domain specific for a tumor cell surface molecule, a customized spacer domain, a transmembrane domain, and an intracellular signaling domain as described herein. In an embodiments, the method further comprises administering to the subject a genetically modified cytotoxic T lymphocyte cell preparation, wherein the modified cytotoxic T lymphocyte cell preparation comprises CD8+ cells that have a chimeric receptor comprising a ligand binding domain specific for a tumor cell surface molecule, a customized spacer domain, a transmembrane domain, and an intracellular signaling domain as described herein.

Another embodiment describes a method of performing cellular immunotherapy in a subject having a disease or disorder comprising: analyzing a biological sample of the subject for the presence of a target molecule associated with the disease or disorder and administering the adoptive immunotherapy compositions described herein, wherein the chimeric receptor specifically binds to the target molecule.

In some embodiments, the CD4+ T helper lymphocyte cell is selected prior to introduction of the chimeric receptor from the group consisting of naïve CD4+ T cells, central memory CD4+ T cells, effector memory CD4+ T cells or bulk CD4+ T cells. In a specific embodiment, CD4+ helper lymphocyte cell is a naïve CD4+ T cell, wherein the naïve CD4+ T cell comprises a CD45RO-, CD45RA+, CD62L+ CD4+ T cell. In yet other embodiments, the CD8+ T cytotoxic lymphocyte cell is selected prior to introduction of the chimeric receptor from the group consisting of naïve CD8+ T cells, central memory CD8+ T cells, effector memory CD8+ T cells or bulk CD8+ T cells. In a specific embodiment, the CD8+ cytotoxic T lymphocyte cell is a central memory T cell wherein the central memory T cell comprises a CD45RO+, CD62L+, CD8+ T cell. In a specific embodiment, the CD8+ cytotoxic T lymphocyte cell is a central memory T cell and the CD4+ helper T lymphocyte cell is a naïve CD4+ T cell.

In embodiments, the CD8+ T cell and the CD4+ T cell are both genetically modified with a chimeric receptor comprising an antibody heavy chain domain that specifically binds a tumor-specific cell surface molecule. In other embodiments, the intracellular signaling domain of the CD8 cytotoxic T cells is the same as the intracellular signaling domain of the CD4 helper T cells. In yet other embodiments, the intracellular signaling domain of the CD8 cytotoxic T cells is different than the intracellular signaling domain of the CD4 helper T cells.

Subjects that can be treated by the present invention are, in general, human and other primate subjects, such as monkeys and apes for veterinary medicine purposes. The subjects can be male or female and can be any suitable age, including infant, juvenile, adolescent, adult, and geriatric subjects.

The methods are useful in the treatment of, for example, hematologic malignancy, melanoma, breast cancer, and other epithelial malignancies or solid tumors. In some embodiments, the molecule associated with the disease or disorder is selected from the group consisting of orphan tyrosine kinase receptor ROR1, Her2, CD19, CD20, CD22, mesothelin, CEA, and hepatitis B surface antigen.

Subjects that can be treated include subjects afflicted with cancer, including but not limited to colon, lung, liver, breast, renal, prostate, ovarian, skin (including melanoma), bone, and brain cancer, etc. In some embodiments the tumor associated antigens or molecules are known, such as melanoma, breast cancer, squamous cell carcinoma, colon cancer, leukemia, myeloma, and prostate cancer. In other embodiments the tumor associated molecules can be targeted with genetically modified T cells expressing an engineered chimeric receptor. Examples include but are not limited to B cell lymphoma, breast cancer, prostate cancer, and leukemia.

Cells prepared as described above can be utilized in methods and compositions for adoptive immunotherapy in accordance with known techniques, or variations thereof that will be apparent to those skilled in the art based on the instant disclosure.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin, fetal bovine serum or other human serum components.

A treatment effective amount of cells in the composition is at least 2 cell subsets (for example, 1 CD8+ central memory T cell subset and 1 CD4+ helper T cell subset) or is more typically greater than $10^2$ cells, and up to $10^6$, up to and including $10^8$ or $10^9$ cells and can be more than $10^{10}$ cells. The number of cells will depend upon the ultimate use for which the composition is intended as will the type of cells included therein. For example, if cells that are specific for a particular antigen are desired, then the population will contain greater than 70%, generally greater than 80%, 85% and 90-95% of such cells. For uses provided herein, the cells are generally in a volume of a liter or less, can be 500 mls or less, even 250 mls or 100 mls or less. Hence the density of the desired cells is typically greater than $10^4$ cells/ml and generally is greater than $10^7$ cells/ml, generally $10^8$ cells/ml or greater. The clinically relevant number of immune cells can be apportioned into multiple infusions that cumulatively equal or exceed $10^6$, $10^7$, $10^8$, $10^8$, $10^9$, $10^{10}$ or $10^{11}$ cells.

In some embodiments, the lymphocytes of the invention may be used to confer immunity to individuals. By "immunity" is meant a lessening of one or more physical symptoms associated with a response to infection by a pathogen, or to a tumor, to which the lymphocyte response is directed. The amount of cells administered is usually in the range present in normal individuals with immunity to the pathogen. Thus, the cells are usually administered by infusion, with each infusion in a range of from 2 cells, up to at least $10^6$ to $3 \times 10^{10}$ cells, preferably in the range of at least $10^7$ to $10^9$ cells. The T cells may be administered by a single infusion, or by multiple infusions over a range of time. However, since different individuals are expected to vary in responsiveness, the type and amount of cells infused, as well as the number of infusions and the time range over which multiple infusions are given are determined by the attending physician, and can be determined by routine examination. The generation of sufficient levels of T lymphocytes (including cytotoxic T lymphocytes and/or helper T lymphocytes) is readily achievable using the rapid expansion method of the present invention, as exemplified herein. See, e.g., U.S. Pat. No. 6,040,177 to Riddell et al. at column 17.

In embodiments, the composition as described herein are administered intravenously, intraperitoneally, intratumorly, into the bone marrow, into the lymph node, and/or into cerebrospinal fluid. In embodiments, the chimeric receptor engineered compositions are delivered to the site of the tumor. Alternatively, the compositions as described herein can be combined with a compound that targets the cells to the tumor or the immune system compartments and avoid sites such as the lung.

In embodiments, the compositions as described herein are administered with chemotherapeutic agents and/or immunosuppressants. In an embodiment, a patient is first treated with a chemotherapeutic agent that inhibits or destroys other immune cells followed by the compositions described herein. In some cases, chemotherapy may be avoided entirely.

The present invention is illustrated further in the examples set forth below.

EXPERIMENTAL

Example I. Customizing Spacer Domain Length and scFv Affinity for Optimal Recognition of ROR1 with Chimeric Receptor Modified T Cells We constructed chimeric receptors specific for the ROR1 molecule that is expressed on a large number of human malignancies including chronic lymphocytic leukemia, mantle cell lymphoma, acute lymphoblastic leukemia, and breast, lung prostate, pancreas and ovarian cancer. The ROR1 chimeric receptors were designed from ROR1 specific scFVs with different affinities and containing extracellular IgG4-Fc spacer domains of different lengths. The ability of T-cells expressing each ROR-1 specific chimeric receptor to recognize ROR1$^+$ hematopoietic and epithelial tumors in vitro, and to eliminate human mantle cell lymphoma engrafted into immunodeficient mice was analyzed.

Materials and Methods

Human Subjects

Peripheral blood mononuclear cells (PBMC) were obtained from healthy donors and patients after written informed consent on research protocols approved by the Institutional Review Board of the Fred Hutchinson Cancer Research Center (FHCRC).

Cell Lines

The K562, Raji, JeKo-1, MDA-MB-231, MDA-MB-468, and 293T cell lines were obtained from the American Type Culture Collection. Dr. Edus H. Warren (FHCRC) kindly provided the renal cell cancer lines FARP, TREP and RWL. K562/ROR1 and Raji/ROR1 were generated by lentiviral transduction with the full-length ROR1-gene. To derive JeKo-1/ffluc, native JeKo-1 cells were transduced with a lentiviral vector encoding the firefly luciferase (ffluc)-gene upstream of a T2A sequence and eGFP. The transduced JeKo-1 cells were sorted for eGFP expression, and expanded for in vivo experiments.

Immunophenotyping

PBMC and cell lines were stained with the following conjugated mAbs: CD3, CD4, CD5, CD8, CD19, CD28, CD45RO, CD62L, CD314 (NKG2D), MICA/B and matched isotype controls (BD Biosciences). Propidium iodide (PI) staining was performed for live/dead cell discrimination. Cell surface expression of ROR1 was analyzed using a polyclonal goat anti-human-ROR1 antibody (R&D Systems).

Surface expression of 2A2 ROR1 chimeric receptor was analyzed using a polyclonal goat anti-mouse-IgG antibody (Fab-specific) (Jackson ImmunoResearch). Flow analyses were done on a FACSCanto®, sort-purifications on a FACSAriaII® (Becton Dickinson) and data analyzed using FlowJo® software (Treestar).

Vector Construction and Preparation of Chimeric Receptor Encoding Lentivirus

Figure 1:
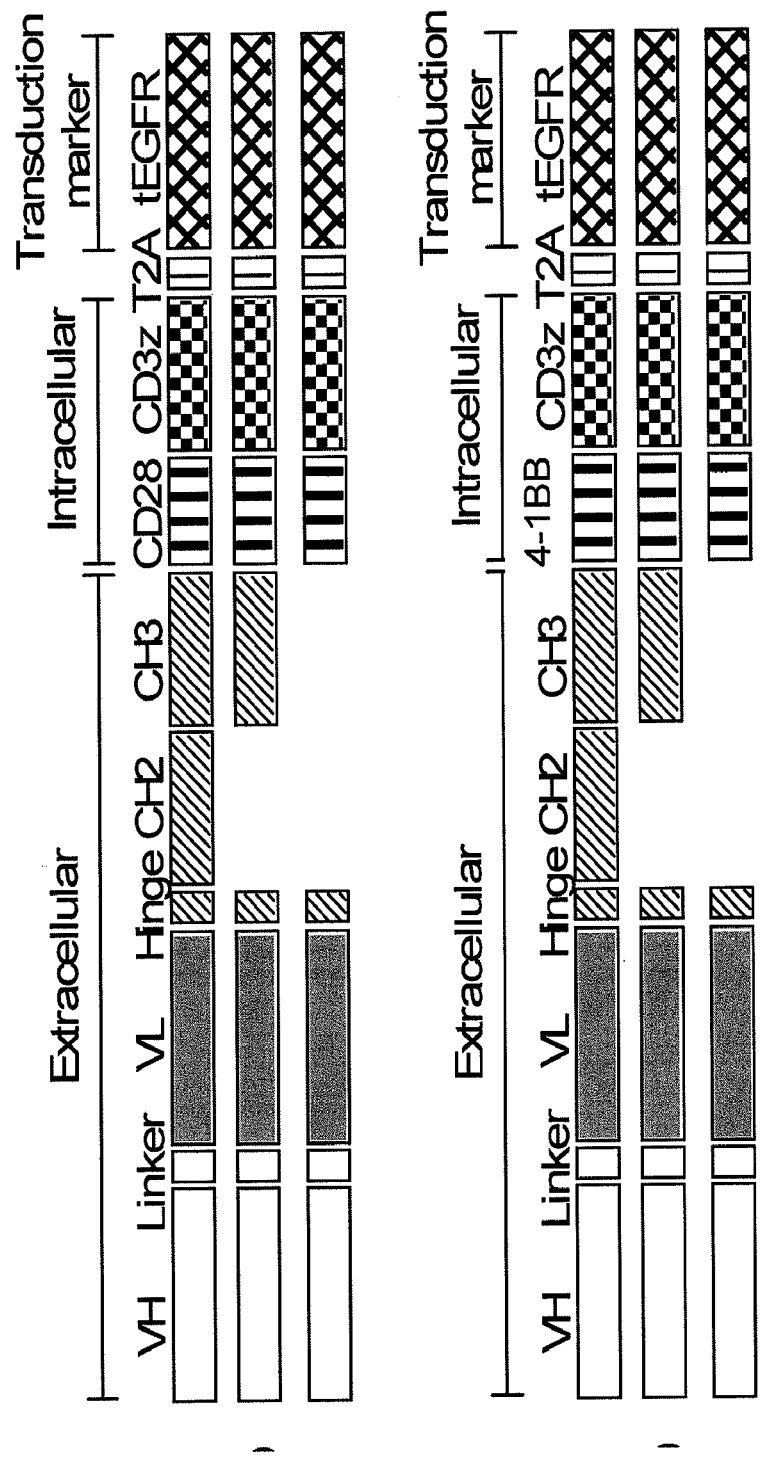
FIG. 1 Library of spacer sequences. We constructed a plasmid library that contain codon optimized DNA sequences that encode extracellular components including of the IgG4 hinge alone, IgG4 hinge linked to CH2 and CH3 domains, or IgG4 hinge linked to the CH3 domain. Any scFV sequence (VH and VL) can be cloned 5' to the sequences encoding this library of variable spacer domains. The spacer domains are in turn linked to CD28 transmembrane and intracellular signaling domains and to CD3 zeta. A T2A sequence in the vector separates the chimeric receptor from a selectable marker encoding a truncated human epidermal growth factor receptor (tEGFR).

ROR1-specific and CD19-specific chimeric receptors were constructed using VL and VH chain segments of the 2A2, R12, and R11 mAbs (ROR1) and FMC63 mAb (CD19). (Variable region sequences for R11 and R12 are provided in Yang et al, Plos One 6(6):e21018, Jun. 15, 2011) Each scFV was linked by a $(G_4S)_3$(SEQ ID NO:12) peptide to a spacer domain derived from IgG4-Fc (Uniprot Database: P01861, SEQ ID NO:13) comprising either 'Hinge-CH2-CH3' (229 AA, SEQ ID NO:), 'Hinge-CH3' (119 AA, SEQ ID NO:) or 'Hinge' only (12 AA, SEQ. ID NO:4) sequences (FIG. 1). All spacers contained a S-P substitution within the 'Hinge' domain located at position 108 of the native IgG4-Fc protein, and were linked to the 27 AA transmembrane domain of human CD28 (Uniprot: P10747, SEQ ID NO: 14) and to a signaling module comprising either (i) the 41 AA cytoplasmic domain of human CD28 with an LL→GG substitution located at positions 186-187 of the native CD28 protein (SEQ ID NO:14) or (ii) the 42 AA cytoplasmic domain of human 4-1BB (Uniprot: Q07011, SEQ ID NO:15), each of which was linked to the 112 AA cytoplasmic domain of isoform 3 of human CD3ζ (Uniprot: P20963, SEQ ID NO; 16). The construct encoded a T2A ribosomal skip element (SEQ ID NO:8)) and a tEGFR sequence (SEQ ID NO:9) downstream of the chimeric receptor. Codon-optimized nucleotide sequences encoding each transgene were synthesized (Life Technologies) and cloned into the epHIV7 lentiviral vector ROR1-chimeric receptor, CD19-chimeric receptor or tEGFR-encoding lentiviruses were produced in 293T cells using the packaging vectors pCHGP-2, pCMV-Rev2 and pCMV-G, and Calphos® transfection reagent (Clontech).

Generation of T-Cell Lines Expressing ROR1 and CD19-Chimeric Receptors

CD8$^+$ CD45RO$^+$ CD62L$^+$ central memory T-cells ($T_{CM}$) or bulk CD4$^+$ T-cells were sorted from PBMC of normal donors, activated with anti-CD3/CD28 beads (Life Technologies), and transduced on day 3 after activation by centrifugation at 800 g for 45 min at 32° C. with lentiviral supernatant (MOI=3) supplemented with 1 µg/mL polybrene (Millipore). T-cells were expanded in RPMI with 10% human serum, 2 mM L-glutamine and 1% penicillin-streptomycin (CTL medium), supplemented with recombinant human IL-2 to a final concentration of 50 U/mL. The tEGFR$^+$ subset of each T-cell line was enriched by immunomagnetic selection with biotin-conjugated anti-EGFR mAb (ImClone Systems) and streptavidin-beads (Miltenyi). ROR1-chimeric receptor and tEGFR control T-cells were expanded using a rapid expansion protocol (Riddell S R, Greenberg P D, The use of anti-CD3 and anti-CD28 monoclonal antibodies to clone and expand human antigen-specific T cells J Immunol Methods. 1990; 128(2):189-201. Epub 1990/04/17.), and CD19-chimeric receptor modified T-cells were expanded by stimulation with irradiated (8,000 rad) B-LCL at a T-cell:LCL ratio of 1:7. T-cells were cultured in CTL medium with 50 U/mL IL-2.

Cytotoxicity, Cytokine Secretion and Proliferation Assays

Target cells were labeled with $^{51}$Cr (PerkinElmer), washed and incubated in triplicate at 1-2×10$^3$ cells/well with effector chimeric receptor modified T-cells at various effector to target (E:T) ratios. Supernatants were harvested for γ-counting after a 4-hour incubation and specific lysis calculated using the standard formula. For analysis of cytokine secretion, 5×10$^4$ T-cells were plated in triplicate with target cells at an E:T ratio of 1:1 (primary CLL), 2:1 (Raji/ROR1; JeKo-1), 4:1 (K562/ROR1, K562/CD19 and K562) or 10:1

(MDA-MB-231), and IFN-γ, TNF-α and IL-2 measured by ELISA or multiplex cytokine immunoassay (Luminex) in supernatant removed after 24-h incubation. In experiments blocking NKG2D signaling, anti-NKG2D (clone 1D11), anti-MICA/B (clone 6D4, all from BD) and anti-ULBP (kindly provided by Dr. Veronika Groh, FHCRC) were used at saturating concentrations. For analysis of proliferation, T-cells were labeled with 0.2 µM carboxyfluorescein succinimidyl ester (CFSE, Invitrogen), washed and plated in triplicate with stimulator cells in medium without exogenous cytokines. After 72-h incubation, cells were labeled with anti-CD8 mAb and PI, and analyzed by flow cytometry to assess cell division of live CD8$^+$ T-cells.

Experiments in NOD/SCID/γc$^{-/-}$ (NSG) Mice

The Institutional Animal Chimeric receptor and Use Committee approved all mouse experiments. Six- to 8-week old female NOD.Cg-Prkdc$^{scid}$Il2rg$^{tm1Wjl}$/SzJ (NSG) mice were obtained from the Jackson Laboratory or bred in-house. Mice were injected with 0.5×10$^6$ JeKo-1/ffluc tumor cells via tail vein and received a subsequent tail vein injection of chimeric receptor-modified or control T-cells.

For bioluminescence imaging of tumor growth, mice received intraperitoneal injections of luciferin substrate (Caliper Life Sciences) resuspended in PBS (15 µg/g body weight). Mice were anesthetized with isoflurane and imaged using an Xenogen IVIS Imaging System (Caliper) 10, 12 and 14 minutes after the injection of luciferin in small binning mode at an acquisition time of 1 s to 1 min to obtain unsaturated images. Luciferase activity was analyzed using Living Image Software (Caliper) and the photon flux analyzed within regions of interest that encompassed the entire body or the thorax of each individual mouse.

Statistical Analyses

Statistical analyses were performed using Prism Software (GraphPad®). Student's t-test was performed as a two-sided paired test with a confidence interval of 95% and results with a p-value of $p<0.05$ were considered significant Statistical analysis of survival were done by log-rank testing and results with a p-value of $p<0.05$ considered significant.

Results

Truncating the Spacer Domain of the 2A2 ROR1-Chimeric Receptor Confers Superior Recognition of ROR1$^+$ Tumors We previously reported the design of a ROR1-specific chimeric receptor using the 2A2 scFV, which binds to an epitope in the NH2-terminal, membrane distal Ig-like/Frizzled portion of ROR1-1. The initial 2A2 ROR1-chimeric receptor had a long 229 AA spacer that included the 'Hinge-CH2-CH3' region of IgG4-Fc, and incorporated CD28 costimulatory and CD3ζ signaling domains (Hudecek M et al. Blood, 2010). This chimeric receptor conferred specific recognition of ROR1$^+$ tumors, but we hypothesized that because of the membrane distal location of the ROR1 epitope, truncating the spacer domain might enhance tumor recognition and T-cell signaling. Therefore, we constructed 2 additional chimeric receptors in which the IgG4-Fe spacer domain was sequentially deleted to derive 'Hinge-CH3' (119 AA, intermediate), and 'Hinge-only' (12 AA, short) variants. Each of the new receptors contained the identical 2A2 scFV, and CD28 and CD3ζ signaling modules. The transgene cassette included a truncated EGFR (tEGFR) to serve as a transduction, selection and in vivo tracking marker for chimeric receptor-modified T-cells.

Figure 2:
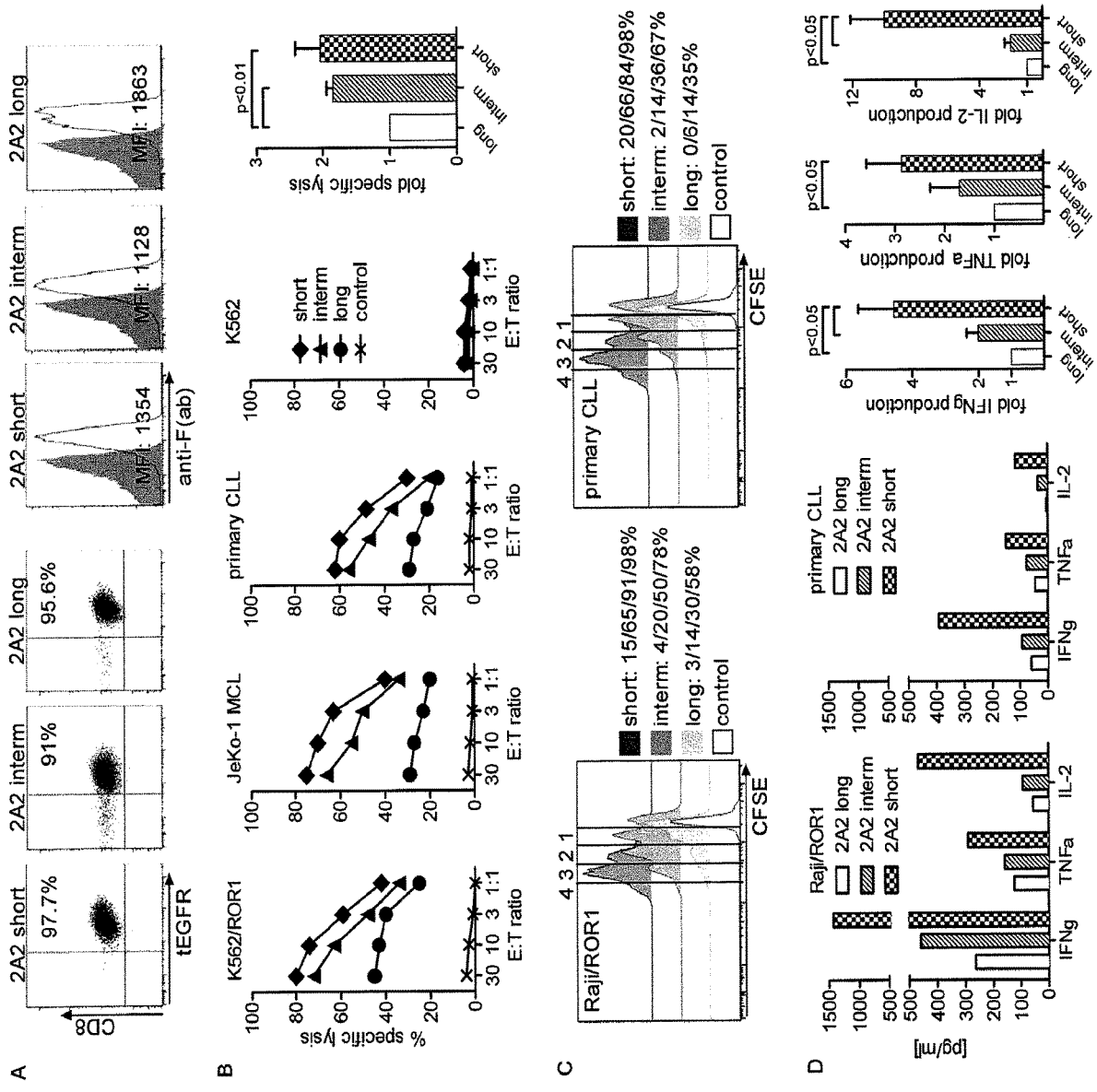
FIG. 2: In vitro cytotoxicity, cytokine production, and proliferation of T-cells modified to express 2A2 ROR1 chimeric receptors with modified spacer length. (A) Phenotype of purified CD8$^+$ T$_{CM}$-derived cell lines modified with each of the 2A2 ROR1 chimeric receptors with long, intermediate and short spacer domain. Staining with anti-F(ab) antibody that binds to an epitope in the 2A2 scFV shows surface expression of ROR1 chimeric receptors with full length or truncated spacer. (B) Cytolytic activity of T-cells expressing the various 2A2 ROR1 chimeric receptors with long (●), intermediate (▲) and short spacer (♦), or a tEGFR control lentiviral vector against ROR1$^+$ (x) and control target cells. The bar diagram summarizes cytotoxicity data from 3 independent experiments (E:T=30:1) normalized to cytolytic activity by 2A2 ROR1 chimeric receptor 'long'=1, and analyzed by Student's t-test. (C) CFSE dye dilution was used to measure proliferation of 2A2 ROR1 chimeric receptor and tEGFR control T-cells, 72 hours after stimulation with Raji/ROR1 (left panel) and primary CLL cells (right panel) without addition of exogenous cytokines. For analysis, triplicate wells were pooled and the proliferation of live (PI−), CD8+ T-cells analyzed. Numbers above each histogram indicate the number of cell divisions the proliferating subset underwent, and the fraction of T-cells in each gate that underwent ≥4/3/2/1 cell divisions is provided next to each plot. (D) Multiplex cytokine assay of supernatants obtained after 24 hours from triplicate co-cultures of 5×10$^4$ T-cells expressing the various 2A2 ROR1 chimeric receptors with Raji/ROR1 and primary CLL cells. Multiplex cytokine data from 3 independent experiments were normalized (cytokine release by 2A2 ROR1 chimeric receptor 'long'=1) and analyzed by Student's t-test (right bar diagram).

We transduced purified CD8$^+$ T$_{CM}$ with the 2A2 ROR1-chimeric receptors containing full length or truncated IgG4-Fc spacers, and with a tEGFR control vector. The mean transduction efficiency was 15% (range 9-22%), and transgene-positive T-cells were enriched to uniform purity (>90%) on day 10 by selection for tEGFR expression, and expanded (FIG. 2A). Surface expression of each of the chimeric receptors was confirmed by staining with F(ab)-specific antibodies (FIG. 2A).

Analysis of the in vitro function of CD8$^+$ T-cells modified to express each of the 2A2 ROR1-chimeric receptors demonstrated that each receptor conferred specific lysis of JeKo-1 MCL and primary CLL cells that naturally express ROR1, and of K562 cells that had been transduced with ROR1, but did not confer recognition of control ROR1$^-$ targets (FIG. 2B). T-cells expressing the short 'Hinge-only' 2A2 ROR1-chimeric receptor had maximum cytolytic activity, and a hierarchy (short>intermediate>>long) of tumor lysis was clearly evident against all ROR1$^+$ tumor targets (FIG. 2B), illustrating the importance of spacer domain length on the recognition of ROR1$^+$ tumor cells.

Anti-tumor efficacy of adoptive T-cell therapy correlates with proliferation and survival of transferred T-cells, which could be altered by signaling through the chimeric receptor. We used CFSE dilution assays to analyze proliferation of T-cells modified with each of the 2A2 ROR1-chimeric receptors after engagement of Raji/ROR1 or CLL, and found that the short spacer construct promoted the greatest T-cell proliferation following stimulation (FIG. 2C). To ensure that the enhanced proliferation was not associated with greater activation induced cell death (AICD), we also analyzed the proportion of 2A2 ROR1 chimeric receptor modified T-cells that stained with propidium iodide (PI) after stimulation with Raji/ROR1 and JeKo-1 tumor cells. We detected a much lower frequency of PI$^+$ CD8$^+$ T-cells in the T-cell line modified with the short (Raji/ROR1: 17.2%/ JeKo-1: 202%) compared to the intermediate (41.6%/ 42.4%) and long (44.5%/48.5%) spacers.

Quantitative analysis of cytokine production in response to stimulation with Raji/ROR1 and primary CLL cells showed production of IFN-γ, TNF-α and IL-2 by T-cells expressing each of the 2A2 ROR1 chimeric receptors. As observed in cytotoxicity assays, the short spacer construct was superior in mediating cytokine secretion after tumor recognition (FIG. 2D). Thus, this analysis shows that truncating the extracellular IgG4-Fc spacer domain of the 2A2 ROR1-chimeric receptor leads to a significant increase in cytotoxicity, proliferation and in vitro effector functions after tumor recognition.

The R11 scFv that is Specific for a Membrane Proximal Epitope in the ROR1 Kringle Domain Requires a Long Extracellular Spacer Domain.

Figure 3:
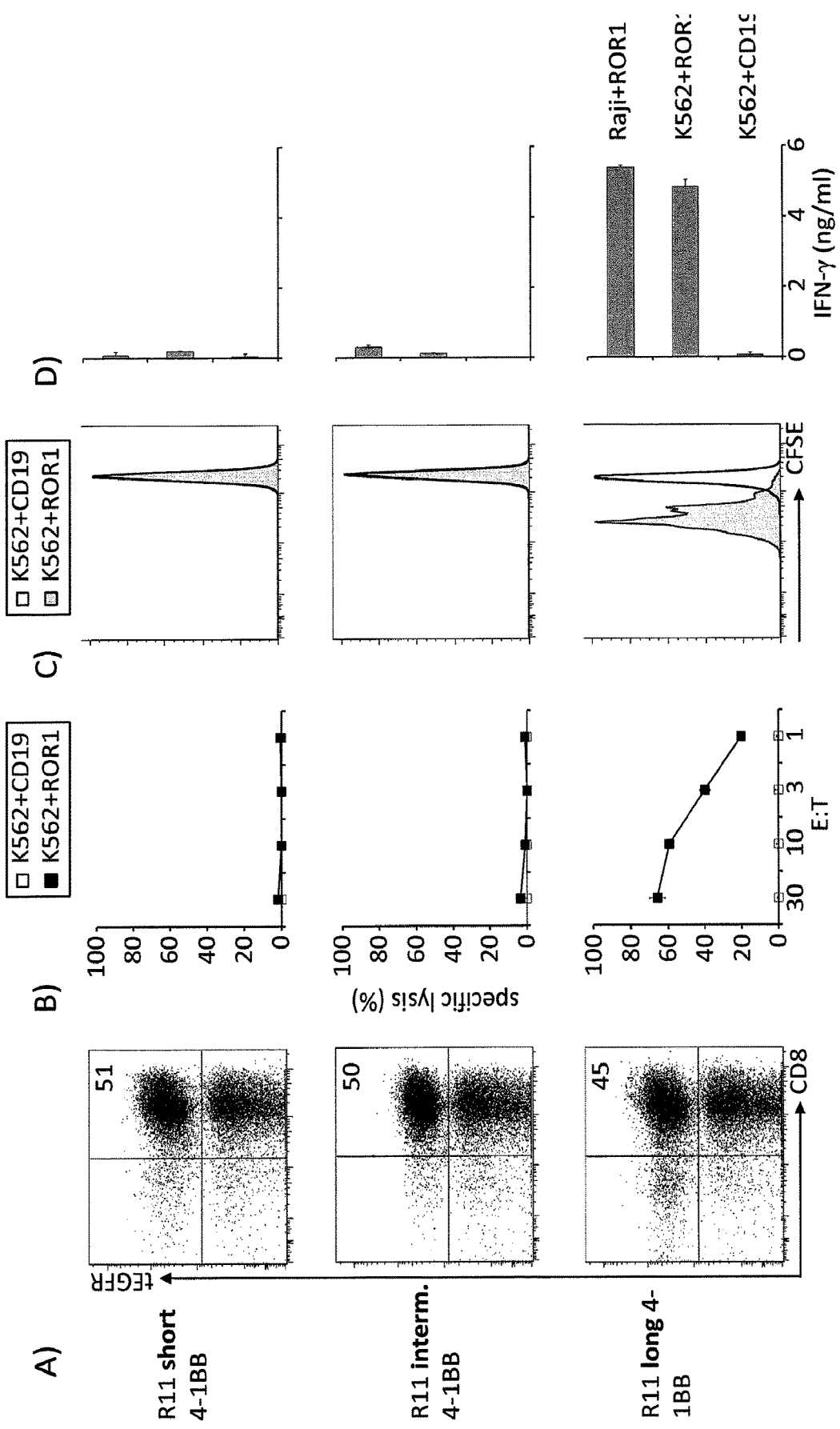
FIG. 3. R11 chimeric receptor requires a long spacer for recognition of ROR1+ tumor cells. The sequences encoding the scFV from the R11 monoclonal antibody that is specific for an epitope in the membrane proximal Kringle domain of the orphan tyrosine kinase receptor ROR1 were cloned upstream of IgG4 hinge only (short), IgG4 hinge/CH3 (intermediate), and IgG4 hinge/CH2/CH3 sequences in our chimeric receptor library containing the 4-1BB costimulatory domains and prepared as lentiviral vectors. A). Human CD8+ T cells were transduced and the transduction efficiency with each of the short, intermediate and long chimeric receptors was determined by staining for the tEGFR marker. B). Transduced T cells expressing the short (top), intermediate (middle), and long (bottom) were assayed for lysis of K562 leukemia cells alone or transfected to express ROR1. Only the T cells expressing the long spacer chimeric receptor efficiently killed ROR1+K562 cells. C). Transduced T cells expressing the short (top), intermediate (middle), and long (bottom) were labeled with CFSE, stimulated with K562 cells expressing ROR1 or CD19 (control) and assayed for cell proliferation over 72 hours. The T cells expressing the long spacer chimeric receptor proliferated specifically to the ROR1+K562 cells. D). Transduced T cells expressing the short (top), intermediate (middle), and long (bottom) were stimulated with Raji lymphoma cells and K562 cells that expressed ROR1 or CD19 (control) and assayed for the secretion of interferon gamma into the supernatant over 24 hours. The T cells expressing the long spacer chimeric receptor proliferated and produced the highest levels of interferon gamma in response to ROR1 positive target cells.

We transduced purified CD8$^+$ T cells with ROR1-chimeric receptors containing the R11 scFv that is specific for the Kringle domain of ROR1 and containing full length or truncated IgG4-Fc spacers (CH3 and hinge only). The transduction efficiency with each of the short (IgG4 hinge only), intermediate (IgG4 hinge/CH3), and long (IgG4 hinge/CH2/CH3) vectors was comparable (45-51%) as measured by EGFR expression. (FIG. 3A). T cells transduced with each of the vectors were assayed for cytolysis (FIG. 3B), proliferation (FIG. 3C), and cytokine production (FIG. 3D) in response to leukemia or lymphoma cells that did or did not express ROR1. As shown, only T cells transduced with the R11 chimeric receptor containing a long spacer sequence were able to efficiently recognize ROR1+ tumors and mediate effector functions.

ROR1 Chimeric Receptors Derived from a mAb R12 with Higher Affinity than 2A2 Mediate Superior Anti-Tumor Reactivity We next examined whether increasing the affinity of the scFV used to construct the ROR1 chimeric receptor might influence tumor recognition and T-cell function. We generated ROR1-specific chimeric receptors from the mAb R12 that like 2A2, binds to an epitope in the NH2-terminal Ig/Frizzled domain of ROR1 but with >50-fold higher monovalent binding affinity.

R12 ROR1 chimeric receptors were constructed with both long and short IgG4-Fc spacers to determine whether the optimal spacer design for this higher affinity scFV differed from that for a lower affinity scFV. We found that similar to 2A2, the short spacer R12 ROR1 chimeric receptor conferred improved cytolytic activity, cytokine secretion and proliferation (data not shown), suggesting that the shorter spacer length provides superior spatial engagement of the T-cell and ROR1$^+$ target cell for T-cell activation.

Figure 4:
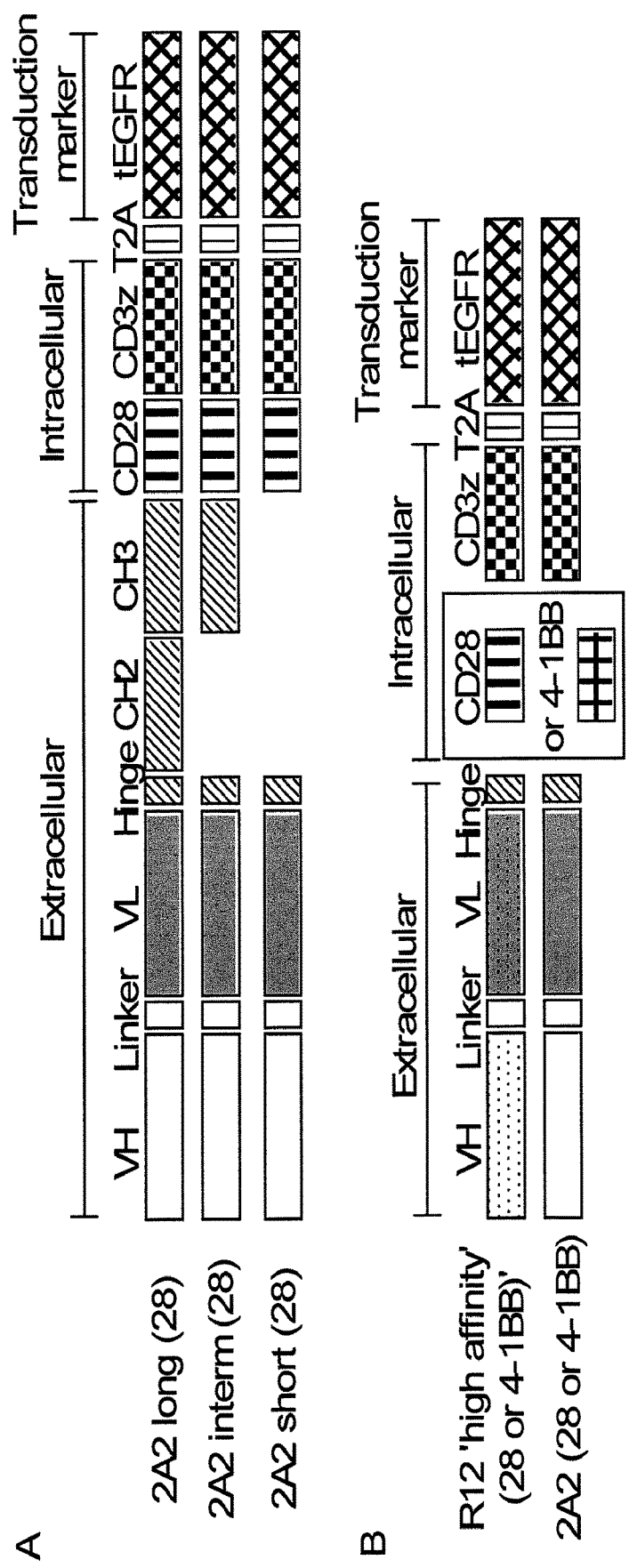
FIG. 4: Design of ROR1 chimeric receptors with modified spacer length and derived from the 2A2 and R12 scFV with different affinity. (A) Design of lentiviral transgene inserts encoding a panel of ROR1 chimeric receptors containing the 2A2 scFV, an IgG4-Fc derived spacer of 'Hinge-CH2-CH3' (long spacer, 229 AA), 'Hinge-CH3' (intermediate, 119 AA), or 'Hinge' only (short, 12 AA), and a signaling module with CD3ζ; and CD28. Each chimeric receptor cassette contains a truncated EGFR marker encoded downstream of a T2A element. (B) Lentiviral transgene inserts encoding ROR1-specific chimeric receptors derived from the R12 and 2A2 scFV with short IgG4-Fc 'Hinge' spacer (12 AA), and a signaling module containing CD28 or 4-1BB and CD3ζ respectively (total: 4 constructs).
Figure 5:
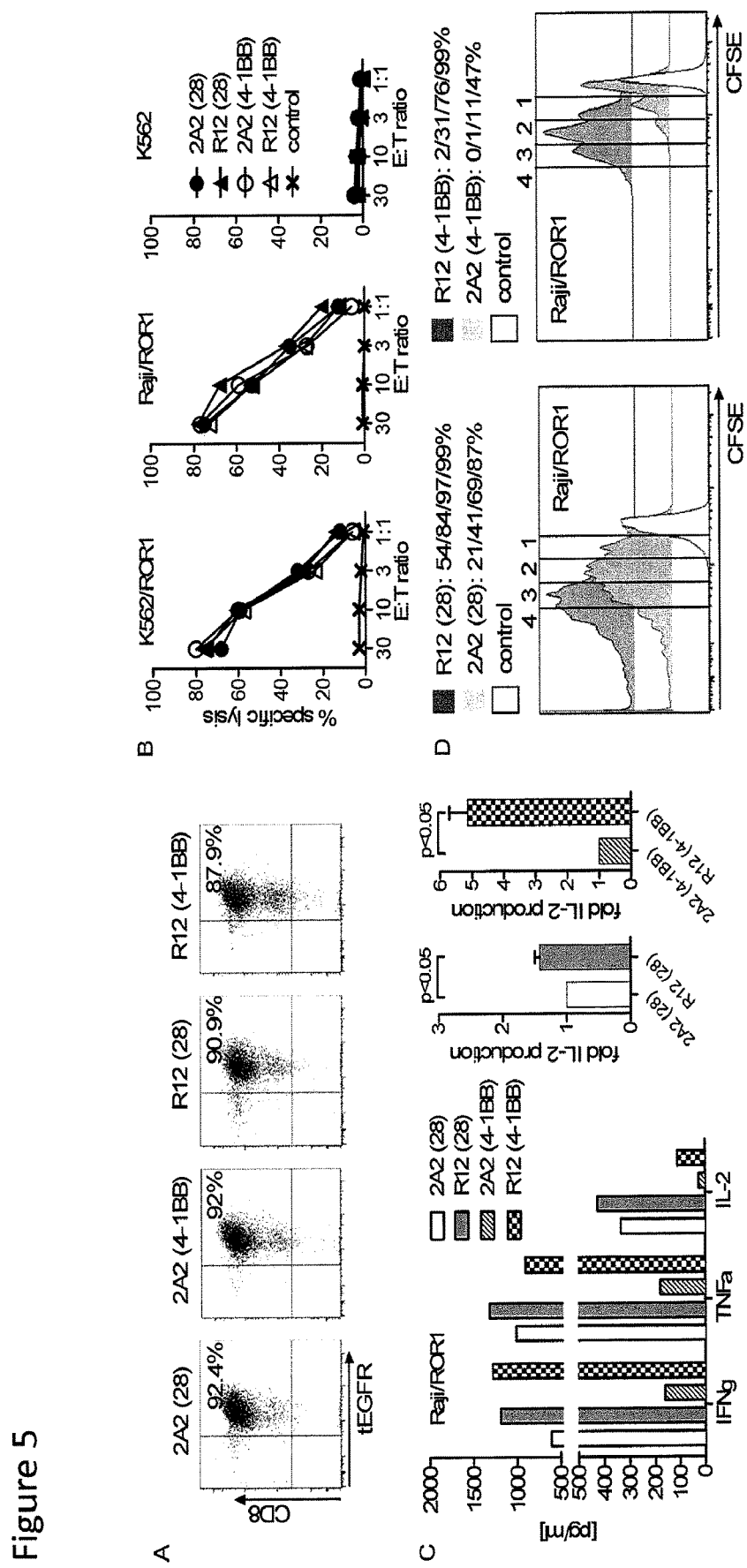
FIG. 5: Anti-tumor reactivity of T-cells modified with ROR1 chimeric receptors derived from mAb R12 with higher affinity than 2A2. (A) tEGFR expression on purified polyclonal CD8+ T$_{CM}$-derived T-cell lines modified with each of the R12 and 2A2 ROR1 chimeric receptors with short IgG4-Fc 'Hinge' spacer, and CD28 or 4-1BB costimulatory domain. (B) Cytotoxicity against ROR1+ and control target cells by T-cells expressing R12 (28-▲; 4-1BB-Δ) and 2A2 ROR1 chimeric receptors (28-●; 4-1BB○) or a tEGFR control vector (x). (C) Multiplex cytokine assay of supernatants obtained after 24 hours from co-cultures of 5×10$^4$ T-cells expressing the various ROR1 chimeric receptors with Raji/ROR1 tumor cells. The middle/right bar diagrams show normalized multiplex data from 3 independent experiments (cytokine release by ROR1 chimeric receptor 2A2=1) analyzed by Student's t-test. (D) Proliferation of ROR1 chimeric receptor T-cells and tEGFR control T-cells 72 hours after stimulation with Raji/ROR1 cells and without addition of exogenous cytokines was assessed by CFSE dye dilution. Numbers above each histogram indicate the number of cell divisions the proliferating subset underwent, and the fraction of T-cells in each gate that underwent ≥4/3/2/1 cell divisions is provided above each plot.

We then designed R12 and 2A2 ROR1 chimeric receptors that contained an optimal (short) extracellular spacer, and either a CD28 or 4-1BB costimulatory domain in tandem with CD3$\zeta$ (4 constructs) for comparison (FIG. 4A,B). These ROR1-chimeric receptor constructs were expressed in purified CD8$^+$ T$_{CM}$ of healthy donors, and we confirmed equivalent transgene expression by tEGFR staining (FIG. 5A). T-cells modified with each of the 2A2 and R12 ROR1-chimeric receptors specifically lysed K562/ROR1 and Raji/ROR1 tumor cells with approximately equivalent efficiency (FIG. 5B). However, analysis of cytokine production showed that the high affinity R12 ROR1 chimeric receptors that contained CD28 or 4-1BB conferred significantly higher IFN-$\gamma$, TNF-$\alpha$ and IL-2 production compared to the corresponding 2A2 constructs (FIG. 5C). We found that T-cells expressing chimeric receptors with a CD28 costimulatory domain produced more IFN-$\gamma$, TNF-$\alpha$ and IL-2 compared to those with 4-1BB.

Experiments to analyze the proliferation of ROR1 chimeric receptor T-cells showed a higher percentage of proliferating T-cells and a higher number of cell divisions in T-cells expressing the high affinity R12 ROR1 chimeric receptors with CD28 and 4-1BB domain compared to T-cells expressing the respective 2A2 counterparts (FIG. 4D). There was more vigorous proliferation in T-cells that expressed chimeric receptors with a CD28 domain, consistent with higher IL-2 production induced by these receptors. There was a lower frequency of AICD as measured by PI staining in T-cell lines modified with R12 compared to 2A2 ROR1-chimeric receptors after stimulation with Raji/ROR1 and JeKo-1 tumor cells respectively (R12: 5.6%/6.9% vs. 2A2: 10%/9.65%). T-cell lines that expressed chimeric receptors with a CD28 domain also had lower AICD compared to 4-1BB in response to Raji/ROR1 and JeKo-1 tumor cells respectively (R12: 16.4%/i 8.4% vs. 2A2 38.1%/39.6%).

To determine if the enhanced function observed with R12 ROR1 chimeric receptors in CD8$^+$ T-cells extended to CD4$^+$ T-cells, we transduced bulk CD4$^+$ T-cells with the 2A2 and R12 ROR1 chimeric receptors containing the short spacer and CD28 costimulatory domain. In response to Raji/ROR1$^+$ tumor cells, CD4$^+$ T-cells that expressed the high affinity R12 scFV produced higher levels of IFN-$\gamma$, TNF-$\alpha$, IL-2, IL-4, and IL-10, and underwent greater proliferation than CD4$^+$ T-cells that expressed 2A2 (FIG. 5A,B). Both cytokine production and proliferation was superior in CD4$^+$ compared to CD8$^+$ T-cells modified with the same ROR1 chimeric receptors. In summary, our data demonstrate that tailoring both the length of the non-signaling extracellular chimeric receptor spacer domain and scFV affinity are independent parameters that affect the function of ROR1-chimeric receptor T-cells.

D8$^+$ T-Cells Modified with a High Affinity ROR1 Chimeric Receptor have Comparable Activity to a CD19 Chimeric Receptor Against Primary CLL In Vitro ROR1 and CD19 are both uniformly expressed on all primary CLL (FIG. 6A), however the absolute number of ROR1-molecules per tumor cell is estimated to be 10-fold lower than that of CD19, which has been successfully targeted in clinical trials with CD19 chimeric receptor T-cells. We compared recognition of primary CLL by CD8$^+$ T-cells expressing the optimized R12 and 2A2 ROR1 chimeric receptors, and a CD19 chimeric receptor derived from the FMC63 scFV. We used purified CD8$^+$ T$_{CM}$ for chimeric receptor-modification to provide a uniform cell product and each chimeric receptor contained a short IgG4-Fc 'Hinge-only' spacer and 4-1BB costimulatory domain. We confirmed our CD19 chimeric receptor (IgG4 Hinge) was at least as and more effective in recognizing CD19$^+$ tumors as a CD19 chimeric receptor with CD8a Hinge spacer and 4-1BB costimulatory domain that is being used in ongoing clinical trials. (FIG. 20). T cells expressing CD19 chimeric receptors with 4-1BB and CD3zeta and a modified IgG4-Fc hinge exhibit superior in vitro and in vivo function compared to T cells expressing CD19 chimeric receptors with 4-1BB and CD3zeta and a CD8 alpha hinge. In FIG. 20D, in vivo antitumor activity of T cells expressing a CD19 chimeric receptor with an IgG4 Fe hinge (group 1) or CD8 alpha hinge (group 2) and T cells that express tEGFR alone (group 3) in NSG mice inoculated with Raji tumor cells expressing firefly luciferase (ffluc) were compared. Mice were imaged 17 days after tumor inoculation and 10 days after T cell inoculation. The data shows greater tumor burden in mice treated with control tEGFR T cells (group 3) or with CD19 chimeric receptor CD8 alpha hinge T cells (group 2) compared with mice treated with CD19 chimeric receptor IgG4 Fc hinge T cells (group 1).

Figure 6:
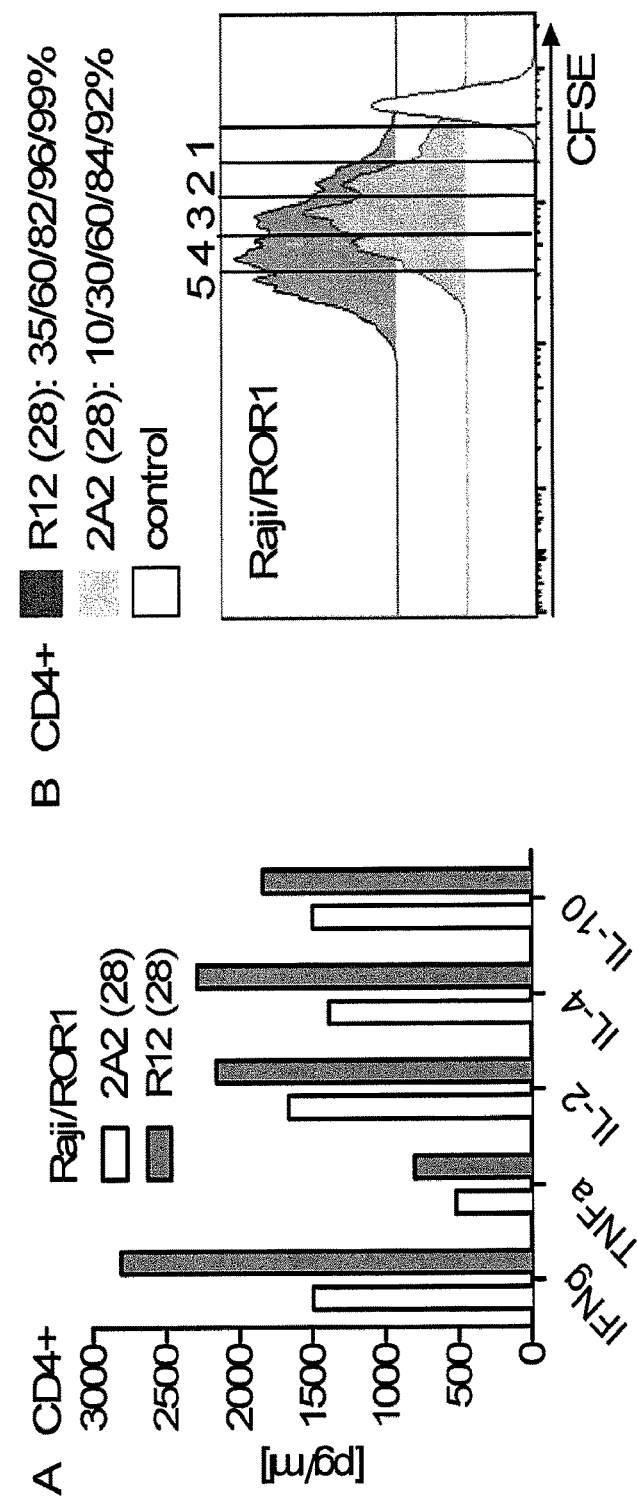
FIG. 6: Analysis of cytokine production and proliferation of CD4+ T-cells lines modified with a ROR1 chimeric receptor derived from mAb R12 with higher affinity than 2A2. (A-B) The 2A2 and R12 ROR1 chimeric receptors had the short spacer and a CD28 costimulatory domain. (A) Multiplex cytokine analysis from supernatants obtained 24 hours after stimulation of 5×10$^4$ CD4+ T-cells expressing the 2A2 and R12 ROR1 chimeric receptor with Raji/ROR1 tumor cells. (B) Proliferation of CD4+ R12 and 2A2 ROR1 chimeric receptor T-cells and tEGFR control T-cells 72 hours after stimulation with Raji/ROR1 cells and without addition of exogenous cytokines was assessed by CFSE dye dilution. Numbers above each histogram indicate the number of cell divisions the proliferating subset underwent, and the fraction of T-cells in each gate that underwent ≥5/4/3/2/1 cell divisions is provided above the histograms.
Figure 7:
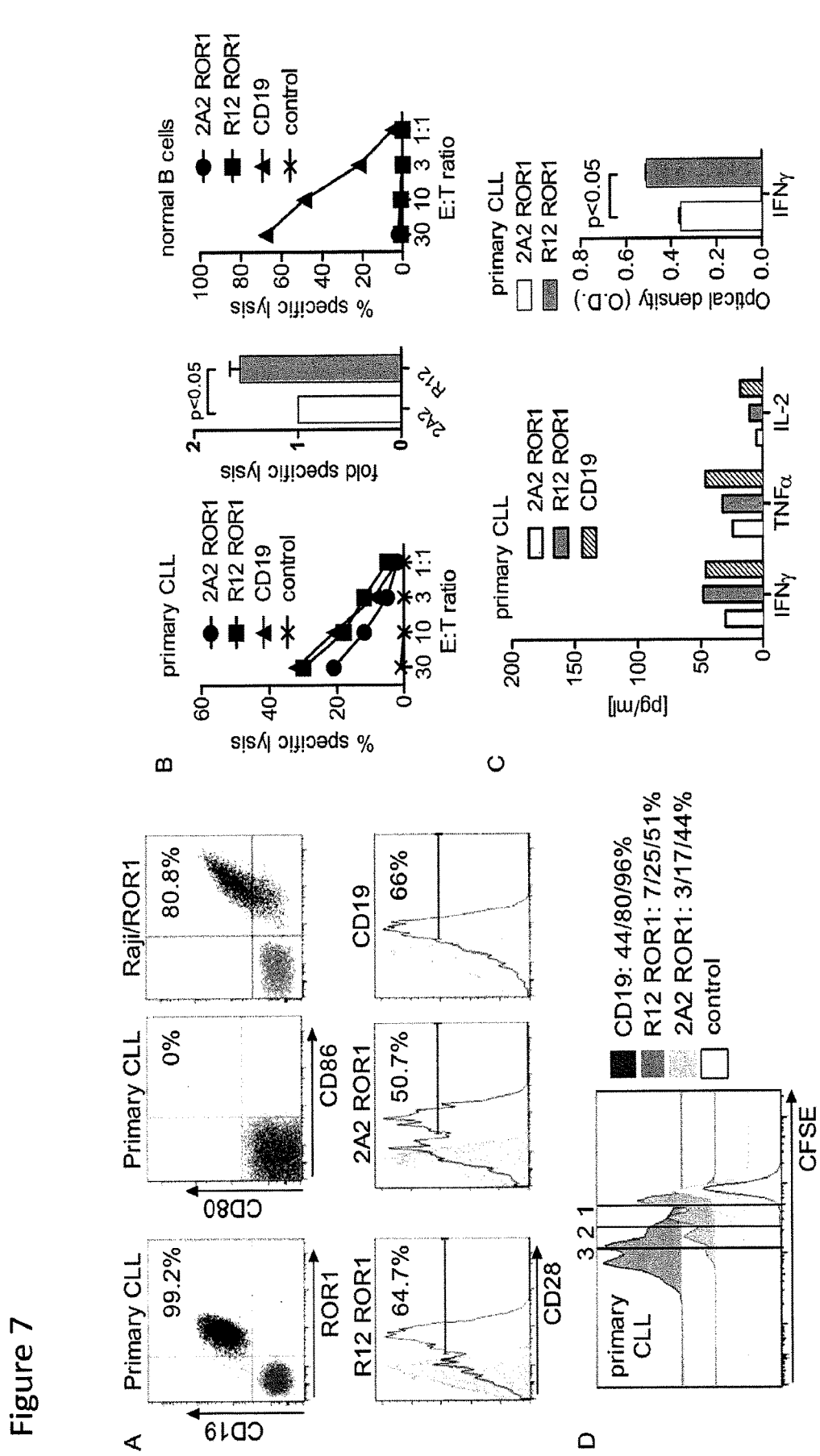
FIG. 7: Recognition of primary CLL by T-cells modified with 2A2 and R12 ROR1 chimeric receptors with optimal short spacer and 4-1BB costimulatory domain or with a CD19-specific chimeric receptor. (A) Expression of ROR1/CD19 on primary CLL, and CD80/86 on primary CLL and Raji/ROR1 tumor cells (black dot plots) that can engage CD28 on chimeric receptor T-cells (white histograms). Staining with matched isotype control mAbs is shown as grey dot plots/histograms. (B) Cytolytic activity of T-cells expressing the 2A2(●) and R12 ROR1 chimeric receptor (■), a CD19-specific chimeric receptor (Δ) and T-cells modified with a tEGFR control vector (x) against primary CLL (left diagram) and normal B cells (right diagram) analyzed by chromium release assay. Cytotoxicity data against primary CLL from 4 independent experiments (E:T=30:1) were normalized (cytolytic activity by ROR1 chimeric receptor 2A2=1) and analyzed by Student's t-test (bar diagram). (C) Multiplex cytokine analysis after a 24-hour stimulation of 5×10$^4$ chimeric receptor T-cells with primary CLL cells. Cytokine release of unstimulated chimeric receptor T-cells was below 3.6 pg/ml (detection limit) (left bar diagram). ELISA for IFN-γ production by 5×10$^4$ 2A2 and R12 ROR1 chimeric receptor T-cells after a 24-hour co-culture with primary CLL. O.D. of 1 corresponds to approximately 250 pg/ml (right bar diagram). (D) Proliferation of CD8+ T-cells modified with the 2A2 ROR1, R12 ROR1 and a CD19 chimeric receptor, 72 hours after stimulation with primary CLL cells. Numbers above each histogram indicate the number of cell divisions, and the fraction of T-cells in each gate that underwent ≥3/2/1 cell divisions is provided next to each plot.

The cytolytic activity of R12 ROR1 chimeric receptor T-cells against primary tumor cells from multiple CLL patients (n=4) was higher compared to T-cells modified with the lower affinity 2A2 ROR1 chimeric receptor, and equivalent to the lysis observed with CD19 chimeric receptor T-cells (FIG. 6B). Multiplex cytokine analysis showed nearly equivalent production of IFN-$\gamma$ and TNF-$\alpha$, but less IL-2 production by CD8$^+$ T-cells expressing the R12 ROR1 compared with those expressing the CD19-chimeric receptor after co-culture with primary CLL (FIG. 6C). 2A2 ROR1 chimeric receptor T-cells produced lower amounts of all cytokines than R12 ROR1 chimeric receptor T-cells as noted previously. Cytokine production by all of the chimeric receptor-transduced T-cells after stimulation with CLL was substantially less than with Raji/ROR1, which unlike CLL expresses both CD80 and CD86 that can engage CD28 expressed on chimeric receptor T-cells (FIG. 6A, C).

Figure 8:
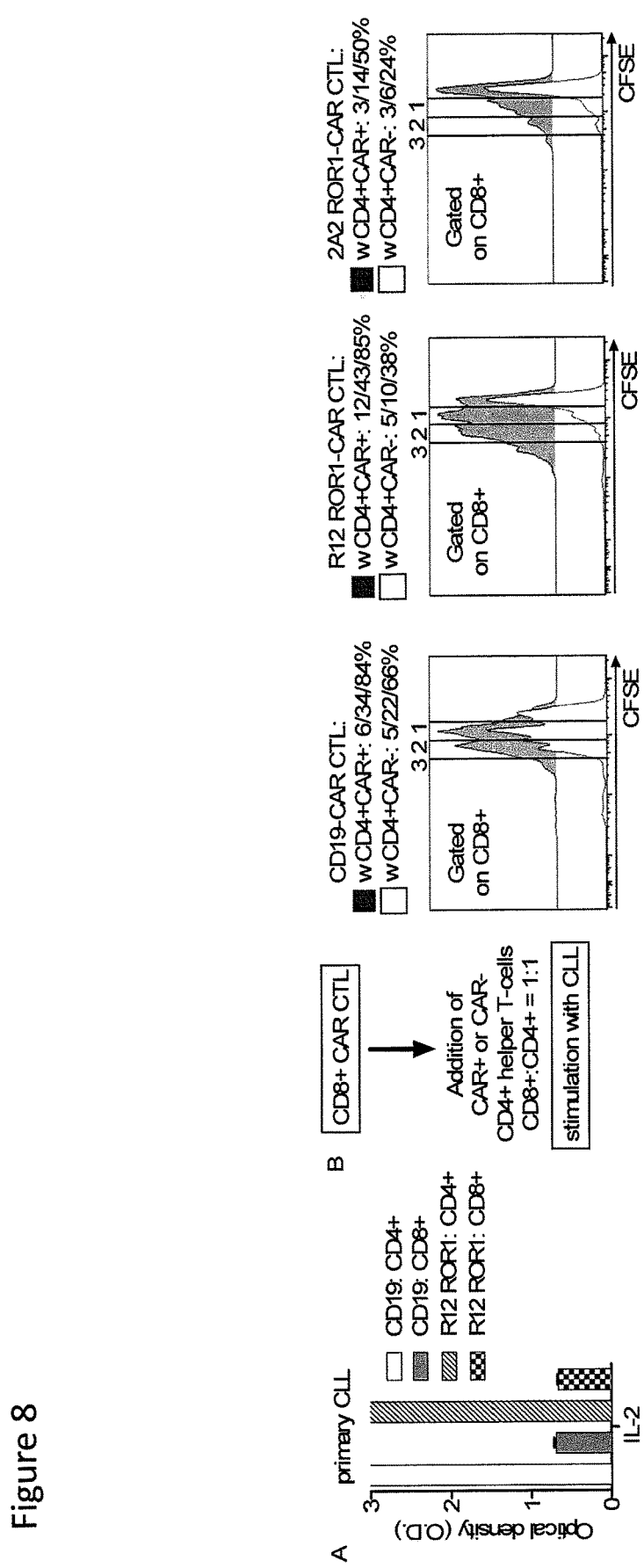
FIG. 8: The function of ROR1-chimeric receptor and CD19-chimeric receptor modified CD8+ T-cells against primary CLL is augmented by chimeric receptor-modified CD4+ helper T-cells. (A) ELISA for IL-2 production from triplicate co-cultures of $5×10^4$ CD8+ and CD4+ T-cells expressing the R12 ROR1 and CD19-chimeric receptor respectively, incubated with primary CLL for 24-hours. O.D. of 1 corresponds to approx. 800 pg/ml. (B) Proliferation of chimeric receptor-modified CD8+ T-cells in response to primary CLL is enhanced by addition of chimeric receptor-modified CD4+ T-cells. CFSE-labeled CD8+ T-cells expressing the 2A2 ROR1, R12 ROR1 and CD19-chimeric receptor respectively, were co-cultured with tumor cells and with 2A2 ROR1, R12 ROR1 and CD19-chimeric receptor transduced or control untranduced CD4+ T-cells (CD8+: CD4+=1:1). Proliferation of the CD8+ subset was analyzed 72 hours after stimulation. Numbers above each histogram indicate the number of cell divisions, and the fraction of T-cells in each gate that underwent ≥3/2/1 cell divisions is provided above each plot.

We observed less proliferation of T-cells expressing the R12 and 2A2 ROR1 chimeric receptor compared to the CD19 chimeric receptor after stimulation with CLL (CD19>R12>2A2) (FIG. 6D). We hypothesized that proliferation of CD8$^+$ ROR1 chimeric receptor T-cells in response to CLL may be augmented in the presence of chimeric receptor-modified CD4$^+$ T-cells because of their higher secretion of IL-2 compared to CD8$^+$ T$_{CM}$ (FIG. 4A; FIG. 8A). To test this possibility, we performed in vitro co-culture experiments where CD4$^+$ and CD8 T$_{CM}$ were separately modified with the R12 ROR1, 2A2 ROR1 and CD19 chimeric receptors respectively, enriched for chimeric receptor expression, and combined at a 1:1 ratio to ensure equivalent proportions of CD8$^+$ and CD4$^+$ T-cells modified with each of the vectors. These cells were CFSE-labeled and stimulated with primary CLL. We observed a dramatic increase in proliferation of CD8$^+$ R12 ROR1 chimeric receptor T-cells after addition of chimeric receptor-transduced, but not untransduced CD4$^+$ T-cells (FIG. 8B). Notably, when provided with CD4-help, we observed equivalent proliferation of R12 ROR1 and CD19 chimeric receptor CD8$^+$ T-cells in response to CLL, whereas proliferation of CD8$^+$ T-cells expressing the lower affinity 2A2 ROR1 chimeric receptor remained less. Collectively, our data show that the high affinity R12 ROR1 chimeric receptor confers superior reactivity compared to 2A2 against primary CLL cells in vitro.

Figure 9:
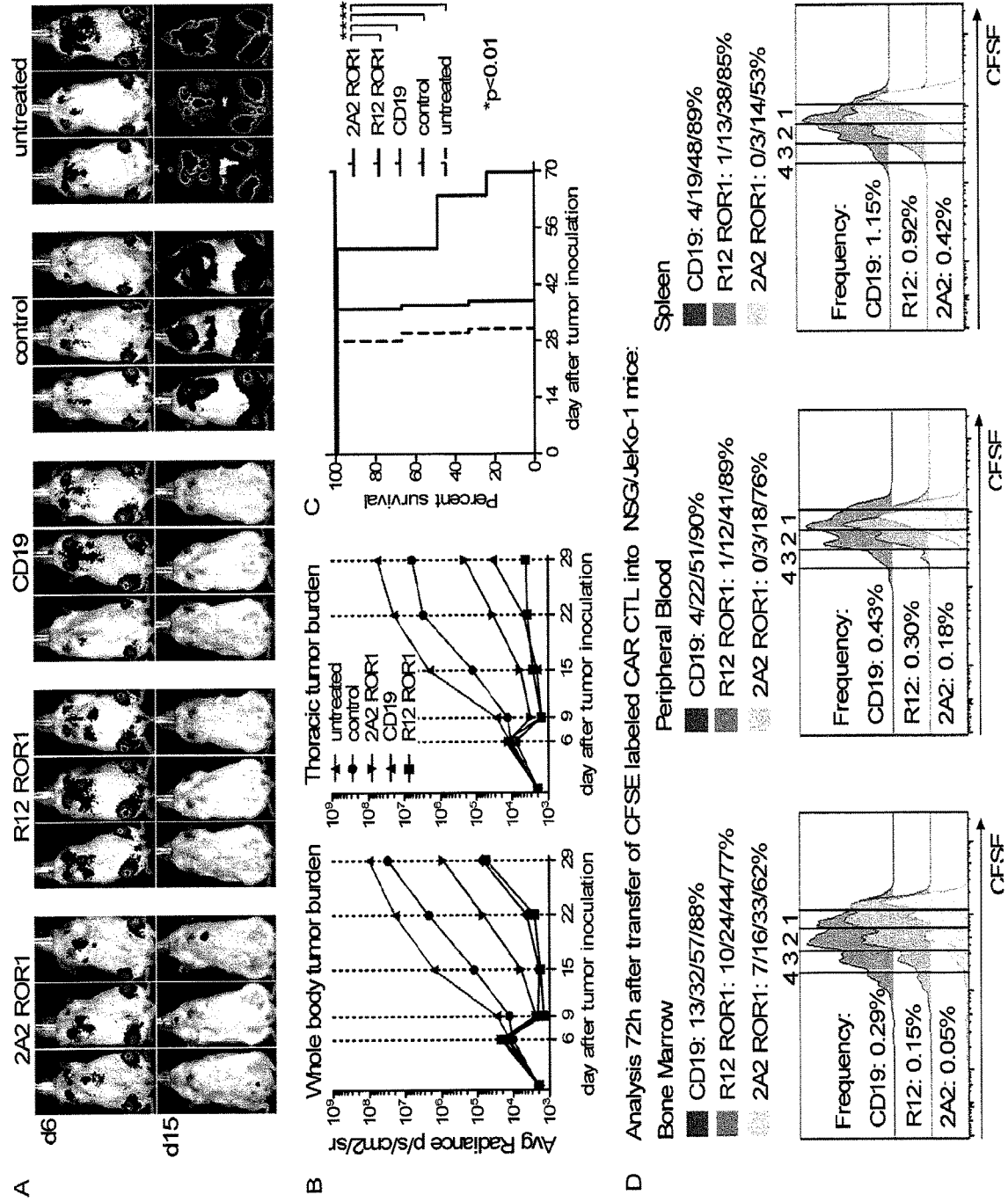
FIG. 9: In vivo anti-tumor efficacy of 2A2 ROR1, R12 ROR1 and CD19 chimeric receptor T-cells. Cohorts of mice were inoculated with $0.5×10^6$ JeKo-1/ffluc MCL via tail vein injection, and $5×10^6$ 2A2 ROR1, R12 ROR1 or CD19 chimeric receptor T-cells, or T-cells expressing a tEGFR control vector were administered 7 days after tumor inoculation. All chimeric receptor constructs had the short IgG4 'Hinge-only' spacer and a 4-1BB costimulatory domain. (A, B) Serial bioluminescence imaging of tumor in cohorts of mice treated with T-cells expressing the 2A2 ROR1 chimeric receptor (▼), the high affinity R12 ROR1 chimeric receptor (■), a CD19-specific chimeric receptor (▲), with T-cells transduced with tEGFR alone (●), and untreated mice. Bioluminescence imaging showed tumor manifestations in the bone marrow and thorax and thus, signal intensity was measured in regions of interest that encompassed the entire body and thorax of each individual mouse. (C) Kaplan-Meier analysis of survival in individual treatment and control groups. Statistical analyses were performed using the log-rank test. The data shown in A-C are representative of results obtained in 2 independent experiments. (D) Proliferation of 2A2 ROR1, R12 ROR1 and CD19 chimeric receptor T-cells in vivo. Tumor bearing NSG/JeKo-1 mice received a single dose of $5×10^6$ CFSE-labeled 2A2 ROR1, R12 ROR1 or CD19 chimeric receptor T-cells on day 7 after tumor inoculation, and 72 h later peripheral blood, bone marrow and spleen were collected from each individual mouse. The frequency and proliferation of live (PI−), CD45+ CD8+ tEGFR+ T-cells was analyzed. The frequency of 2A2 ROR1, R12 ROR1 and CD19 chimeric receptor T-cells respectively is provided on the left of each histogram as percentage of live cells, and the fraction of T-cells that underwent ≥4/3/2/1 cell divisions is provided above each plot.

ROR1-Chimeric Receptor T-Cells Mediate in Vivo Anti-Tumor Activity in a Mouse Model of Systemic Mantle Cell Lymphoma It remained uncertain whether the superior in vitro activity of T-cells modified with the higher affinity R12 chimeric receptor would translate into improved anti-tumor activity in vivo, and how targeting ROR1 would compare to targeting CD19. To address these questions, we inoculated cohorts of immunodeficient NSG mice with the human MCL line JeKo-1/ffluc by tail vein injection, and seven days later when tumor was disseminated, treated the mice with a single intravenous dose of R12 ROR1, 2A2 ROR1 or CD19 chimeric receptor CD8$^+$ T-cells. Control mice were treated with tEGFR T-cells or untreated. All chimeric receptors had the optimal short spacer and the 4-1BB costimulatory domain. Untreated NSG/JeKo-1 mice developed a rapidly progressive systemic lymphoma necessitating euthanasia approximately 4 weeks after tumor inoculation (FIG. 9A-C).

We observed tumor regression and improved survival in all mice treated with R12 ROR1, 2A2 ROR1 and CD19 chimeric receptor T-cells. Mice treated with R12 ROR1 chimeric receptor T-cells had a superior anti-tumor response and survival compared to mice treated with 2A2 ROR1 chimeric receptor T-cells (p<0.01), and comparable anti-tumor activity to mice treated with CD19 chimeric receptor T-cells (FIG. 9A-C).

We analyzed the frequency of chimeric receptor T-cells in the peripheral blood following adoptive transfer and detected higher numbers of tEGFR$^+$ T-cells in mice treated with the R12 ROR1 chimeric receptor compared to the 2A2 ROR1 chimeric receptor, suggesting more vigorous proliferation in vivo improved tumor control. To confirm this, we administered CFSE-labeled CD19 chimeric receptor, R12 and 2A2 ROR1 chimeric receptor T-cells to cohorts of NSG mice bearing JeKo-1/ffluc, and analyzed T-cell proliferation in the peripheral blood, bone marrow and spleen 72 hours after transfer. A higher percentage of the R12 and CD19 chimeric receptor T-cells proliferated and underwent a greater number of cell divisions compared to 2A2 ROR1 chimeric receptor T-cells (FIG. 9D). The JeKo-1 tumor eventually recurred in all mice treated with ROR1 or CD19 chimeric receptor T-cells (FIG. 9A-C). Tumor recurrence was not a result of the selection of ROR1 or CD19 loss variants, as recurrent tumors were positive for both molecules.

For comparison, we analyzed anti-tumor efficacy of CD19 chimeric receptor T-cells in NSG mice engrafted with Raji tumors and observed complete tumor eradication, indicating the recurrence of JeKo-1 reflects difficulty eradicating this tumor (data not shown). In summary, this data is the first to show that ROR1 chimeric receptor T-cells have anti-tumor efficacy in vivo, and suggest that for B-cell malignancies, an optimized ROR1 chimeric receptor such as R12 may be effective and spare normal CD19$^+$ B-cells that lack ROR1 expression.

Figure 10:
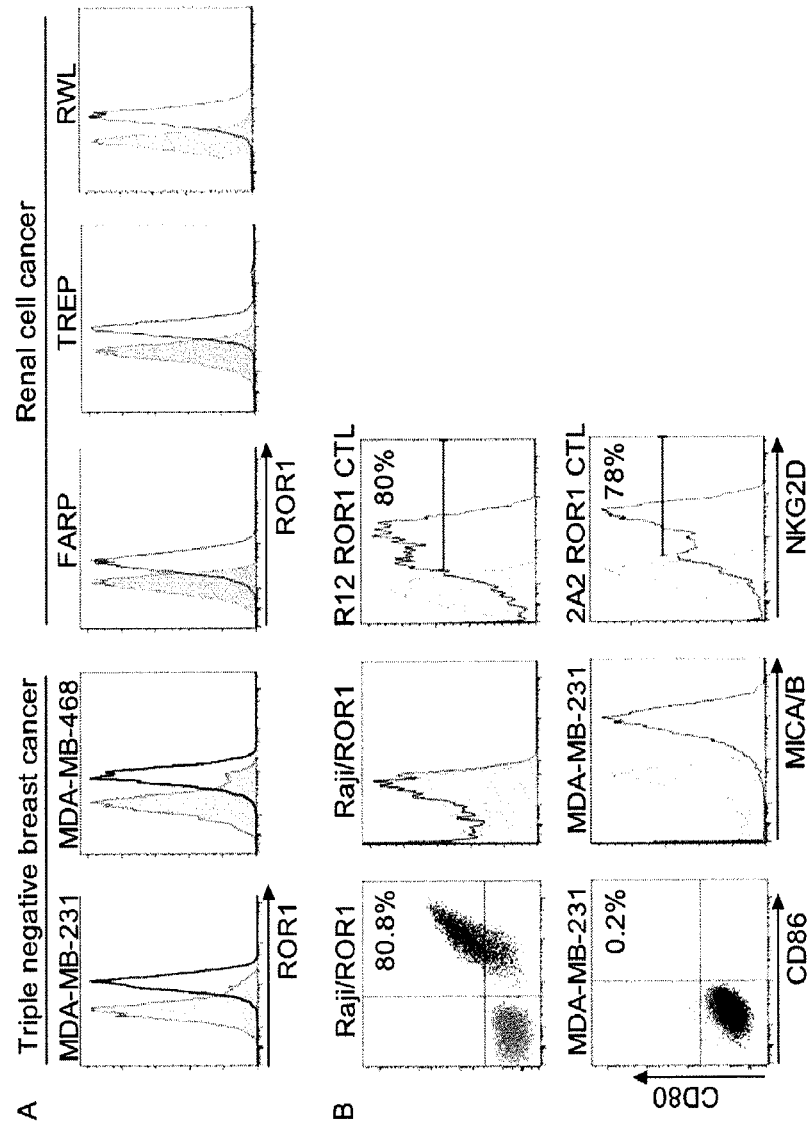
FIG. 10 Expression of ROR1 and NKG2D ligands on epithelial cancer cell lines. (A) Expression of ROR1 on the triple negative breast cancer cell lines MDA-MB-231 and 468, and the renal cell cancer lines FARP, TREP and RWL (black histograms). Staining with matched isotype control antibody is shown as grey histograms. (B) Expression of CD80/86 and the NKG2D ligands MICA/B on MDA-MB-231 and Raji/ROR1 tumor cells, and NKG2D (CD314) on 2A2 and R12 ROR1-chimeric receptor T-cells. Staining with matched isotype control mAbs is shown as grey dot plots/histograms.
Figure 11:
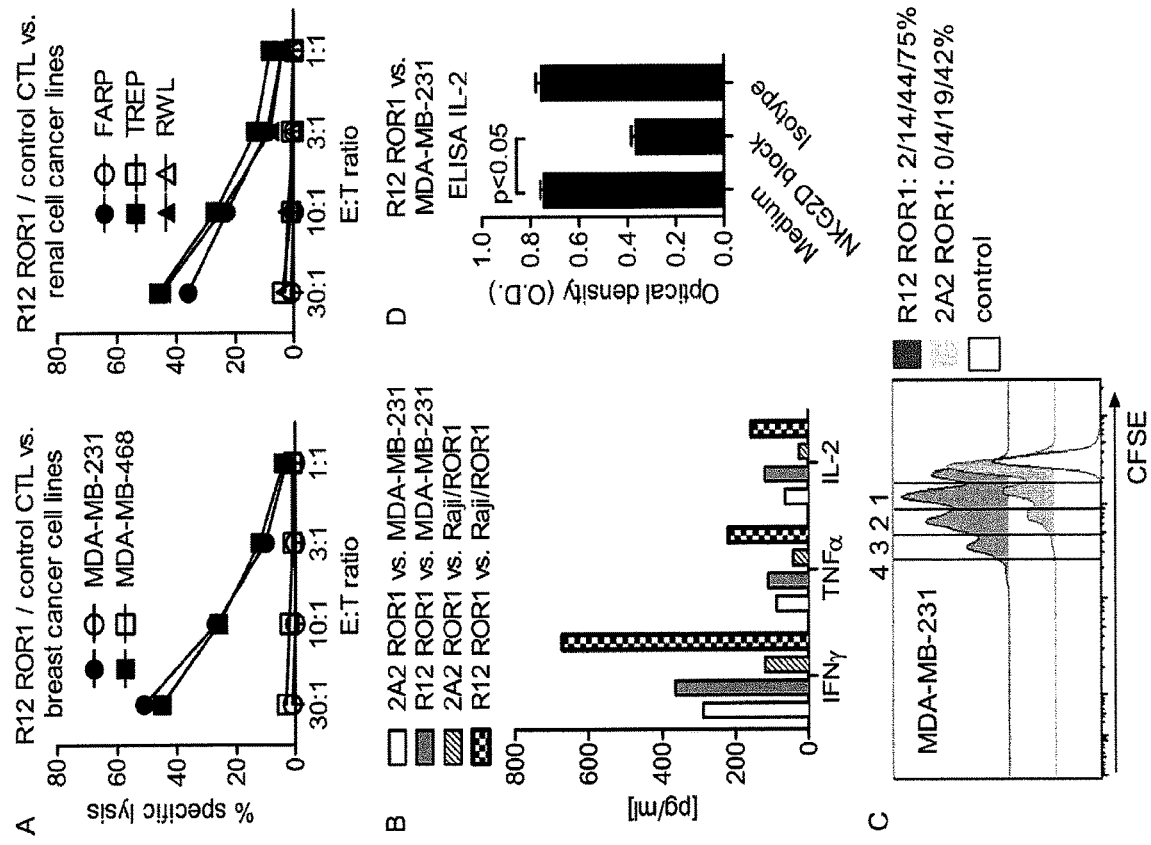
FIG. 11: ROR1-chimeric receptor modified T-cells recognize ROR1+ epithelial tumor cells in vitro. (A) Chromium release assay to evaluate the cytolytic activity of R12 ROR1-chimeric receptor modified T-cells (short spacer/4-1BB costimulatory domain, closed symbols) and tEGFR control T-cells (open symbols) against ROR1+ breast cancer and renal cell cancer lines. (A-D) The 2A2 and R12 ROR1-chimeric receptors had the optimal short spacer and a 4-1BB costimulatory domain. (B) Multiplex cytokine analysis after stimulation of T-cells expressing the 2A2 and R12 ROR1-chimeric receptor with MDA-MB-231 and Raji/ROR1 tumor cells. (C) Proliferation of CD8+ T-cells modified with the 2A2 and R12 ROR1-chimeric receptor 72 hours after stimulation with MDA-MB-231 tumor cells. For analysis, triplicate wells were pooled and the proliferation of live (PI−), CD8+ T-cells analyzed. Numbers above each histogram indicate the number of cell divisions the proliferating subset underwent, and the fraction of T-cells in each gate that underwent ≥4/3/2/1 cell divisions is provided next to each histogram. (D) ELISA for IL-2 production by R12 ROR1-chimeric receptor T-cells after a 24-hour co-culture with MDA-MB-231 in plain medium, and after addition of an antibody cocktail blocking of the NKG2D pathway [anti-NKG2D (clone 1D11), anti-MICA/B (clone 6D4) and anti-ULBP] or matched isotype control mAbs. O.D. of 0.6 corresponds to approximately 1900 pg/ml.

T-Cells Expressing the R12 ROR1 Chimeric Receptor have Superior Reactivity Compared to 2A2 Against ROR1$^+$ Epithelial Tumor Cells ROR1 has been detected on many epithelial tumors, although it is unknown whether ROR1 expression is sufficient for recognition by ROR1 chimeric receptor T-cells. Using flow cytometry, we confirmed ROR1 expression on breast cancer lines MDA-MB-231 and 468, and on the renal cell carcinoma lines FARP, TREP, and RWL (FIG. 10A). We then analyzed tumor recognition by CD8$^+$ T-cells transduced with the R12 ROR1 chimeric receptors with the optimal short spacer and 4-1BB domain, and observed efficient recognition of MDA-MB-231, MDA-MB-468, FARP, TREP and RWL (FIG. 11A). We analyzed cytokine secretion and proliferation of T-cells modified with the R12 and 2A2 ROR1-chimeric receptors after co-culture with MDA-MB-231, and observed greater cytokine production and proliferation with the R12 ROR1 chimeric receptor (FIG. 11 B, C). Similar to what we observed with ROR1$^+$ B cell malignancies, the superior activation of R12 ROR1 chimeric receptor T cells after stimulation with MDA-MB-231 was not associated with increased AICD (R12: 9.8% vs. 2A2: 10.9%).

Discussion

ROR1 has attracted interest as a potential target for cancer immunotherapy due to its expression on the surface of many B-lymphoid and epithelial cancers, including subsets of lung, colorectal and renal cell cancer. We previously showed that CLL and MCL were specifically recognized by T-cells modified to express a ROR1-specific chimeric receptor (Hudecek M, et al. Blood. 2010; 116(22):4532-41. Epub 2010/08/13). The design and function of ROR1-chimeric receptors has been improved through modification of the extracellular spacer domain and deriving the chimeric receptor from a scFV of higher affinity, and demonstrate that T-cells modified with designed ROR1 chimeric receptors have in vivo activity against ROR1$^+$ B-cell lymphoma and in vitro activity against a wide range of epithelial tumors.

We compared the function of T-cells modified with ROR1 chimeric receptors derived from the 2A2 mAb that contained either the original long IgG4-Fc 'Hinge-CH2-CH3' spacer that we have shown enables high level cell surface expression, or truncated intermediate 'Hinge-CH3' and short 'Hinge-only' spacer variants. We preserved the 12 AA Hinge domain in our short spacer construct based on prior data that a flexible spacer was required for separating the scFV from the T-cell membrane and allowing antigen recognition on tumor cells (Fitzer-Attas C J, et al., Harnessing Syk family tyrosine kinases as signaling domains for chimeric single chain of the variable domain receptors: optimal design for T cell activation. J Immunol. 1998; 160(1):145-54. Epub 1998/04/29.)

Our studies with the 2A2 ROR1 chimeric receptor show that T-cell cytokine secretion and proliferation after tumor cell recognition are superior with the intermediate and short spacer constructs compared to the long spacer construct. Staining with anti-F(ab) Abs showed equivalent chimeric receptor expression of all three receptors, demonstrating the improved T-cell function with the short spacer chimeric receptor was not due to differences in chimeric receptor density. This data supports the principle that the design of extracellular spacers should be tailored for each target molecule and epitope.

The affinity of the scFV selected for designing a chimeric receptor is an additional parameter that could affect T-cell recognition. We generated and characterized a panel of ROR1-specific mAbs of different affinities and selected the R12 mAb, which recognizes an epitope in the Ig-like/Frizzled region as 2A2. R12 has a higher affinity for ROR1-protein due to a much slower dissociation. The R12 chimeric receptor, like the 2A2 chimeric receptor conferred optimal T-cell recognition and function when designed with a short extracellular spacer. A direct comparison of proliferation and cytokine production after tumor engagement by T-cells modified with the 2A2 and R12 chimeric receptors demonstrated that the R12 chimeric receptor derived from the higher affinity mAb was superior. We were concerned that the slower dissociation of R12 from ROR1 could prolong T-cell activation and confer an increased susceptibility to AICD. However, we detected a lower rate of AICD in T-cells modified with the R12 ROR1-chimeric receptor compared to 2A2, demonstrating that the increased affinity of R12 had no detrimental effect on T-cell survival in our preclinical models.

ROR1 has a potential advantage over CD19 as a target for CLL and MCL since it is not expressed on normal mature naïve and memory B-cells. However, there is a lower number of ROR1 molecules on B-cell tumors compared with CD19 and it is uncertain if an optimized ROR1 chimeric receptor would be as effective as a CD19 chimeric receptor similar in design to those being used in the clinic. Unfortunately, B-cell tumor xenograft models used previously in NSG mice to evaluate the function of CD19 chimeric receptor T-cells including Raji, Daudi and Nalm-6, are not derived from CLL or MCL and do not constitutively express ROR1. Thus, to compare targeting CD19 and ROR1 in vivo, we used the JeKo-1 MCL cell line, which naturally expresses both CD19 and ROR1 and engrafts in NSG mice. To make our model clinically relevant, we inoculated JeKo-1 lymphoma cells intravenously to generate systemic tumors, and treated mice with T-cell products of uniform consistency once tumors were established. We found that T-cells expressing the high affinity R12 chimeric receptor conferred equivalent anti-tumor activity in vivo as CD19 chimeric receptor T-cells. Consistent with our in vitro analysis, the R12 ROR1 chimeric receptor also mediated superior activity in vivo compared to the optimal 2A2 ROR1-chimeric receptor. These results should be interpreted cautiously since murine tumor models may not predict the efficacy of adoptive therapy in clinical settings. However, the results suggest that ROR1 warrants consideration as an alternative to CD19, or to provide an additional target to minimize the potential for CD19 loss variants to emerge.

ROR1 appears to play a decisive role in survival of some epithelial tumors. Thus, an advantage of targeting ROR1 is that a single chimeric receptor may be useful to treat patients with a large number of hematopoietic and non-hematopoietic tumors.

Our data shows for the first time that T-cells that express a designed ROR1 chimeric receptor efficiently recognize epithelial cancers in vitro. Cytokine secretion and T-cell proliferation induced by ROR1+ breast cancer cells were higher than that induced by leukemia cells, despite the absence of the CD80/86 costimulatory ligand. The studies reported here demonstrate that the design of the extracellular spacer domain and chimeric receptor affinity are parameters that can be modulated to enhance the recognition of ROR1+ hematologic and epithelial tumors in vitro and in vivo by ROR1-chimeric receptor modified T-cells. The development of ROR1-chimeric receptors with enhanced tumor reactivity provides the opportunity for clinical applications in a variety of human cancers.

Example 2

Figure 12:
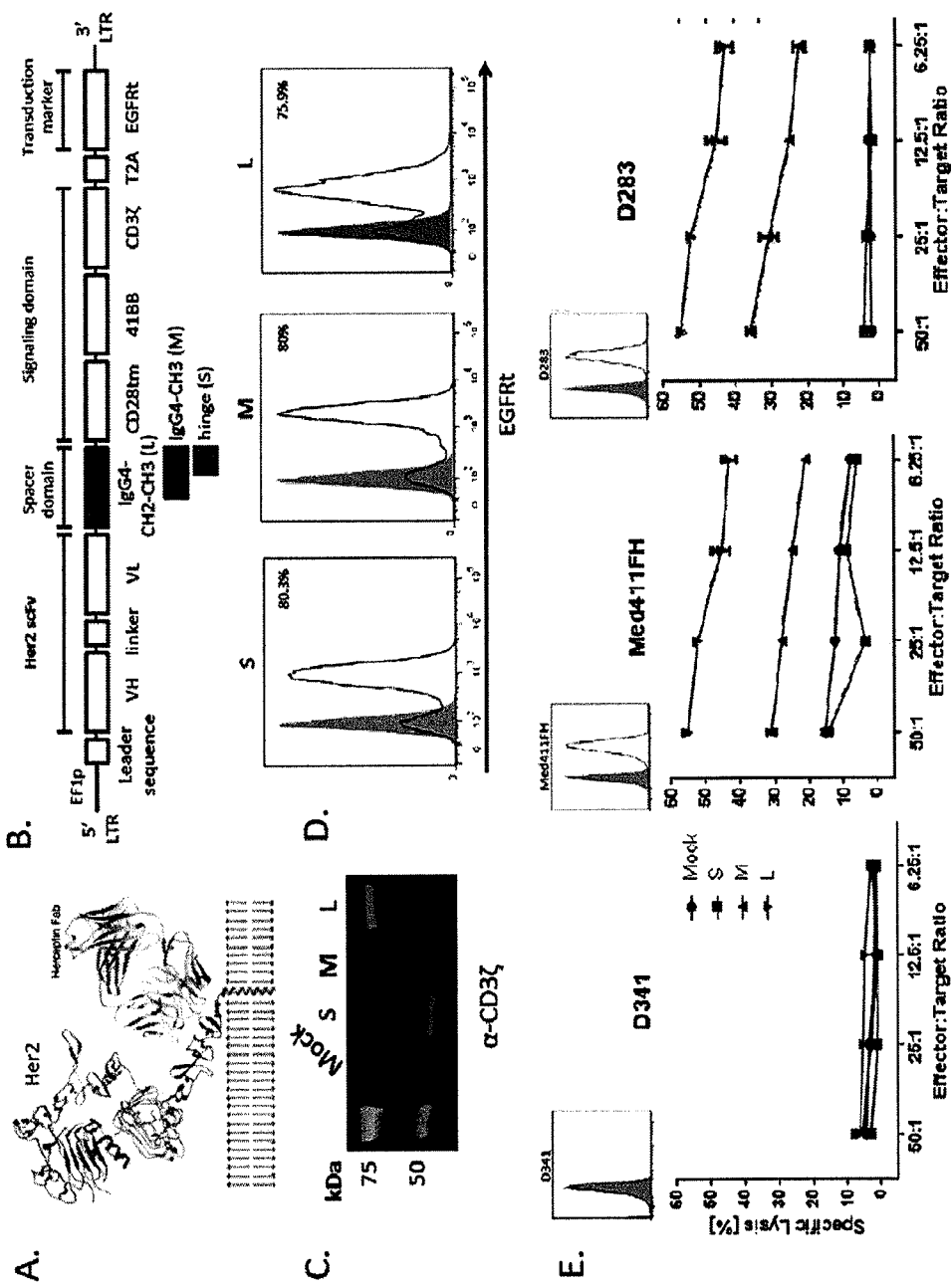
FIG. 12. Effect of extracellular spacer length on recognition and triggering of tumor cell lysis by CD8+ human T cells that express a HER2-specific chimeric receptor. A.) Depiction of Herceptin Fab epitope location on tumor cell membrane proximal epitope on human HER2, B.) Structural formats of Herceptin scFv CAR spacer length variants as -T2A-linked polypeptides with the carboxyl EGFRt marker transmembrane protein, C.) Western blot detection of short, medium, and long spacer Herceptin-CAR variant expression in human CD8+CTL's, D.) Flow cytometric detection of EGFRt by transduced human CD8+CTL's transduced with Herceptin CAR variants then immunomagnetically purified by Herceptin-biotin, anti-biotin microbeads, E.) Distinct cytolytic function by T cells transduced to express the Herceptin CAR variants (short—S; medium—M; and long—L) against HER2+ Med411FH and D283 human medulloblastoma cell lines (D341 is a HER2− control medulloblastoma cell line, inset flow plots are tumor target lines stained with anti-HER2 specific mAb). Green-full IgG4 (Long Spacer, ▼), Blue=IgG4hinge:CH3 (Medium Spacer, ▲), Red=IgG4hinge only (Short Spacer; ■).

Effect of Extracellular Spacer Domain Length on Triggering of Tumor Cell Lysis with a Her2-Specific Chimeric Receptor that Recognizes an Epitope Located Proximal to the Tumor Cell Membrane The effect of CAR spacer length on recognition and triggering of tumor cell recognition by CD8+ human T lymphocytes that expressed a HER2-specific chimeric receptor was examined using similar methods to those described above for ROR1. HER2-specific chimeric receptors were constructed using VL and VH chain segments of a HER2-specific mAb that recognized a membrane proximal epitope on HER2 (FIG. 12A), and the scFVs were linked to IgG4 hinge/CH2/CH3, IgG4 hinge/CH3, and IgG4 hinge only extracellular spacer domains and to the CD28 transmembrane domain, 4-1BB and CD3 zeta signaling domains (FIG. 12B). Primary CD8+ T cells were transduced with each of the HER2 chimeric receptors and selected for expression of the EGFR transduction marker (FIG. 12D). Expression of the HER 2 chimeric receptors and the size of each receptor was confirmed by Western Blot (FIG. 12C). The T cells were then expanded with anti CD3 mAb and feeder cells and examined for their ability to recognize HER2+ tumor cells. As observed with the R11 ROR1 specific chimeric receptor, the HER2 chimeric receptor that contained a long extracellular spacer domain conferred superior T cell recognition of HER2+ tumor cells (FIG. 12E).

Discussion

This example of the effect of extracellular spacer length on chimeric receptor modified T cell recognition of tumor cells used a chimeric receptor comprising a scFv built from the $V_{H+L}$ sequences of the Herceptin chimeric mAb. Studies by Cho et al (Nature 421:756, 2003) localized to epitope location of Herceptin to a membrane proximal location on the HER2 (ERRB2) extracellular domain (FIG. 12A). Based on our understanding of the structure of human IgG4 hinge: Fc variants (FIG. 12B), we hypothesize that a membrane proximal location of the targeting epitope on an extracellular tumor cell antigen would best recognized by effector T cells that express a chimeric receptor encoding a long spacer. Our data demonstrating a gradient of cytolytic activity from near back ground activity by T cells expressing a short spacer Herceptin chimeric receptor, to intermediate activity by T cells expressing a medium length spacer chimeric receptor, and maximal lysis by T cells that expressed the long spacer chimeric receptor. Thus, the extracellular spacer has definitive effects on tumor recognition by T cells, and this data provides further support for the need to tailor chimeric receptor design based on epitope location of tumor expressed target molecules.

Example 3

Customizing Spacer Length and Sequence for Optimal Recognition and In Vivo Efficacy of CD19 with Chimeric Receptor Modified T Cells Materials and Methods
Human Subjects Blood samples were obtained from healthy donors who provided written informed consent to participate in research protocols approved by the Institutional Review Board of the Fred Hutchinson Cancer Research Center (FHCRC). Peripheral blood mononuclear cells (PBMC) were isolated by centrifugation over Ficoll-Hypaque (Sigma, St. Louis, Mo.), and cryopreserved in RPMI, 20% human serum and 10% dimethyl sulfoxide.

Cell Lines

The K562, Raji, JeKo-1, and 293T cell lines were obtained from the American Type Culture Collection (Manassas, Va.) and cultured as directed. A lentivirus encoding the ffluc-gene upstream of a T2A sequence and eGFP was produced in 293T cells and used to transduce Raji and JeKo-1 tumor cells. Raji, and JeKo-1 cells were expanded after lentiviral transduction and the eGFP positive subset sort-purified.

Immunophenotyping

PBMC and T-cell lines were stained with one or more of the following conjugated monoclonal antibodies: CD3, CD4, CD8, CD25, CD45RA, CD45RO, CD62L, CD69 and matched isotype controls (BD Biosciences). Staining with propidium iodide (PI, BD Biosciences) was performed for live/dead cell discrimination as directed by the manufacturer. Flow analyses were done on a FACSCanto, sort-purifications on a FACSAriaII (Becton Dickinson) and data analyzed using FlowJo software (Treestar).

Vector Construction and Preparation of CD19 Chimeric Receptor Encoding Lentivirus CD19 specific chimeric receptors were constructed using: (1) the VL and VH chain segments of the CD19-specific mAb FMC63 (SEQ ID NO:3), linked by a $(G_4S)_3$ linker (SEQ ID NO:12) peptide (VL-linker-VH); (2) a spacer domain derived from IgG4-Fc (Uniprot Database: P01861, (SEQ ID NO:13)) comprising either the Hinge-CH2-CH3 portion (229 AA, (SEQ ID NO:)) or Hinge only (12 AA; (SEQ ID NO:4)). Both spacers contained a S→P substitution within the Hinge domain located at position 108 of the native IgG4-Fe protein; the 27 AA transmembrane domain of human CD28 (Uniprot Database: P10747, (SEQ ID NO:14)); (4) a signaling module comprising either (i) the 41 AA cytoplasmic domain of human CD28 with an LL→GG substitution located at position 186-187 of the native CD28 protein (SEQ ID NO:14); and/or (ii) the 42 AA cytoplasmic domain of human 4-1BB (Uniprot Database: Q07011, (SEQ ID NO:15)); linked to (iii) the 112 AA cytoplasmic domain of isoform 3 of human CD3ζ (Uniprot Database: P20963, (SEQ ID NO:16)); the self cleaving T2A sequence (SEQ ID NO:8); and (6) a truncated epidermal growth factor receptor (EGFR) sequence (SEQ ID NO:9).

Codon-optimized nucleotide sequences encoding each trans gene were synthesized (LifeTechnologies, Carlsbad, Calif.) and cloned into the epHIV7 lentiviral vector using NheI and NotI restriction sites. The epHIV7 lentiviral vector had been derived from the pHIV7 vector by replacing the cytomegalovirus promoter of pHIV7 with an EF-1 promoter.

CD19 chimeric receptor or tEGFR-encoding lentivirus was produced in 293T cells co-transfected with the lentiviral vector and the packaging vectors pCHGP-2, pCMV-Rev2 and pCMV-G using Calphos transfection reagent (Clontech). Medium was changed 16 h after transfection, and lentivirus collected after 24, 48 and 72 h.

Generation of T-Cell Lines Expressing the CD19 Chimeric Receptors

Sort-purified CD8$^+$ CD45RA$^-$ CD45RO$^+$ CD62L$^+$ central memory T-cells ($T_{CM}$) of normal donors were activated with anti-CD3/CD28 beads (Life Technologies) according to the manufacturer's instructions, and transduced with lentiviral supernatant (MOI=3) supplemented with 1 μg/mL polybrene (Millipore) on day 3 after activation by centrifugation at 2,100 rpm for 45 min at 32° C. T cells were expanded in RPMI, 10% human serum, 2 mM L-glutamine and 1% penicillin-streptomycin (CTL medium), supplemented with recombinant human (rh) IL-2 to a final concentration of 50 U/mL every 48 h. After expansion, an aliquot of each transduced T cell line was stained with biotin-conjugated anti-EGFR (epithelial growth factor receptor) antibody and streptavidin-beads (Miltenyi), and tEGFR+ T cells isolated by immunomagnetic selection.

The tEGFR+ T-cell subset was then stimulated with irradiated (8,000 rad) TM EBV-LCL at a T cell:LCL ratio of 1:7, and expanded for 8 days in CTL medium with addition of 50 U/mL rh IL-2 every 48 h.

Chromium Release, Cytokine Secretion and CFSE Proliferation Assays

Target cells were labeled with $^{51}$Cr (PerkinElmer) overnight, washed and incubated in triplicate at $1-2\times10^3$ cells/well with effector T cells at various effector to target (E:T) ratios. Supernatants were harvested for γ counting after a 4-hour incubation and specific lysis calculated using the standard formula. For analyses of cytokine secretion, target and effector cells were plated in triplicate wells at an E:T ratio of 2:1 (Raji) or 4:1 (K562/CDI9 and K562), and INF-γ, TNF-α, IL-2, IL-4, IL-6 and IL-10 measured by multiplex cytokine immunoassay (Luminex) in supernatant removed after a 24-hour incubation.

For analysis of proliferation, T cells were labeled with 0.2 μM carboxyfluorescein succinimidyl ester (CFSE, Invitrogen), washed and plated in triplicate wells with stimulator cells at a ratio of 2:1 (Raji) or 4:1 (K562/CD19 and K562) in CTL medium without exogenous cytokines. After 72 h of incubation, cells were labeled with anti-CD3 mAb and propidium iodide (PI) to exclude dead cells from analysis. Samples were analyzed by flow cytometry and cell division of live CD3+ T-cells assessed by CFSE dilution.

Experiments in NOD/SCID and NOD/SCID/γc$^{-/-}$ (NSG) Mice

All mouse experiments were approved by the FRCRC Institutional Animal Chimeric receptore and Use Committee. Six- to 8-week old female NOD.CBI7-Prkdc$^{scid}$/J (NOD/SCID) and NOD.Cg-Prkdc$^{scid}$ Il2rg$^{tm1Wjl}$/SzJ (NSG) mice were obtained from the Jackson Laboratory or bred in-house (FRCRC. Mice were injected intravenously (i. v.) with $0.5\times10^6$ Raji-ffluc tumor cells via tail vein injection, and received injections of chimeric receptor-modified T cells, control T cells, or PBS via tail vein injection as indicated.

For bioluminescence imaging, mice received intraperitoneal (i.p.) injections of freshly prepared luciferin substrate (Caliper Life Sciences, MA) resuspended in PBS (15 μg/g body weight) and were then anesthetized with isoflurane in an induction chamber. After induction of deep anesthesia, mice were imaged using an Xenogen IVIS In Vivo Imaging System (Caliper Life Sciences, MA) at 10, 12 and 14 minutes post i.p. injection of luciferin at an acquisition time of 1 second to 1 minute in small binning mode to obtain unsaturated images. Luciferase activity was analyzed using Living Image Software (Caliper Life Sciences, MA) and the photon flux analyzed within regions of interest that encompassed the entire body of each individual mouse.

Statistical Analyses

Statistical analyses were performed using Prism Software (GraphPad, Calif.). Student's t-test was performed as a two-sided test with a confidence interval of 95% and results considered significant with a p-value of $p<0.05$. Statistical analysis of survival were done by Log-rank testing and results considered significant with a p-value of $p<0.05$.

Results

Figure 13:
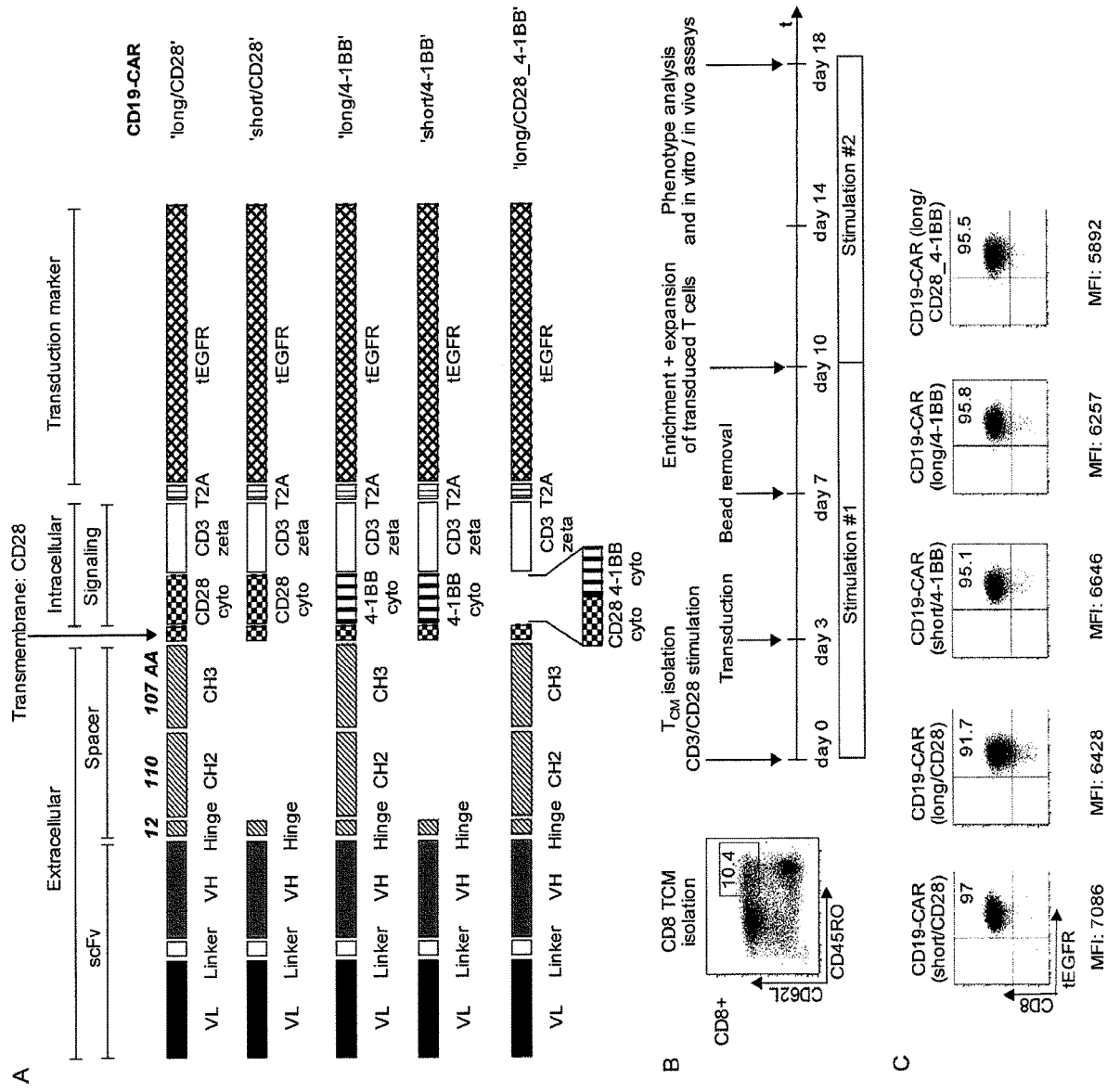
FIG. 13: CD19-chimeric receptor vectors and generation of CD19-chimeric receptor T cells.

Preparation of Polyclonal CD8+ $T_{CM}$-Derived Cell Lines that Express CD19 Chimeric Receptors with Long and Short Extracellular Spacers We constructed individual lentiviral vectors encoding a panel of codon-optimized CD19 chimeric receptor genes to examine the influence of extracellular spacer length on the in vitro function and in vivo antitumor activity of CD19 chimeric receptor-modified T cells. Each chimeric receptor was comprised of a single chain variable fragment corresponding to the sequence of the CD19-specific mAb FMC63 (scFv: VL-VH), a spacer derived from IgG4-Fc including either the 'Hinge-CH2-CH3' domain (229 AA, long spacer) or the 'Hinge' domain only (12 AA, short spacer), and a signaling module of CD3ζ with membrane proximal CD28 or 4-1 BB costimulatory domains, either alone or in tandem (FIG. 13A). The transgene cassette included a truncated EGFR (tEGFR) downstream from the chimeric receptor gene and separated by a cleavable T2A element, to serve as a transduction, selection and in vivo tracking marker for chimeric receptor-modified T cells.

We isolated a CD8+ CD45RO+ CD62L+ central memory T cell ($T_{CM}$) cell population by cell sorting from the blood of normal donors for transduction and expansion, because of the superior ability of $T_{CM}$ to persist in vivo after adoptive transfer. CD8+ T cells were stimulated with anti CD3/28 beads, transduced with each of the lentiviral vectors, and expanded in culture for 18 days before being used for in vitro and in vivo experiments. (FIG. 13B) Similar transduction efficiencies were achieved with each of the lentiviral vectors (mean 25%) and transgene-positive T cells were enriched to uniform purity by immunomagnetic selection using a biotinylated anti-EGFR mAb and streptavidin beads. Following tEGFR-enrichment, each of the CD19 chimeric receptor T cell lines were expanded by a single stimulation with CD19+B-LCL, without apparent differences in in vitro growth kinetics between T cell lines expressing the various CD 19 chimeric receptor constructs. After expansion, the tEGFR marker was expressed at equivalent levels on >90% of the T cells transduced with each of the vectors (FIG. 13C).

CD19 Chimeric Receptors with Long and Short Extracellular Spacer Domain Confer Specific Anti-Tumor Reactivity In Vitro We compared the effector function of $T_{CM}$-derived T cell lines modified to express CD19 chimeric receptors with CD28 and 4-1BB costimulatory signaling moieties, and either a short ('short/CD28'; 'short/4-1BB') or long ('long/CD28'; 'long/4-1BB') extracellular spacer domain respectively. T cells expressing each of the 4 CD19 chimeric receptor constructs conferred specific cytolytic activity against CD19+ Raji and JeKo-1 lymphoma cells, and against K562 cells that had been stably transfected with CD19, but not native CD19- K562 cells (FIG. 14A). Quantitative analyses of cytokine production in response to stimulation with K562/CD19 or Raji tumor cells by multiplex cytokine assay (Luminex) showed production of IFN-γ, TNF-α, IL-2, IL-4, IL-6, and IL-10 by T cells expressing each of the CD19 chimeric receptors (FIG. 14B). T cells expressing CD19 chimeric receptors with a CD28 costimulatory domain produced significantly higher levels of IFN-γ, TNF-α, IL-2 and IL-10 compared to the corresponding constructs with a 4-1BB costimulatory domain (FIG. 14B, C). There was significantly higher IFN-y production and significantly less IL-4 production by T cells expressing the CD19 'long/CD28' chimeric receptor compared with those expressing the 'short/CD28' chimeric receptor. Amongst the CD19 chimeric receptors with 4-1BB costimulatory signaling module, we detected significantly higher levels of IFN-γ, TNF-α, IL-2, IL-4, and IL-10 secretion in T cells expressing the construct with the short spacer domain (FIG. 14B, C).

We used CFSE dye dilution to analyze proliferation of T cells modified with each of the CD19 chimeric receptors after engagement of CD 19+ tumor cells. Specific and vigorous proliferation of each of the CD19 chimeric receptor T cell lines was observed 72 hours following stimulation with either K562/CD19 or Raji. The average number of cell divisions was higher for CD19 chimeric receptor T cells with a CD28 costimulatory domain compared to those with 4-1BB, consistent with greater IL-2 production by T cells expressing a CD28 containing chimeric receptor (FIG. 14B-D). We also analyzed the proportion of chimeric receptor T cells that underwent activation induced cell death after stimulation with K562/CD19 and Raji tumor cells at the end of the 72-hours by costaining the culture with CD3+ and PI. We detected a higher frequency of CD3+ CD8+ PI+ T cells in the CD19 chimeric receptor cell line 'long/4-1 BB', but few PI+ cells were observed with the other CD19 chimeric receptors. (FIG. 14E).

This analysis of in vitro effector functions was consistent with prior studies that have compared CD28 and 4-1BB costimulatory domains, and did not reveal differences in T cell function that would suggest that a particular CD19 chimeric receptor construct from this panel would lack anti-tumor efficacy in vivo.

T Cells Expressing CDl9 Chimeric Receptors with Short Extracellular Spacer Domains but not Long Extracellular Spacer Domains Eradicate Rail Tumors in Immunodeficient Mouse Models We next evaluated the in vivo antitumor efficacy of T cells modified with each of the CD19 chimeric receptors in immunodeficient (NOD/SCID) mice engrafted with firefly luciferase transfected Raji cells (Raji-ffluc), which enables sequential quantitative analyses of tumor burden and distribution using bioluminescence imaging. NOD/SCID mice inoculated with $0.5 \times 10^6$ Raji-ffluc cells via tail vein injection developed disseminated lymphoma, which if untreated led to hind limb paralysis after approximately 3.5 weeks, necessitating euthanasia. Tumor bearing mice were treated with 2 doses of CD8+ $T_{CM}$-derived T cells modified with each of the CD19 chimeric receptors or with a tEGFR control vector administered on day 2 and day 9 after tumor inoculation (FIG. 15A).

Surprisingly, only T cells modified to express CD19 chimeric receptors with short extracellular spacer domain ('short/CD28' and 'short/4-1BB') eradicated Raji tumors in this model, whereas mice treated with T cells expressing CD19 chimeric receptors with long spacer ('long/CD28' and 'long/4-1BB') developed systemic lymphoma and hind limb paralysis with nearly identical kinetics as untreated mice or mice treated with control tEGFR+ T cells (FIG. 15B, C). The striking difference in antitumor activity between CD19 chimeric receptors with short and long spacer domains was highly significant and reproducible in multiple experiments with chimeric receptor T cell lines generated from 3 different normal donors.

The NOD/SCID lymphoma model may be suboptimal for predicting anti-tumor activity in a clinical setting because of the short interval between tumor inoculation and T cell administration and the greater resistance to engraftment of human cells compared to more immunodeficient mouse strains such as NOD/SCID/γc$^{-/-}$ (NSG). Thus, we evaluated antitumor activity of adoptive therapy in a more clinically relevant model in which Raji-ffluc lymphoma was established in NSG mice, and the CD19 chimeric receptor T cells were administered after 7 days when the tumor was readily detectable in the bone marrow by bioluminescence imaging (FIG. 16A). We performed initial dose titration experiments to determine the minimal dose of T cells transduced with the CD19 'short/4-1BB'chimeric receptor that was required for eradication of established Raji tumors. A single dose of $2.5 \times 10^6$ T cells expressing CD19-chimeric receptor 'short/4-1BB' promoted complete regression of established Raji tumors and resulted in long-term tumor-free survival in 100% of mice (FIG. 16B,C). At the $2.5 \times 10^6$ dose level, the T-cells were easily detected in the peripheral blood of NSG mice for at least 3 weeks following adoptive transfer and tumor eradication. Thus, this model enabled comparative studies both of antitumor activity and persistence of T cells modified with each of the CD19-chimeric receptors in our panel (FIG. 16D).

We then treated cohorts of NSG mice that were engrafted with Raji lymphoma with PBS alone, with a single dose of $2.5 \times 10^6$ T cells expressing each of the CD19 chimeric receptors or with T cells modified with a tEGFR encoding control vector (FIG. 17A). In this model of established lymphoma, T cells expressing CD19 chimeric receptors with a short extracellular spacer domain and either 4-1BB or CD28 costimulatory domains ('short/CD28' and 'short/4-1BB') mediated complete tumor regression over 7-10 days and all mice survived tumor free for >56 days. By contrast, mice treated with T cells modified to express CD19 chimeric receptors with a long spacer domain ('long/CD28' and 'long/4-1BB') exhibited tumor progression and had to be sacrificed at a similar time as mice that had received control tEGFR T cells (FIG. 17B, C). The lack of in vivo antitumor activity of the chimeric receptor constructs with long spacers was unexpected given the ability of T cells expressing these constructs to lyse tumor cells in vitro, and the enhanced IL-2 production and proliferation after engagement of T cells expressing the 'long/CD28' CD19 chimeric receptor compared to the 4-1BB constructs.

To provide insight into the basis for the lack of efficacy, we performed sequential flow cytometry on peripheral blood samples of mice at intervals after the T cell infusion. All mice treated with T cells expressing the 'short/CD28' and 'short/4-1BB' CD19 chimeric receptors had significantly higher levels of transferred T cells in the blood at all time points after adoptive transfer, compared to mice treated with T cells that expressed corresponding CD19 chimeric receptors with long extracellular spacer ($p<0.01$) (FIG. 17D). We did not observe significant differences in T-cell persistence in the peripheral blood of mice that had received T cells expressing CD19 chimeric receptors with CD28 or 4-1BB co-stimulatory domains and short spacer domains (FIG. 17D).

The In Vivo Anti-Tumor Efficacy of CD19 Chimeric Receptors with Long Spacers is not Improved by Increasing T Cell Dose or Providing an Additional Costimulatory domain The lack of in vivo anti-tumor efficacy and the lower level of persisting chimeric receptor T cells in mice treated with T cells modified with CD19 chimeric receptors with long spacer domains suggested that efficacy might be improved by increasing the chimeric receptor T cell dose or by including both CD28 and 4-1BB domains into the chimeric receptor to augment costimulatory signaling. To evaluate this possibility we modified CD8+ $T_{CM}$ with 'long/CD28', 'short CD28', and 'long/CD28_4-1BB' CD19 chimeric receptor vectors and confirmed that the long/CD28_4-1BB' CD19 chimeric receptor conferred specific lysis and cytokine production in vitro after recognition of CD19+ target cells (FIG. 18A-C). Consistent with previous studies of CD19 chimeric receptors, the level of cytokine production and proliferation in vitro in T cells expressing the CD28_4-1BB'CD19 chimeric receptor was inferior compared to the identical construct with CD28 alone, and superior to T cells expressing the 'long 4-IBB' CD19 chimeric receptor (FIG. 18B, C).

Groups of NSG mice with established Raji tumors were then treated with a high dose of T cells ($10 \times 10^6$) T cells expressing the 'long/CD28' CD19 chimeric receptor, the 'long/CD28_4-IBB' CD19 chimeric receptor, the 'short/CD28' CD19-chimeric receptor, and tEGFR alone. Tumor burden was measured by bioluminescence imaging and serial flow cytometric analyses of peripheral blood samples performed to determine the frequency of transferred T cells. Consistent with the results of our prior experiments using much lower doses of T cells, Raji tumors were completely eradicated in mice treated with T cells expressing the 'short/CD28' CD19-chimeric receptor. However, even with a 4-fold higher T cell dose, treatment with T cells expressing the 'long/CD28' CD19 chimeric receptor or the 'long/CD28_4-1BB' CD19 chimeric receptor did not provide a discernible antitumor effect (FIG. 18D,E).

Thus, increasing the chimeric receptor T cell dose and adding a 4-1BB costimulatory domain to CD19 chimeric receptors failed to overcome the negative impact of the longer spacer domain on antitumor activity in vivo. Thus, in this model, anti-tumor reactivity of CD19 chimeric receptors is dictated to a great extent by the length of the extracellular spacer domain, and not by the intracellular costimulatory signaling modules.

T Cells Modified with CD19 Chimeric Receptors that Possess Long Extracellular Spacers Undergo Activation Induced Cell Death In Vivo We sought to determine potential mechanisms underlying the inferior in vivo antitumor activity of T cells that express CD19 chimeric receptors with long spacer domains. Because lower numbers of transferred T cells modified to express CD19 chimeric receptors with long spacer domains were present in the blood, we considered the possibility that the T cells were not efficiently activated by tumor cells in vivo or conversely, that they underwent activation induced T cell death in vivo. Therefore, we labeled CD19 chimeric receptor modified and corresponding control T cells with CFSE and administered these T cells to tumor bearing NSG/Raji mice to examine activation, proliferation and survival of T cells modified with each of the CD19 chimeric receptor constructs at tumor sites in vivo (FIG. 19A). At the end of their in vitro expansion and immediately prior to CFSE labeling and infusion into NSG mice bearing established Raji tumors, T cells transduced with each of the CD19 chimeric receptors expressed low levels of the activation markers CD69 and CD25 (FIG. 19B).

Bone marrow was obtained from subgroups of mice 24 and 72 hours after the T cell infusion to examine the frequency, activation and proliferation of transferred T cells. At 24 hours, tumor cells (CD45+CD3−) were present in the bone marrow in all treatment groups and a large fraction of chimeric receptor T cells, but not control T cells, had upregulated CD69 and CD25. There was no measurable dilution of CFSE in the transferred chimeric receptor T cells. (FIG. 19C) Both CD69 and CD25 were expressed in a higher proportion of T cells modified with 'long space'CD19 chimeric receptors, suggesting these cells may have received a stronger stimulus compared to T cells with 'short spacer' CD19 chimeric receptors (FIG. C). Despite evidence of T cell activation at 24 hours there were significantly lower numbers of chimeric receptor T cells in the bone marrow of mice treated with T cells modified with the CD28 and 4-1BB 'long spacer' constructs compared to those modified with the CD28 and 4-1BB 'short space' constructs, or with the control tEGFR vector (FIG. 19C, E).

At 72 hours after T cell transfer, T cells expressing the 'short/CD28' and 'short/4-1BB'CD19 chimeric receptors had increased 3 to >10 fold in frequency in the bone marrow and spleen, and had undergone several cell divisions (FIG. 19D,E). Control tEGFR+ T cells remained present in the bone marrow and spleen at 72 hours at a level similar to that observed at 24 hours, and had not divided as measured by CFSE dilution. By contrast, the numbers of T cells expressing the 'long/CD28' and 'long/4-1BB' CD19 chimeric receptors had not increased in the bone marrow and spleen. (FIG. 19D, E) Consistent with lower cell numbers, analysis of CFSE staining in viable PI– 'long/CD28' and 'long/4-1BB'CD19 chimeric receptor T cells demonstrated these cells had undergone a much lower number of cell divisions compared with 'short/CD28' and 'short/4-1BB'CD19 chimeric receptor T cells. (FIG. 19D) When the flow data was analyzed to include PI+ T cells, we detected a much higher frequency of PI+ CD3+ T cells in bone marrow and spleen of mice that received CD19 chimeric receptor T cells with 'long spacer' domains, demonstrating that a significant proportion of T cells, despite being activated by tumor in vivo had undergone cell death (FIG. 19F). Consistent with the bioluminescence imaging, CD45+ CD3– Raji tumor cells were present in greater numbers in the bone marrow of mice treated with T cells expressing CD19 chimeric receptors with long spacer domains or expressing tEGFR only compared to mice treated with CD19 chimeric receptors with short spacer domains (FIG. 19D,E, G).

Collectively, the data provides evidence that CD19 chimeric receptors with long extracellular spacer domain, despite mediating equivalent or superior effector function in vitro and recognizing tumor in vivo, induce a high level of activation induced cell death in vivo and fail to eradicate established lymphoma.

Discussion

Chimeric receptors are artificial receptors that include an extracellular antigen-binding scFv, a spacer domain that provides separation of the scFv from the cell membrane and an intracellular signaling module that mediates T cell activation. Chimeric receptors that contain a scFv derived from the CD19-specific FMC63 mAb studied here, have advanced to testing in clinical trials in patients with B-cell malignancies. Antitumor activity and T cell persistence have varied substantially in different trials. Each of these clinical trials differed in potentially critical variables, including different gene transfer vectors, cell culture methodologies, and conditioning regimens prior to CD19 chimeric receptor T cell transfer.

We examined the possibility that the extracellular spacer domain of CD19 chimeric receptors may be an important determinant of anti-tumor activity in vivo, independent of the costimulatory signaling provided by the chimeric receptor. We derived spacer domains from IgG4-Fc, which enables high levels of chimeric receptor cell surface expression and is less likely to provoke recognition by innate immune cells compared to other IgG isotypes. We used the IgG4 'Hinge-CH2-CH3' in the design of the long (229 AA) spacer constructs and the IgG4 'Hinge' domain in our short (12 AA) spacer chimeric receptors. To compare the individual chimeric receptor constructs, we used purified (>90%) chimeric receptor positive CD8+ $T_{CM}$-derived T cells to remove differences in the cellular composition and transduction frequency as a potential source of bias in the analysis of in vitro and in vivo function. CD8+ $T_{CM}$ have been shown to have superior traits for adoptive immunotherapy, compared with other more prevalent T cell subsets in blood that persist poorly and are ineffective in tumor therapy. The CD19 chimeric receptor T cells were generated using a standardized culture protocol that is similar to that used to derive chimeric receptor T cells for clinical trials. Our data show that CD19 chimeric receptors with a short IgG4 'Hinge' spacer conferred potent anti-tumor reactivity in vitro and in vivo, whereas corresponding CD19 chimeric receptors with a long spacer of IgG4 'Hinge-CH2-CH3', despite equivalent or superior reactivity in vitro, failed to confer significant anti-tumor effects in murine lymphoma models. Surprisingly, the length of the spacer domain proved to be a decisive element for in vivo antitumor activity, and the lack of efficacy of the 'long spacer' chimeric receptor could not be overcome by increasing the T cell dose.

We also observed major differences in cytokine secretion and proliferation in vitro between T cells expressing CD19 chimeric receptors containing CD28 and 4-1BB costimulatory domains, with CD28 augmenting secretion of IFN-γ, IL-2, and TNF-α compared with 4-1BB. CD19 chimeric receptors that possessed a tandem CD28_4-1BB also produced higher levels of these cytokines compared to chimeric receptors encoding 4-1BB only. However, our data shows that these differences in in vitro function were not predictive of in vivo anti-tumor efficacy, since CD19 chimeric receptors with either CD28 or 4-1BB costimulatory domain and a short spacer were similarly effective at eradicating advanced established Raji tumors in NSG mice. In contrast, CD19 chimeric receptors with suboptimal spacer length and CD28, 4-1BB, or both costimulatory domains, despite conferring similar in vitro function as the identical chimeric receptor construct with a short spacer domain, lacked significant anti-tumor activity in vivo, demonstrating the contribution of spacer length to in vivo function of chimeric receptor T cells.

Our studies provide insight into the mechanism responsible for the lack of in vivo efficacy of CD19 chimeric receptors with long spacer domains. T cells expressing CD19 chimeric receptors with both long and short spacer domains could be detected in the bone marrow and spleen after adoptive transfer into NSG mice bearing established Raji lymphoma, and the majority were activated as demonstrated by upregulation of CD25 and CD69. However, T cells modified to express a CD19 chimeric receptor with a long spacer domain exhibited a steep decline in cell number, in contrast to the marked in vivo expansion of T cells expressing CD19 chimeric receptors with a short spacer domain. The decline in T cell number was a consequence of much higher levels of cell death in the first 72 hours after adoptive transfer compared with T cells with short spacer domains, and control T cells that did not express a CD19 chimeric receptor. Collectively, these data indicate that recognition of tumor cells in vivo resulted in death of T cells expressing CD19-chimeric receptors with long spacer domains. A similar mechanism may explain the short duration and low levels of T cell persistence in the clinical trials that employed long spacer CD19-chimeric receptors (14).

The studies reported here are the first to show that the spacer domains of CD19 chimeric receptors that lack intrinsic signaling properties have dramatic effects on in vivo antitumor activity independent of costimulatory signaling, and identify the importance of analyzing the optimal composition of this region in the design of chimeric receptors for clinical applications.

The foregoing is illustrative of the present invention, and is not to be construed as limiting thereof. The invention is defined by the following claims, with equivalents of the claims to be included therein. All references and documents referred to herein are hereby incorporated by reference.

TABLE 1

Sequence of anti-CD19 short spacer chimeric receptor

GMCSFRss-CD19scFv-IgG4hinge-CD28tm-41BB-Zeta-T2A-EGFRt
*At*gctgctgctggtgaccagcctgctgctgtgcgagctgccccaccccgcctttctgctgatcccc
(GMCSFRss) (SEQ ID NO: 2)

Gacatccagatgacccagaccacctccagcctgagcgccagcctgggcgaccgggtgaccatcagctgccggg
ccagccaggacatcagcaagtacctgaactggtatcagcagaagcccgacggcaccgtcaagctgctgatctac
cacaccagccggctgcacagcggcgtgcccagccggtttagcggcagcggctccggcaccgactacagcctgac
catctccaacctggaacaggaagatatcgccacctactttttgccagcagggcaacacactgccctacacctttggc
ggcggaacaaagctggaaatcaccggcagcacctccggcagcggcaagcctggcagcggcgagggcagcacc
aagggcgaggtgaagagcaggaaagcggccctggcctggtggccccagccagagcctgagcgtgacctgca
ccgtgagcggcgtgagcctgcccgactacggcgtgagctggatccggcagccccccaggaagggcctggaatg
gctgggcgtgatagggcagcgagaccacctactacaacagcgccctgaagagccggctgaccatcatcaag
gacaacagcaagagccaggtgttcctgaagatgaacagcctgcagaccgacgacaccgccatctactactgcgc
caagcactactactacggcggcagctacgccatggactactggggccagggcaccagcgtgaccgtgagcagc
(CD19scFv) (SEQ ID NO: 3)

Gaatctaagtacggaccgccctgccccccttgccct (IgG4hinge) (SEQ ID NO: 4)

Atgttctgggtgctggtggtggtcggaggcgtgctggcctgctacagcctgctggtcaccgtggccttcatcatctt
ttgggtg (CD28tm-) (SEQ ID NO: 5)

Aaacggggcagaaagaaactcctgtatatattcaaacaaccatttatgagaccagtacaaactactcaagagg
aagatggctgtagctgccgatttccagaagaagaagaaggaggatgtgaactg (41BB) (SEQ ID NO: 6)
Cgggtgaagttcagcagaagcgccgacgcccctgcctaccagcagggccagaatcagctgtacaacgagctga
acctgggcagaagggaagagtacgacgtcctggataagcggagaggccctgagatgggcggcaaac
ctcggcggaagaaccccaggaaggcctgtataacgaactgcagaaagacaagatggccgaggcctacagcg
agatcggcatgaagggcgagcggaggcggggcaagggccacgacggcctgtatcagggcctgtccaccgcca
ccaaggatacctacgacgccctgcacatgcaggccctgcccccaagg (CD3Zeta)- (SEQ ID NO: 7)
Ctcgagggcggcggagagggcagaggaagtcttctaacatgcggtgacgtggaggagaatcccggccctagg
(T2A) (SEQ ID NO: 8)

Atgcttctcttggtgacaagccttctgctctgtgagttaccacacccagcattcctcctgatcccacgcaaagtgtg
taacggaataggtattggtgaatttaaagactcactctccataaatgctacgaatattaaacacttcaaaaactgc
acctccatcagtggcgatctccacatcctgccggtggcatttaggggtgactccttcacacatactcctcctctggat
ccacaggaactggatattctgaaaaccgtaaaggaaatccacagggtttttgctgattcaggcttggcctgaaaac
aggacggacctccatgcctttgagaacctagaaatcatacgcggcaggaccaagcaacatggtcagtttttctctt
gcagtcgtcagcctgaacataacatccttgggattacgctccacaaggagataagtgatggagatgtgataattt
caggaaacaaaaatttgtgctatgcaaatacaataaaactggaaaaaactgtttgggacctccggtcagaaaacc
aaaattataagcaacagaggtgaaaacagctgcaaggccacaggccaggtctgccatgccttgtgctcccccga
gggctgctggggcccggagcccagggactgcgtctcttgccggaatgtcagccgaggcagggaatgcgtggac
aagtgcaaccttctggagggtgagccaaggagtttgtggagaactctgagtgcatacagtgccaccccagagtg
cctgcctcaggccatgaacatcacctgcacaggacgggaccagacaactgtatccagtgtgcccactacattga
cggccccactgcgtcaagacctgcccggcaggagtcatgggagaaaacaacaccaggtctggaagtacgca
gacgccggccatgtgtgccacctgtgccatccaaactgcacctacggatgcactgggccaggtcttgaaggctgt
ccaacgaatgggcctaagatcccgtccatcgccactgggatggtggggccctcctcttgctgctggtggtggccc
tggggatcggcctcttcat*gtga* (EGFRt) (SEQ ID NO: 9)

TABLE 2

```
          GMCSFRss
DNA: ATGCTGCTGCTGGTGACCAGCCTGCTGCTGTGCGAGCTGCCCCACCCCGCC
AA:   M   L   L   L   V   T   S   L   L   L   C   E   L   P   H   P   A

CD19scFv
DNA: TTTCTGCTGATCCCC:GACATCCAGATGACCCAGACCACCTCCAGCCTGAGC
AA:   F   L   L   I   P   D   I   Q   M   T   Q   T   T   S   S   L   S

DNA: GCCAGCCTGGGCGACCGGGTGACCATCAGCTGCCGGGCCAGCCAGGACATC
AA:   A   S   L   G   D   R   V   T   I   S   C   R   A   S   Q   D   I

DNA: AGCAAGTACCTGAACTGGTATCAGCAGAAGCCCGACGGCACCGTCAAGCTG
AA:   S   K   Y   L   N   W   Y   Q   Q   K   P   D   G   T   V   K   L

DNA: CTGATCTACCACACCAGCCGGCTGCACAGCGGCGTGCCCAGCCGGTTTAGC
AA:   L   I   Y   H   T   S   R   L   H   S   G   V   P   S   R   F   S

DNA: GGCAGCGGCTCCGGCACCGACTACAGCCTGACCATCTCCAACCTGGAACAG
AA:   G   S   G   S   G   T   D   Y   S   L   T   I   S   N   L   E   Q

DNA: GAAGATATCGCCACCTACTTTTGCCAGCAGGGCAACACACTGCCCTACACC
AA:   E   D   I   A   T   Y   F   C   Q   Q   G   N   T   L   P   Y   T

DNA: TTTGGCGGCGGAACAAAGCTGGAAATCACCGGCAGCACCTCCGGCAGCGGC
AA:   F   G   G   G   T   K   L   E   I   T   G   S   T   S   G   S   G
```

TABLE 2-continued

```
DNA: AAGCCTGGCAGCGGCGAGGGCAGCACCAAGGGCGAGGTGAAGCTGCAGGAA
AA:   K  P  G  S  G  E  G  S  T  K  G  E  V  K  L  Q  E

DNA: AGCGGCCCTGGCCTGGTGGCCCCCAGCCAGAGCCTGAGCGTGACCTGCACC
AA:   S  G  P  G  L  V  A  P  S  Q  S  L  S  V  T  C  T

DNA: GTGAGCGGCGTGAGCCTGCCCGACTACGGCGTGAGCTGGATCCGGCAGCCC
AA:   V  S  G  V  S  L  P  D  Y  G  V  S  W  I  R  Q  P

DNA: CCCAGGAAGGGCCTGGAATGGCTGGGCGTGATCTGGGGCAGCGAGACCACC
AA:   P  R  K  G  L  E  W  L  G  V  I  W  G  S  E  T  T

DNA: TACTACAACAGCGCCCTGAAGAGCCGGCTGACCATCATCAAGGACAACAGC
AA:   Y  Y  N  S  A  L  K  S  R  L  T  I  I  K  D  N  S

DNA: AAGAGCCAGGTGTTCCTGAAGATGAACAGCCTGCAGACCGACGACACCGCC
AA:   K  S  Q  V  F  L  K  M  N  S  L  Q  T  D  D  T  A

DNA: ATCTACTACTGCGCCAAGCACTACTACTACGGCGGCAGCTACGCCATGGAC
AA:   I  Y  Y  C  A  K  H  Y  Y  Y  G  G  S  Y  A  M  D
                                                    IgG4hinge
DNA: TACTGGGGCCAGGGCACCAGCGTGACCGTGAGCAGC:GAGAGCAAGTACGGA
AA:   Y  W  G  Q  G  T  S  V  T  V  S  S   E  S  K  Y  G
                     CD28tm
DNA: CCGCCCTGCCCCCCTTGCCCT:ATGTTCTGGGTGCTGGTGGTGGTCGGAGGC
AA:   P  P  C  P  P  C  P   M  F  W  V  L  V  V  V  G  G DNA: GTGCTGGCCTGCTACAGCCTGCTGGTCACCGTGGCCTTCATCATCTTTTGG
AA:   V  L  A  C  Y  S  L  L  V  T  V  A  F  I  I  F  W
         41BB
DNA: GTG:AAACGGGGCAGAAAGAAACTCCTGTATATATTCAAACAACCATTTATG
AA:   V   K  R  G  R  K  K  L  L  Y  I  F  K  Q  P  F  M DNA: AGACCAGTACAAACTACTCAAGAGGAAGATGGCTGTAGCTGCCGATTTCCA
AA:   R  P  V  Q  T  T  Q  E  E  D  G  C  S  C  R  F  P
                                              CD3Zeta
DNA: GAAGAAGAAGAAGGAGGATGTGAACTGCGGGTGAAG:TTCAGCAGAAGCGCC
AA:   E  E  E  E  G  G  C  E  L  R  V  K   F  S  R  S  A DNA: GACGCCCCTGCCTACCAGCAGGGCCAGAATCAGCTGTACAACGAGCTGAAC
AA:   D  A  P  A  Y  Q  Q  G  Q  N  Q  L  Y  N  E  L  N DNA: CTGGGCAGAAGGGAAGAGTACGACGTCCTGGATAAGCGGAGAGGCCGGGAC
AA:   L  G  R  R  E  E  Y  D  V  L  D  K  R  R  G  R  D DNA: CCTGAGATGGGCGGCAAGCCTCGGCGGAAGAACCCCCAGGAAGGCCTGTAT
AA:   P  E  M  G  G  K  P  R  R  K  N  P  Q  E  G  L  Y DNA: AACGAACTGCAGAAAGACAAGATGGCCGAGGCCTACAGCGAGATCGGCATG
AA:   N  E  L  Q  K  D  K  M  A  E  A  Y  S  E  I  G  M DNA: AAGGGCGAGCGGAGGCGGGGCAAGGGCCACGACGGCCTGTATCAGGGCCTG
AA:   K  G  E  R  R  R  G  K  G  H  D  G  L  Y  Q  G  L DNA: TCCACCGCCACCAAGGATACCTACGACGCCCTGCACATGCAGGCCCTGCCC
AA:   S  T  A  T  K  D  T  Y  D  A  L  H  M  Q  A  L  P
          T2A
DNA: CCAAGG:CTCGAGGGCGGCGGAGAGGGCAGAGGAAGTCTTCTAACATGCGGT
AA:   P  R   L  E  G  G  G  E  G  R  G  S  L  L  T  C  G
                                    EGFRt
DNA: GACGTGGAGGAGAATCCCGGCCCTAGG:ATGCTTCTCCTGGTGACAAGCCTT
AA:   D  V  E  E  N  P  G  P  R   M  L  L  L  V  T  S  L DNA: CTGCTCTGTGAGTTACCACACCCAGCATTCCTCCTGATCCCACGCAAAGTG
AA:   L  L  C  E  L  P  H  P  A  F  L  L  I  P  R  K  V DNA: TGTAACGGAATAGGTATTGGTGAATTTAAAGACTCACTCTCCATAAATGCT
AA:   C  N  G  I  G  I  G  E  F  K  D  S  L  S  I  N  A DNA: ACGAATATTAAACACTTCAAAAACTGCACCTCCATCAGTGGCGATCTCCAC
AA:   T  N  I  K  H  F  K  N  C  T  S  I  S  G  D  L  H DNA: ATCCTGCCGGTGGCATTTAGGGGTGACTCCTTCACACATACTCCTCCTCTG
AA:   I  L  P  V  A  F  R  G  D  S  F  T  H  T  P  P  L
```

TABLE 2-continued

```
DNA: GATCCACAGGAACTGGATATTCTGAAAACCGTAAAGGAAATCACAGGGTTT
AA:   D  P  Q  E  L  D  I  L  K  T  V  K  E  I  T  G  F

DNA: TTGCTGATTCAGGCTTGGCCTGAAAACAGGACGGACCTCCATGCCTTTGAG
AA:   L  L  I  Q  A  W  P  E  N  R  T  D  L  H  A  F  E

DNA: AACCTAGAAATCATACGCGGCAGGACCAAGCAACATGGTCAGTTTTCTCTT
AA:   N  L  E  I  I  R  G  R  T  K  Q  H  G  Q  F  S  L

DNA: GCAGTCGTCAGCCTGAACATAACATCCTTGGGATTACGCTCCCTCAAGGAG
AA:   A  V  V  S  L  N  I  T  S  L  G  L  R  S  L  K  E

DNA: ATAAGTGATGGAGATGTGATAATTTCAGGAAACAAAAATTTGTGCTATGCA
AA:   I  S  D  G  D  V  I  I  S  G  N  K  N  L  C  Y  A

DNA: AATACAATAAACTGGAAAAAACTGTTTGGGACCTCCGGTCAGAAAACCAAA
AA:   N  T  I  N  W  K  K  L  F  G  T  S  G  Q  K  T

DNA: ATTATAAGCAACAGAGGTGAAAACAGCTGCAAGGCCACAGGCCAGGTCTGC
AA:   I  I  S  N  R  G  E  N  S  C  K  A  T  G  Q  V  C

DNA: CATGCCTTGTGCTCCCCCGAGGGCTGCTGGGGCCCGGAGCCCAGGGACTGC
AA:   H  A  L  C  S  P  E  G  C  W  G  P  E  P  R  D  C

DNA: GTCTCTTGCCGGAATGTCAGCCGAGGCAGGGAATGCGTGGACAAGTGCAAC
AA:   V  S  C  R  N  V  S  R  G  R  E  C  V  D  K  C  N

DNA: CTTCTGGAGGGTGAGCCAAGGGAGTTTGTGGAGAACTCTGAGTGCATACAG
AA:   L  L  E  G  E  P  R  E  F  V  E  N  S  E  C  I  Q

DNA: TGCCACCCAGAGTGCCTGCCTCAGGCCATGAACATCACCTGCACAGGACGG
AA:   C  H  P  E  C  L  P  Q  A  M  N  I  T  C  T  G  R

DNA: GGACCAGACAACTGTATCCAGTGTGCCCACTACATTGACGGCCCCCACTGC
AA:   G  P  D  N  C  I  Q  C  A  H  Y  I  D  G  P  H  C

DNA: GTCAAGACCTGCCCGGCAGGAGTCATGGGAGAAAACAACACCCTGGTCTGG
AA:   V  K  T  C  P  A  G  V  M  G  E  N  N  T  L  V  W

DNA: AAGTACGCAGACGCCGGCCATGTGTGCCACCTGTGCCATCCAAACTGCACC
AA:   K  Y  A  D  A  G  H  V  C  H  L  C  H  P  N  C  T

DNA: TACGGATGCACTGGGCCAGGTCTTGAAGGCTGTCCAACGAATGGGCCTAAG
AA:   Y  G  C  T  G  P  G  L  E  G  C  P  T  N  G  P  K

DNA: ATCCCGTCCATCGCCACTGGGATGGTGGGGGCCCTCCTCTTGCTGCTGGTG
AA:   I  P  S  I  A  T  G  M  V  G  A  L  L  L  L  L  V

DNA: GTGGCCCTGGGGATCGGCCTCTTCATG*TGA*___ (SEQ ID NO: 10)
AA:   V  A  L  G  I  G  L  F  M  *  (SEQ ID NO: 11)
```

TABLE 3

ZXR-014 Nucleotide and amino acid sequences (map of sections)

GMCSFRss: nt2084-2149
CD19scFv: nt2150-2884
Igg4Hinge: nt2885-2920
CD28tm: nt2921-3004
41BB: nt3005-3130
Zeta: nt3131-3466
T2A: nt3467-3538
EGFRt: nt3539-4612

Primers for sequencing:

| Oligo name | Sequence | Region |
|---|---|---|
| oJ02649 | ATCAAAAGAATAGACC GAGATAGGGT | pre-U5 (SEQ ID NO: 22) |
| oJ02648 | CCGTACCTTTAAGACCA ATGACTTAC | delU3 (SEQ ID NO: 23) |
| oJ02650 | TTGAGAGTTTTCGCCCCG | mid-Ampr (SEQ ID NO: 24) |
| oJ02651 | AATAGACAGATCGCTG AGATAGGT | post-Ampr (SEQ ID NO: 25) |
| oJ02652 | CAGGTATCCGGTAAGCGG | CoE1 ori (SEQ ID NO: 26) |
| oJ02653 | CGACCAGCAACCATAGTCC | SV40 (SEQ ID NO: 27) |
| oJ02654 | TAGCGGTTTGACTCACGG | CMV (SEQ ID NO: 28) |
| oJ02655 | GCAGGGAGCTAGAACGATTC | psi (SEQ ID NO: 29) |
| oJ02656 | ATTGTCTGGTATAGT GCAGCAG | RRE (SEQ ID NO: 30) |

TABLE 3-continued

ZXR-014 Nucleotide and amino acid sequences (map of sections)

| oJ02657 | TCGCAACGGGTTTGCC | EF1p (SEQ ID NO: 31) |
| --- | --- | --- |
| oJ02658 | AGGAAGATATCGCCACCTACT | CD19Rop (SEQ ID NO: 32) |
| oJ02601 | CGGGTGAAGTTCAGCAGAAG | Zeta (SEQ ID NO: 33) |
| oJ02735 | ACTGTGTTTGCTGACGCAAC | WPRE (SEQ ID NO: 34) |
| oJ02715 | ATGCTTCTCCTGGTGACAAG | EGFRt (SEQ ID NO: 35) |

TABLE 4

Uniprot P0861 IgG4-Fc (SEQ ID NO: 13)

```
        10         20         30         40
ASTKGPSVFP LAPCSRSTSE STAALGCLVK DYFPEPVTVS
        50         60         70         80
WNSGALTSGV HTFPAVLQSS GLYSLSSVVT VPSSSLGTKT
        90        100        110        120
YTCNVDHKPS NTKVDKRVES KYGPPCPSCP APEFLGGPSV
       130        140        150        160
FLFPPKPKDT LMISRTPEVT CVVVDVSQED PEVQFNWYVD
       170        180        190        200
GVEVHNAKTK PREEQFNSTY RVVSVLTVLH QDWLNGKEYK
       210        220        230        240
CKVSNKGLPS SIEKTISKAK GQPREPQVYT LPPSQEEMTK
       250        260        270        280
NQVSLTCLVK GFYPSDIAVE WESNGQPENN YKTTPPVLDS
       290        300        310        320
DGSFFLYSRL TVDKSRWQEG NVFSCSVMHE ALHNHYTQKS
LSLSLGK
```

1-98 CH1
99-110 Hinge
111-220 CH2
221-327 CH3
Position 108 S → P

TABLE 5

Uniprot P10747 CD28 (SEQ ID NO: 14)

```
        10         20         30         40
MLRLLLALNL FPSIQVTGNK ILVKQSPMLV AYDNAVNLSC
        50         60         70         80
KYSYNLFSRE FRASLHKGLD SAVEVCVVYG NYSQQLQVYS
        90        100        110        120
KTGFNCDGKL GNESVTFYLQ NLYVNQTDIY FCKIEVMYPP
       130        140        150        160
PYLDNEKSNG TIIHVKGKHL CPSPLFPGPS KPFWVLVVVG
       170        180        190        200
GVLACYSLLV TVAFIIFWVR SKRSRLLHSD YMNMTPRRPG
```

```
       210        220
PTRKHYQPYA PPRDFAAYRS
```

1-18 signal peptide
19-152 extracellular domain
153-179 transmembrane domain
180-220 intracellular domain
Position 186-187 LL→GC

TABLE 6

Uniprot Q07011 4-1BB (SEQ ID NO: 15)

```
        10         20         30         40
MGNSCYNIVA TLLLVLNFER TRSLQDPCSN CPAGTFCDNN
        50         60         70         80
RNQICSPCPP NSFSSAGGQR TCDICRQCKG VFRTRKECSS
        90        100        110        120
TSNAECDCTP GFHCLGAGCS MCEQDCKQGQ ELTKKGCKDC
       130        140        150        160
CFGTFNDQKR GICRPWTNCS LDGKSVLVNG TKERDVVCGP
       170        180        190        200
SPADLSPGAS SVTPPAPARE PGHSPQIISF FLALTSTALL
       210        220        230        240
FLLFFLTLRF SVVKRGRKKL LYIFKQPFMR PVQTTQEEDG
       250
CSCRFPEEEE GGCEL
```

1-23 signal peptide
24-186 extracellular domain
187-213 transmembrane domain
214-255 intracellular domain

TABLE 7

Uniprot P20963 human CD3ζ isoform 3 (SEQ ID NO: 16)

```
        10         20         30         40
MKWKALFTAA ILQAQLPITE AQSFGLLDPK LCYLLDGILF
        50         60         70         80
IYGVILTALF LRVKFSRSAD APAYQQGQNQ LYNELNLGRR
        90        100        110        120
EEYDVLDKRR GRDPEMGGKP QRRKNPQEGL YNELQKDKMA
       130        140        150        160
EAYSEIGMKG ERRRGKGHDG LYQGLSTATK DTYDALHMQA
LPPR
```

1-21 signal peptide
22-30 extracellular
31-51 transmembrane
52-164 intracellular domain
61-89 ITAM1
100-128 ITAM2
131-159 ITAM3

TABLE 8

Exemplary Hinge region Sequences

| Human IgG1 | EPKSCDKTHTCPPCP | (SEQ ID NO: 17) |
| --- | --- | --- |
| Human IgG2 | ERKCCVECPPCP | (SEQ ID NO: 18) |

TABLE 8-continued

Exemplary Hinge region Sequences

| | | |
|---|---|---|
| Human IgG3 | ELKTPLGDTHTCPRCP (EPKSCDTPPPCPRCP)$_3$ | (SEQ ID NO: 19) |
| Human IgG4 | ESKYGPPCPSCP | (SEQ ID NO: 20) |
| Modified Human IgG4 | ESKYGPPCPPCP | (SEQ ID NO: 21) |
| Modified Human IgG4 | YGPPCPPCP | (SEQ ID NO: 51) |
| Modified Human IgG4 | KYGPPCPPCP | (SEQ ID NO: 52) |
| Modified Human IgG4 | EVVKYGPPCPPCP | (SEQ ID NO: 53) |

TABLE 9

R12 long spacer CAR:
PJ_R12-CH2—CH3-41BB-Z-T2A-tEGFR
(SEQ ID NO: 37)
GTTAGACCAGATCTGAGCCTGGGAGCTCTCTGGCTAACTAGGGAACCCACT
GCTTAAGCCTCAATAAAGCTTGCCTTGAGTGCTTCAAGTAGTGTGTGCCCG
TCTGTTGTGTGACTCTGGTAACTAGAGATCCCTCAGACCCTTTTAGTCAGT
GTGGAAAATCTCTAGCAGTGGCGCCCGAACAGGGACTTGAAAGCGAAAGGG
AAACCAGAGGAGCTCTCTCGACGCAGGACTCGGCTTGCTGAAGCGCGCACG
GCAAGAGGCGAGGGGCGGCGACTGGTGAGTACGCCAAAAATTTTGACTAGC
GGAGGCTAGAAGGAGAGAGATGGGTGCGAGAGCGTCAGTATTAAGCGGGGG
AGAATTAGATCGATGGGAAAAAATTCGGTTAAGGCCAGGGGGAAAGAAAAA
ATATAAAATTAAAACATATAGTATGGGCAAGCAGGGAGCTAGAACGATTCGC
AGTTAATCCTGGCCTGTTAGAAACATCAGAAGGCTGTAGACAAATACTGGG
ACAGCTACAACCATCCCTTCAGACAGGATCAGAAGAACTTAGATCATTATA
TAATACAGTAGCAACCCTCTATTGTGTGCATCAAAGGATAGAGATAAAAGA
CACCAAGGAAGCTTTAGACAAGATAGAGGAAGAGCAAAACAAAAGTAAGAA
AAAAGCACAGCAAGCAGCAGCTGACACAGGACACAGCAATCAGGTCAGCCA
AAATTACCCTATAGTGCAGAACATCCAGGGGCAAATGGTACATCAGGCCAT
ATCACCTAGAACTTTAAATGCATGGGTAAAAGTAGTAGAAGAGAAGGCTTT
CAGCCCAGAAGTGATACCCATGTTTTCAGCATTATCAGAAGGAGCCACCCC
ACAAGATTTAAACACCATGCTAAACACAGTGGGGGGACATCAAGCAGCCAT
GCAAATGTFAAAAGAGACCATCAATGAGGAAGCTGCAGGCAAAGAGAAGAG
TGGTGCAGAGAGAAAAAAGAGCAGTGGGAATAGGAGCTTTGTTCCTTGGGT
TCTTGGGAGCAGCAGGAAGCACTATGGGCGCAGCGTCAATGACGCTGACGG
TACAGGCCAGACAATTATTGTCTGGTATAGTGCAGCAGCAGAACAATTTGC
TGAGGGCTATTGAGGCGCAACAGCATCTGTTGCAACTCACAGTCTGGGGCA
TCAAGCAGCTCCAGGCAAGAATCCTGGCTGTGGAAAGATACCTAAAGGATC
AACAGCTCCTGGGGATTTGGGGTTGCTCTGGAAAACTCATTTGCACCACTG
CTGTGCCTTGGATCTACAAATGGCAGTATTCATCCACAATTTTAAAAGAAA
AGGGGGGATTGGGGGGTACAGTGCAGGGGAAAGAATAGTAGACATAATAGC

TABLE 9-continued

AACAGACATACAAACTAAAGAATTACAAAAACAAATTACAAAAATTCAAAA
TTTTCGGGTTTATTACAGGGACAGCAGAGATCCAGTTTGGGGATCAATTGC
ATGAAGAATCTGCTTAGGGTTAGGCGTTTTGCGCTGCTTCGCGAGGATCTG
CGATCGCTCCGGTGCCCGTCAGTGGGCAGAGCGCACATCGCCCACAGTCCC
CGAGAAGTTGGGGGGAGGGGTCGGCAATTGAACCGGTGCCTAGAGAAGGTG
GCGCGGGGTAAACTGGGAAAGTGATGTCGTGTACTGGCTCCGCCTTTTTCC
CGAGGGTGGGGGAGAACCGTATATAAGTGCAGTAGTCGCCGTGAACGTTCT
TTTTCGCAACGGGTTTGCCGCCAGAACACAGCTGAAGCTTCGAGGGGCTCG
CATCTCTCCTTCACGCGCCCGCCGCCCTACCTGAGGCCGCCATCCACGCCG
GTTGAGTCGCGTTCTGCCGCCTCCCGCCTGTGGTGCCTCCTGAACTGCGTC
CGCCGTCTAGGTAAGTTTAAAGCTCAGGTCGAGACCGGGCCTTTGTCCGGC
GCTCCCTTGGAGCCTACCTAGACTCAGCCGGCTCTCCACGCTTTGCCTGAC
CCTGCTTGCTCAACTCTACGTCTTTGTTTCGTTTTCTGTTCTGCGCCGTTA
CAGATCCAAGCTGTGACCGGCGCCTACG
[GCTAGC]GAATTCCTCGAGGCC
ACC[ATG]CTGCTGCTGGTGACAAGCCTGCTGCTGTGCGAGCTGCCCCACCCC
GCCTTTCTGCTGATCCCCCAGGAACAGCTCGTCGAAAGCGGCGGCAGACTG
GTGACACCTGGCGGCAGCCTGACCCTGAGCTGCAAGGCCAGCGGCTTCGAC
TTCAGCGCCTACTACATGAGCTGGGTCCGCCAGGCCCCTGGCAAGGGACTG
GAATGGATCGCCACCATCTACCCCAGCAGCGGCAAGACCTACTACGCCACC
TGGGTGAACGGACGGTTCACCATCTCCAGCGACAACGCCCAGAACACCGTG
GACCTGCAGATGAACGCCTGACAGCCGCCGACCGGGCCACCTACTTTTGC
GCCAGAGACAGCTACGCCGACGACGGCGCCCTGTTCAACATCTGGGGCCCT
GGCACCCTGGTGACAATCTCTAGCGGCGGAGGCGGATCTGGTGGCGGAGGA
AGTGGCGGCGGAGGATCTGAGCTGGTGCTGACCCAGAGCCCCTCTGTGTCT
GCTGCCCTGGGAAGCCCTGCCAAGATCACCTGTACCCTGAGCAGCGCCCAC
AAGACCGACACCATCGACTGGTATCAGCAGCTGCAGGGCGAGGCCCCCAGA
TACCTGATGCAGGTGCAGAGCGACGGCAGCTACACCAAGAGGCCAGGCGTG
CCCGACCGGTTCAGCGGATCTAGCTCTGGCGCCGACCGCTACCTGATCATC
CCCAGCGTGCAGGCCGATGACGAGGCCGATTACTACTGTGGCGCCGACTAC
ATCGGCGGCTACGTGTTCGGCGGAGGCACCCAGCTGACCGTGACCGGCGAG
TCTAAG

IgG4 spacer
[TA]CGGACCGCCCTGCCCCCCTTGCCCT
CH2
GCCCCCGAGTTCCTGGGCGGACCCAGCGTGTTCCTGTTCCCCCCCAAGCCC
AAGGACACCCTGATGATCAGCCGGACCCCCGAGGTGACCTGCGTGGTGGTG
GACGTGAGCCAGGAAGATCCCGAGGTCCAGTTCAATTGGTACGTGGACGGC
GTGGAAGTGCACAACGCCAAGACCAAGCCCAGAGAGGAACAGTTCAACAGC
ACCTACCGGGTGGTGTCTGTGCTGACCGTGCTGCACCAGGACTGGCTGAAC TABLE 9-continued

GGCAAAGAATACAAGTGCAAGGTGTCCAACAAGGGCCTGCCCAGCAGCATC

GAAAAGACCATCAGCAAGGCCAAG

CH3
GGCCAGCCTCGCGAGCCCCAGGTGTACACCCTGCCTCCCTCCCAGGAAGAG

ATGACCAAGAACCAGGTGTCCCTGACCTGCCTGGTGAAGGGCTTCTACCCC

AGCGACATCGCCGTGGAGTGGGAGAGCAACGGCCAGCCTGAGAACAACTAC

AAGACCACCCCTCCCGTGCTGGACAGCGACGGCAGCTTCTTCCTGTACAGC

CGGCTGACCGTGGACAAGAGCCGGTGGCAGGAAGGCAACGTCTTTAGCTGC

AGCGTGATGCACGAGGCCCTGCACAACCACTACACCCAGAAGAGCCTGAGC

CTGTCCCTGGGCAAG 4-1BB
ATGTTCTGGGTGCTGGTGGTGGTGGGCGGGGTGCTGGCCTGCTACAGCCTG

CTGGTGACAGTGGCCTTCATCATCTTTTGGGTGAAACGGGGCAGAAAGAAA

CTCCTGTATATATTCAAACAACCATTTATGAGACCAGTACAAACTACTCAA

GAGGAAGATGGCTGTAGCTGCCGATTTCCAGAAGAAGAAGAAGGAGGATGT

GAACTG

CD3 zeta
CGGGTGAAGTTCAGCAGAAGCGCCGACGCCCCTGCCTACCAGCAGGGCCAG

AATCAGCTGTACAACGAGCTGAACCTGGGCAGAAGGGAAGAGTACGACGTC

CTGGATAAGCGGAGAGGCCGGGACCCTGAGATGGGCGGCAAGCCTCGGCGG

AAGAACCCCCAGGAAGGCCTGTATAACGAACTGCAGAAAGACAAGATGGCC

GAGGCCTACAGCGAGATCGGCATGAAGGGCGAGCGGAGGCGGGGCAAGGGC

CACGACGGCCTGTATCAGGGCCTGTCCACCGCCACCAAGGATACCTACGAC

GCCCTGCACATGCAGGCCCTGCCCCCAAGG

T2A
CTCGAGGGCGGCGGAGAGGGCAGAGGAAGTCTTCTAACATGCGGTGACGTG

GAGGAGAATCCCGGCCCTAGG tEGFR
ATGCTTCTCCTGGTGACAAGCCTTCTGCTCTGTGAGTTACCACACCCAGCA

TTCCTCCTGATCCCACGCAAAGTGTGTAACGGAATAGGTATTGGTGAATTT

AAAGACTCACTCTCCATAAATGCTACGAATATTAAACACTTCAAAAACTGC

ACCTCCATCAGTGGCGATCTCCACATCCTGCCGGTGGCATTTAGGGGTGAC

TCCTTCACACATACTCCTCCTCTGGATCCACAGGAACTGGATATTCTGAAA

ACCGTAAAGGAAATCACAGGGTTTTTGCTGATTCAGGCTTGGCCTGAAAAC

AGGACGGACCTCCATGCCTTTGAGAACCTAGAAATCATACGCGGCAGGACC

AAGCAACATGGTCAGTTTTCTCTTGCAGTCGTCAGCCTGAACATAACATCC

TTGGGATTACGCTCCCTCAAGGAGATAAGTGATGGAGATGTGATAATTTCA

GGAAACAAAAATTTGTGCTATGCAAATACAATAAACTGGAAAAAACTGTTT

GGGACCTCCGGTCAGAAAACCAAAATTATAAGCAACAGAGGTGAAAACAGC

TGCAAGGCCACAGGCCAGGTCTGCCATGCCTTGTGCTCCCCCGAGGGCTGC

TGGGGCCCGGAGCCCAGGGACTGCGTCTCTTGCCGGAATGTCAGCCGAGGC

AGGGAATGCGTGGACAAGTGCAACCTTCTGGAGGGTGAGCCAAGGGAGTTT

GTGGAGAACTCTGAGTGCATACAGTGCCACCCAGAGTGCCTGCCTCAGGCC

ATGAACATCACCTGCACAGGACGGGACCAGACAACTGTATCCAGTGTGCC

CACTACATTGACGGCCCCCACTGCGTCAAGACCTGCCCGGCAGGAGTCATG

GGAGAAAACAACACCCTGGTCTGGAAGTACGCAGACGCCGGCCATGTGTGC

CACCTGTGCCATCCAAACTGCACCTACGGATGCACTGGGCCAGGTCTTGAA

GGCTGTCCAACGAATGGGCCTAAGATCCCGTCCATCGCCACTGGGATGGTG

GGGCCCTCCTCTTGCTGCTGGTGGTGGCCCTGGGGATCGGCCTCTTCATG

TGAGCGGCCGCTCTAGACCCGGGCTGCAGGAATTCGATATCAAGCTTATC

GATAATCAACCTCTGGATTACAAAATTTGTGAAAGATTGACTGGTATTCTT

AACTATGTTGCTCCTTTTACGCTATGTGGATACGCTGCTTTAATGCCTTTG

TATCATGCTATTGCTTCCCGTATGGCTTTCATTTTCTCCTCCTTGTATAAA

TCCTGGTTGCTGTCTCTTTATGAGGAGTTGTGGCCCGTTGTCAGGCAACGT

GGCGTGGTGTGCACTGTGTTTGCTGACGCAACCCCCACTGGTTGGGGCATT

GCCACCACCTGTCAGCTCCTTTCCGGGACTTTCGCTTTCCCCCTCCCTATT

GCCACGGCGGAACTCATCGCCGCCTGCCTTGCCCGCTGCTGGACAGGGGCT

CGGCTGTTGGGCACTGACAATTCCGTGGTGTTGTCGGGGAAATCATCGTCC

TTTCCTTGGCTGCTCGCCTGTGTTGCCACCTGGATTCTGCGCGGGACGTCC

TTCTGCTACGTCCCTTCGGCCCTCAATCCAGCGGACCTTCCTTCCCGCGGC

CTGCTGCCGGCTCTGCGGCCTCTTCCGCGTCTTCGCCTTCGCCCTCAGACG

AGTCGGATCTCCCTTTGGGCCGCCTCCCCGCATCGATACCGTCGACTAGCC

GTACCTTTAAGACCAATGACTTACAAGGCAGCTGTAGATCTTAGCCACTTT

TTAAAAGAAAAGGGGGGACTGGAAGGGCTAATTCACTCCCAAAGAAGACAA

GATCTGCTTTTTGCCTGTACTGGGTCTCTCTGGTTAGACCAGATCTGAGCC

TGGGAGCTCTCTGGCTAACTAGGGAACCCACTGCTTAAGCCTCAATAAAGC

TTGCCTTGAGTGCTTCAAGTAGTGTGTGCCCGTCTGTTGTGTGACTCTGGT

AACTAGAGATCCCTCAGACCCTTTTAGTCAGTGTGGAAAATCTCTAGCAGA

ATTCGATATCAAGCTTATCGATACCGTCGACCTCGAGGGGGGCCCGGTAC

CCAATTCGCCCTATAGTGAGTCGTATTACAATTCACTGGCCGTCGTTTTAC

AACGTCGTGACTGGGAAAACCCTGGCGTTACCCAACTTAATCGCCTTGCAG

CACATCCCCCTTTCGCCACCTGGCGTAATAGCGAAGAGGCCCGCACCGATC

GCCCTTCCCAACAGTTGCGCAGCCTGAATGGCGAATGGAAATTGTAAGCGT

TAATATTTTGTTAAAATTCGCGTTAAATTTTGTTAAATCAGCTCATTTTT

TAACCAATAGGCCGAAATCGGCAAAATCCCTTATAAATCAAAAGAATAGAC

CGAGATAGGGTTGAGTGTTGTTCCAGTTTGGAACAAGAGTCCACTATTAAA

GAACGTGGACTCCAACGTCAAAGGGCGAAAAACCGTCTATCAGGGCGATGG

CCCACTACGTGAACCATCACCCTAATCAAGTTTTTTGGGGTCGAGGTGCCG

TAAAGCACTAAATCGGAACCCTAAAGGGAGCCCCCGATTTAGAGCTTGACG

GGGAAAGCCGGCGAACGTGGCGAGAAAGGAAGGGAAGAAAGCGAAAGGAGC

GGGCGCTAGGGCGCTGGCAAGTGTAGCGGTCACGCTGCGCGTAACCACCAC

ACCCGCCGCGCTTAATGCGCCGCTACAGGGCGCGTCAGGTGGCACTTTTCG

TABLE 9-continued

```
GGGAAATGTGCGCGGAACCCCTATTTGTTTATTTTTCTAAATACATTCAAA
TATGTATCCGCTCATGAGACAATAACCCTGATAAATGCTTCAATAATATTG
AAAAAGGAAGAGTATGAGTATTCAACATTTCCGTGTCGCCCTTATTCCCTT
TTTTGCGGCATTTTGCCTTCCTGTTTTTGCTCACCCAGAAACGCTGGTGAA
AGTAAAAGATGCTGAAGATCAGTTGGGTGCACGAGTGGGTTACATCGAACT
GGATCTCAACAGCGGTAAGATCCTTGAGAGTTTTCGCCCCGAAGAACGTTT
TCCAATGATGAGCACTTTTAAAGTTCTGCTATGTGGCGCGGTATTATCCCG
TATTGACGCCGGGCAAGAGCAACTCGGTCGCCGCATACACTATTCTCAGAA
TGACTTGGTTGAGTACTCACCAGTCACAGAAAAGCATCTTACGGATGGCAT
GACAGTAAGAGAATTATGCAGTGCTGCCATAACCATGAGTGATAACACTGC
GGCCAACTTACTTCTGACAACGATCGGAGGACCGAAGGAGCTAACCGCTTT
TTTGCACAACATGGGGGATCATGTAACTCGCCTTGATCGTTGGGAACCGGA
GCTGAATGAAGCCATACCAAACGACGAGCGTGACACCACGATGCCTGTAGC
AATGGCAACAACGTTGCGCAAACTATTAACTGGCGAACTACTTACTCTAGC
TTCCCGGCAACAATTAATAGACTGGATGGAGGCGGATAAAGTTGCAGGACC
ACTTCTGCGCTCGGCCCTTCCGGCTGGCTGGTTTATTGCTGATAAATCTGG
AGCCGGTGAGCGTGGGTCTCGCGGTATCATTGCAGCACTGGGGCCAGATGG
TAAGCCCTCCCGTATCGTAGTTATCTACACGACGGGGAGTCAGGCAACTAT
GGATGAACGAAATAGACAGATCGCTGAGATAGGTGCCTCACTGATTAAGCA
TTGGTAACTGTCAGACCAAGTTTACTCATATATACTTTAGATTGATTTAAA
ACTTCATTTTTAATTTAAAAGGATCTAGGTGAAGATCCTTTTTGATAATCT
CATGACCAAAATCCCTTAACGTGAGTTTTCGTTCCACTGAGCGTCAGACCC
CGTAGAAAAGATCAAAGGATCTTCTTGAGATCCTTTTTTTCTGCGCGTAAT
CTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGC
GCAGATACCAAATACTGTTCTTCTAGTGTAGCCGTAGTTAGGCCACCACTT
CAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAG
ACGATAGTTACCGGATAAGGCGCAGCGGTCGGGCTGAACGGGGGGTTCGTG
CACACAGCCCAGCTTGGAGCGAACGACCTACACCGAACTGAGATACCTACA
GCGTGAGCTATGAGAAAGCGCCACGCTTCCCGAAGGGAGAAAGGCGGACAG
GTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTG
ACTTGAGCGTCGATTTTTGTGATGCTCGTCAGGGGGCGGAGCCTATGGAA
AAACGCCAGCAACGCGGCCTTTTTACGGTTCCTGGCCTTTTGCTGGCCTTT
TGCTCACATGTTCTTTCCTGCGTTATCCCCTGATTCTGTGGATAACCGTAT
TACCGCCTTTGAGTGAGCTGATACCGCTCGCCGCAGCCGAACGACCGAGCG
CAGCGAGTCAGTGAGCGAGGAAGCGGAAGAGCGCCCAATACGCAAACCGCC
TCTCCCCGCGCGTTGGCCGATTCATTAATGCAGCTGGCACGACAGGTTTCC
CGACTGGAAAGCGGGCAGTGAGCGCAACGCAATTAATGTGAGTTAGCTCAC
TCATTAGGCACCCCAGGCTTTACACTTTATGCTTCCGGCTCGTATGTTGTG
TGGAATTGTGAGCGGATAACAATTTCACACAGGAAACAGCTATGACCATGA
TTACGCCAAGCTCGAAATTAACCCTCACTAAAGGGAACAAAAGCTGGAGCT
CCACCGCGGTGGCGGCCTCGAGGTCGAGATCCGGTCGACCAGCAACCATA
GTCCCGCCCCTAACTCCGCCCATCCCGCCCCTAACTCCGCCCAGTTCCGCC
CATTCTCCGCCCCATGGCTGACTAATTTTTTTTATTTATGCAGAGGCCGAG
GCCGCCTCGGCCTCTGAGCTATTCCAGAAGTAGTGAGGAGGCTTTTTTGGA
GGCCTAGGCTTTTGCAAAAAGCTTCGACGGTATCGATTGGCTCATGTCCAA
CATTACCGCCATGTTGACATTGATTATTGACTAGTTATTAATAGTAATCAA
TTACGGGTCATTAGTTCATAGCCCATATATGGAGTTCCGCGTTACATAAC
TTACGGTAAATGGCCCGCCTGGCTGACCGCCCAACGACCCCCGCCCATTGA
CGTCAATAATGACGTATGTTCCCATAGTAACGCCAATAGGGACTTTCCATT
GACGTCAATGGGTGGAGTATTTACGGTAAACTGCCCACTTGGCAGTACATC
AAGTGTATCATATGCCAAGTACGCCCCCTATTGACGTCAATGACGGTAAAT
GGCCCGCCTGGCATTATGCCCAGTACATGACCTTATGGGACTTTCCTACTT
GGCAGTACATCTACGTATTAGTCATCGCTATTACCATGGTGATGCGGTTTT
GGCAGTACATCAATGGGCGTGGATAGCGGTTTGACTCACGGGGATTTCCAA
GTCTCCACCCCATTGACGTCAATGGGAGTTTGTTTTGGCACCAAAATCAAC
GGGACTTTCCAAAATGTCGTAACAACTCCGCCCCATTGACGCAAATGGGCG
GTAGGCGTGTACGGAATTCGGAGTGGCGAGCCCTCAGATCCTGCATATAAG
CAGCTGCTTTTTGCCTGTACTGGGTCTCTCTG
```

TABLE 10

Leader_R12-Hinge-CH2—CH3-CD28ttn/41BB-Z-T2A-tEGFR
(SEQ ID NO: 38)

Leader
MLLLVTSLLLCELPHPAFLLIP

R12 scFv
QEQLVESGGRLVTPGGSLTLSCKASGFDFSAYYMSWVRQAPGKGLEWIATI
YPSSGKTYYATWVNGRFTISSDNAQNTVDLQMNSLTAADRATYFCARDSYA
DDGALFNIWGPGTLVTISSGGGGSGGGGSGGGGSELVLTQSPSVSAALGSP
AKITCTLSSAHKTDTIDWYQQLQGEAPRYLMQVQSDGSYTKRPGVPDRFSG
SSSGADRYLIIPSVQADDEADYYCGADYIGGYVFGGGTQLTVTG

Hinge Spacer
ESKYGPPCPPCP

CH2
APEFLGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGL
PSSIEKTISKAK

CH3
GQPREPQVYTLPPSQEEMTKNQVSLTCLVKGFYPSDIAVEWESNGQPEN
NYKTTPPVLDSDGSFFLYSRLTVDKSRWQEGNVFSCSVMHEALHNHYTQK
SLSLSLGK

TABLE 10-continued

CD28
MFWVLVVVGGVLACYSLLVTVAFIIFWV 4-1BB
KRGRKKLLYIFKQPFMRPVQTTQEEDGCSCRFPEEEEGGCEL

CD3 zeta
RVKFSRSADAPAYQQGQNQLYNELNLGRREEYDVLDKRRGRDPEMGGKPRR
KNPQEGLYNELQKDKMAEAYSEIGMKGERRRGKGHDGLYQGLSTATKDTYD
ALHMQALPPR

T2A
LEGGGEGRGSLLTCGDVEENPGPR tEGFR
MLLLVTSLLLCELPHPAFLLIPRKVCNGIGIGEFKDSLSINATNIKHFKNC
TSISGDLHILPVAFRGDSFTHTPPLDPQELDILKTVKEITGFLLIQAWPEN
RTDLHAFENLEIIRGRTKQHGQFSLAVVSLNITSLGLRSLKEISDGDVIIS
GNKNLCYANTINWKKLFGTSGQKTKIISNRGENSCKATGQVCHALCSPEGC
WGPEPRDCVSCRNVSRGRECVDKCNLLEGEPREFVENSECIQCHPECLPQA
MNITCTGRGPDNCIQCAHYIDGPHCVKTCPAGVMGENNTLVWKYADAGHVC
HLCHPNCTYGCTGPGLEGCPTNGPKIPSIATGMVGALLLLLVVALGIGLFM

TABLE 11

R12 intermediate spacer
CAR: PJ_R12-CH3-41BB-Z-T2A-tEGFR
(SEQ ID NO: 39)
GTTAGACCAGATCTGAGCCTGGGAGCTCTCTGGCTAACTAGGGAACCCACT
GCTTAAGCCTCAATAAAGCTTGCCTTGAGTGCTTCAAGTAGTGTGTGCCCG
TCTGTTGTGTGACTCTGGTAACTAGAGATCCCTCAGACCCTTTTAGTCAGT
GTGGAAAATCTCTAGCAGTGGCGCCCGAACAGGGACTTGAAAGCGAAAGGG
AAACCAGAGGAGCTCTCTCGACGCAGGACTCGGCTTGCTGAAGCGCGCACG
GCAAGAGGCGAGGGGCGGCGACTGGTGAGTACGCCAAAAATTTTGACTAGC
GGAGGCTAGAAGGAGAGAGATGGGTGCGAGAGCGTCAGTATTAAGCGGGGG
AGAATTAGATCGATGGGAAAAAATTCGGTTAAGGCCAGGGGGAAAGAAAAA
ATATAAAATTAAAACATATAGTATGGGCAAGCAGGGAGCTAGAACGATTCGC
AGTTAATCCTGGCCTGTTAGAAACATCAGAAGGCTGTAGACAAATACTGGG
ACAGCTACAACCATCCCTTCAGACAGGATCAGAAGAACTTAGATCATTATA
TAATACAGTAGCAACCCTCTATTGTGTGCATCAAAGGATAGAGATAAAAGA
CACCAAGGAAGCTTTAGACAAGATAGAGGAAGAGCAAAACAAAAGTAAGAA
AAAAGCACAGCAAGCAGCAGCTGACACAGGACACAGCAATCAGGTCAGCCA
AAATTACCCTATAGTGCAGAACATCCAGGGGCAAATGGTACATCAGGCCAT
ATCACCTAGAACTTTAAATGCATGGGTAAAAGTAGTAGAAGAGAAGGCTTT
CAGCCCAGAAGTGATACCCATGTTTTCAGCATTATCAGAAGGAGCCACCCC
ACAAGATTTAAACACCATGCTAAACACAGTGGGGGGACATCAAGCAGCCAT
GCAAATGTTAAAAGAGACCATCAATGAGGAAGCTGCAGGCAAAGAGAAGAG
TGGTGCAGAGAGAAAAAAGAGCAGTGGGAATAGGAGCTTTGTTCCTTGGGT
TCTTGGGAGCAGCAGGAAGCACTATGGGCGCAGCGTCAATGACGCTGACGG
TACAGGCCAGACAATTATTGTCTGGTATAGTGCAGCAGCAGAACAATTTGC
TGAGGGCTATTGAGGCGCAACAGCATCTGTTGCAACTCACAGTCTGGGGCA
TCAAGCAGCTCCAGGCAAGAATCCTGGCTGTGGAAAGATACCTAAAGGATC
AACAGCTCCTGGGGATTTGGGGTTGCTCTGGAAAACTCATTTGCACCACTG
CTGTGCCTTGGATCTACAAATGGCAGTATTCATCCACAATTTTAAAAGAAA
AGGGGGGATTGGGGGGTACAGTGCAGGGGAAAGAATAGTAGACATAATAGC
AACAGACATACAAACTAAAGAATTACAAAAACAAATTACAAAAATTCAAAA
TTTTCGGGTTTATTACAGGGACAGCAGAGATCCAGTTTGGGGATCAATTGC
ATGAAGAATCTGCTTAGGGTTAGGCGTTTTGCGCTGCTTCGCGAGGATCTG
CGATCGCTCCGGTGCCCGTCAGTGGGCAGAGCGCACATCGCCCACAGTCCC
CGAGAAGTTGGGGGGAGGGGTCGGCAATTGAACCGGTGCCTAGAGAAGGTG
GCGCGGGGTAAACTGGGAAAGTGATGTCGTGTACTGGCTCCGCCTTTTTCC
CGAGGGTGGGGGAGAACCGTATATAAGTGCAGTAGTCGCCGTGAACGTTCT
TTTTCGCAACGGGTTTGCCGCCAGAACACAGCTGAAGCTTCGAGGGGCTCG
CATCTCTCCTTCACGCGCCCGCCGCCCTACCTGAGGCCGCCATCCACGCCG
GTTGAGTCGCGTTCTGCCGCCTCCCGCCTGTGGTGCCTCCTGAACTGCGTC
CGCCGTCTAGGTAAGTTTAAAGCTCAGGTCGAGACCGGGCCTTTGTCCGGC
GCTCCCTTGGAGCCTACCTAGACTCAGCCGGCTCTCCACGCTTTGCCTGAC
CCTGCTTGCTCAACTCTACGTCTTTGTTTCGTTTTCTGTTCTGCGCCGTTA
CAGATCCAAGCTGTGACCGGCGCCTACG

GCTAGC GAATTCCTCGAGGCC

R12 ScFv
ACC ATG CTGCTGCTGGTGACAAGCCTGCTGCTGTGCGAGCTGCCCCACCCC
GCCTTTCTGCTGATCCCCCAGGAACAGCTCGTCGAAAGCGGCGGCAGACTG
GTGACACCTGGCGGCAGCCTGACCCTGAGCTGCAAGGCCAGCGGCTTCGAC
TTCAGCGCCTACTACATGAGCTGGGTCCGCCAGGCCCCTGGCAAGGGACTG
GAATGGATCGCCACCATCTACCCCAGCAGCGGCAAGACCTACTACGCCACC
TGGGTGAACGGACGGTTCACCATCTCCAGCGACAACGCCCAGAACACCGTG
GACCTGCAGATGAACAGCCTGACAGCCGCCGACCGGGCCACCTACTTTTGC
GCCAGAGACAGCTACGCCGACGACGGCGCCCTGTTCAACATCTGGGGCCCT
GGCACCCTGGTGACAATCTCTAGCGGCGGAGGCGGATCTGGTGGCGGAGGA
AGTGGCGGCGGAGGATCTGAGCTGGTGCTGACCCAGAGCCCTCTGTGTCT
GCTGCCCTGGGAAGCCCTGCCAAGATCACCTGTACCCTGAGCAGCGCCCAC
AAGACCGACACCATCGACTGGTATCAGCAGCTGCAGGGCGAGGCCCCCAGA
TACCTGATGCAGGTGCAGAGCGACGGCAGCTACACCAAGAGGCCAGGCGTG
CCCGACCGGTTCAGCGGATCTAGCTCTGGCGCCGACCGCTACCTGATCATC
CCCAGCGTGCAGGCCGATGACGAGGCCGATTACTACTGTGGCGCCGACTAC
ATCGGCGGCTACGTGTTCGGCGGAGGCACCCAGCTGACCGTGACCGGC GAG
TCTAAG

TABLE 11-continued

Hinge Spacer
TACCGGACCGCCCTGCCCCCCTTGCCCT

CH3
GGCCAGCCTCGCGAGCCCCAGGTGTACACCCTGCCTCCCTCCCAGGAAGAG
ATGACCAAGAACCAGGTGTCCCTGACCTGCCTGGTGAAGGGCTTCTACCCC
AGCGACATCGCCGTGGAGTGGGAGAGCAACGGCCAGCCTGAGAACAACTAC
AAGACCACCCCTCCCGTGCTGGACAGCGACGGCAGCTTCTTCCTGTACAGC
CGGCTGACCGTGGACAAGAGCCGGTGGCAGGAAGGCAACGTCTTTAGCTGC
AGCGTGATGCACGAGGCCCTGCACAACCACTACACCCAGAAGAGCCTGAGC
CTGTCCCTGGGCAAG 4-1BB
ATGTTCTGGGTGCTGGTGGTGGTGGGCGGGGTGCTGGCCTGCTACAGCCTG
CTGGTGACAGTGGCCTTCATCATCTTTTGGGTGAAACGGGGCAGAAAGAAA
CTCCTGTATATATTCAAACAACCATTTATGAGACCAGTACAAACTACTCAA
GAGGAAGATGGCTGTAGCTGCCGATTTCCAGAAGAAGAAGAAGGAGGATGT
GAACTG

CD3zeta
CGGGTGAAGTTCAGCAGAAGCGCCGACGCCCCTGCCTACCAGCAGGGCCAG
AATCAGCTGTACAACGAGCTGAACCTGGGCAGAAGGGAAGAGTACGACGTC
CTGGATAAGCGGAGAGGCCGGGACCCTGAGATGGGCGGCAAGCCTCGGCGG
AAGAACCCCCAGGAAGGCCTGTATAACGAACTGCAGAAAGACAAGATGGCC
GAGGCCTACAGCGAGATCGGCATGAAGGGCGAGCGGAGGCGGGGCAAGGGC
CACGACGGCCTGTATCAGGGCCTGTCCACCGCCACCAAGGATACCTACGAC
GCCCTGCACATGCAGGCCCTGCCCCCAAGG

T2A
CTCGAGGGCGGCGGAGAGGGCAGAGGAAGTCTTCTAACATGCGGTGACGT
GGAGGAGAATCCCGGCCCTAGG tEGFR
ATGCTTCTCCTGGTGACAAGCCTTCTGCTCTGTGAGTTACCACACCCAGCA
TTCCTCCTGATCCCACGCAAAGTGTGTAACGGAATAGGTATTGGTGAATTT
AAAGACTCACTCTCCATAAATGCTACGAATATTAAACACTTCAAAAACTGC
ACCTCCATCAGTGGCGATCTCCACATCCTGCCGGTGGCATTTAGGGGTGAC
TCCTTCACACATACTCCTCCTCTGGATCCACAGGAACTGGATATTCTGAAA
ACCGTAAAGGAAATCACAGGGTTTTTGCTGATTCAGGCTTGGCCTGAAAAC
AGGACGGACCTCCATGCCTTTGAGAACCTAGAAATCATACGCGGCAGGACC
AAGCAACATGGTCAGTTTTCTCTTGCAGTCGTCAGCCTGAACATAACATCC
TTGGGATTACGCTCCCTCAAGGAGATAAGTGATGGAGATGTGATAATTTCA
GGAAACAAAAATTTGTGCTATGCAAATACAATAAACTGGAAAAAACTGTTT
GGGACCTCCGGTCAGAAAACCAAAATTATAAGCAACAGAGGTGAAAACAGC
TGCAAGGCCACAGGCCAGGTCTGCCATGCCTTGTGCTCCCCCGAGGGCTGC
TGGGGCCCGGAGCCCAGGGACTGCGTCTCTTGCCGGAATGTCAGCCGAGGC
AGGGAATGCGTGGACAAGTGCAACCTTCTGGAGGGTGAGCCAAGGGAGTTT

GTGGAGAACTCTGAGTGCATACAGTGCCACCCAGAGTGCCTGCCTCAGGCC
ATGAACATCACCTGCACAGGACGGGACCAGACAACTGTATCCAGTGTGCC
CACTACATTGACGGCCCCCACTGCGTCAAGACCTGCCCGGCAGGAGTCATG
GGAGAAAACAACACCCTGGTCTGGAAGTACGCAGACGCCGGCCATGTGTGC
CACCTGTGCCATCCAAACTGCACCTACGGATGCACTGGGCCAGGTCTTGAA
GGCTGTCCAACGAATGGGCCTAAGATCCCGTCCATCGCCACTGGGATGGTG
GGGGCCCTCCTCTTGCTGCTGGTGGTGGCCCTGGGGATCGGCCTCTTCATG
TGAGCGGCCGCTCTAGACCCGGGCTGCAGGAATTCGATATCAAGCTTATC
GATAATCAACCTCTGGATTACAAAATTTGTGAAAGATTGACTGGTATTCTT
AACTATGTTGCTCCTTTTACGCTATGTGGATACGCTGCTTTAATGCCTTTG
TATCATGCTATTGCTTCCCGTATGGCTTTCATTTTCTCCTCCTTGTATAAA
TCCTGGTTGCTGTCTCTTTATGAGGAGTTGTGGCCCGTTGTCAGGCAACGT
GGCGTGGTGTGCACTGTGTTTGCTGACGCAACCCCCACTGGTTGGGGCATT
GCCACCACCTGTCAGCTCCTTTCCGGGACTTTCGCTTTCCCCCTCCCTATT
GCCACGGCGGAACTCATCGCCGCCTGCCTTGCCCGCTGCTGGACAGGGGCT
CGGCTGTTGGGCACTGACAATTCCGTGGTGTTGTCGGGGAAATCATCGTCC
TTTCCTTGGCTGCTCGCCTGTGTTGCCACCTGGATTCTGCGCGGGACGTCC
TTCTGCTACGTCCCTTCGGCCCTCAATCCAGCGGACCTTCCTTCCCGCGGC
CTGCTGCCGGCTCTGCGGCCTCTTCCGCGTCTTCGCCTTCGCCCTCAGACG
AGTCGGATCTCCCTTTGGGCCGCCTCCCCGCATCGATACCGTCGACTAGCC
GTACCTTTAAGACCAATGACTTACAAGGCAGCTGTAGATCTTAGCCACTTT
TTAAAAGAAAAGGGGGGACTGGAAGGGCTAATTCACTCCCAAAGAAGACAA
GATCTGCTTTTTGCCTGTACTGGGTCTCTCTGGTTAGACCAGATCTGAGCC
TGGGAGCTCTCTGGCTAACTAGGGAACCCACTGCTTAAGCCTCAATAAAGC
TTGCCTTGAGTGCTTCAAGTAGTGTGTGCCCGTCTGTTGTGTGACTCTGGT
AACTAGAGATCCCTCAGACCCTTTTAGTCAGTGTGGAAAATCTCTAGCAGA
ATTCGATATCAAGCTTATCGATACCGTCGACCTCGAGGGGGGGCCCGGTA
CCCAATTCGCCCTATAGTGAGTCGTATTACAATTCACTGGCCGTCGTTTTA
CAACGTCGTGACTGGGAAAACCCTGGCGTTACCCAACTTAATCGCCTTGCA
GCACATCCCCCTTTCGCCAGCTGGCGTAATAGCGAAGAGGCCCGCACCGAT
CGCCCTTCCCAACAGTTGCGCAGCCTGAATGGCGAATGGAAATTGTAAGCG
TTAATATTTTGTTAAAATTCGCGTTAAATTTTTGTTAAATCAGCTCATTTT
TTAACCAATAGGCCGAAATCGGCAAAATCCCTTATAAATCAAAAGAATAGA
CCGAGATAGGGTTGAGTGTTGTTCCAGTTTGGAACAAGAGTCCACTATTAA
AGAACGTGGACTCCAACGTCAAAGGGCGAAAAACCGTCTATCAGGGCGATG
GCCCACTACGTGAACCATCACCCTAATCAAGTTTTTTGGGGTCGAGGTGCC
GTAAAGCACTAAATCGGAACCCTAAAGGGAGCCCCCGATTTAGAGCTTGAC
GGGGAAAGCCGGCGAACGTGGCGAGAAAGGAAGGGAAGAAAGCGAAAGGAG
CGGGCGCTAGGGCGCTGGCAAGTGTAGCGGTCACGCTGCGCGTAACCACCA
CACCCGCCGCGCTTAATGCGCCGCTACAGGGCGCGTCAGGTGGCACTTTTC

TABLE 11-continued

```
GGGGAAATGTGCGCGGAACCCCTATTTGTTTATTTTTTCTAAATACATTCA
AATATGTATCCGCTCATGAGACAATAACCCTGATAAATGCTTCAATAATAT
TGAAAAAGGAAGAGTATGAGTATTCAACATTTCCGTGTCGCCCTTATTCCC
TTTTTTGCGGCATTTTGCCTTCCTGTTTTTGCTCACCCAGAAACGCTGGTG
AAAGTAAAAGATGCTGAAGATCAGTTGGGTGCACGAGTGGGTTACATCGAA
CTGGATCTCAACAGCGGTAAGATCCTTGAGAGTTTTCGCCCCGAAGAACGT
TTTCCAATGATGAGCACTTTTAAAGTTCTGCTATGTGGCGCGGTATTATCC
CGTATTGACGCCGGGCAAGAGCAACTCGGTCGCCGCATACACTATTCTCAG
AATGACTTGGTTGAGTACTCACCAGTCACAGAAAAGCATCTTACGGATGGC
ATGACAGTAAGAGAATTATGCAGTGCTGCCATAACCATGAGTGATAACACT
GCGGCCAACTTACTTCTGACAACGATCGGAGGACCGAAGGAGCTAACCGCT
TTTTTGCACAACATGGGGGATCATGTAACTCGCCTTGATCGTTGGGAACCG
GAGCTGAATGAAGCCATACCAAACGACGAGCGTGACACCACGATGCCTGTA
GCAATGGCAACAACGTTGCGCAAACTATTAACTGGCGAACTACTTACTCTA
GCTTCCCGGCAACAATTAATAGACTGGATGGAGGCGGATAAAGTTGCAGGA
CCACTTCTGCGCTCGGCCCTTCCGGCTGGCTGGTTTATTGCTGATAAATCT
GGAGCCGGTGAGCGTGGGTCTCGCGGTATCATGCAGCACTGGGGCCAGATG
GTAAGCCCTCCCGTATCGTAGTTATCTACACGACGGGGAGTCAGGCAACTA
TGGATGAACGAAATAGACAGATCGCTGAGATAGGTGCCTCACTGATTAAGC
ATTGGTAACTGTCAGACCAAGTTTACTCATATATACTTTAGATTGATTTAA
AACTTCATTTTTAATTTAAAAGGATCTAGGTGAAGATCCTTTTTGATAATC
TCATGACCAAAATCCCTTAACGTGAGTTTTCGTTCCACTGAGCGTCAGACC
CCGTAGAAAAGATCAAAGGATCTTCTTGAGATCCTTTTTTTCTGCGCGTAA
TCTGCTGCTTGCAAACAAAAAAACCACCGCTACCAGCGGTGGTTTGTTTGC
CGGATCAAGAGCTACCAACTCTTTTTCCGAAGGTAACTGGCTTCAGCAGAG
CGCAGATACCAAATACTGTTCTTCTAGTGTAGCCGTAGTTAGGCCACCACT
TCAAGAACTCTGTAGCACCGCCTACATACCTCGCTCTGCTAATCCTGTTAC
CAGTGGCTGCTGCCAGTGGCGATAAGTCGTGTCTTACCGGGTTGGACTCAA
GACGATAGTTACCGGATAAGGCGCAGCGGTCGGGCTGAACGGGGGGTTCGT
GCACACAGCCCAGCTTGGAGCGAACGACCTACACCGAACTGAGATACCTAC
AGCGTGAGCTATGAGAAAGCGCCACGCTTCCCGAAGGGAGAAAGGCGGACA
GGTATCCGGTAAGCGGCAGGGTCGGAACAGGAGAGCGCACGAGGGAGCTTC
CAGGGGGAAACGCCTGGTATCTTTATAGTCCTGTCGGGTTTCGCCACCTCT
GACTTGAGCGTCGATTTTTGTGATGCTCGTCAGGGGGCGGAGCCTATGGA
AAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTA
TTACCGCCTTTGAGTGAGCTGATACCGCTCGCCGCAGCCGAACGACCGAGC
GCAGCGAGTCAGTGAGCGAGGAAGCGGAAGAGCGCCCAATACGCAAACCGC
CTCTCCCCGCGCGTTGGCCGATTCATTAATGCAGCTGGCACGACAGGTTTC
CCGACTGGAAAGCGGGCAGTGAGCGCAACGCAATTAATGTGAGTTAGCTCA
CTCATTAGGCACCCCAGGCTTTACACTTTATGCTTCCGGCTCGTATGTTGT
GTGGAATTGTGAGCGGATAACAATTTCACACAGGAAACAGCTATGACCATG
ATTACGCCAAGCTCGAAATTAACCCTCACTAAAGGGAACAAAAGCTGGAGC
TCCACCGCGGTGGCGGCCTCGAGGTCGAGATCCGGTCGACCAGCAACCAT
AGTCCCGCCCCTAACTCCGCCCATCCCGCCCCTAACTCCGCCCAGTTCCGC
CCATTCTCCGCCCCATGGCTGACTAATTTTTTTATTTATGCAGAGGCCGA
GGCCGCCTCGGCCTCTGAGCTATTCCAGAAGTAGTGAGGAGGCTTTTTTGG
AGGCCTAGGCTTTTGCAAAAAGCTTCGACGGTATCGATTGGCTCATGTCCA
ACATTACCGCCATGTTGACATTGATTATTGACTAGTTATTAATAGTAATCA
ATTACGGGGTCATTAGTTCATAGCCCATATATGGAGTTCCGCGTTACATAA
CTTACGGTAAATGGCCCGCCTGGCTGACCGCCCAACGACCCCCGCCCATTG
ACGTCAATAATGACGTATGTTCCCATAGTAACGCCAATAGGGACTTTCCAT
TGACGTCAATGGGTGGAGTATTTACGGTAAACTGCCCACTTGGCAGTACAT
CAAGTGTATCATATGCCAAGTACGCCCCCTATTGACGTCAATGACGGTAAA
TGGCCCGCCTGGCATTATGCCCAGTACATGACCTTATGGGACTTTCCTACT
TGGCAGTACATCTACGTATTAGTCATCGCTATTACCATGGTGATGCGGTTT
TGGCAGTACATCAATGGGCGTGGATAGCGGTTTGACTCACGGGGATTTCCA
AGTCTCCACCCCATTGACGTCAATGGGAGTTTGTTTTGGCACCAAAATCAA
CGGGACTTTCCAAAATGTCGTAACAACTCCGCCCCATTGACGCAAATGGGC
GGTAGGCGTGTACGGAATTCGGAGTGGCGAGCCCTCAGATCCTGCATATAA
GCAGCTGCTTTTTGCCTGTACTGGGTCTCTCTG
```

TABLE 12

Leader_R12-Hinge-CH3-CD28tm/41BB-Z-T2A-tEGFR
(SEQ ID NO: 40)

Leader
MLLLVTSLLLCELPHPAFLLIP

R12 scFV
QEQLVESGGRLVTPGGSLTLSCKASGFDFSAYYMSWVRQAPGKGLEWIATI
YPSSGKTYYATWVNGRFTISSDNAQNTVDLQMNSLTAADRATYFCARDSYA
DDGALFNIWGPGTLVTISSGGGGSGGGGSGGGGSELVLTQSPSVSAALGSP
AKITCTLSSAHKTDTIDWYQQLQGEAPRYLMQVSDGSYTKRPGVPDRFSG
SSSGADRYLIIPSVQADDEADYYCGADYIGGYVFGGGTQLTVTG

Hinge Spacer
ESKYGPPCPPCP

CH3
GQPREPQVYTLPPSQEEMTKNQVSLTCLVKGFYPSDIAVEWESNGQPENN
YKTTPPVLDSDGSFFLYSRLTVDKSRWQEGNVFSCSVMHEALHNHYTQKS
LSLSLGK

CD28tm
MFWVLVVVGGVLACYSLLVTVAFIIFWV 4-1BB
KRGRKKLLYIFKQPFMRPVQTTQEEDGCSCRFPEEEEGGCEL

TABLE 12-continued

CD3 zeta
RVKFSRSADAPAYQQGQNQLYNELNLGRREEYDVLDKRRGRDPEMGGKPRR
KNPQEGLYNELQKDKMAEAYSEIGMKGERRRGKGHDGLYQGLSTATKDTYD
ALHMQALPPR

T2A
LEGGGEGRGSLLTCGDVEENPGPR tEGFR
MLLLVTSLLLCELPHPAFLLIPRKVCNGIGIGEFKDSLSINATNIKHFKNC
TSISGDLHILPVAFRGDSFTHTPPLDPQELDILKTVKEITGFLLIQAWPEN
RTDLHAFENLEIIRGRTKQHGQFSLAVVSLNITSLGLRSLKEISDGDVIIS
GNKNLCYANTINWKKLFGTSGQKTKIISNRGENSCKATGQVCHALCSPEGC
WGPEPRDCVSCRNVSRGRECVDKCNLLEGEPREFVENSECIQCHPECLPQA
MNITCTGRGPDNCIQCAHYIDGPHCVKTCPAGVMGENNTLVWKYADAGHVC
HLCHPNCTYGCTGPGLEGCPTNGPKIPSIATGMVGALLLLLVVALGIGLFM

TABLE 13

R12 short spacer CAR: PJ_R12-Hinge-41BB-Z-T2A-tEGFR
(SEQ ID NO: 41)
GTTAGACCAGATCTGAGCCTGGGAGCTCTCTGGCTAACTAGGGAACCCACT
GCTTAAGCCTCAATAAAGCTTGCCTTGAGTGCTTCAAGTAGTGTGTGCCCG
TCTGTTGTGTGACTCTGGTAACTAGAGATCCCTCAGACCCTTTTAGTCAGT
GTGGAAAATCTCTAGCAGTGGCGCCCGAACAGGGACTTGAAAGCGAAAGGG
AAACCAGAGGAGCTCTCTCGACGCAGGACTCGGCTTGCTGAAGCGCGCACG
GCAAGAGGCGAGGGGCGGCGACTGGTGAGTACGCCAAAAATTTTGACTAGC
GGAGGCTAGAAGGAGAGAGATGGGTGCGAGAGCGTCAGTATTAAGCGGGGG
AGAATTAGATCGATGGGAAAAAATTCGGTTAAGGCCAGGGGGAAAGAAAAA
ATATAAATTAAAACATATAGTATGGGCAAGCAGGGAGCTAGAACGATTCGC
AGTTAATCCTGGCCTGTTAGAAACATCAGAAGGCTGTAGACAAATACTGGG
ACAGCTACAACCATCCCTTCAGACAGGATCAGAAGAACTTAGATCATTATA
TAATACAGTAGCAACCCTCTATTGTGTGCATCAAAGGATAGAGATAAAAGA
CACCAAGGAAGCTTTAGACAAGATAGAGGAAGAGCAAAACAAAAGTAAGAA
AAAAGCACAGCAAGCAGCAGCTGACACAGGACACAGCAATCAGGTCAGCCA
AAATTACCCTATAGTGCAGAACATCCAGGGGCAAATGGTACATCAGGCCAT
ATCACCTAGAACTTTAAATGCATGGGTAAAAGTAGTAGAAGAGAAGGCTTT
CAGCCCAGAAGTGATACCCATGTTTTCAGCATTATCAGAAGGAGCCACCCC
ACAAGATTTAAACACCATGCTAAACACAGTGGGGGGACATCAAGCAGCCAT
GCAAATGTTAAAAGAGACCATCAATGAGGAAGCTGCAGGCAAAGAGAAGAG
TGGTGCAGAGAGAAAAAGAGCAGTGGGAATAGGAGCTTTGTTCCTTGGGT
TCTTGGGAGCAGCAGGAAGCACTATGGGCGCAGCGTCAATGACGCTGACGG
TACAGGCCAGACAATTATTGTCTGGTATAGTGCAGCAGCAGAACAATTTGC
TGAGGGCTATTGAGGCGCAACAGCATCTGTTGCAACTCACAGTCTGGGGCA
TCAAGCAGCTCCAGGCAAGAATCCTGGCTGTGGAAAGATACCTAAAGGATC
AACAGCTCCTGGGGATTTGGGGTTGCTCTGGAAAACTCATTTGCACCACTG
CTGTGCCTTGGATCTACAAATGGCAGTATTCATCCACAATTTTAAAAGAAA
AGGGGGGATTGGGGGGTACAGTGCAGGGGAAAGAATAGTAGACATAATAGC
AACAGACATACAAACTAAAGAATTACAAAAACAAATTACAAAAATTCAAAA
TTTTCGGGTTTATTACAGGGACAGCAGAGATCCAGTTTGGGGATCAATTGC
ATGAAGAATCTGCTTAGGGTTAGGCGTTTTGCGCTGCTTCGCGAGGATCTG
CGATCGCTCCGGTGCCCGTCAGTGGGCAGAGCGCACATCGCCCACAGTCCC
CGAGAAGTTGGGGGGAGGGGTCGGCAATTGAACCGGTGCCTAGAGAAGGTG
GCGCGGGGTAAACTGGGAAAGTGATGTCGTGTACTGGCTCCGCCTTTTTCC
CGAGGGTGGGGGAGAACCGTATATAAGTGCAGTAGTCGCCGTGAACGTTCT
TTTTCGCAACGGGTTTGCCGCCAGAACACAGCTGAAGCTTCGAGGGGCTCG
CATCTCTCCTTCACGCGCCCGCCGCCCTACCTGAGGCCGCCATCCACGCCG
GTTGAGTCGCGTTCTGCCGCCTCCCGCCTGTGGTGCCTCCTGAACTGCGTC
CGCCGTCTAGGTAAGTTTAAAGCTCAGGTCGAGACCGGGCCTTTGTCCGGC
GCTCCCTTGGAGCCTACCTAGACTCAGCCGGCTCTCCACGCTTTGCCTGAC
CCTGCTTGCTCAACTCTACGTCTTTGTTTCGTTTTCTGTTCTGCGCCGTTA
CAGATCCAAGCTGTGACCGGCGCCTACG

GCTAGC

R12 scFV
ACCATGCTGCTGCTGGTGACAAGCCTGCTGCTGTGCGAGCTGCCCCACCC
CGCCTTTCTGCTGATCCCCCAGGAACAGCTCGTCGAAAGCGGCGGCAGACT
GGTGACACCTGGCGGCAGCCTGACCCTGAGCTGCAAGGCCAGCGGCTTCGA
CTTCAGCGCCTACTACATGAGCTGGGTCCGCCAGGCCCCTGGCAAGGGACT
GGAATGGATCGCCACCATCTACCCCAGCAGCGGCAAGACCTACTACGCCAC
CTGGGTGAACGGACGGTTCACCATCTCCAGCGACAACGCCCAGAACACCGT
GGACCTGCAGATGAACAGCCTGACAGCCGCCGACCGGGCCACCTACTTTTG
CGCCAGAGACAGCTACGCCGACGACGGCGCCCTGTTCAACATCTGGGGCCC
TGGCACCCTGGTGACAATCTCTAGCGGCGGAGGCGGATCTGGTGGCGGAGG
AAGTGGCGGCGGAGGATCTGAGCTGGTGCTGACCCAGAGCCCCTCTGTGTC
TGCTGCCCTGGGAAGCCCTGCCAAGATCACCTGTACCCTGAGCAGCGCCCA
CAAGACCGACACCATCGACTGGTATCAGCAGCTGCAGGGCGAGGCCCCCAG
ATACCTGATGCAGGTGCAGAGCGACGGCAGCTACACCAAGAGGCCAGGCGT
GCCCGACCGGTTCAGCGGATCTAGCTCTGGCGCCGACCGCTACCTGATCAT
CCCCAGCGTGCAGGCCGATGACGAGGCCGATTACTACTGTGGCGCCGACTA
CATCGGCGGCTACGTGTTCGGCGGAGGCACCCAGCTGACCGTGACCGGCGA
GTCTAAG

Hinge/Spacer
TACGGACCGCCCTGCCCCCCTTGCCCT 4-1BB
ATGTTCTGGGTGCTGGTGGTGGTGGGCGGGGTGCTGGCCTGCTACAGCCTG
CTGGTGACAGTGGCCTTCATCATCTTTTGGGTGAAACGGGGCAGAAAGAAA TABLE 13-continued

```
CTCCTGTATATATTCAAACAACCATTTATGAGACCAGTACAAACTACTCAA

GAGGAAGATGGCTGTAGCTGCCGATTTCCAGAAGAAGAAGAAGGAGGATGT

GAACTG
```

CD3 zeta
```
CGGGTGAAGTTCAGCAGAAGCGCCGACGCCCCTGCCTACCAGCAGGGCCAG

AATCAGCTGTACAACGAGCTGAACCTGGGCAGAAGGGAAGAGTACGACGTC

CTGGATAAGCGGAGAGGCCGGGACCCTGAGATGGGCGGCAAGCCTCGGCGG

AAGAACCCCCAGGAAGGCCTGTATAACGAACTGCAGAAAGACAAGATGGCC

GAGGCCTACAGCGAGATCGGCATGAAGGGCGAGCGGAGGCGGGGCAAGGGC

CACGACGGCCTGTATCAGGGCCTGTCCACCGCCACCAAGGATACCTACGAC

GCCCTGCACATGCAGGCCCTGCCCCCCAAGG
```

T2A
```
CTCGAGGGCGGCGGAGAGGGCAGAGGAAGTCTTCTAACATGCGGTGACGT

GGAGGAGAATCCCGGCCCTAGG
``` tEGFR
```
ATGCTTCTCCTGGTGACAAGCCTTCTGCTCTGTGAGTTACCACACCCAGCA

TTCCTCCTGATCCCACGCAAAGTGTGTAACGGAATAGGTATTGGTGAATTT

AAAGACTCACTCTCCATAAATGCTACGAATATTAAACACTTCAAAAACTGC

ACCTCCATCAGTGGCGATCTCCACATCCTGCCGGTGGCATTTAGGGGTGAC

TCCTTCACACATACTCCTCCTCTCGATCCACAGGAACTGGATATTCTGAAA

ACCGTAAAGGAAATCACAGGGTTTTTGCTGATTCAGGCTTGGCCTGAAAAC

AGGACGGACCTCCATGCCTTTGAGAACCTAGAAATCATACGCGGCAGGACC

AAGCAACATGGTCAGTTTTCTCTTGCAGTCGTCAGCCTGAACATAACATCC

TTGGGATTACGCTCCCTCAAGGAGATAAGTGATGGAGATGTGATAATTTCA

GGAAACAAAAATTTGTGCTATGCAAATACAATAAACTGGAAAAAACTGTTT

GGGACCTCCGGTCAGAAAACCAAAATTATAAGCAACAGAGGTGAAAACAGC

TGCAAGGCCACAGGCCAGGTCTGCCATGCCTTGTGCTCCCCCGAGGGCTGC

TGGGGCCCGGAGCCCAGGGACTGCGTCTCTTGCCGGAATGTCAGCCGAGGC

AGGGAATGCGTGGACAAGTGCAACCTTCTGGAGGGTGAGCCAAGGGAGTTT

GTGGAGAACTCTGAGTGCATACAGTGCCACCCAGAGTGCCTGCCTCAGGCC

ATGAACATCACCTGCACAGGACGGGGACCAGACAACTGTATCCAGTGTGCC

CACTACATTGACGGCCCCCACTGCGTCAAGACCTGCCCGGCAGGAGTCATG

GGAGAAAACAACACCCTGGTCTGGAAGTACGCAGACGCCGGCCATGTGTGC

CACCTGTGCCATCCAAACTGCACCTACGGATGCACTGGGCCAGGTCTTGAA

GGCTGTCCAACGAATGGGCCTAAGATCCCGTCCATCGCCACTGGGATGGTG

GGGGCCCTCCTCTTGCTGCTGGTGGTGGCCCTGGGGATCGGCCTCTTCATG

TGAGCGGCCGCTCTAGACCCGGGCTGCAGGAATTCGATATCAAGCTTATC

GATAATCAACCTCTGGATTACAAAATTTGTGAAAGATTGACTGGTATTCTT

AACTATGTTGCTCCTTTTACGCTATGTGGATACGCTGCTTTAATGCCTTTG

TATCATGCTATTGCTTCCCGTATGGCTTTCATTTTCTCCTCCTTGTATAAA

TCCTGGTTGCTGTCTCTTTATGAGGAGTTGTGGCCCGTTGTCAGGCAACGT

GGCGTGGTGTGCACTGTGTTTGCTGACGCAACCCCCACTGGTTGGGGCATT

GCCACCACCTGTCAGCTCCTTTCCGGGACTTTCGCTTTCCCCCTCCCTATT

GCCACGGCGGAACTCATCGCCGCCTGCCTTGCCCGCTGCTGGACAGGGGCT

CGGCTGTTGGGCACTGACAATTCCGTGGTGTTGTCGGGGAAATCATCGTCC

TTTCCTTGGCTGCTCGCCTGTGTTGCCACCTGGATTCTGCGCGGGACGTCC

TTCTGCTACGTCCCTTCGGCCCTCAATCCAGCGGACCTTCCTTCCCGCGGC

CTGCTGCCGGCTCTGCGGCCTCTTCCGCGTCTTCGCCTTCGCCCTCAGACG

AGTCGGATCTCCCTTTGGGCCGCCTCCCCGCATCGATACCGTCGACTAGCC

GTACCTTTAAGACCAATGACTTACAAGGCAGCTGTAGATCTTAGCCACTTT

TTAAAAGAAAAGGGGGGACTGGAAGGGCTAATTCACTCCCAAAGAAGACAA

GATCTGCTTTTTGCCTGTACTGGGTCTCTCTGGTTAGACCAGATCTGAGCC

TGGGAGCTCTCTGGCTAACTAGGGAACCCACTGCTTAAGCCTCAATAAAGC

TTGCCTTGAGTGCTTCAAGTAGTGTGTGCCCGTCTGTTGTGTGACTCTGGT

AACTAGAGATCCCTCAGACCCTTTTAGTCAGTGTGGAAAATCTCTAGCAGA

ATTCGATATCAAGCTTATCGATACCGTCGACCTCGAGGGGGGGCCCGGTA

CCCAATTCGCCCTATAGTGAGTCGTATTACAATTCACTGGCCGTCGTTTTA

CAACGTCGTGACTGGGAAAACCCTGGCGTTACCCAACTTAATCGCCTTGCA

GCACATCCCCCTTTCGCCAGCTGGCGTAATAGCGAAGAGGCCCGCACCGAT

CGCCCTTCCCAACAGTTGCGCAGCCTGAATGGCGAATGGAAATTGTAAGCG

TTAATATTTTGTTAAAATTCGCGTTAAATTTTTGTTAAATCAGCTCATTTT

TTAACCAATAGGCCGAAATCGGCAAAATCCCTTATAAATCAAAAGAATAGA

CCGAGATAGGGTTGAGTGTTGTTCCAGTTTGGAACAAGAGTCCACTATTAA

AGAACGTGGACTCCAACGTCAAAGGGCGAAAAACCGTCTATCAGGGCGATG

GCCCACTACGTGAACCATCACCCTAATCAAGTTTTTTGGGGTCGAGGTGCC

GTAAAGCACTAAATCGGAACCCTAAAGGGAGCCCCCGATTTAGAGCTTGAC

GGGGAAAGCCGGCGAACGTGGCGAGAAAGGAAGGGAAGAAAGCGAAAGGAG

CGGGCGCTAGGGCGCTGGCAAGTGTAGCGGTCACGCTGCGCGTAACCACCA

CACCCGCCGCGCTTAATGCGCCGCTACAGGGCGCGTCAGGTGGCACTTTTC

GGGGAAATGTGCGCGGAACCCCTATTTGTTTATTTTTCTAAATACATTCAA

ATATGTATCCGCTCATGAGACAATAACCCTGATAAATGCTTCAATAATATT

GAAAAAGGAAGAGTATGAGTATTCAACATTTCCGTGTCGCCCTTATTCCCT

TTTTTGCGGCATTTTGCCTTCCTGTTTTTGCTCACCCAGAAACGCTGGTGA

AAGTAAAAGATGCTGAAGATCAGTTGGGTGCACGAGTGGGTTACATCGAAC

TGGATCTCAACAGCGGTAAGATCCTTGAGAGTTTTCGCCCCGAAGAACGTT

TTCCAATGATGAGCACTTTTAAAGTTCTGCTATGTGGCGCGGTATTATCCC

GTATTGACGCCGGGCAAGAGCAACTCGGTCGCCGCATACACTATTCTCAGA

ATGACTTGGTTGAGTACTCACCAGTCACAGAAAAGCATCTTACGGATGGCA

TGACAGTAAGAGAATTATGCAGTGCTGCCATAACCATGAGTGATAACACTG

CGGCCAACTTACTTCTGACAACGATCGGAGGACCGAAGGAGCTAACCGCTT

TTTTGCACAACATGGGGGATCATGTAACTCGCCTTGATCGTTGGGAACCGG
```

TABLE 13-continued

```
AGCTGAATGAAGCCATACCAAACGACGAGCGTGACACCACGATGCCTGTAG
CAATGGCAACAACGTTGCGCAAACTATTAACTGGCGAACTACTTACTCTAG
CTTCCCGGCAACAATTAATAGACTGGATGGAGGCGGATAAAGTTGCAGGAC
CACTTCTGCGCTCGGCCCTTCCGGCTGGCTGGTTTATTGCTGATAAATCTG
GAGCCGGTGAGCGTGGGTCTCGCGGTATCATTGCAGCACTGGGGCCAGATG
GTAAGCCCTCCCGTATCGTAGTTATCTACACGACGGGGAGTCAGGCAACTA
TGGATGAACGAAATAGACAGATCGCTGAGATAGGTGCCTCACTGATTAAGC
ATTGGTAACTGTCAGACCAAGTTTACTCATATATACTTTAGATTGATTTAA
AACTTCATTTTTAATTTAAAAGGATCTAGGTGAAGATCCTTTTTGATAATC
TCATGACCAAAATCCCTTAACGTGAGTTTTCGTTCCACTGAGCGTCAGACC
CCGTAGAAAAGATCAAAGGATCTTCTTGAGATCCTTTTTTTCTGCGCGTAA
TCTGCTGCTTGCAAACAAAAAAACCACCGCTACCAGCGGTGGTTTGTTTGC
CGGATCAAGAGCTACCAACTCTTTTTCCGAAGGTAACTGGCTTCAGCAGAG
CGCAGATACCAAATACTGTTCTTCTAGTGTAGCCGTAGTTAGGCCACCACT
TCAAGAACTCTGTAGCACCGCCTACATACCTCGCTCTGCTAATCCTGTTAC
CAGTGGCTGCTGCCAGTGGCGATAAGTCGTGTCTTACCGGGTTGGACTCAA
GACGATAGTTACCGGATAAGGCGCAGCGGTCGGGCTGAACGGGGGGTTCGT
GCACACAGCCCAGCTTGGAGCGAACGACCTACACCGAACTGAGATACCTAC
AGCGTGAGCTATGAGAAAGCGCCACGCTTCCCGAAGGGAGAAAGGCGGACA
GGTATCCGGTAAGCGGCAGGGTCGGAACAGGAGAGCGCACGAGGGAGCTTC
CAGGGGGAAACGCCTGGTATCTTTATAGTCCTGTCGGGTTTCGCCACCTCT
GACTTGAGCGTCGATTTTGTGATGCTCGTCAGGGGGGCGGAGCCTATGGA
AAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTA
TTACCGCCTTTGAGTGAGCTGATACCGCTCGCCGCAGCCGAACGACCGAGC
GCAGCGAGTCAGTGAGCGAGGAAGCGGAAGAGCGCCCAATACGCAAACCGC
CTCTCCCCGCGCGTTGGCCGATTCATTAATGCAGCTGGCACGACAGGTTTC
CCGACTGGAAAGCGGGCAGTGAGCGCAACGCAATTAATGTGAGTTAGCTCA
CTCATTAGGCACCCCAGGCTTTACACTTTATGCTTCCGGCTCGTATGTTGT
GTGGAATTGTGAGCGGATAACAATTTCACACAGGAAACAGCTATGACCATG
ATTACGCCAAGCTCGAAATTAACCCTCACTAAAGGGAACAAAAGCTGGAGC
TCCACCGCGGTGGCGGCCTCGAGGTCGAGATCCGGTCGACCAGCAACCAT
AGTCCCGCCCCTAACTCCGCCCATCCCGCCCCTAACTCCGCCCAGTTCCGC
CCATTCTCCGCCCCATGGCTGACTAATTTTTTTTATTTATGCAGAGGCCGA
GGCCGCCTCGGCCTCTGAGCTATTCCAGAAGTAGTGAGGAGGCTTTTTTGG
AGGCCTAGGCTTTTGCAAAAAGCTTCGACGGTATCGATTGGCTCATGTCCA
ACATTACCGCCATGTTGACATTGATTATTGACTAGTTATTAATAGTAATCA
ATTACGGGGTCATTAGTTCATAGCCCATATATGGAGTTCCGCGTTACATAA
CTTACGGTAAATGGCCCGCCTGGCTGACCGCCCAACGACCCCCGCCCATTG
ACGTCAATAATGACGTATGTTCCCATAGTAACGCCAATAGGGACTTTCCAT
TGACGTCAATGGGTGGAGTATTTACGGTAAACTGCCCACTTGGCAGTACAT
CAAGTGTATCATATGCCAAGTACGCCCCCTATTGACGTCAATGACGGTAAA
TGGCCCGCCTGGCATTATGCCCAGTACATGACCTTATGGGACTTTCCTACT
TGGCAGTACATCTACGTATTAGTCATCGCTATTACCATGGTGATGCGGTTT
TGGCAGTACATCAATGGGCGTGGATAGCGGTTTGACTCACGGGGATTTCCA
AGTCTCCACCCCATTGACGTCAATGGGAGTTTGTTTTGGCACCAAAATCAA
CGGGACTTTCCAAAATGTCGTAACAACTCCGCCCCATTGACGCAAATGGGC
GGTAGGCGTGTACGGAATTCGGAGTGGCGAGCCCTCAGATCCTGCATATAA
GCAGCTGCTTTTTGCCTGTACTGGGTCTCTCTG
```

TABLE 14

Leader_R12-CD28tm/41BB-Z-T2A-tEGFR(SEQ ID NO: 42)

Leader
MLLLVTSLLLCELPHPAFLLIP scFv R12
QEQLVESGGRLVTPGGSLTLSCKASGFDFSAYYMSWVRQAPGKGLEWIATIYPSSG
KTYYATWVNGRFTISSDNAQNTVDLQMNSLTAADRATYFCARDSYADDGALFNI
WGPGTLVTISSGGGGSGGGGSGGGGSELVLTQSPSVSAALGSPAKITCTLSSAHKTD
TIDWYQQLQGEAPRYLMQVQSDGSYTKRPGVPDRFSGSSSGADRYLIIPSVQADDE
ADYYCGADYIGGYVFGGGTQLTVTG Hinge/spacer
ESKYGPPCPPCP CD28tm
MFWVLVVVGGVLACYSLLVTVAFIIFWV 4-1BB
KRGRKKLLYIFKQPFMRPVQTTQEEDGCSCRFPEELEGGCEL CD3zeta
RVKFSRSADAPAYQQGQNQLYNELNLGRREEYDVLDKRRGRDPEMGGKPRRKNP
QEGLYNELQKDKMAEAYSEIGMKGERRRGKGHDGLYQGLSTATKDTYDALHMQ
ALPPR

TABLE 14-continued

Leader_R12-CD28tm/41BB-Z-T2A-tEGFR(SEQ ID NO: 42)

T2A
LEGGGEGRGSLLTCGDVEENPGPR tEGFR
MLLLVTSLLLCELPHPAFLLIPRKVCNGIGIGEFKDSLSINATNIKHFKNCTSISGDLHI
LPVAFRGDSFTHTPPLDPQELDILKTVKEITGFLLIQAWPENRTDLHAFENLEIIRGRT
KQHGQFSLAVVSLNITSLGLRSLKEISDGDVIISGNKNLCYANTINWKKLFGTSGQK
TKIISNRGENSCKATGQVCHALCSPEGCWGPEPRDCVSCRNVSRGRECVDKCNLLE
GEPREFVENSECIQCHPECLPQAMNITCTGRGPDNCIQCAHYIDGPHCVKTCPAGVM
GENNTLVWKYADAGHVCHLCHPNCTYGCTGPGLEGCPTNGPKIPSIATGMVGALL
LLLVVALGIGLFM

TABLE 15

R11 long spacer CAR:
PJ_R11—CH2—CH3-41BB-Z-T2A-tEGFR
(SEQ ID NO: 43)

GTTAGACCAGATCTGAGCCTGGGAGCTCTCTGGCTAACTAGGGAACCCACT

GCTTAAGCCTCAATAAAGCTTGCCTTGAGTGCTTCAAGTAGTGTGTGCCCG

TCTGTTGTGTGACTCTGGTAACTAGAGATCCCTCAGACCCTTTTAGTCAGT

GTGGAAAATCTCTAGCAGTGGCGCCCGAACAGGGACTTGAAAGCGAAAGGG

AAACCAGAGGAGCTCTCTCGACGCAGGACTCGGCTTGCTGAAGCGCGCACG

GCAAGAGGCGAGGGGCGGCGACTGGTGAGTACGCCAAAAATTTTGACTAGC

GGAGGCTAGAAGGAGAGAGATGGGTGCGAGAGCGTCAGTATTAAGCGGGGG

AGAATTAGATCGATGGGAAAAAATTCGGTTAAGGCCAGGGGGAAAGAAAAA

ATATAAATTAAAACATATAGTATGGGCAAGCAGGGAGCTAGAACGATTCGC

AGTTAATCCTGGCCTGTTAGAAACATCAGAAGGCTGTAGACAAATACTGGG

ACAGCTACAACCATCCCTTCAGACAGGATCAGAAGAACTTAGATCATTATA

TAATACAGTAGCAACCCTCTATTGTGTGCATCAAAGGATAGAGATAAAGA

CACCAAGGAAGCTTTAGACAAGATAGAGGAAGAGCAAAACAAAAGTAAGAA

AAAAGCACAGCAAGCAGCAGCTGACACAGGACACAGCAATCAGGTCAGCCA

AAATTACCCTATAGTGCAGAACATCCAGGGGCAAATGGTACATCAGGCCAT

ATCACCTAGAACTTTAAATGCATGGGTAAAAGTAGTAGAAGAGAAGGCTTT

CAGCCCAGAAGTGATACCCATGTTTTCAGCATTATCAGAAGGAGCCACCCC

ACAAGATTTAAACACCATGCTAAACACAGTGGGGGGACATCAAGCAGCCAT

GCAAATGTTAAAAGAGACCATCAATGAGGAAGCTGCAGGCAAAGAGAAGAG

TGGTGCAGAGAGAAAAAAGAGCAGTGGGAATAGGAGCTTTGTTCCTTGGGT

TCTTGGGAGCAGCAGGAAGCACTATGGGCGCAGCGTCAATGACGCTGACGG

TACAGGCCAGACAATTATTGTCTGGTATAGTGCAGCAGCAGAACAATTTGC

TGAGGGCTATTGAGGCGCAACAGCATCTGTTGCAACTCACAGTCTGGGGCA

TCAAGCAGCTCCAGGCAAGAATCCTGGCTGTGGAAAGATACCTAAAGGATC

AACAGCTCCTGGGGATTTGGGGTTGCTCTGGAAAACTCATTTGCACCACTG

CTGTGCCTTGGATCTACAAATGGCAGTATTCATCCACAATTTTAAAAGAAA

AGGGGGGATTGGGGGGTACAGTGCAGGGGAAGAATAGTAGACATAATAGC

AACAGACATACAAACTAAAGAATTACAAAAACAAATTACAAAATTCAAA

TTTTCGGGTTTATTACAGGGACAGCAGAGATCCAGTTTGGGATCAATTGC

ATGAAGAATCTGCTTAGGGTTAGGCGTTTTGCGCTGCTTCGCGAGGATCTG

CGATCGCTCCGGTGCCCGTCAGTGGGCAGAGCGCACATCGCCCACAGTCCC

CGAGAAGTTGGGGGAGGGGTCGGCAATTGAACCGGTGCCTAGAGAAGGTG

GCGCGGGGTAAACTGGGAAAGTGATGTCGTGTACTGGCTCCGCCTTTTTCC

CGAGGGTGGGGGAGAACCGTATATAAGTGCAGTAGTCGCCGTGAACGTTCT

TTTTCGCAACGGGTTTGCCGCCAGAACACAGCTGAAGCTTCGAGGGGCTCG

CATCTCTCCTTCACGCGCCCGCCGCCCTACCTGAGGCCGCCATCCACGCCG

GTTGAGTCGCGTTCTGCCGCCTCCCGCCTGTGGTGCCTCCTGAACTGCGTC

CGCCGTCTAGGTAAGTTTAAAGCTCAGGTCGAGACCGGGCCTTTGTCCGGC

GCTCCCTTGGAGCCTACCTAGACTCAGCCGGCTCTCCACGCTTTGCCTGAC

CCTGCTTGCTCAACTCTACGTCTTTGTTTCGTTTTCTGTTCTGCGCCGTTA

CAGATCCAAGCTGTGACCGGCGCCTACG

GCTAGC scFv R12
GAATTCGCCACCATGCTGCTGCTGGTGACAAGCCTGCTGCTGTGCGAGCTG

CCCCACCCCGCCTTTCTGCTGATCCCCCAGAGCGTGAAAGAGTCCGAGGGC

GACCTGGTCACACCAGCCGGCAACCTGACCCTGACCTGTACCGCCAGCGGC

AGCGACATCAACGACTACCCCATCTCTTGGGTCCGCCAGGCTCCTGGCAAG

GGACTGGAATGGATCGGCTTCATCAACAGCGGCGGCAGCACTTGGTACGCC

AGCTGGGTCAAAGGCCGGTTCACCATCAGCCGGACCAGCACCACCGTGGAC

CTGAAGATGACAAGCCTGACCACCGACGACACCGCCACCTACTTTTGCGCC

AGAGGCTACAGCACCTACTACGGCGACTTCAACATCTGGGGCCCTGGCACC

CTGGTCACAATCTCTAGCGGCGGAGGCGGCAGCGGAGGTGGAGGAAGTGG

GGCGGAGGATCCGAGCTGGTCATGACCCAGACCCCCAGCAGCACATCTGGC

GCCGTGGGCGGCACCGTGACCATCAATTGCCAGGCCAGCCAGAGCATCGAC

AGCAACCTGGCCTGGTTCCAGCAGAAGCCCGGCCAGCCCCCCACCCTGCTG

ATCTACAGAGCCTCCAACCTGGCCAGCGGCGTGCCAAGCAGATTCAGCGGC

AGCAGATCTGGCACCGAGTACACCCTGACCATCTCCGGCGTGCAGAGAGAG

GACGCCGCTACCTATTACTGCCTGGGCGGCGTGGGCAACGTGTCCTACAGA

ACCAGCTTCGGCGGAGGTACTGAGGTGGTCGTCAAA

TABLE 15-continued

Hinge/Spacer
TA`CGGACCG`CCCTGCCCCCCTTGCCCT

CH2
GCCCCCGAGTTCCTGGGCGGACCCAGCGTGTTCCTGTTCCCCCCCAAGCCC

AAGGACACCCTGATGATCAGCCGGACCCCCGAGGTGACCTGCGTGGTGGTG

GACGTGAGCCAGGAAGATCCCGAGGTCCAGTTCAATTGGTACGTGGACGGC

GTGGAAGTGCACAACGCCAAGACCAAGCCCAGAGAGGAACAGTTCAACAGC

ACCTACCGGGTGGTGTCTGTGCTGACCGTGCTGCACCAGGACTGGCTGAAC

GGCAAAGAATACAAGTGCAAGGTGTCCAACAAGGGCCTGCCCAGCAGCATC

GAAAAGACCATCAGCAAGGCCAAG

CH3
GGCCAGCCTCGCGAGCCCCAGGTGTACACCCTGCCTCCCTCCCAGGAAGAG

ATGACCAAGAACCAGGTGTCCCTGACCTGCCTGGTGAAGGGCTTCTACCCC

AGCGACATCGCCGTGGAGTGGGAGAGCAACGGCCAGCCTGAGAACAACTAC

AAGACCACCCCTCCCGTGCTGGACAGCGACGGCAGCTTCTTCCTGTACAGC

CGGCTGACCGTGGACAAGAGCCGGTGGCAGGAAGGCAACGTCTTTAGCTGC

AGCGTGATGCACGAGGCCCTGCACAACCACTACACCCAGAAGAGCCTGAGC

CTGTCCCTGGGCAAG 4-1BB
ATGTTCTGGGTGCTGGTGGTGGTGGGCGGGGTGCTGGCCTGCTACAGCCTG

CTGGTGACAGTGGCCTTCATC`ATCTTTTGGGTG`AAACGGGGCAGAAAGAAA

CTCCTGTATATATTCAAACAACCATTTATGAGACCAGTACAAACTACTCAA

GAGGAAGATGGCTGTAGCTGCCGATTTCCAGAAGAAGAAGAAGGAGGATGT

GAACT`G`

CD3zeta
CGGGTGAAGTTCAGCAGAAGCGCCGACGCCCCTGCCTACCAGCAGGGCCAG

AATCAGCTGTACAACGAGCTGAACCTGGGCAGAAGGGAAGAGTACGACGTC

CTGGATAAGCGGAGAGGCCGGGACCCTGAGATGGGCGGCAAGCCTCGGCGG

AAGAACCCCCAGGAAGGCCTGTATAACGAACTGCAGAAAGACAAGATGGCC

GAGGCCTACAGCGAGATCGGCATGAAGGGCGAGCGGAGGCGGGGCAAGGGC

CACGACGGCCTGTATCAGGGCCTGTCCACCGCCACCAAGGATACCTACGAC

GCCCTGCACATGCAGGCCCTGCCCCCAAGG

T2A
`CTCGAG`GGCGGCGGAGAGGGCAGAGGAAGTCTTCTAACATGCGGTGACGT

GGAGGAGAATCCCGGCCCTAGG tEGFR
ATGCTTCTCCTGGTGACAAGCCTTCTGCTCTGTGAGTTACCACACCCAGCA

TTCCTCCTGATCCCACGCAAAGTGTGTAACGGAATAGGTATTGGTGAATTT

AAAGACTCACTCTCCATAAATGCTACGAATATTAAACACTTCAAAAACTGC

ACCTCCATCAGTGGCGATCTCCACATCCTGCCGGTGGCATTTAGGGGTGAC

TCCTTCACACATACTCCTCCTCT`GGATCC`ACAGGAACTGGATATTCTGAAA

ACCGTAAAGGAAATCACAGGGTTTTTGCTGATTCAGGCTTGGCCTGAAAAC

AGGACGGACCTCCATGCCTTTGAGAACCTAGAAATCATACGCGGCAGGACC

AAGCAACATGGTCAGTTTTCTCTTGCAGTCGTCAGCCTGAACATAACATCC

TTGGGATTACGCTCCCTCAAGGAGATAAGTGATGGAGATGTGATAATTTCA

GGAAACAAAAATTTGTGCTATGCAAATACAATAAACTGGAAAAAACTGTTT

GGGACCTCCGGTCAGAAAACCAAAATTATAAGCAACAGAGGTGAAAACAGC

TGCAAGGCCACAGGCCAGGTCTGCCATGCCTTGTGCTCCCCCGAGGGCTGC

TGGGGCCCGGAGCCCAGGGACTGCGTCTCTTGCCGGAATGTCAGCCGAGGC

AGGGAATGCGTGGACAAGTGCAACCTTCTGGAGGGTGAGCCAAGGGAGTTT

GTGGAGAACTCTGAGTGCATACAGTGCCACCCAGAGTGCCTGCCTCAGGCC

ATGAACATCACCTGCACAGGACGGGGACCAGACAACTGTATCCAGTGTGCC

CACTACATTGACGGCCCCCACTGCGTCAAGACCTGCCCGGCAGGAGTCATG

GGAGAAAACAACACCCTGGTCTGGAAGTACGCAGACGCCGGCCATGTGTGC

CACCTGTGCCATCCAAACTGCACCTACGGATGCACTGGGCCAGGTCTTGAA

GGCTGTCCAACGAATGGGCCTAAGATCCCGTCCATCGCCACTGGGATGGTG

GGGGCCCTCCTCTTGCTGCTGGTGGTGGCCCTGGGGATCGGCCTCTTCATG

`TGA``GCGGCCGC`TCTAGACCCGGGCTGCAGGAATTCGATATCAAGCTTATCG

ATAATCAACCTCTGGATTACAAAATTTGTGAAAGATTGACTGGTATTCTTA

ACTATGTTGCTCCTTTTACGCTATGTGGATACGCTGCTTTAATGCCTTTGT

ATCATGCTATTGCTTCCCGTATGGCTTTCATTTTCTCCTCCTTGTATAAAT

CCTGGTTGCTGTCTCTTTATGAGGAGTTGTGGCCCGTTGTCAGGCAACGTG

GCGTGGTGTGCACTGTGTTTGCTGACGCAACCCCCACTGGTTGGGGCATTG

CCACCACCTGTCAGCTCCTTTCCGGGACTTTCGCTTTCCCCCTCCCTATTG

CCACGCGGAACTCATCGCCGCCTGCCTTGCCCGCTGCTGGACAGGGGCTC

GGCTGTTGGGCACTGACAATTCCGTGGTGTTGTCGGGGAAATCATCGTCCT

TTCCTTGGCTGCTCGCCTGTGTTGCCACCTGGATTCTGCGCGGGACGTCCT

TCTGCTACGTCCCTTCGGCCCTCAATCCAGCGGACCTTCCTTCCCGCGGCC

TGCTGCCGGCTCTGCGGCCTCTTCCGCGTCTTCGCCTTCGCCCTCAGACGA

GTCGGATCTCCCTTTGGGCCGCCTCCCCGCATCGATACCGTCGACTAGCCG

TACCTTTAAGACCAATGACTTACAAGGCAGCTGTAGATCTTAGCCACTTTT

TAAAAGAAAAGGGGGGACTGGAAGGGCTAATTCACTCCCAAAGAAGACAAG

ATCTGCTTTTTGCCTGTACTGGGTCTCTCTGGTTAGACCAGATCTGAGCCT

GGGAGCTCTCTGGCTAACTAGGGAACCCACTGCTTAAGCCTCAATAAAGCT

TGCCTTGAGTGCTTCAAGTAGTGTGTGCCCGTCTGTTGTGTGACTCTGGTA

ACTAGAGATCCCTCAGACCCTTTTAGTCAGTGTGGAAAATCTCTAGCAGAA

TTCGATATCAAGCTTATCGATACCGTCGAC`CTCGAG`GGGGGGCCCGGTAC

CCAATTCGCCCTATAGTGAGTCGTATTACAATTCACTGGCCGTCGTTTTAC

AACGTCGTGACTGGGAAAACCCTGGCGTTACCCAACTTAATCGCCTTGCAG

CACATCCCCCTTTCGCCAGCTGGCGTAATAGCGAAGAGGCCCGCACCGATC

GCCCTTCCCAACAGTTGCGCAGCCTGAATGGCGAATGGAAATTGTAAGCGT

TAATATTTTGTTAAAATTCGCGTTAAATTTTTGTTAAATCAGCTCATTTTT

TAACCAATAGGCCGAAATCGGCAAAATCCCTTATAAATCAAAAGAATAGAC

TABLE 15-continued

CGAGATAGGGTTGAGTGTTGTTCCAGTTTGGAACAAGAGTCCACTATTAAA
GAACGTGGACTCCAACGTCAAAGGGCGAAAAACCGTCTATCAGGGCGATGG
CCCACTACGTGAACCATCACCCTAATCAAGTTTTTTGGGGTCGAGGTGCCG
TAAAGCACTAAATCGGAACCCTAAAGGAGCCCCCGATTTAGAGCTTGACG
GGGAAAGCCGGCGAACGTGGCGAGAAAGGAAGGGAAGAAAGCGAAAGGAGC
GGGCGCTAGGGCGCTGGCAAGTGTAGCGGTCACGCTGCGCGTAACCACCAC
ACCCGCCGCGCTTAATGCGCCGCTACAGGGCGCGTCAGGTGGCACTTTTCG
GGGAAATGTGCGCGGAACCCCTATTTGTTTATTTTTCTAAATACATTCAAA
TATGTATCCGCTCATGAGACAATAACCCTGATAAATGCTTCAATAATATTG
AAAAAGGAAGAGTATGAGTATTCAACATTTCCGTGTCGCCCTTATTCCCTT
TTTTGCGGCATTTTGCCTTCCTGTTTTTGCTCACCCAGAAACGCTGGTGAA
AGTAAAAGATGCTGAAGATCAGTTGGGTGCACGAGTGGGTTACATCGAACT
GGATCTCAACAGCGGTAAGATCCTTGAGAGTTTTCGCCCCGAAGAACGTTT
TCCAATGATGAGCACTTTTAAAGTTCTGCTATGTGGCGCGGTATTATCCCG
TATTGACGCCGGGCAAGAGCAACTCGGTCGCCGCATACACTATTCTCAGAA
TGACTTGGTTGAGTACTCACCAGTCACAGAAAAGCATCTTACGGATGGCAT
GACAGTAAGAGAATTATGCAGTGCTGCCATAACCATGAGTGATAACACTGC
GGCCAACTTACTTCTGACAACGATCGGAGGACCGAAGGAGCTAACCGCTTT
TTTGCACAACATGGGGGATCATGTAACTCGCCTTGATCGTTGGGAACCGGA
GCTGAATGAAGCCATACCAAACGACGAGCGTGACACCACGATGCCTGTAGC
AATGGCAACAACGTTGCGCAAACTATTAACTGGCGAACTACTTACTCTAGC
TTCCCGGCAACAATTAATAGACTGGATGGAGGCGGATAAAGTTGCAGGACC
ACTTCTGCGCTCGGCCCTTCCGGCTGGCTGGTTTATTGCTGATAAATCTGG
AGCCGGTGAGCGTGGGTCTCGCGGTATCATTGCAGCACTGGGGCCAGATGG
TAAGCCCTCCCGTATCGTAGTTATCTACACGACGGGGAGTCAGGCAACTAT
GGATGAACGAAATAGACAGATCGCTGAGATAGGTGCCTCACTGATTAAGCA
TTGGTAACTGTCAGACCAAGTTTACTCATATATACTTTAGATTGATTTAAA
ACTTCATTTTTAATTTAAAAGGATCTAGGTGAAGATCCTTTTTGATAATCT
CATGACCAAAATCCCTTAACGTGAGTTTTCGTTCCACTGAGCGTCAGACCC
CGTAGAAAAGATCAAAGGATCTTCTTGAGATCCTTTTTTTCTGCGCGTAAT
CTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGC
GCAGATACCAAATACTGTTCTTCTAGTGTAGCCGTAGTTAGGCCACCACTT
CAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAG
ACGATAGTTACCGGATAAGGCGCAGCGGTCGGGCTGAACGGGGGGTTCGTG
CACACAGCCCAGCTTGGAGCGAACGACCTACACCGAACTGAGATACCTACA
GCGTGAGCTATGAGAAAGCGCCACGCTTCCCGAAGGGAGAAAGGCGGACAG
GTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTG

TABLE 15-continued

ACTTGAGCGTCGATTTTTGTGATGCTCGTCAGGGGGCGGAGCCTATGGAA
AAACGCCAGCAACGCGGCCTTTTTACGGTTCCTGGCCTTTTGCTGGCCTTT
TGCTCACATGTTCTTTCCTGCGTTATCCCCTGATTCTGTGGATAACCGTAT
TACCGCCTTTGAGTGAGCTGATACCGCTCGCCGCAGCCGAACGACCGAGCG
CAGCGAGTCAGTGAGCGAGGAAGCGGAAGAGCGCCCAATACGCAAACCGCC
TCTCCCCGCGCGTTGGCCGATTCATTAATGCAGCTGGCACGACAGGTTTCC
CGACTGGAAAGCGGGCAGTGAGCGCAACGCAATTAATGTGAGTTAGCTCAC
TCATTAGGCACCCCAGGCTTTACACTTTATGCTTCCGGCTCGTATGTTGTG
TGGAATTGTGAGCGGATAACAATTTCACACAGGAAACAGCTATGACCATGA
TTACGCCAAGCTCGAAATTAACCCTCA
CTAAAGGGAACAAAAGCTGGAGCTCCACCGCGGTGGCGG<u>CTCGAG</u>GTCGA
GATCCGGTCGACCAGCAACCATAGTCCCGCCCCTAACTCCGCCCATCCCGC
CCCTAACTCCGCCCAGTTCCGCCCATTCTCCGCCCCATGGCTGACTAATTT
TTTTTATTTATGCAGAGGCCGAGGCCGCCTCGGCCTCTGAGCTATTCCAGA
AGTAGTGAGGAGGCTTTTTTGGAGGCCTAGGCTTTTGCAAAAAGCTTCGAC
GGTATCGATTGGCTCATGTCCAACATTACCGCCATGTTGACATTGATTATT
GACTAGTTATTAATAGTAATCAATTACGGGGTCATTAGTTCATAGCCCATA
TATGGAGTFCCGCGTTACATAACTTACGGTAAATGGCCCGCCTGGCTGACC
GCCCAACGACCCCCGCCCATTGACGTCAATAATGACGTATGTTCCCATAGT
AACGCCAATAGGGACTTTCCATTGACGTCAATGGGTGGAGTATTTACGGTA
AACTGCCCACTTGGCAGTACATCAAGTGTATCATATGCCAAGTACGCCCCC
TATTGACGTCAATGACGGTAAATGGCCCGCCTGGCATTATGCCCAGTACAT
GACCTTATGGGACTTTCCTACTTGGCAGTACATCTACGTATTAGTCATCGC
TATTACCATGGTGATGCGGTTTTGGCAGTACATCAATGGGCGTGGATAGCG
GTTTGACTCACGGGGATTTCCAAGTCTCCACCCCATTGACGTCAATGGGAG
TTTGTTTTGGCACCAAAATCAACGGGACTTTCCAAAATGTCGTAACAACTC
CGCCCCATTGACGCAAATGGGCGGTAGGCGTGTACGGTGGGAGGTCTATATAAGCAGCTGCTTTTTGCCTGTACTGGGTCTC
CGCCCCATTGACGCAAATGGGCGGTAGGCGTGTACGGAATTCGGAGTGGCG
AGCCCTCAGATCCTGCATATAAGCAGCTGCTTTTTGCCTGTACTGGGTCTC
TCTG

TABLE 16

Leader_R11-Hinge-CH2—CH3-CD28tm/41BB-Z-T2A-tEGFR
(SEQ ID NO: 44)
Leader
MLLLVTSLLLCELPHPAFLLIP R11 scFv
QSVKESEGDLVTPAGNLTLTCTASGSDINDYPISWVRQAPGKGLEWIGFIN
SGGSTWYASWVKGRFTISRTSTTVDLKMTSLTTDDTATYFCARGYSTYYGD
FNIWGPGTLVTISSGGGGSGGGGSGGGGSELVMTQTPSSTSGAVGGTVTIN
CQASQSIDSNLAWFQQKPGQPPTLLIYRASNLASGVPSRFSGSRSGTEYTL
TISGVQREDAATYYCLGGVGNVSYRTSFGGGTEVVVK

TABLE 16-continued

```
Hinge/Spacer
ESKYGPPCPPCP

CH2
APEFLGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPS

SIEKTISKAK

CH3
GQPREPQVYTLPPSQEEMTKNQVSLTCLVKGFYPSDIAVEWESNGQPENN

YKTTPPVLDSDGSFFLYSRLTVDKSRWQEGNVFSCSVMHEALHNHYTQKS

LSLSLGK

CD28tm
MFWVLVVVGGVLACYSLLVTVAFIIFWV 4-1BB
KRGRKKLLYIFKQPFMRPVQTTQEEDGCSCRFPEEEEGGCEL

CD3zeta
RVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYD

ALHMQALPPR

T2A
LEGGGEGRGSLLTCGDVEENPGPR tEGFR
MLLLVTSLLLCELPHPAFLLIPRKVCNGIGIGEFKDSLSINATNIKHFKNC

TSISGDLHILPVAFRGDSFTHTPPLDPQELDILKTVKEITGFLLIQAWPEN

RTDLHAFENLEIIRGRTKQHGQFSLAVVSLNITSLGLRSLKEISDGDVIIS

GNKNLCYANTINWKKLEGISGQKTKIISNRGENSCKATGQVCHALCSPEGC

WGPEPRDCVSCRNVSRGRECVDKCNLLEGEPREFVENSECIQCHPECLPQA

MNITCTGRGPDNCIQCAHYIDGPHCVKTCPAGVMGENNTLVWKYADAGHVC

HLCHPNCTYGCTGPGLEGCPTNGPKIPSIATGMVGALLLLLVVALGIGLFM
```

TABLE 17

```
R11 intermediate spacer CAR:
PJ_R11-CH3-41BB-Z-T2A-tEGFR
                                      (SEQ ID NO: 45)
GTTAGACCAGATCTGAGCCTGGGAGCTCTCTGGCTAACTAGGGAACCCACT

GCTTAAGCCTCAATAAAGCTTGCCTTGAGTGCTTCAAGTAGTGTGTGCCCG

TCTGTTGTGTGACTCTGGTAACTAGAGATCCCTCAGACCCTTTTAGTCAGT

GTGGAAAATCTCTAGCAGTGGCGCCCGAACAGGGACTTGAAAGCGAAAGGG

AAACCAGAGGAGCTCTCTCGACGCAGGACTCGGCTTGCTGAAGCGCGCACG

GCAAGAGGCGAGGGGCGGCGACTGGTGAGTACGCCAAAAATTTTGACTAGC

GGAGGCTAGAAGGAGAGAGATGGGTGCGAGAGCGTCAGTATTAAGCGGGGG

AGAATTAGATCGATGGGAAAAAATTCGGTTAAGGCCAGGGGGAAAGAAAA

ATATAAATTAAAACATATAGTATGGGCAAGCAGGGAGCTAGAACGATTCGC

AGTTAATCCTGGCCTGTTAGAAACATCAGAAGGCTGTAGACAAATACTGGG

ACAGCTACAACCATCCCTTCAGACAGGATCAGAAGAACTTAGATCATTATA

TAATACAGTAGCAACCCTCTATTGTGTGCATCAAAGGATAGAGATAAAGA

CACCAAGGAAGCTTTAGACAAGATAGAGGAAGAGCAAAACAAAAGTAAGAA

AAAGCACAGCAAGCAGCAGCTGACACAGGACACAGCAATCAGGTCAGCCA

AAATTACCCTATAGTGCAGAACATCCAGGGGCAAATGGTACATCAGGCCAT

ATCACCTAGAACTTTAAATGCATGGGTAAAAGTAGTAGAAGAGAAGGCTTT

CAGCCCAGAAGTGATACCCATGTTTTCAGCATTATCAGAAGGAGCCACCCC

ACAAGATTTAAACACCATGCTAAACACAGTGGGGGGACATCAAGCAGCCAT

GCAAATGTTAAAAGAGACCATCAATGAGGAAGCTGCAGGCAAAGAGAAGAG

TGGTGCAGAGAGAAAAAAGAGCAGTGGGAATAGGAGCTTTGTTCCTTGGGT

TCTTGGGAGCAGCAGGAAGCACTATGGGCGCAGCGTCAATGACGCTGACGG

TACAGGCCAGACAATTATTGTCTGGTATAGTGCAGCAGCAGAACAATTTGC

TGAGGGCTATTGAGGCGCAACAGCATCTGTTGCAACTCACAGTCTGGGGCA

TCAAGCAGCTCCAGGCAAGAATCCTGGCTGTGGAAAGATACCTAAAGGATC

AACAGCTCCTGGGGATTTGGGGTTGCTCTGGAAAACTCATTTGCACCACTG

CTGTGCCTTGGATCTACAAATGGCAGTATTCATCCACAATTTTAAAAGAAA

AGGGGGGATTGGGGGGTACAGTGCAGGGGAAAGAATAGTAGACATAATAGC

AACAGACATACAAACTAAAGAATTACAAAAACAAATTACAAAAATTCAAAA

TTTTCGGGTTTATTACAGGGACAGCAGAGATCCAGTTTGGGGATCAATTGC

ATGAAGAATCTGCTTAGGGTTAGGCGTTTTGCGCTGCTTCGCGAGGATCTG

CGATCGCTCCGGTGCCCGTCAGTGGGCAGAGCGCACATCGCCCACAGTCCC

CGAGAAGTTGGGGGGAGGGGTCGGCAATTGAACCGGTGCCTAGAGAAGGTG

GCGCGGGGTAAACTGGGAAAGTGATGTCGTGTACTGGCTCCGCCTTTTTCC

CGAGGGTGGGGGAGAACCGTATATAAGTGCAGTAGTCGCCGTGAACGTTCT

TTTTCGCAACGGGTTTGCCGCCAGAACACAGCTGAAGCTTGAGGGGCTCG

CATCTCTCCTTCACGCGCCCGCCGCCCTACCTGAGGCCGCCATCCACGCCG

GTTGAGTCGCGTTCTGCCGCCTCCCGCCTGTGGTGCCTCCTGAACTGCGTC

CGCCGTCTAGGTAAGTTTAAAGCTCAGGTCGAGACCGGGCCTTTGTCCGGC

GCCTGACCCTGCTTGCTCAACTCTACGTCTTTGTTTCGTTTTCTGTTCTGC

GCTCCCTTGGAGCCTACCTAGACTCAGCCGGCTCTCCACGCTTTGCCGTTA

CAGATCCAAGCTGTGACCGGCGCCTACG

GCTAGC

R11 scFV
GAATTCGCCACCATGCTGCTGCTGGTGACAAGCCTGCTGCTGTGCGAGCTG

CCCCACCCCGCCTTTCTGCTGATCCCCCAGAGCGTGAAAGAGTCCGAGGGC

GACCTGGTCACACCAGCCGGCAACCTGACCCTGACCTGTACCGCCAGCGGC

AGCGACATCAACGACTACCCCATCTCTTGGGTCCGCCAGGCTCCTGGCAAG

GGACTGGAATGGATCGGCTTCATCAACAGCGGCGGCAGCACTTGGTACGCC

AGCTGGGTCAAGGCCGGTTCACCATCAGCCGGACCAGCACCACCGTGGAC

CTGAAGATGACAAGCCTGACCACCGACGACACCGCCACCTACTTTTGCGCC

AGAGGCTACAGCACCTACTACGGCGACTTCAACATCTGGGGCCCTGGCACC
```

TABLE 17-continued

CTGGTCACAATCTCTAGCGGCGGAGGCGGCAGCGGAGGTGGAGGAAGTGGC

GGCGGAGGATCCGAGCTGGTCATGACCCAGACCCCCAGCAGCACATCTGGC

GCCGTGGGCGGCACCGTGACCATCAATTGCCAGGCCAGCCAGAGCATCGAC

AGCAACCTGGCCTGGTTCCAGCAGAAGCCCGGCCAGCCCCCCACCCTGCTG

ATCTACAGAGCCTCCAACCTGGCCAGCGGCGTGCCAAGCAGATTCAGCGGC

AGCAGATCTGGCACCGAGTACACCCTGACCATCTCCGGCGTGCAGAGAGAG

GACGCCGCTACCTATTACTGCCTGGGCGGCGTGGGCAACGTGTCCTACAGA

ACCAGCTTCGGCGGAGGTACTGAGGTGGTCGTCAAA

Hinge/spacer
TAGGACCGCCCTGCCCCCCTTGCCCT

GCCCCCGAGTTCCTGGGCGGACCCAGCGTGTTCCTGTTCCCCCCCAAGCCC

AAGGACACCCTGATGATCAGCCGGACCCCCGAGGTGACCTGCGTGGTGGTG

GACGTGAGCCAGGAAGATCCCGAGGTCCAGTTCAATTGGTACGTGGACGGC

GTGGAAGTGCACAACGCCAAGACCAAGCCCAGAGAGGAACAGTTCAACAGC

ACCTACCGGGTGGTGTCTGTGCTGACCGTGCTGCACCAGGACTGGCTGAAC

GGCAAAGAATACAAGTGCAAGGTGTCCAACAAGGGCCTGCCCAGCAGCATC

GAAAAGACCATCAGCAAGGCCAAG

CH3
GGCCAGCCTCGCGAGCCCCAGGTGTACACCCTGCCTCCCTCCCAGGAAGAG

ATGACCAAGAACCAGGTGTCCCTGACCTGCCTGGTGAAGGGCTTCTACCCC

AGCGACATCGCCGTGGAGTGGGAGAGCAACGGCCAGCCTGAGAACAACTAC

AAGACCACCCCTCCCGTGCTGGACAGCGACGGCAGCTTCTTCCTGTACAGC

CGGCTGACCGTGGACAAGAGCCGGTGGCAGGAAGGCAACGTCTTTAGCTGC

AGCGTGATGCACGAGGCCCTGCACAACCACTACACCCAGAAGAGCCTGAGC

CTGTCCCTGGGCAAG 4-1BB
ATGTTCTGGGTGCTGGTGGTGGTGGGCGGGGTGCTGGCCTGCTACAGCCTG

CTGGTGACAGTGGCCTTCATCATCTTTTGGGTGAAACGGGGCAGAAAGAAA

CTCCTGTATATATTCAAACAACCATTTATGAGACCAGTACAAACTACTCAA

GAGGAAGATGGCTGTAGCTGCCGATTTCCAGAAGAAGAAGAAGGAGGATGT

GAACTG

CD3zeta
CGGGTGAAGTTCAGCAGAAGCGCCGACGCCCCTGCCTACCAGCAGGGCCAG

AATCAGCTGTACAACGAGCTGAACCTGGGCAGAAGGGAAGAGTACGACGTC

CTGGATAAGCGGAGAGGCCGGGACCCTGAGATGGGCGGCAAGCCTCGGCGG

AAGAACCCCCAGGAAGGCCTGTATAACGAACTGCAGAAAGACAAGATGGCC

GAGGCCTACAGCGAGATCGGCATGAAGGGCGAGCGGAGGCGGGGCAAGGGC

CACGACGGCCTGTATCAGGGCCTGTCCACCGCCACCAAGGATACCTACGAC

GCCCTGCACATGCAGGCCCTGCCCCCAAGG

T2A
CTCGAGGGCGGCGGAGAGGGCAGAGGAAGTCTTCTAACATGCGGTGACGT

GGAGGAGAATCCCGGCCCTAGG tEGFR
ATGCTTCTCCTGGTGACAAGCCTTCTGCTCTGTGAGTTACCACACCCAGCA

TTCCTCCTGATCCCACGCAAAGTGTGTAACGGAATAGGTATTGGTGAATTT

AAAGACTCACTCTCCATAAATGCTACGAATATTAAACACTTCAAAAACTGC

ACCTCCATCAGTGGCGATCTCCACATCCTGCCGGTGGCATTTAGGGGTGAC

TCCTTCACACATACTCCTCCTCTGGATCGGACAGGAACTGGATATTCTGAA

AACCGTAAAGGAAATCACAGGGTTTTTGCTGATTCAGGCTTGGCCTGAAAA

CAGGACGGACCTCCATGCCTTTGAGAACCTAGAAATCATACGCGGCAGGAC

CAAGCAACATGGTCAGTTTTCTCTTGCAGTCGTCAGCCTGAACATAACATC

CTTGGGATTACGCTCCCTCAAGGAGATAAGTGATGGAGATGTGATAATTTC

AGGAAACAAAAATTTGTGCTATGCAAATACAATAAACTGGAAAAAACTGTT

TGGGACCTCCGGTCAGAAAACCAAAATTATAAGCAACAGAGGTGAAAACAG

CTGCAAGGCCACAGGCCAGGTCTGCCATGCCTTGTGCTCCCCCGAGGGCTG

CTGGGGCCCGGAGCCCAGGGACTGCGTCTCTTGCCGGAATGTCAGCCGAGG

CAGGGAATGCGTGGACAAGTGCAACCTTCTGGAGGGTGAGCCAAGGGAGTT

TGTGGAGAACTCTGAGTGCATACAGTGCCACCCAGAGTGCCTGCCTCAGGC

CATGAACATCACCTGCACAGGACGGGACCAGAACTGTATCCAGTGTGC

CCACTACATTGACGGCCCCCACTGCGTCAAGACCTGCCCGGCAGGAGTCAT

GGGAGAAAACAACACCCTGGTCTGGAAGTACGCAGACGCCGGCCATGTGTG

CCACCTGTGCCATCCAAACTGCACCTACGGATGCACTGGGCCAGGTCTTGA

AGGCTGTCCAACGAATGGGCCTAAGATCCCGTCCATCGCCACTGGGATGGT

GGGGGCCCTCCTCTTGCTGCTGGTGGTGGCCCTGGGGATCGGCCTCTTCAT

GTGAGCGGCCGCTCTAGACCCGGGCTGCAGGAATTCGATATCAAGCTTAT

CGATAATCAACCTCTGGATTACAAAATTTGTGAAAGATTGACTGGTATTCT

TAACTATGTTGCTCCTTTTACGCTATGTGGATACGCTGCTTTAATGCCTTT

GTATCATGCTATTGCTTCCCGTATGGCTTTCATTTTCTCCTCCTTGTATAA

ATCCTGGTTGCTGTCTCTTTATGAGGAGTTGTGGCCCGTTGTCAGGCAACG

TGGCGTGGTGTGCACTGTGTTTGCTGACGCAACCCCCACTGGTTGGGGCAT

TGCCACCACCTGTCAGCTCCTTTCCGGGACTTTCGCTTTCCCCCTCCCTAT

TGCCACGGCGGAACTCATCGCCGCCTGCCTTGCCCGCTGCTGGACAGGGGC

TCGGCTGTTGGGCACTGACAATTCCGTGGTGTTGTCGGGGAAATCATCGTC

CTTTCCTTGGCTGCTCGCCTGTGTTGCCACCTGGATTCTGCGCGGGACGTC

CTTCTGCTACGTCCCTTCGGCCCTCAATCCAGCGGACCTTCCTTCCCGCGG

CCTGCTGCCGGCTCTGCGGCCTCTTCCGCGTCTTCGCCTTCGCCCTCAGAC

GAGTCGGATCTCCCTTTGGGCCGCCTCCCCGCATCGATACCGTCGACTAGC

CGTACCTTTAAGACCAATGACTTACAAGGCAGCTGTAGATCTTAGCCACTT

TTTAAAAGAAAAGGGGGGACTGGAAGGGCTAATTCACTCCCAAAGAAGACA

AGATCTGCTTTTTGCCTGTACTGGGTCTCTCTGGTTAGACCAGATCTGAGC

CTGGGAGCTCTCTGGCTAACTAGGGAACCCACTGCTTAAGCCTCAATAAAG

CTTGCCTTGAGTGCTTCAAGTAGTGTGTGCCCGTCTGTTGTGTGACTCTGG

TABLE 17-continued

```
TAACTAGAGATCCCTCAGACCCTTTTAGTCAGTGTGGAAAATCTCTAGCAG
AATTCGATATCAAGCTTATCGATACCGTCGACCTCGAGGGGGGGCCCGGT
ACCCAATTCGCCCTATAGTGAGTCGTATTACAATTCACTGGCCGTCGTTTT
ACAACGTCGTGACTGGGAAAACCCTGGCGTTACCCAACTTAATCGCCTTGC
AGCACATCCCCCTTTCGCCAGCTGGCGTAATAGCGAAGAGGCCCGCACCGA
TCGCCCTTCCCAACAGTTGCGCAGCCTGAATGGCGAATGGAAATTGTAAGC
GTTAATATTTTGTTAAAATTCGCGTTAAATTTTTGTTAAATCAGCTCATTT
TTTAACCAATAGGCCGAAATCGGCAAAATCCCTTATAAATCAAAAGAATAG
ACCGAGATAGGGTTGAGTGTTGTTCCAGTTTGGAACAAGAGTCCACTATTA
AAGAACGTGGACTCCAACGTCAAAGGGCGAAAAACCGTCTATCAGGGCGAT
GGCCCACTACGTGAACCATCACCCTAATCAAGTTTTTTGGGGTCGAGGTGC
CGTAAAGCACTAAATCGGAACCCTAAAGGGAGCCCCCGATTTAGAGCTTGA
CGGGGAAAGCCGGCGAACGTGGCGAGAAAGGAAGGGAAGAAAGCGAAAGGA
GCGGGCGCTAGGGCGCTGGCAAGTGTAGCGGTCACGCTGCGCGTAACCACC
ACACCCGCCGCGCTTAATGCGCCGCTACAGGGCGCGTCAGGTGGCACTTTT
CGGGGAAATGTGCGCGGAACCCCTATTTGTTTATTTTTCTAAATACATTCA
AATATGTATCCGCTCATGAGACAATAACCCTGATAAATGCTTCAATAATAT
TGAAAAAGGAAGAGTATGAGTATTCAACATTTCCGTGTCGCCCTTATTCCC
TTTTTTGCGGCATTTTGCCTTCCTGTTTTTGCTCACCCAGAAACGCTGGTG
AAAGTAAAAGATGCTGAAGATCAGTTGGGTGCACGAGTGGGTTACATCGAA
CTGGATCTCAACAGCGGTAAGATCCTTGAGAGTTTTCGCCCCGAAGAACGT
TTTCCAATGATGAGCACTTTTAAAGTTCTGCTATGTGGCGCGGTATTATCC
CGTATTGACGCCGGGCAAGAGCAACTCGGTCGCCGCATACACTATTCTCAG
AATGACTTGGTTGAGTACTCACCAGTCACAGAAAAGCATCTTACGGATGGC
ATGACAGTAAGAGAATTATGCAGTGCTGCCATAACCATGAGTGATAACACT
GCGGCCAACTTACTTCTGACAACGATCGGAGGACCGAAGGAGCTAACCGCT
TTTTTGCACAACATGGGGGATCATGTAACTCGCCTTGATCGTTGGGAACCG
GAGCTGAATGAAGCCATACCAAACGACGAGCGTGACACCACGATGCCTGTA
GCAATGGCAACAACGTTGCGCAAACTATTAACTGGCGAACTACTTACTCTA
GCTTCCCGGCAACAATTAATAGACTGGATGGAGGCGGATAAAGTTGCAGGA
CCACTTCTGCGCTCGGCCCTTCCGGCTGGCTGGTTTATTGCTGATAAATCT
GGAGCCGGTGAGCGTGGGTCTCGCGGTATCATTGCAGCACTGGGGCCAGAT
GGTAAGCCCTCCCGTATCGTAGTTATCTACACGACGGGGAGTCAGGCAACT
ATGGATGAACGAAATAGACAGATCGCTGAGATAGGTGCCTCACTGATTAAG
CATTGGTAACTGTCAGACCAAGTTTACTCATATATACTTTAGATTGATTTA
AAACTTCATTTTTAATTTAAAAGGATCTAGGTGAAGATCCTTTTTGATAAT
CTCATGACCAAAATCCCTTAACGTGAGTTTTCGTTCCACTGAGCGTCAGAC
CCCGTAGAAAAGATCAAAGGATCTTCTTGAGATCCTTTTTTTCTGCGCGTA
ATCTGCTGCTTGCAAACAAAAAAACCACCGCTACCAGCGGTGGTTTGTTTG
CCGGATCAAGAGCTACCAACTCTTTTTCCGAAGGTAACTGGCTTCAGCAGA
GCGCAGATACCAAATACTGTTCTTCTAGTGTAGCCGTAGTTAGGCCACCAC
TTCAAGAACTCTGTAGCACCGCCTACATACCTCGCTCTGCTAATCCTGTTA
CCAGTGGCTGCTGCCAGTGGCGATAAGTCGTGTCTTACCGGGTTGGACTCA
AGACGATAGTTACCGGATAAGGCGCAGCGGTCGGGCTGAACGGGGGGTTCG
TGCACACAGCCCAGCTTGGAGCGAACGACCTACACCGAACTGAGATACCTA
CAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTT
CCAGGGGGAAACGCCTGGTATCTTTATAGTCCTGTCGGGTTTCGCCACCTC
TGACTTGAGCGTCGATTTTTGTGATGCTCGTCAGGGGGGCGGAGCCTATGG
AAAAACGCCAGCAACGCGGCCTTTTTACGGTTCCTGGCCTTTTGCTGGCCT
TTTGCTCACATGTTCTTTCCTGCGTTATCCCCTGATTCTGTGGATAACCGT
ATTACCGCCTTTGAGTGAGCTGATACCGCTCGCCGCAGCCGAACGACCGAG
CGCAGCGAGTCAGTGAGCGAGGAAGCGGAAGAGCGCCCAATACGCAAACCG
CCTCTCCCCGCGCGTTGGCCGATTCATTAATGCAGCTGGCACGACAGGMCC
CGACTGGAAAGCGGGCAGTGAGCGCAACGCAATTAATGTGAGTTAGCTCAC
TCATTAGGCACCCCAGGCTTTACACTTTATGCTTCCGGCTCGTATGTTGTG
TGGAATTGTGAGCGGATAACAATTTCACACAGGAAACAGCTATGACCATGA
TTACGCCAAGCTCGAAATTAACCCTCACTAAAGGGAACAAAAGCTGGAGCT
CCACCGCGGTGGCGGCCTCGAGGTCGAGATCCGGTCGACCAGCAACCATAG
TCCCGCCCCTAACTCCGCCCATCCCGCCCCTAACTCCGCCCAGTTCCGCCC
ATTCTCCGCCCCATGGCTGACTAATTTTTTTATTTATGCAGAGGCCGAGG
CCGCCTCGGCCTCTGAGCTATTCCAGAAGTAGTGAGGAGGCTTTTTTGGAG
GCCTAGGCTTTTGCAAAAAGCTTCGACGGTATCGATTGGCTCATGTCCAAC
ATTACCGCCATGTTGACATTGATTATTGACTAGTTATTAATAGTAATCAAT
TACGGGGTCATTAGTTCATAGCCCATATATGGAGTTCCGCGTTACATAACT
TACGGTAAATGGCCCGCCTGGCTGACCGCCCAACGACCCCCGCCCATTGAC
GTCAATAATGACGTATGTTCCCATAGTAACGCCAATAGGGACTTTCCATTG
ACGTCAATGGGTGGAGTATTTACGGTAAACTGCCCACTTGGCAGTACATCA
AGTGTATCATATGCCAAGTACGCCCCCTATTGACGTCAATGACGGTAAATG
GCCCGCCTGGCATTATGCCCAGTACATGACCTTATGGGACTTTCCTACTTG
GCAGTACATCTACGTATTAGTCATCGCTATTACCATGGTGATGCGGTTTTG
GCAGTACATCAATGGGCGTGGATAGCGMTTGACTCACGGGGATTTCCAAGT
CTCCACCCCATTGACGTCAATGGGAGTTTGTTTTGGCACCAAAATCAACGG
GACTTTCCAAAATGTCGTAACAACTCCGCCCCATTGACGCAAATGGGCGGT
AGGCGTGTACGGAATTCGGAGTGGCGAGCCCTCAGATCCTGCATATAAGCA
GCTGCTTTTTGCCTGTACTGGGTCTCTCTG
```

TABLE 18

Leader_R11-Hinge-CH3-CD28tm/41BB-Z-T2A-tEGFR
(SEQ ID NO: 46)

Leader
MLLLVTSLLLCELPHPAFLLIP scFV R11
QSVKESEGDLVTPAGNLTLTCTASGSDINDYPISWVRQAPGKGLEWIGFIN
SGGSTWYASWVKGRFTISRTSTTVDLKMTSLTTDDTATYFCARGYSTYYGD
FNIWGPGTLVTISSGGGGSGGGGSGGGGSELVMTQTPSSTSGAVGGTVTIN
CQASQSIDSNLAWFQQKPGQPPTLLIYRASNLASGVPSRFSGSRSGTEYTL
TISGVQREDAATYYCLGGVGNVSYRTSFGGGTEVVVK Hinge/spacer
ESKYGPPCPPCP CH3
GQPREPQVYTLPPSQEEMTKNQVSLTCLVKGFYPSDIAVEWESNGQPENN
YKTTPPVLDSDGSFFLYSRLTVDKSRWQEGNVFSCSVMHEALHNHYTQKSL
SLSLGK CD28tm
MFWVLVVVGGVLACYSLENTVAFIIFWV 4-1BB
KRGRKKLLYIFKQPFMRPVQTTQEEDGCSCRFPEEEEGGCEL CD3zeta
RVKFSRSADAPAYQQGQNQLYNELNLGRREEYDVLDKRRGRDPEMGGKPRR
KNPQEGLYNELQKDKMAEAYSEIGMKGERRRGKGHDGLYQGLSTATKDTYD
ALHMQALPPR

T2A
LEGGGEGRGSLLTCGDVEENPGPRM tEGFR
LLLVTSLLLCELPHPAFLLIPRKVCNGIGIGEFKDSLSINATNIKHFKNCT
SISGDLHILPVAFRGDSFTHTPPLDPQELDILKTVKEITGFLLIQAWPENR
TDLHAFENLEIIRGRTKQHGQFSLAVVSLNITSLGLRSLKEISDGDVIISG
NKNLCYANTINWKKLFGTSGQKTKIISNRGENSCKATGQVCHALCSPEGCW
GPEPRDCVSCRNVSRGRECVDKCNLLEGEPREFVENSECIQCHPECLPQAM
NITCTGRGPDNCIQCAHYIDGPHCVKTCPAGVMGENNTLVWKYADAGHVCH
LCHPNCTYGCTGPGLEGCPTNGPKIPSIATGMVGALLLLLVVALGIGLFM

TABLE 19

R11 short spacer CAR: PJ_R11-41BB-Z-T2A-tEGFR
(SEQ ID NO: 47)
GTTAGACCAGATCTGAGCCTGGGAGCTCTCTGGCTAACTAGGGAACCCACT
GCTTAAGCCTCAATAAAGCTTGCCTTGAGTGCTTCAAGTAGTGTGTGCCCG
TCTGTTGTGTGACTCTGGTAACTAGAGATCCCTCAGACCCTTTTAGTCAGT
GTGGAAAATCTCTAGCAGTGGCGCCCGAACAGGGACTTGAAAGCGAAAGGG
AAACCAGAGGAGCTCTCTCGACGCAGGACTCGGCTTGCTGAAGCGCGCACG
GCAAGAGGCGAGGGGCGGCGACTGGTGAGTACGCCAAAAATTTTGACTAGC
GGAGGCTAGAAGGAGAGAGATGGGTGCGAGAGCGTCAGTATTAAGCGGGGG
AGAATTAGATCGATGGGAAAAAATTCGGTTAAGGCCAGGGGGAAAGAAAAA TABLE 19-continued ATATAAATTAAAACATATAGTATGGGCAAGCAGGGAGCTAGAACGATTCGC
AGTTAATCCTGGCCTGTTAGAAACATCAGAAGGCTGTAGACAAATACTGGG
ACAGCTACAACCATCCCTTCAGACAGGATCAGAAGAACTTAGATCATTATA
TAATACAGTAGCAACCCTCTATTGTGTGCATCAAAGGATAGAGATAAAAGA
CACCAAGGAAGCTTTAGACAAGATAGAGGAAGAGCAAAACAAAAGTAAGAA
AAAAGCACAGCAAGCAGCAGCTGACACAGGACACAGCAATCAGGTCAGCCA
AAATTACCCTATAGTGCAGAACATCCAGGGGCAAATGGTACATCAGGCCAT
ATCACCTAGAACTTTAAATGCATGGGTAAAAGTAGTAGAAGAGAAGGCTTT
CAGCCCAGAAGTGATACCCATGTTTTCAGCATTATCAGAAGGAGCCACCCC
ACAAGATTTAAACACCATGCTAAACACAGTGGGGGGACATCAAGCAGCCAT
GCAAATGTTAAAAGAGACCATCAATGAGGAAGCTGCAGGCAAAGAGAAGAG
TGGTGCAGAGAGAAAAAAGAGCAGTGGGAATAGGAGCTTTGTTCCTTGGGT
TCTTGGGAGCAGCAGGAAGCACTATGGGCGCAGCGTCAATGACGCTGACGG
TACAGGCCAGACAATTATTGTCTGGTATAGTGCAGCAGCAGAACAATTTGC
TGAGGGCTATTGAGGCGCAACAGCATCTGTTGCAACTCACAGTCTGGGGCA
TCAAGCAGCTCCAGGCAAGAATCCTGGCTGTGGAAAGATACCTAAAGGATC
AACAGCTCCTGGGGATTTGGGGTTGCTCTGGAAAACTCATTTGCACCACTG
CTGTGCCTTGGATCTACAAATGGCAGTATTCATCCACAATTTTAAAAGAAA
AGGGGGGATTGGGGGGTACAGTGCAGGGGAAAGAATAGTAGACATAATAGC
AACAGACATACAAACTAAAGAATTACAAAAACAAATTACAAAAATTCAAAA
TTTTCGGGTTTATTACAGGGACAGCAGAGATCCAGTTTGGGGATCAATTGC
ATGAAGAATCTGCTTAGGGTTAGGCGTTTTGCGCTGCTTCGCGAGGATCTG
CGATCGCTCCGGTGCCCGTCAGTGGGCAGAGCGCACATCGCCCACAGTCCC
CGAGAAGTTGGGGGGAGGGGTCGGCAATTGAACCGGTGCCTAGAGAAGGTG
GCGCGGGGTAAACTGGGAAAGTGATGTCGTGTACTGGCTCCGCCTTTTTCC
CGAGGGTGGGGGAGAACCGTATATAAGTGCAGTAGTCGCCGTGAACGTTCT
TTTTCGCAACGGGTTTGCCGCCAGAACACAGCTGAAGCTTCGAGGGGCTCG
CATCTCTCCTTCACGCGCCCGCCGCCCTACCTGAGGCCGCCATCCACGCCG
GTTGAGTCGCGTTCTGCCGCCTCCCGCCTGTGGTGCCTCCTGAACTGCGTC
CGCCGTCTAGGTAAGTTTAAAGCTCAGGTCGAGACCGGGCCTTTGTCCGGC
GCTCCCTTGGAGCCTACCTAGACTCAGCCGGCTCTCCACGCTTTGCCTGAC
CCTGCTTGCTCAACTCTACGTCTTTGTTTCGTTTTCTGTTCTGCGCCGTTA
CAGATCCAAGCTGTGACCGGCGCCTACG

GCTAGC scFV R11
GAATTCGCCACCATGCTGCTGCTGGTGACAAGCTGCTGCTGTGCGAGCT
GCCCCACCCCGCCTTTCTGCTGATCCCCCAGAGCGTGAAAGAGTCCGAGGG
CGACCTGGTCACACCAGCCGGCAACCTGACCCTGACCTGTACCGCCAGCGG
CAGCGACATCAACGACTACCCCATCTCTTGGGTCCGCCAGGCTCCTGGCAA
GGGACTGGAATGGATCGGCTTCATCAACAGCGGCGGCAGCACTTGGTACGC

TABLE 19-continued

CAGCTGGGTCAAAGGCCGGTTCACCATCAGCCGGACCAGCACCACCGTGGA

CCTGAAGATGACAAGCCTGACCACCGACGACACCGCCACCTACTTTTGCGC

CAGAGGCTACAGCACCTACTACGGCGACTTCAACATCTGGGGCCCTGGCAC

CCTGGTCACAATCTCTAGCGGCGGAGGCGGCAGCGGAGGTGGAGGAAGTGG

CGGCGGAGGATCCGAGCTGGTCATGACCCAGACCCCCAGCAGCACATCTGG

CGCCGTGGGCGGCACCGTGACCATCAATTGCCAGGCCAGCCAGAGCATCGA

CAGCAACCTGGCCTGGTTCCAGCAGAAGCCCGGCCAGCCCCCCACCCTGCT

GATCTACAGAGCCTCCAACCTGGCCAGCGGCGTGCCAAGCAGATTCAGCGG

CAGCAGATCTGGCACCGAGTACACCCTGACCATCTCCGGCGTGCAGAGAGA

GGACGCCGCTACCTATTACTGCCTGGGCGGCGTGGGCAACGTGTCCTACAG

AACCAGCTTCGGCGGAGGTACTGAGGTGGTCGTCAAA

Hinge/spacer
TACGGACCGCCCTGCCCCCCTTGCCCT

GGCCAGCCTCGCGAGCCCCAGGTGTACACCCTGCCTCCCTCCCAGGAAGAG

ATGACCAAGAACCAGGTGTCCCTGACCTGCCTGGTGAAGGGCTTCTACCCC

AGCGACATCGCCGTGGAGTGGGAGAGCAACGGCCAGCCTGAGAACAACTAC

AACACCACCCCTCCCGTGCTGGACAGCGACGGCAGCTTCTTCCTGTACAGC

CGGCTGACCGTGGACAAGAGCCGGTGGCAGGAAGGCAACGTCTTTAGCTGC

AGCGTGATGCACGAGGCCCTGCACAACCACTACACCCAGAAGAGCCTGAGC

CTGTCCCTGGGCAAG 4-1BB
ATGTTCTGGGTGCTGGTGGTGGTGGGCGGGGTGCTGGCCTGCTACAGCCTG

CTGGTGACAGTGGCCTTCATCATCTTTTGGGTGAAACGGGGCAGAAAGAAA

CTCCTGTATATATTCAAACAACCATTTATGAGACCAGTACAAACTACTCAA

GAGGAAGATGGCTGTAGCTGCCGATTTCCAGAAGAAGAAGAAGGAGGATGT

GAACTG

CD3zeta
CGGGTGAAGTTCAGCAGAAGCGCCGACGCCCCTGCCTACCAGCAGGGCCAG

AATCAGCTGTACAACGAGCTGAACCTGGGCAGAAGGGAAGAGTACGACGTC

CTGGATAAGCGGAGAGGCCGGGACCCTGAGATGGGCGGCAAGCCTCGGCGG

AAGAACCCCCAGGAAGGCCTGTATAACGAACTGCAGAAAGACAAGATGGCC

GAGGCCTACAGCGAGATCGGCATGAAGGGCGAGCGGAGGCGGGGCAAGGGC

CACGACGGCCTGTATCAGGGCCTGTCCACCGCCACCAAGGATACCTACGAC

GCCCTGCACATGCAGGCCCTGCCCCCAAGG

T2A
CTCGAGGGCGGCGGAGAGGGCAGAGGAAGTCTTCTAACATGCGGTGACGT

GGAGGAGAATCCCGGCCCTAGG tEGFR
ATGCTTCTCCTGGTGACAAGCCTTCTGCTCTGTGAGTTACCACACCCAGCA

TTCCTCCTGATCCCACGCAAAGTGTGTAACGGAATAGGTATTGGTGAATTT

AAAGACTCACTCTCCATAAATGCTACGAATATTAAACACTTCAAAAACTGC

ACCTCCATCAGTGGCGATCTCCACATCCTGCCGGTGGCATTTAGGGGTGAC

TABLE 19-continued

TCCTTCACACATACTCCTCCTCTGGATCCACAGGAACTGGATATTCTGAA

AACCGTAAAGGAAATCACAGGGTTTTTGCTGATTCAGGCTTGGCCTGAAA

CAGGACGGACCTCCATGCCTTTGAGAACCTAGAAATCATACGCGGCAGGAC

CAAGCAACATGGTCAGTTTTCTCTTGCAGTCGTCAGCCTGAACATAACATC

CTTGGGATTACGCTCCCTCAAGGAGATAAGTGATGGAGATGTGATAATTTC

AGGAAACAAAAATTTGTGCTATGCAAATACAATAAACTGGAAAAAACTGTT

TGGGACCTCCGGTCAGAAAACCAAAATTATAAGCAACAGAGGTGAAAACAG

CTGCAAGGCCACAGGCCAGGTCTGCCATGCCTTGTGCTCCCCCGAGGGCTG

CTGGGGCCCGGAGCCCAGGGACTGCGTCTCTTGCCGGAATGTCAGCCGAGG

CAGGGAATGCGTGGACAAGTGCAACCTTCTGGAGGGTGAGCCAAGGGAGTT

TGTGGAGAACTCTGAGTGCATACAGTGCCACCCAGAGTGCCTGCCTCAGGC

CATGAACATCACCTGCACAGGACGGGACCAGACAACTGTATCCAGTGTGC

CCACTACATTGACGGCCCCCACTGCGTCAAGACCTGCCCGGCAGGAGTCAT

GGGAGAAAACAACACCCTGGTCTGGAAGTACGCAGACGCCGGCCATGTGTG

CCACCTGTGCCATCCAAACTGCACCTACGGATGCACTGGGCCAGGTCTTGA

AGGCTGTCAACGAATGGGCCTAAGATCCCGTCCATCGCCACTGGGATGGT

GGGGGCCCTCCTCTTGCTGCTGGTGGTGGCCCTGGGGATCGGCCTCTTCA

TGTGAGCGGCCGCTCTAGACCCGGGCTGCAGGAATTCGATATCAAGCTTA

TCGATAATCAACCTCTGGATTACAAAATTTGTGAAAGATTGACTGGTATTC

TTAACTATGTTGCTCCTTTTACGCTATGTGGATACGCTGCTTTAATGCCTT

TGTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAAC

GTGGCGTGGTGTGCACTGTGTTTGCTGACGCAACCCCCACTGGTTGGGGCA

TTGCCACCACCTGTCAGCTCCTTTCCGGGACTTTCGCTTTCCCCCTCCCTA

TTGCCACGGCGGAACTCATCGCCGCCTGCCTTGCCCGCTGCTGGACAGGGG

CTCGGCTGTTGGGCACTGACAATTCCGTGGTGTTGTCGGGGAAATCATCGT

CCTTTCCTTGGCTGCTCGCCTGTGTTGCCACCTGGATTCTGCGCGGGACGT

CCTTCTGCTACGTCCCTTCGGCCCTCAATCCAGCGGACCTTCCTTCCCGCG

GCCTGCTGCCGGCTCTGCGGCCTCTTCCGCGTCTTCGCCTTCGCCCTCAGA

CGAGTCGGATCTCCCTTTGGGCCGCCTCCCCGCATCGATACCGTCGACTAG

CCGTACCTTTAAGACCAATGACTTACAAGGCAGCTGTAGATCTTAGCCACT

TTTTAAAAGAAAAGGGGGGACTGGAAGGGCTAATTCACTCCCAAAGAAGAC

AAGATCTGCTTTTTGCCTGTACTGGGTCTCTCTGGTTAGACCAGATCTGAG

CCTGGGAGCTCTCTGGCTAACTAGGGAACCCACTGCTTAAGCCTCAATAAA

GCTTGCCTTGAGTGCTTCAAGTAGTGTGTGCCCGTCTGTTGTGTGACTCTG

GTAACTAGAGATCCCTCAGACCCTTTTAGTCAGTGTGGAAAATCTCTAGCA

GAATTCGATATCAAGCTTATCGATACCGTCGACCTCGAGGGGGGGCCCGG

TACCCAATTCGCCCTATAGTGAGTCGTATTACAATTCACTGGCCGTCGTTT

TACAACGTCGTGACTGGGAAAACCCTGGCGTTACCCAACTTAATCGCCTTG

CAGCACATCCCCCTTTCGCCAGCTGGCGTAATAGCGAAGAGGCCCGCACCG

TABLE 19-continued

```
ATCGCCCTTCCCAACAGTTGCGCAGCCTGAATGGCGAATGGAAATTGTAAG
CGTTAATATTTTGTTAAAATTCGCGTTAAATTTTTGTTAAATCAGCTCATT
TTTTAACCAATAGGCCGAAATCGGCAAAATCCCTTATAAATCAAAAGAATA
GACCGAGATAGGGTTGAGTGTTGTTCCAGTTTGGAACAAGAGTCCACTATT
AAAGAACGTGGACTCCAACGTCAAAGGGCGAAAAACCGTCTATCAGGGCGA
TGGCCCACTACGTGAACCATCACCCTAATCAAGTTTTTTGGGGTCGAGGTG
CCGTAAAGCACTAAATCGGAACCCTAAAGGGAGCCCCCGATTTAGAGCTTG
ACGGGGAAAGCCGGCGAACGTGGCGAGAAAGGAAGGGAAGAAAGCGAAAGG
AGCGGGCGCTAGGGCGCTGGCAAGTGTAGCGGTCACGCTGCGCGTAACCAC
CACACCCGCCGCGCTTAATGCGCCGCTACAGGGCGCGTCAGGTGGCACTTT
TCGGGGAAATGTGCGCGGAACCCCTATTTGTTTATTTTTCTAAATACATTC
AAATATGTATCCGCTCATGAGACAATAACCCTGATAAATGCTTCAATAATA
TTGAAAAAGGAAGAGTATGAGTATTCAACATTTCCGTGTCGCCCTTATTCC
CTTTTTTGCGGCATTTTGCCTTCCTGTTTTTGCTCACCCAGAAACGCTGGT
GAAAGTAAAAGATGCTGAAGATCAGTTGGGTGCACGAGTGGGTTACATCGA
ACTGGATCTCAACAGCGGTAAGATCCTTGAGAGTTTTCGCCCCGAAGAACG
TTTTCCAATGATGAGCACTTTTAAAGTTCTGCTATGTGGCGCGGTATTATC
CCGTATTGACGCCGGGCAAGAGCAACTCGGTCGCCGCATACACTATTCTCA
GAATGACTTGGTTGAGTACTCACCAGTCACAGAAAAGCATCTTACGGATGG
CATGACAGTAAGAGAATTATGCAGTGCTGCCATAACCATGAGTGATAACAC
TGCGGCCAACTTACTTCTGACAACGATCGGAGGACCGAAGGAGCTAACCGC
TTTTTTGCACAACATGGGGGATCATGTAACTCGCCTTGATCGTTGGGAACC
GGAGCTGAATGAAGCCATACCAAACGACGAGCGTGACACCACGATGCCTGT
AGCAATGGCAACAACGTTGCGCAAACTATTAACTGGCGAACTACTTACTCT
AGCTTCCCGGCAACAATTAATAGACTGGATGGAGGCGGATAAAGTTGCAGG
ACCACTTCTGCGCTCGGCCCTTCCGGCTGGCTGGTTTATTGCTGATAAATC
TGGAGCCGGTGAGCGTGGGTCTCGCGGTATCATTGCAGCACTGGGGCCAGA
TGGTAAGCCCTCCCGTATCGTAGTTATCTACACGACGGGGAGTCAGGCAAC
TATGGATGAACGAAATAGACAGATCGCTGAGATAGGTGCCTCACTGATTAA
GCATTGGTAACTGTCAGACCAAGTTTACTCATATATACTTTAGATTGATTT
AAAACTTCATTTTTAATTTAAAAGGATCTAGGTGAAGATCCTTTTTGATAA
TCTCATGACCAAAATCCCTTAACGTGAGTTTTCGTTCCACTGAGCGTCAGA
CCCCGTAGAAAAGATCAAAGGATCTTCTTGAGATCCTTTTTTTCTGCGCGT
AATCTGCTGCTTGCAAACAAAAAAACCACCGCTACCAGCGGTGGTTTGTTT
GCCGGATCAAGAGCTACCAACTCTTTTTCCGAAGGTAACTGGCTTCAGCAG
AGCGCAGATACCAAATACTGTTCTTCTAGTGTAGCCGTAGTTAGGCCACCA
CTTCAAGAACTCTGTAGCACCGCCTACATACCTCGCTCTGCTAATCCTGTT
ACCAGTGGCTGCTGCCAGTGGCGATAAGTCGTGTCTTACCGGGTTGGACTC
AAGACGATAGTTACCGGATAAGGCGCAGCGGTCGGGCTGAACGGGGGGTTC
GTGCACACAGCCCAGCTTGGAGCGAACGACCTACACCGAACTGAGATACCT
```

```
ACAGCGTGAGCTATGAGAAAGCGCCACGCTTCCCGAAGGGAGAAAGGCGGA
CAGGTATCCGGTAAGCGGCAGGGTCGGAACAGGAGAGCGCACGAGGGAGCT
TCCAGGGGGAAACGCCTGGTATCTTTATAGTCCTGTCGGGTTTCGCCACCT
CTGACTTGAGCGTCGATTTTTGTGATGCTCGTCAGGGGGCGGAGCCTATG
GAAAAACGCCAGCAACGCGGCCTTTTTACGGTTCCTGGCCTTTTGCTGGCC
TTTTGCTCACATGTTCTTTCCTGCGTTATCCCCTGATTCTGTGGATAACCG
TATTACCGCCTTTGAGTGAGCTGATACCGCTCGCCGCAGCCGAACGACCGA
GCGCAGCGAGTCAGTGAGCGAGGAAGCGGAAGAGCGCCCAATACGCAAACC
GCCTCTCCCCGCGCGTTGGCCGATTCATTAATGCAGCTGGCACGACAGGTT
TCCCGACTGGAAAGCGGGCAGTGAGCGCAACGCAATTAATGTGAGTTAGCT
CACTCATTAGGCACCCCAGGCTTTACACTTTATGCTTCCGGCTCGTATGTT
GTGTGGAATTGTGAGCGGATAACAATTTCACACAGGAAACAGCTATGACCA
TGATTACGCCAAGCTCGAAATTAACCCTCACTAAAGGGAACAAAAGCTGG
AGCTCCACCGCGGTGGCGGCCTCGAGGTCGAGATCCGGTCGACCAGCAAC
CATAGTCCCGCCCCTAACTCCGCCCATCCCGCCCCTAACTCCGCCCAGTTC
CGCCCATCCTCCGCCCCATGGCTGACTAATTTTTTTATTTATGCAGAGGC
CGAGGCCGCCTCGGCCTCTGAGCTATTCCAGAAGTAGTGAGGAGGCTTTTT
TGGAGGCCTAGGCTTTTGCAAAAAGCTTCGACGGTATCGATTGGCTCATGT
CCAACATTACCGCCATGTTGACATTGATTATTGACTAGTTATTAATAGTAA
TCAATTACGGGGTCATTAGTTCATAGCCCATATATGGAGTTCCGCGTTACA
TAACTTACGGTAAATGGCCCGCCTGGCTGACCGCCCAACGACCCCCGCCCA
TTGACGTCAATAATGACGTATGTTCCCATAGTAACGCCAATAGGGACTTTC
CATTGACGTCAATGGGTGGAGTATTTACGGTAAACTGCCCACTTGGCAGTA
CATCAAGTGTATCATATGCCAAGTACGCCCCCTATTGACGTCAATGACGGT
AAATGGCCCGCCTGGCATTATGCCCAGTACATGACCTTATGGGACTTTCCT
ACTTGGCAGTACATCTACGTATTAGTCATCGCTATTACCATGGTGATGCGG
TTTTGGCAGTACATCAATGGGCGTGGATAGCGGTTTGACTCACGGGGATTT
CCAAGTCTCCACCCCATTGACGTCAATGGGAGTTTGTTTTGGCACCAAAAT
CAACGGGACTTTCCAAAATGTCGTAACAACTCCGCCCCATTGACGCAAATG
GGCGGTAGGCGTGTACGGAATTCGGAGTGGCGAGCCCTCAGATCCTGCATA
TAAGCAGCTGCTTTTTGCCTGTACTGGGTCTCTCTG
```

TABLE 20

Leader_R11-Hinge-CD28tm/41BB-Z-T2A-tEGFR (SEQ ID NO: 48)

Leader
MLLLVTSLLLCELPHPAFLLIP

ScFv R11
QSVKESEGDLVTPAGNLTLTCTASGSDINDYPISWVRQAPGKGLEWIGFINSGGSTW
YASWVKGRFTISRTSTTVDLKMTSLTTDDTATYFCARGYSTYYGDFNIWGPGTLVT
ISSGGGGSGGGGSGGGGSELVMTQTPSSTSGAVGGTVTINCQASQSIDSNLAWFQQ
KPGQPPTLLIYRASNLASGVPSRFSGSRSGTEYTLTISGVQREDAATYYCLGGVGNV
SYRTSFGGGTEVVVK

Spacer/Hinge
ESKYGPPCPPCP

CD28tm
MFWVLVVVGGVLACYSLLVTVAFIIFWV 4-1BB
KRGRKKLLYIFKQPFMRPVQTTQEEDGCSCRFPEEEEGGCEL

CD3zeta
RVKFSRSADAPAYQQGQNQLYNELNLGRREEYDVLDKRRGRDPEMGGKPRRKNP
QEGLYNELQKDKMAEAYSEIGMKGERRRGKGHDGLYQGLSTATKDTYDALHMQ
ALPPR

T2A
LEGGGEGRGSLLTCGDVEENPGPR tEGFR
MLLLVTSLLLCELPHPAFLLIPRKVCNGIGIGEFKDSLSINATNIKHFKNCTSISGDLHI
LPVAFRGDSFTHTPPLDPQELDILKTVKEITGFLLIQAWPENRTDLHAFENLEIIRGRT
KQHGQFSLAVVSLNITSLGLRSLKEISDGDVIISGNKNLCYANTINWKKLFGTSGQK
TKIISNRGENSCKATGQVCHALCSPEGCWGPEPRDCVSCRNVSRGRECVDKCNLLE
GEPREFVENSECIQCHPECLPQAMNITCTGRGPDNCIQCAHYIDGPHCVKTCPAGVM
GENNTLVWKYADAGHVCHLCHPNCTYGCTGPGLEGCPTNGPKIPSIATGMVGALL
LLLVVALGIGLFM

TABLE 21

Intermediate Spacer (SEQ ID NO: 49)

Hinge/spacer
ESKYGPPCPPCP

CH3
GQPREPQVYTLPPSQEEMTKNQVSLTCLVKGFYPSDIAVEWESNGQPENN
YKTTPPVLDSDGSFFLYSRLTVDKSRWQEGNVFSCSVMHEALHNHYTQKS
LSLSLGK

Long spacer (SEQ ID NO: 50)

Hinge
ESKYGPPCPPCP

CH2
APEFLGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPS
SIEKTISKAK

CH3
GQPREPQVYTLPPSQEEMTKNQVSLTCLVKGFYPSDIAVEWESNGQPENN
YKTTPPVLDSDGSFFLYSRLTVDKSRWQEGNVFSCSVMHEALHNHYTQK
SLSLSLGK

TABLE 22

Her 2 construct-short spacer (SEQ Id No: 54)
GMCSFss-Her2scFv-IgG4hinge-CD28tm-41BB-Zeta-T2A-EGFRt Leader
Atgcttctcctggtgacaagccttctgctctgtgagttaccacacccagcattcctcctgatccca Her2scFV
gatatccagatgacccagtccccgagctccctgtccgcctctgtgggcgatagggtcaccatcacctgccgtgccagtcaggatgtg
aatactgctgtagcctggtatcaacagaaaccaggaaaagctccgaaactactgatttactcggcatccttcctctactctggagtccct
tctcgcttctctggttccagatctgggacggatttcactcttaccatcagcagtctgcagccgaagacttcgcaacttattactgtcag
caacattatactactcctcccacgttcggacagggtaccaaggtggagatcaaaggcagtactagcggcggtggctccggggggcg
gatccggtggggggcagcagcgaggttcagctggtggagtctggcggtggcctggtgcagcaggggctcactccgtttgtc
ctgtgcagcttctggcttcaacattaaagacacctatatacactgggtgcgtcaggccccgggtaaggcctggaatgggttgcaag
gatttatcctacgaatggttatactagatatgccgatagcgtcaagggccgtttcactataagcgcagacacatccaaaaacacagcct
acctgcagatgaacagcctgcgtgctgaggacactgccgtctattattgttctagatgggagggggacggcttctatgctatggacta
ctggggtcaaggaaccctggtcaccgtctcgagt TABLE 22-continued Her 2 construct-short spacer (SEQ Id No: 54)
GMCSFss-Her2scFv-IgG4hinge-CD28tm-41BB-Zeta-T2A-EGFRt Hinge spacer
Gagagcaagtacggaccgccctgccccccttgccct CD28tm
atgttctgggtgctggtggtggtcggaggcgtgctggcctgctacagcctgctggtcaccgtggccttcatcatcttttgggtg 4-1BB
Aaacggggcagaaagaaactcctgtatatattcaaacaaccatttatgagaccagtacaaactactcaagaggaagatggctgtagc
tgccgatttccagaagaagaagaaggaggatgtgaactg CD3 zeta
Cgggtgaagttcagcagaagcgccgacgcccctgcctaccagcagggccagaatcagctgtacaacgagctgaacctgggcag
aagggaagagtacgacgtcctggataagcggagaggcccgggaccctgagatgggcggcaagcctcggcgaagaaccccag
gaaggcctgtataacgaactgcagaaagacaagatggccgaggcctacagcgagatcggcatgaagggcgagcggaggcggg
gcaagggccacgacggcctgtatcagggcctgtccaccgccaccaaggatacctacgacgccctgcacatgcaggccctgccc
caagg T2A
Ctcgagggcggcggagagggcagaggaagtcttctaacatgcggtgacgtggaggagaatcccggccctagg tEGFR
atgcttctcctggtgacaagccttctgctctgtgagttaccacacccagcattcctcctgatcccacgcaaagtgtgtaacggaataggt
attggtgaatttaaagactcactctccataaatgctacgaatattaaacacttcaaaaactgcacctccatcagtggcgatctccacatcc
tgccggtggcatttaggggtgactccttcacacatactcctcctctggatccacaggaactggatattctgaaaaccgtaaaggaaatc
acaggttttttgctgattcaggcttggcctgaaaacaggacggacctccatgcctttgagaacctagaaatcatacgcggcaggacc
aagcaacatggtcagttttctcttgcagtcgtcagcctgaacataacatccttgggattacgtccctcaaggagataagtgatggaga
tgtgataatttcaggaaacaaaaatttgtgctatgcaaatacaataaactgaaaaactgtttggacctccggtcagaaaaccaaaa
ttataagcaacagaggtgaaaacagctgcaaggccacaggccaggtctgccatgccttgtgctccccgagggctgctgggccc
ggagcccagggactgcgtctcttgccggaatgtcagccgaggcagggaatgcgtggacaagtgcaaccttctggagggtgagcc
aagggagtttgtggagaactctgagtgcatacagtgccacccagagtgcctgcctcaggccatgaacatcacctgcacaggacgg
ggaccagacaactgtatccagtgtgccactacattgacggccccactgcgtcaagacctgcccggcaggagtcatgggagaaa
acaacaccctggtctggaagtacgcagacgccggccatgtgtgccacctgtgccatccaaactgcacctacggatgcactgggcca
ggtcttgaaggctgtccaacgaatgggcctaagatcccgtccatcgccactgggatggtgggggcctcctcttgctgctggtggtg
gccctggggatcggcctcttcatgtga

TABLE 23

Her 2 construct-intermediate spacer (SEQ Id No: 55)

Leader
Atgcttctcctggtgacaagccttctgctctgtgagttaccacaccca

Her2scFv
Gcattcctcctgatcccagatatccagatgacccagtccccgagctccctgtccgcctctgtgggcgatagggtcaccatcacctgc
cgtgccagtcaggatgtgaatactgctgtagcctggtatcaacagaaaccaggaaaagctccgaaactactgatttactcggcatcct
tcctctactctggagtcccttctcgcttctctggttccagatctgggacggattttcactctgaccatcagcagtctgcagccggaagactt
cgcaacttattactgtcagcaacattatactactcctcccacgttcggacagggtaccaaggtggagatcaaaggcagtactagcggc
ggtggctccggggcggatccggtggggcggcagcagcggaggttcagctggtgcggttggcctggtggtgcagccagg
gggctcactccgtttgtcctgtgcagcttctggcttcaacattaaagacacctatatacactgggtgcgtcaggcccccgggtaaggggc
ctggaatgggttgcaaggatttatcctacgaatggttatactagatatgccgatagcgtcaagggccgtttcactataagcgcagacac
atccaaaacacagcctacctgcagatgaacagcctgcgtgctgaggacactgccgtctattattgttctagatggggagggggacgg
cttctatgctatggactactggggtcaaggaaccctggtcaccgtctcgagt Hinge spacer
GagagcaagtacggaccgccctgccccccttgccctGgccagcctagagaacccaggtgtacaccctgcctcccagccagga
agagatgaccaagaaccaggtgtccctgacctgcctggtcaaaggcttctaccccagcgatatcgccgtggaatgggagagcaac
ggccagcccgagaacaactacaagaccacccccctgtgctggacagcgacggcagcttcttcctgtactcccggctgaccgtgg
acaagagccggtggcaggaaggcaacgtcttcagctgcagcgtgatgcacgaggccctgcacaaccactacacccagaagtccc
tgagcctgagcctgggcaag CD28tm
Atgttctgggtgctggtggtggtcggaggcgtgctggcctgctacagcctgctggtcaccgtggccttcatcatcttttgggtg 4-1BB
Aaacggggcagaaagaaactcctgtatatattcaaacaaccatttatgagaccagtacaaactactcaagaggaagatggctgtagc
tgccgatttccagaagaagaagaaggaggatgtgaactg CD3 zeta
Cgggtgaagttcagcagaagcgccgacgcccctgcctaccagcagggccagaatcagctgtacaacgagctgaacctgggcag
aagggaagagtacgacgtcctggataagcggagaggcccgggaccctgagatgggcggcaagcctcggcgaagaaccccag
gaaggcctgtataacgaactgcagaaagacaagatggccgaggcctacagcgagatcggcatgaagggcgagcggaggcggg
gcaagggccacgacggcctgtatcagggcctgtccaccgccaccaaggatacctacgacgccctgcacatgcaggccctgccc
caagg

TABLE 23-continued

Her 2 construct-intermediate spacer (SEQ Id No: 55)

T2A
Ctcgagggcggcggagagggcagaggaagtcttctaacatgcggtgacgtggaggagaatcccggccctagg tEGFR
atgcttctcctggtgacaagccttctgctctgtgagttaccacacccagcattcctcctgatcccacgcaaagtgtgtaacggaataggt
attggtgaatttaaagactcactctccataaatgctacgaatattaaacacttcaaaaactgcacctccatcagtggcgatctccacatcc
tgccggtggcatttaggggtgactccttcacacatactcctcctctggatccacaggaactggatattctgaaaaccgtaaaggaaatc
acagggttttttgctgattcaggcttggcctgaaaacaggacggacctccatgcctttgagaacctagaaatcatacgcggcaggacc
aagcaacatggtcagttttctcttgcagtcgtcagcctgaacataacatccttgggattacgctccctcaaggagataagtgatggaga
tgtgataatttcaggaaacaaaaatttgtgctatgcaaatacaataaactggaaaaaactgtttgggacctccggtcagaaaaccaaaa
ttataagcaacagaggtgaaaacagctgcaaggccacaggccaggtctgccatgccttgtgctccccgagggctgctgggccc
ggagcccagggactgcgtctcttgccggaatgtcagccgaggcagggaatgcgtggacaagtgcaacccttctggagggtgagcc
aagggagtttgtggagaactctgagtgcatacagtgccacccagagtgcctgcctcaggccatgaacatcacctgcacaggacgg
ggaccagacaactgtatccagtgtgcccactacattgacggcccccactgcgtcaagacctgcccggcaggagtcatgggagaaa
acaacacccctggtctggaagtacgcagacgccggccatgtgtgccacctgtgccatccaaactgcacctacggatgcactgggcca
ggtcttgaaggctgtccaacgaatgggcctaagatcccgtccatcgccactgggatggtgggggcctcctcttgctgctggtggtg
gccctggggatcggcctcttcatgtga

TABLE 24

Her 2 construct-long spacer (SEQ Id No: 56)

leader
<u>Atgcttctcctggtgacaagccttctgctctgtgagttaccacaccca</u>

Her2scFV
gcattcctcctgatcccagatatccagatgacccagtccccgagctccctgtccgcctctgtgggcgatagggtcaccatcacctgcc
gtgccagtcaggatgtgaatactgctgtagcctggtatcaacagaaaccaggaaaagctccgaaactactgatttactcggcatcctt
cctctactctggagtccctctcctgcttctcggttccagatctggagtcacttcactgaccatcagcactctgcagccggaagactt
cgcaacttattactgtcagcaacattatactactcctcccacgttcggacagggtaccaaggtggagatcaaaggcagtactagcggc
ggtggctccggggggcggatccggtgggggcggcagcagcgaggttcagctggtggagtctggcggtggcctggtgcagccagg
gggctcactccgtttgtcctgtgcagcttctggcttcaacattaaagacacctatatacactgggtgcgtcaggcccgggtaagggc
ctggaatgggttgcaaggatttatcctacgaatggttatactagatatgccgatagcgtcaagggccgtttcactataagcgcagacac
atccaaaaacacagcctacctgcagatgaacagcctgcgtgctgaggacactgccgtctattattgttctagatggggaggggacgg
cttctatgctatggactactggggtcaaggaacccctggtcaccgtctcgagt long spacer
gagagcaagtacggaccgccctgcccccccttgccctgcccccgagttcctgggcggaccccagcgtgttcctgttccccccaagcc
caaggacaccctgatgatcagccggaccccgaggtgacctgcgtggtggtggacgtgagccaggaagatcccgaggtccagtt
caattggtacgtggacggcgtggaagtgcacaacgccaagaccaagcccagagaggaacagttcaacagcacctacccgggtggt
gtctgtgctgaccgtgctgcaccaggactggctgaacggcaaagaatacaagtgcaaggtgtccaacaagggcctgcccagcagc
atcgaaaagaccatcagcaaggccaagggccagcctcgcgagccccaggtgtacaccctgcctccctcccaggaagatgatgacc
<u>aagaaccaggtgtccctgacctgcctggtgaagggcttctaccccagcgacatcgccgtggagtgggagagcaacggccagcct</u>
<u>gagaacaactacaagaccacccctcccgtgctggacagcgacggcagcttcttcctgtacagccggctgaccgtggacaagagcc</u>
<u>ggtggcaggaaggcaacgtctttagctgcagcgtgatgcacgaggccctgcacaaccactacacccagaagagcctgagcctgtc</u>
<u>cctgggcaag</u>

CD28tm
atgttctgggtgctggtggtggtgggcggggtgctggcctgctacagcctgctggtgacagtggccttcatcatcttttggtg 4-1BB
aaacggggcagaaagaaactcctgtatatattcaaacaaccatttatgagaccagtacaaactactcaagaggaagatggctgtagct
gccgatttccagaagaagaagaaggaggatgtgaactg CD3zeta
Cgggtgaagttcagcagaagcgccgacgcccctgcctaccagcagggccagaatcagctgtacaacgagctgaacctgggcag
aagggaagagtacgacgtcctggataagcggagaggccgggaccctgagatgggcggcaagcctcggcggaagaaccccag
gaaggcctgtataacgaactgcagaaagacaagatggccgaggcctacagcgagatcggcatgaagggcgagcggaggcggg
gcaagggccacgacggcctgtatcagggcctgtccaccgccaccaaggatacctacgacgccctgcacatgcaggccctgcccc
caagg T2A
Ctcgagggcggcggagagggcagaggaagtcttctaacatgcggtgacgtggaggagaatcccggccctagg tEGFR
atgcttctcctggtgacaagccttctgctctgtgagttaccacacccagcattcctcctgatcccacgcaaagtgtgtaacggaataggt
attggtgaatttaaagactcactctccataaatgctacgaatattaaacacttcaaaaactgcacctccatcagtggcgatctccacatcc
tgccggtggcatttaggggtgactccttcacacatactcctcctctggatccacaggaactggatattctgaaaaccgtaaaggaaatc
acagggttttttgctgattcaggcttggcctgaaaacaggacggacctccatgcctttgagaacctagaaatcatacgcggcaggacc
aagcaacatggtcagttttctcttgcagtcgtcagcctgaacataacatccttgggattacgctccctcaaggagataagtgatggaga
tgtgataatttcaggaaacaaaaatttgtgctatgcaaatacaataaactggaaaaaactgtttgggacctccggtcagaaaaccaaaa
ttataagcaacagaggtgaaaacagctgcaaggccacaggccaggtctgccatgccttgtgctccccgagggctgctgggccc
ggagcccagggactgcgtctcttgccggaatgtcccgaggcagggaatgcgtggacaagtgcaacccttctggagggtgagcc
aagggagtttgtggagaactctgagtgcatacagtgccacccagagtgcctgcctcaggccatgaacatcacctgcacaggacgg
ggaccagacaactgtatccagtgtgcccactacattgacggcccccactgcgtcaagacctgcccggcaggagtcatgggagaaa TABLE 24-continued Her 2 construct-long spacer (SEQ Id No: 56)

acaacaccctggtctggaagtacgcagacgccggccatgtgtgccacctgtgccatccaaactgcacctacggatgcactgggcca
ggtcttgaaggctgtccaacgaatgggcctaagatcccgtccatcgccactgggatggtgggggccctcctcttgctgctggtggtg
gccctggggatcggcctcttcatgtga

That which is claimed is:

1. A nucleic acid encoding a chimeric receptor, wherein the chimeric receptor comprises:
   (a) an scFv that binds to an epitope in the extracellular region of CD19, wherein the scFv comprises the variable heavy (VH) chain and the variable light (VL) chain encoded by SEQ ID NO:3;
   (b) a transmembrane domain;
   (c) a polypeptide spacer located between the scFv and the transmembrane domain, wherein the polypeptide spacer consists of the amino acid sequence set forth in SEQ ID NO:21; and
   (d) an intracellular signaling domain that comprises the signaling domain of CD3ζ and a costimulatory domain.

2. The nucleic acid of claim 1, wherein the scFv has a VL-linker-VH orientation.

3. The nucleic acid of claim 1, wherein the scFv consists of the amino acid sequence encoded by SEQ ID NO:3.

4. A T cell comprising the nucleic acid of claim 1.

5. The T cell of claim 4, wherein the T cell is a CD8+ T cell or a CD4+ T cell.

6. A composition, comprising the T cell of claim 4 in a pharmaceutically acceptable excipient.

7. The composition of claim 6, wherein at least 30% of the T cells in the composition expressing the chimeric receptor are capable of proliferating through at least two generations in vitro.

8. The composition of claim 6, wherein the T cell in the composition is a CD8+ T cell selected from the group consisting of nave CD8+ T cells, central memory CD8+ T cells, effector memory CD28+ T cells, and bulk CD8+ T cells; or a CD4+ T cell selected from the group consisting of naïve CD4+ T cells, central memory CD4+ T cells, effector memory CD4+ T cells, and bulk CD4+ T cells.

9. The composition of claim 8, wherein the composition comprises a plurality of T cells, wherein the plurality of T cells comprise a plurality of the CD8+ T cells and a plurality of the CD4+ T cells.

10. A nucleic acid encoding a chimeric receptor wherein the chimeric receptor comprises:
    (a) an scFv that binds to an epitope in the extracellular region of CD19, wherein the scFv comprises a VL chain domain comprising the sequences RASQDIS-KYLN (SEQ ID NO:57), SRLHSGV (SEQ ID NO:58), and GNTLPYTFG (SEQ ID NO:59) and a VH chain domain comprising the sequences DYGVS (SEQ ID NO:74), VIWGSETTYYNSALKS (SEQ ID NO:60), and YAMDYWG (SEQ ID NO:61);
    (b) a transmembrane domain;
    (c) a polypeptide spacer located between the scFv and the transmembrane domain, wherein the polypeptide spacer consists of the amino acid sequence set forth in SEQ ID NO:21; and
    (d) an intracellular signaling domain that comprises the signaling domain of CD3ζ and a costimulatory domain.

11. The nucleic acid of claim 10, wherein the scFv has a VL-linker-VH orientation.

12. The nucleic acid of claim 10, wherein:
    the scFv comprises the VH chain and the VL chain encoded by SEQ ID NO:3;
    the transmembrane domain consists of the amino acid sequence encoded by SEQ ID NO:5; and
    the intracellular signaling domain comprises the amino acid sequence encoded by SEQ ID NO:6 and the amino acid sequence encoded by SEQ ID NO:7.

13. The nucleic acid of claim 10, wherein the transmembrane domain consists of the transmembrane domain of CD8 or of CD28, and the costimulatory domain comprises the signaling domain of 4-1BB.

14. The nucleic acid of claim 10, wherein:
    the scFv has a VL-linker-VH orientation;
    the transmembrane domain consists of the amino acid sequence encoded by SEQ ID NO:5; and
    the intracellular signaling domain comprises the amino acid sequence encoded by SEQ ID NO:6 and the amino acid sequence encoded by SEQ ID NO:7.

15. The nucleic acid of claim 1, wherein:
    the transmembrane domain consists of the transmembrane domain of CD28; and
    the costimulatory domain comprises the signaling domain of 4-1BB or the signaling domain of CD28.

16. A chimeric receptor encoded by the nucleic acid of claim 1.

17. An expression vector comprising the nucleic acid of claim 1.

18. The nucleic acid of claim 10, wherein:
    the transmembrane domain consists of the transmembrane domain of CD28; and
    the costimulatory domain comprises the signaling domain of 4-1BB or the signaling domain of CD28.

19. The nucleic acid of claim 1, wherein the nucleic acid is set forth by SEQ ID NO:10, or a sequence having at least 95% identity to SEQ ID NO:10.

20. The expression vector of claim 17, further comprising a polynucleotide encoding a marker sequence, wherein the polynucleotide encoding the marker sequence is operably linked in frame with the polynucleotide encoding the chimeric receptor.

21. The expression vector of claim 20, wherein the polynucleotide encoding the chimeric receptor and the polynucleotide encoding the marker sequence are separated by a polynucleotide encoding a cleavable linker sequence.

22. The expression vector of claim 20, wherein the marker sequence is a truncated EGFR sequence.

23. The expression vector of claim 21, wherein the cleavable linker sequence is a T2A peptide.

24. A chimeric receptor encoded by the nucleic acid of claim 10.

25. A T cell comprising the nucleic acid of claim 10.

26. An expression vector comprising the nucleic acid of claim 10.

27. A chimeric receptor encoded by SEQ ID NO:10.

28. The nucleic acid of claim 1, wherein the polynucleotide encoding the chimeric receptor comprises:
    the scFv encoded by SEQ ID NO:3;
    the polypeptide spacer encoded by SEQ ID NO:4;
    the transmembrane domain encoded by SEQ ID NO:5;
    the costimulatory domain encoded by SEQ ID NO:6; and
    the CD3 signaling domain encoded by SEQ ID NO:7.

29. The nucleic acid of claim 10, wherein the intracellular signaling domain consists of the signaling domain of CD3ζ and the costimulatory domain of 4-1BB.

30. The nucleic acid of claim 1, wherein:
    the scFv consists of the amino acid sequence encoded by SEQ ID NO:3;
    the transmembrane domain consists of the amino acid sequence encoded by SEQ ID NO:5; and
    the intracellular signaling domain comprises the amino acid sequence encoded by SEQ ID NO:6 and the amino acid sequence encoded by SEQ ID NO:7.

31. The composition of claim 9, wherein the CD8+ T cells and the CD4+ T cells are present at about a 1:1 ratio in the composition.

32. A chimeric receptor encoded by the nucleic acid of claim 28.

33. An expression vector comprising the nucleic acid of claim 28.

34. A T cell comprising the nucleic acid of claim 28.

35. A chimeric receptor encoded by the nucleic acid of claim 30.

36. An expression vector comprising the nucleic acid of claim 30.

37. A T cell comprising the nucleic acid of claim 30.

* * * * *

UNITED STATES PATENT AND TRADEMARK OFFICE
CERTIFICATE OF CORRECTION

PATENT NO. : 10,780,118 B2  
APPLICATION NO. : 14/422640  
DATED : September 22, 2020  
INVENTOR(S) : Michael C. Jensen et al.

Page 1 of 2

It is certified that error appears in the above-identified patent and that said Letters Patent is hereby corrected as shown below:

In the Specification

Column 7, Line 13, replace "untranduced" with -- untransduced --;

Column 11, Line 6, replace "Pr" with -- PI⁻ --;

Column 11, Line 23, replace "binge" with -- hinge --;

Column 12, Line 29, replace "ore more" with -- or more --;

Column 17, Line 16, replace "inetermediate" with -- intermediate --;

Column 20, Line 39, replace "68$" with -- 68 --;

Column 29, Line 52, replace "1000%" with -- 100% --;

Column 35, Line 41, replace "an cell" with -- a cell --;

Column 41, Line 55, replace "IgG4-Fe" with -- IgG4-Fc --;

Column 43, Line 51, replace "16.4%/i 8.4%" with -- 16.4%/18.4% --;

Column 44, Line 26, replace "IgG4 Fe" with -- IgG4 Fc --;

Column 49, Line 35, replace "IgG4-Fe" with -- IgG4-Fc --;

Column 54, Line 5, replace "4-IBB" with -- 4-1BB --;

Column 54, Line 10, replace "4-IBB" with -- 4-1BB --;

Signed and Sealed this  
Ninth Day of March, 2021

Drew Hirshfeld  
*Performing the Functions and Duties of the  
Under Secretary of Commerce for Intellectual Property and  
Director of the United States Patent and Trademark Office*

CERTIFICATE OF CORRECTION (continued)
U.S. Pat. No. 10,780,118 B2

Column 55, Line 1, replace "4-IBB" with -- 4-1BB --;

Column 55, Line 3, replace "4-IBB" with -- 4-1BB --;

Column 55, Line 6, replace "4-IBB" with -- 4-1BB --;

Column 55, Line 13, replace "4-IBB" with -- 4-1BB --;

Column 55, Line 18, replace "4-IBB" with -- 4-1BB --;

In the Claims

Claim 8, Column 228, Line 66, replace "nave" with -- naïve --;

Claim 8, Column 228, Line 67, replace "CD28+" with -- CD8+ --;

Claim 10, Column 229, Line 8, replace "receptor wherein" with -- receptor, wherein --;

Claim 20, Column 230, Lines 9-10, replace "polynucleotide encoding the chimeric receptor." with -- nucleic acid encoding the chimeric receptor. --;

Claim 21, Column 230, Line 12, replace "polynucleotide encoding the chimeric receptor" with -- nucleic acid encoding the chimeric receptor --;

Claim 28, Column 230, Line 32, replace "CD3" with -- CD3ζ --.